(12) United States Patent
Wang et al.

(10) Patent No.: US 10,858,659 B2
(45) Date of Patent: Dec. 8, 2020

(54) BIOSYNTHETIC GENE CLUSTER OF CARRIMYCIN

(71) Applicant: SHENYANG FUYANG PHARMACEUTICAL TECHNOLOGY CO., LTD., Shenyang, Liaoning (CN)

(72) Inventors: Yiguang Wang, Liaoning (CN); Yang Jiang, Liaoning (CN); Xiaofeng Zhao, Liaoning (CN); Weiqing He, Liaoning (CN); Jianlu Dai, Liaoning (CN)

(73) Assignee: SHENYANG FUYANG PHARMACEUTICAL TECHNOLOGY CO., LTD., Shenyang (CN)

(*) Notice: Subject to any disclaimer, the term of this patent is extended or adjusted under 35 U.S.C. 154(b) by 52 days.

(21) Appl. No.: 16/067,392

(22) PCT Filed: Nov. 24, 2016

(86) PCT No.: PCT/CN2016/107039
§ 371 (c)(1),
(2) Date: Jun. 29, 2018

(87) PCT Pub. No.: WO2017/114034
PCT Pub. Date: Jul. 6, 2017

(65) Prior Publication Data
US 2019/0093112 A1  Mar. 28, 2019

(30) Foreign Application Priority Data
Dec. 31, 2015 (CN) .......................... 2015 1 1028754

(51) Int. Cl.
| | | |
|---|---|---|
| *C12N 9/04* | (2006.01) | |
| *C12N 15/52* | (2006.01) | |
| *C12P 19/62* | (2006.01) | |
| *C12N 9/02* | (2006.01) | |
| *C12N 9/10* | (2006.01) | |
| *C12N 9/16* | (2006.01) | |
| *C12N 9/86* | (2006.01) | |

(52) U.S. Cl.
CPC ............ *C12N 15/52* (2013.01); *C12N 9/001* (2013.01); *C12N 9/0006* (2013.01); *C12N 9/1029* (2013.01); *C12N 9/16* (2013.01); *C12N 9/86* (2013.01); *C12P 19/62* (2013.01); *C12Y 101/01064* (2013.01); *C12Y 101/01188* (2013.01); *C12Y 103/01008* (2013.01); *C12Y 203/01013* (2013.01); *C12Y 301/02007* (2013.01); *C12Y 305/02003* (2013.01)

(58) Field of Classification Search
CPC ........ C12N 15/52; C12N 9/116; C12N 9/001; C12N 9/1029; C12N 9/16; C12N 9/86
See application file for complete search history.

(56) References Cited

U.S. PATENT DOCUMENTS

| 7,070,980 B2 | 7/2006 | Midoh et al. |
| 7,795,001 B2 | 9/2010 | Midoh et al. |
| 2004/0016182 A1 | 8/2004 | Shen et al. |

FOREIGN PATENT DOCUMENTS

| CN | 1174238 A | 2/1998 |
| CN | 1405299 A | 3/2003 |
| CN | 1554355 A | 12/2004 |
| CN | 101649325 A | 2/2010 |
| CN | 102115757 A | 7/2011 |
| CN | 103820474 A1 | 5/2014 |
| CN | 105505954 A | 4/2016 |
| EP | 0 354 641 | 2/1990 |
| EP | 0 791 656 | 8/1997 |
| EP | 2 597 152 | 5/2013 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Guangdong et al., *Construction of a Stable Bioengineered Strain of Biotechmycin*, 15(2) Chinese Journal of Biotechnology 171-175 (Apr. 1999) (English translation abstract on p. 175).
Ma et al., *Construction of 4"-Isovalerylspiramycin-I-Producing Strain by In-Frame Partial Deletion of 3-O-Acyltransferase Gene in Streptomyces spiramyceticus WSJ-1, the Bitespiramycin Producer*, 62 Curr. Microbiol 16-20 (2011).
International Search Report (PCT/ISA/210) dated Feb. 27, 2017, by the Chinese Patent Office as the International Searching Authority for International Application No. PCT/CN2016/107039.
Chunyan et al., *Construction of 4" Isovalerylspiramycin-I-Producing Straining by In-Frame Partial Deletion of 3-O-Acyltransferase Gene in Streptomyces spiramyceticus WSJ-1, the Bitespiramycin Producer*, 62(1) Current Microbiology 16-20 (2011).
Shang et al., *Construction and Physiological Studies on a Stable Bioengineered Strain of Shengjimycin*, 54(1) The Journal of Antibiotics 66-73 (Feb. 2001).

(Continued)

Primary Examiner — Richard G Hutson
(74) Attorney, Agent, or Firm — Buchanan Ingersoll & Rooney PC

(57) ABSTRACT

The present disclosure provides a biosynthetic gene cluster of carrimycin. The biosynthetic gene cluster comprises 44 gene open reading frames (orf), i.e., 5 orfs (orf10-14) encoding polyketide synthase, 9 orfs (orf1, 4-6, 15 and 36-39) related to polyketone synthesis extension unit and modification, 16 orfs (orf9, 16-22, 24, 26, 28, 29, 33-35 and 41) related to glycosyl synthesis, 6 orfs (orf7, 8, 30-32 and 40) related to glycosyl transfer, 2 orfs (orf3 and 25) related to resistance, 4 orfs (orf2, 23, 27 and 42) possibly related to regulation, a tsr resistance marker gene orf (orf43) and a 4"-mycaroseglucoside isovaleryl transferase gene orf (orf44).

8 Claims, 3 Drawing Sheets
Specification includes a Sequence Listing.

(56) References Cited

OTHER PUBLICATIONS

Wang et al., *Regulation of branched-chain amino acid catabolism: glucose limitation enhances the component of isovalerylspiramycin for the bitespiramycin production*, 33 Bioprocess and Biosystems Engineering 257-265 (201).

* cited by examiner

BIOSYNTHETIC GENE CLUSTER OF CARRIMYCIN

TECHNICAL FIELD

The present disclosure belongs to the fields of microbial gene resources and gene engineering, specifically relates to clone, analysis and function research of antibiotic biosynthetic gene clusters in gene engineering and an application of the antibiotic biosynthetic gene clusters.

BACKGROUND

Carrimycin has used names, i.e., shengjimycin and biotechspiramycin, is a 16-membered macrolide antibiotic developed by using a synthetic biology technology [described in patents with number ZL971044406 and ZL021487715]. Carrimycinis a spiramycin with multi-acylated 4"-hydroxyl, which takes 4"-isovaleryl spiramycin III, II and I as main ingredients, wherein the ingredient III accounts for about 30% or more, the ingredient II accounts for about 25%, and the content of ingredient I does not exceed 10%.

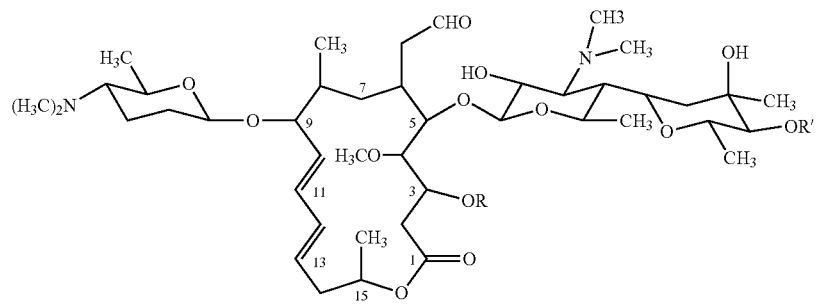

Structural formula of carrimycin

Isovalerylspiramycin III: R = COCH$_2$CH$_3$ R' = COCH$_2$CH(CH$_3$)$_2$
Isovalerylspiramycin II: R = COCH$_3$ R' = COCH$_2$CH(CH$_3$)$_2$
Isovalerylspiramycin I: R = H R' = COCH$_2$CH(CH$_3$)$_2$ Carrimycin has relatively high activity to Gram-positive bacteria and has antibacterial activity to erythromycin, beta-lactam antibiotic-resistant bacteria, bacillus influenzae, gonococcus, legionella, Bacteroides fragilis and Clostridium perfringens. Particularly, carrimycin has relatively high activity to Mycoplasma pneumoniae, Chlamydia trachomatis and Chlamydia pneumoniae [Yu, Lanxiang, et al., Sichuan Journal of Physiological Sciences; 1998, 20 (3), patent number: 2003101224209] and has better post-antibiotic effects and antibiotic sub-MIC effects. Carrimycin is free of complete drug cross resistance with similar drugs. Shown by pharmacokinetics researches, carrimycin has higher lipophicity and is high in intracellular antibacterial activity, high in oral administration absorption speed, high in absolute bioavailability, high in tissue penetrability, wide in tissue distribution, long in elimination half-life and long in in-vivo retention time, and tissue concentration of the carrimycinis higher than blood plasma concentration [Sun, Liwen, et al., Chinese Pharmacological Bulletin 2000, 16 (6): 694-8; Zhong, Dafang, et al., J chromatography B. 2003, 791: 45; Shi, Xiangguo, et al., Asian Journal of Drug Metabolism and Pharmacokinetics. 2003, 3 (2): 134; Shi, Xiangguo, et al., Chinese Chemical letter 2004, 15: 431; Shi, Xiangguo, et al., ActaPharmacologicaSinica, 2004, 25: 1396]. Shown by pharmacologic, toxicologic and completed clinical three-stage research results, carrimycin is used for treating respiratory tract infections, is definite in treatment effect and low in adverse reaction rate, particularly has little injury to livers and is good in safety [Lin, Futian, et al., Eighth nationwide antibiotic academic conference paper compilation 1997, p. 167; Zhao, Chunyan, et al., Chinese Journal of Antibiotics, 1998, 23 (4): 306; Sun, Tao, et al., Chinese Journal of Antibiotics, 2001, 26 (1): 49-51]. Carrimycin is a direct fermented product of gene engineering bacterium obtained by using gene recombination technology. The preparation process is simple and convenient, and it can effectively avoid chemical contamination and save energy source. Oral preparations of carrimycin are convenient to take and only required to be taken once per day, which is helpful to improve the compliance of patients with medications, and is also convenient to enter the basic medical insurance drug series.

Carrimycin is a fermented product of gene engineering bacteria (Streptomyces spiramyceticus WSJ-1), which is obtained through subjecting 4"-isovaleryl transferasegenes of carbomycin producing bacteria to clone expression in spiramycin producing bacteria (Streptomyces spiramyceticus F21). The spiramycin producing bacteria (Streptomyces spiramyceticus F21) was isolated from soil in Yongchang County, Gansu Province, China in 1982 by our laboratory. The morphological characteristics, physiologic biochemical characteristics, cell wall chemical composition, 16S rRNA gene sequence and 5 housekeeping gene protein levels of the bacteria in phylogenetic tree analysis has nothing in common with abroad-reported spiramycin producing bacteria Streptomyces ambofaciens ATCC23877 and reported streptomycete. Thus, the spiramycin producing bacteria (Streptomyces spiramyceticus F21) is extremely possibly a new streptomycete species [Dai, Jianlu, et al., Journal of Microbiology, 2012, 39 (4): 503-514].

Sequencing of gene clusters related to spiramycin biosynthesis in the spiramycin producing bacteria Streptomyces ambofaciens ATCC23877 has been completed [Karray F., Microbiology, 2007, 153: 4111-4122], and sequences of biosynthetic gene clusters of other macrolide antibiotics such as avermectin, canavaliamycin, erythromycin, chalcomycin, tylosin and medemycin have also been reported [Ikeda H. et al., Nat. Biotechnol. 2003, 21(5): 526-531, Haydock et al., Microbiology, 2005, 151, 3161-3169; Oliynyk M. et al., Nat. Biotechnol. 2007, 25(4): 447-453;

Wards L. et al., Antimicrob. Agents & Chemotherapy, 2004, 48(12): 4703-4712; Cundiffe E. et al., Antonie Van Leeuwenhoek, 2001, 79(3-4): 229-234; Midoh Naoki et al., U.S. Pat. No. 7,070,980]. Biosynthetic gene clusters of macrolide antibiotics have the full length of about 50-80 kb and have the common characteristics of being composed of polyketide synthase (PKS) for encoding a biosynthetic modular structure of a 16-membered macrolide ring, polyketone synthesis extension unit related enzymes, enzymes responsible for modification of different radical groups of a lactone ring, genes of glycosyl synthesis and transfer related enzymes and resistance and regulation and control function related genes, etc. Macrolides are formed through carrying out a continuous condensation reaction to catalyze some simple carboxylic acid molecules by PKS composed of modular structures in a manner similar to biosynthesis of fatty acids. Each module is only responsible for one-step condensation reaction in a polyketone chain forming process, and the module at least contains a beta-ketoacylsynthetase (KS) structural domain, an acyltransferase (AT) structural domain and an acyl carrier protein (ACP) structural domain. In addition, the module further possibly contains a beta-ketoacyl reductase (KR) structural domain, a dehydrase (DH) structural domain and an ester acyl reductase (ER) structural domain, and the structural domains decide a reduction step of added extension units. Meanwhile, the action of a thioesterase (TE) structural domain is also required to catalyze the cyclization and release of polyketone chains. Finally, modification steps such as hydroxylation, methylation, methoxylation and acylation are also required to be carried out to form various structures of macrolide antibiotics. Generally, all the macrolides are connected with glycosyl groups (or glycosylamino) of different quantities, for example, carrimycin contains three glycosyl groups, i.e., forosamine, mycaminose and mycarose. The glycosyl groups are undertaken by glycosyl synthesis and transfer related enzymes. Resistant genes endow the producing bacteria with capability for resisting antibiotic producted by itself and are generally related to ABC transport protein. Regulation and control function related genes participate in regulation and control of self-biosynthetic antibiotics.

Through gene cluster sequence information and structural analysis, the genetic manipulations can be further performed on producing bacteria to obtain novel and more effective antibiotics. For example, new macrolide antibiotics are created through changing PKS synthesis modular structures of macrolide antibiotics by genetic manipulation, changing lactone ring after-modification and replacing or modifying glycosyl groups. And the yield of the antibiotics can be increased through carrying out genetic operation on resistant genes or regulatory genes. [Wilkinson B. et al., Chem Biol. 2000, 7 (2): 111-117; Kalz L. et al., Med Res Rev. 1999, 19 (6): 543-58; Goodman C D et al., Antimicrobial Agents and Chemotherapy, 2013, 57(2): 907-913; Wang W et al., ProcNatlAcadSci USA, 2014, 111(15): 5688-93; Stratigopoulos G et al., Mol Microbiol. 2004, 54(5): 1326-34; Novakova R et al., Folia Microbiol. 2011, 56(3): 276-82].

SUMMARY

The present disclosure provides a biosynthetic linkage gene cluster of carrimycin. The gene cluster has 44 gene open reading frames (orf) in all, the full length of nucleotide sequences is 89315 bp (Seq. 1). The gene cluster contains 5 orfs encoding polyketide synthase (orf 10-14), comprising 8 modules and 37 structural domains, 9 orfs related to polyketone synthesis extension unit and modification (1, 4-6, 15 and 36-39), 16 orfs related to glycosyl synthesis (9, 16-22, 24, 26, 28, 29, 33-35 and 41) and 6 orfs related to glycosyl transfer (7, 8, 30-32 and 40). In addition, the gene cluster further comprises 2 orfs related to resistance (3 and 25) and 4 orfs possibly-related to regulation and control (2, 23, 27 and 42). The nucleotide sequences are separately selected from a group consisting of orf1(1-645), orf2(1810-1208), orf3(3133-2285), orf4(3614-4840), orf5(4846-5511), orf6 (7150-5801), orf7(8444-7179), orf8(9729-8482), orf9 (10543-9830), orf10(16215-10543), orf11(21076-16328), orf12(32511-21124), orf13(38599-32585), orf14(52259-38643), orf15(53099-54310), orf16(54495-54845), orf17 (54842-56041), orf18(56038-56946), orf19(56930-57967), orf20(57937-60174), orf21(60836-61984), orf22(62796-62077), orf23 (63633-65645), orf24(67379-66318), orf25 (69004-67352), orf26(69349-70650), orf27(72156-70708), orf28(72422-73462), orf29(74601-73561), orf30(74913-76160), orf31(76218-77486), orf32(77606-78781), orf33 (78783-79775), orf34(79772-80779), orf35(82055-80823), orf36(83164-82052), orf37(84400-83279), orf38(84713-84393), orf39(85576-84710), orf40(85825-87042), orf41 (87094-87702) and orf42(89315-88143) in Seq. 1. In addition, the gene cluster further comprises orf43 (866-60) and orf44 (2337-1174) in an exogenous gene Seq. 2 unlinked to Seq. 1 with the full length of 2337 bp.

The present disclosure further provides an amino acid sequence of 4'-phosphopantetheinyl transferase (PPT), the amino acid sequence consists of 214 amino acids in Seq. 3 and is called as IA-W1, and nucleotide sequence of an encoding gene is selected from 1-645 bases in Seq. 1.

The present disclosure further provides an amino acid sequence of a TetR family transcription regulation and control factor, the amino acid sequence consists of 200 amino acids in Seq. 4 and is called as IA-W2, and nucleotide sequence of an encoding gene is selected from 1810-1208 bases in Seq. 1.

The present disclosure further provides an amino acid sequence of 23S rRNA methyltransferase, the amino acid sequence consists of 282 amino acids in Seq. 5 and is called as IA-W3, and nucleotide sequence of an encoding gene is selected from 3133-2285 bases in Seq. 1.

The present disclosure further provides an amino acid sequence of 3-O-acyltransferase, the amino acid sequence consists of 408 amino acids in Seq. 6 and is called as IA-W4, and nucleotide sequence of an encoding gene is selected from 3614-4840 bases in Seq. 1.

The present disclosure further provides an amino acid sequence of O-methyltransferase, the amino acid sequence consists of 221 amino acids in Seq. 7 and is called as IA-W5, and nucleotide sequence of an encoding gene is selected from 4846-5511 bases in Seq. 1.

The present disclosure further provides an amino acid sequence of crotonyl coenzyme A reductase, the amino acid sequence consists of 449 amino acids in Seq. 8 and is called as IA-W6, and nucleotide sequence of an encoding gene is selected from 7150-5801 bases in Seq. 1.

The present disclosure further provides an amino acid sequence of glycosyltransferase, the amino acid sequence consists of 421 amino acids in Seq. 9 and is called as IA-W7, and nucleotide sequence of an encoding gene is selected from 8444-7179 bases in Seq. 1.

The present disclosure further provides an amino acid sequence of glycosyltransferase accessory protein, the amino acid sequence consists of 415 amino acids in Seq. 10 and is called as IA-W8, and nucleotide sequence of an encoding gene is selected from 9729-8482 bases in Seq. 1.

The present disclosure further provides an amino acid sequence of NDP-aminohexose N-dimethyltransferase, the amino acid sequence consists of 237 amino acids in Seq. 11 and is called as IA-W9, and nucleotide sequence of an encoding gene is selected from 10543-9830 bases in Seq. 1.

The present disclosure further provides an amino acid sequence comprising a polyketidesynthase structural domain of ketosynthase $(KS)_8$-acyltransferase $(AT)_8$-ketoreductase $(KR)_8$-acyl carrier protein $(ACP)_8$-chain-release thioesterase (TE), the amino acid sequence consists of 1890 amino acids in Seq. 12 and is called as IA-W10, and nucleotide sequence of an encoding gene is selected from 16215-10543 bases in Seq. 1.

The present disclosure further provides an amino acid sequence comprising a polyketide synthase structural domain of $KS_7$-$AT_7$-$KR_7$-$ACP_7$, the amino acid sequence consists of 1582 amino acids in Seq. 13 and is called as IA-W11, and nucleotide sequence of an encoding gene is selected from 21076-16328 bases in Seq. 1.

The present disclosure further provides an amino acid sequence comprising a polyketide synthase structural domain of $KS_5$-$AT_5$-$KR_5$-$ACP_5$-$KS_6$-$AT_6$-$DH_6$ (dehydrase)-$ER_6$ (enoylreductase)-$KR_6$-$ACP_6$, the amino acid sequence consists of 3795 amino acids in Seq. 14 and is called as IA-W12, and nucleotide sequence of an encoding gene is selected from 32511-21124 bases in Seq. 1.

The present disclosure further provides an amino acid sequence comprising a polyketide synthase structural domain of $KS_4$-$AT_4$-$DH_4$-$KR_4$-$ACP_4$, the amino acid sequence consists of 2004 amino acids in Seq. 15 and is called as IA-W13, and nucleotide sequence of an encoding gene is selected from 38599-32585 bases in Seq. 1.

The present disclosure further provides an amino acid sequence comprising a polyketide synthase structural domain of $KS_1$-$AT_1$-$ACP_1$-$KS_2$-$AT_2$-$KR_2$-$ACP_2$-$KS_3$-$AT_3$-$DH_3$-$KR_3$-$ACP_3$, the amino acid sequence consists of 4538 amino acids in Seq. 16 and is called as IA-W14, and nucleotide sequence of an encoding gene is selected from 52259-38643 bases in Seq. 1.

The present disclosure further provides an amino acid sequence of cytochrome P-450 oxidase, the amino acid sequence consists of 403 amino acids in Seq. 17 and is called as IA-W15, and nucleotide sequence of an encoding gene is selected from 53099-54310 bases in Seq. 1.

The present disclosure further provides an amino acid sequence of NDP-hexoseisomerase, the amino acid sequence consists of 116 amino acids in Seq. 18 and is called as IA-W16, and nucleotide sequence of an encoding gene is selected from 54495-54845 bases in Seq. 1.

The present disclosure further provides an amino acid sequence of NDP-hexoseaminotransferase, the amino acid sequence consists of 399 amino acids in Seq. 19 and is called as IA-W17, and nucleotide sequence of an encoding gene is selected from 54842-56041 bases in Seq. 1.

The present disclosure further provides an amino acid sequence of NDP-glucosesynthase, the amino acid sequence consists of 302 amino acids in Seq. 20 and is called as IA-W18, and nucleotide sequence of an encoding gene is selected from 56038-56946 bases in Seq. 1.

The present disclosure further provides an amino acid sequence of NDP-glucose-4,6-dehydrase, the amino acid sequence consists of 345 amino acids in Seq. 21 and is called as IA-W19, and nucleotide sequence of an encoding gene is selected from 56930-57967 bases in Seq. 1.

The present disclosure further provides an amino acid sequence of NDP-hexose-2,3-dehydrase/thioesterase, the amino acid sequence consists of 745 amino acids in Seq. 22 and is called as IA-W20, and nucleotide sequence of an encoding gene is selected from 57937-60174 bases in Seq. 1.

The present disclosure further provides an amino acid sequence of NDP-hexoseaminotransferase, the amino acid sequence consists of 382 amino acids in Seq. 23 and is called as IA-W21, and nucleotide sequence of an encoding gene is selected from 60836-61984 bases in Seq. 1.

The present disclosure further provides an amino acid sequence of NDP-aminohexose N-dimethyltransferase, the amino acid sequence consists of 239 amino acids in Seq. 24 and is called as IA-W22, and nucleotide sequence of an encoding gene is selected from 62796-62077 bases in Seq. 1.

The present disclosure further provides an amino acid sequence of a transcription regulation and control factor, the amino acid sequence consists of 670 amino acids in Seq. 25 and is called as IA-W23, and nucleotide sequence of an encoding gene is selected from 63633-65645 bases in Seq. 1.

The present disclosure further provides an amino acid sequence of NDP-aminohexoseisomerase, the amino acid sequence consists of 354 amino acids in Seq. 26 and is called as IA-W24, and nucleotide sequence of an encoding gene is selected from 67379-66318 bases in Seq. 1.

The present disclosure further provides an amino acid sequence of ABC transport protein, the amino acid sequence consists of 550 amino acids in Seq. 27 and is called as IA-W25, and nucleotide sequence of an encoding gene is selected from 69004-67352 bases in Seq. 1.

The present disclosure further provides an amino acid sequence of NDP-hexosedehydrase, the amino acid sequence consists of 433 amino acids in Seq. 28 and is called as IA-W26, and nucleotide sequence of an encoding gene is selected from 69349-70650 bases in Seq. 1.

The present disclosure further provides an amino acid sequence of similar GTP enzyme, the amino acid sequence consists of 482 amino acids in Seq. 29 and is called as IA-W27, and nucleotide sequence of an encoding gene is selected from 72156-70708 bases in Seq. 1.

The present disclosure further provides an amino acid sequence of NDP-hexoseisomerase, the amino acid sequence consists of 346 amino acids in Seq. 30 and is called as IA-W28, and nucleotide sequence of an encoding gene is selected from 72422-73462 bases in Seq. 1.

The present disclosure further provides an amino acid sequence of NDP-hexoseketoreductase, the amino acid sequence consists of 346 amino acids in Seq. 31 and is called as IA-W29, and nucleotide sequence of an encoding gene is selected from 74601-73561 bases in Seq. 1.

The present disclosure further provides an amino acid sequence of glycosyltransferase accessory protein, the amino acid sequence consists of 415 amino acids in Seq. 32 and is called as IA-W30, and nucleotide sequence of an encoding gene is selected from 74913-76160 bases in Seq. 1.

The present disclosure further provides an amino acid sequence of glycosyltransferase, the amino acid sequence consists of 422 amino acids in Seq. 33 and is called as IA-W31, and nucleotide sequence of an encoding gene is selected from 76218-77486 bases in Seq. 1.

The present disclosure further provides an amino acid sequence of glycosyltransferase, the amino acid sequence consists of 391 amino acids in Seq. 34 and is called as IA-W32, and nucleotide sequence of an encoding gene is selected from 77606-78781 bases in Seq. 1.

The present disclosure further provides an amino acid sequence of NDP-hexoseketoreductase, the amino acid sequence consists of 330 amino acids in Seq. 35 and is called as IA-W33, and nucleotide sequence of an encoding gene is selected from 78783-79775 bases in Seq. 1.

The present disclosure further provides an amino acid sequence of NDP-hexose reductase, the amino acid sequence consists of 335 amino acids in Seq. 36 and is called as IA-W34, and nucleotide sequence of an encoding gene is selected from 79772-80779 bases in Seq. 1.

The present disclosure further provides an amino acid sequence of NDP-hexose methyltransferase, the amino acid sequence consists of 410 amino acids in Seq. 37 and is called as IA-W35, and nucleotide sequence of an encoding gene is selected from 82055-80823 bases in Seq. 1.

The present disclosure further provides an amino acid sequence of methoxymalonylsynthetase, the amino acid sequence consists of 370 amino acids in Seq. 38 and is called as IA-W36, and nucleotide sequence of an encoding gene is selected from 83164-82052 bases in Seq. 1.

The present disclosure further provides an amino acid sequence of dehydrogenase, the amino acid sequence consists of 373 amino acids in Seq. 39 and is called as IA-W37, and nucleotide sequence of an encoding gene is selected from 84400-83279 bases in Seq. 1.

The present disclosure further provides an amino acid sequence of acyl carrying protein, the amino acid sequence consists of 106 amino acids in Seq. 40 and is called as IA-W38, and nucleotide sequence of an encoding gene is selected from 84713-84393 bases in Seq. 1.

The present disclosure further provides an amino acid sequence of methoxymalonyl dehydrogenase, the amino acid sequence consists of 288 amino acids in Seq. 41 and is called as IA-W39, and nucleotide sequence of an encoding gene is selected from 85576-84710 bases in Seq. 1.

The present disclosure further provides an amino acid sequence of glycosyltransferase, the amino acid sequence consists of 405 amino acids in Seq. 42 and is called as IA-W40, and nucleotide sequence of an encoding gene is selected from 85825-87042 bases in Seq. 1.

The present disclosure further provides an amino acid sequence of NDP-hexose isomerase, the amino acid sequence consists of 202 amino acids in Seq. 43 and is called as IA-W41, and nucleotide sequence of an encoding gene is selected from 87094-87702 bases in Seq. 1.

The present disclosure further provides an amino acid sequence of a transcription regulation and control factor protein, the amino acid sequence consists of 390 amino acids in Seq. 44 and is called as IA-W42, and nucleotide sequence of an encoding gene is selected from 89315-88143 bases in Seq. 1.

The present disclosure further provides an amino acid sequence of an exogenous 23S rRNAmethylase (Thiostrepton and tsr resistance marker related), the amino acid sequence consists of 269 amino acids in Seq. 45 and is called as IA-W43, and nucleotide sequence of an encoding gene is selected from 866-57 bases in Seq. 2.

The present disclosure further provides an amino acid sequence of exogenous 4"-mycaroseglucoside isovaleryl transferase, the amino acid sequence consists of 388 amino acids in Seq. 46 and is called as IA-W44, and nucleotide sequence of an encoding gene is selected from 2337-1171 bases in Seq. 2.

On the basis of obtaining information of the biosynthetic gene cluster of carrimycin, and analyzing the possible functions of encoded proteins of each gene through gene blocking and homologous comparation, the whole 44 genes of the biosynthetic gene cluster of carrimycin of the present disclosure are further described, and the gene cluster has a structure shown in FIG. 1, specifically:

(1) five polyketide synthase genes, including orf10-14;
(2) nine genes related to polyketone synthesis extension unit and modification related genes, including orf1, orf4-6, 15 and 36-39;
(3) sixteen genes related to glycosyl synthesis, including orf9, 16-22, 24, 26, 28, 29, 33-35 and 41;
(4) six genes related to glycosyl transfer, including orf7, 8, 30-32 and 40;
(5) two genes related to resistance, including orf3 and 25;
(6) 4 genes related to biosynthesis regulation and control in all, including orf2, 23, 27 and 42; and
(7) two genes, including an exogenous gene engineering marker gene orf43 (thiostrepton and a tsr resistant gene) and a mycarose 4"-O-isovaleryl transferase gene orf44 linked to the orf43.

Five polyketide synthase genes (orf10-14) in Seq. 1, complementary nucleotide sequences and amino acid sequences thereof are essential to synthesis of a lactone ring of carrimycin. The 5 polyketide synthase genes comprises 8 modules and 37 structural domains shown in FIG. 2. Orf14 comprises 3 modules: a loading structural domain 1, a module 2 and a module 3; in a loading module domain, $KS_1$, $AT_1$ and $ACP_1$ are responsible for the initial synthesis of the lactone ring, and acetic acid is catalyzed as an initiation unit. The module 2 comprises structural domains $KS_2$, $AT_2$, $KR_2$ and $ACP_2$; and the module 3 comprises structural domains $KS_3$, $AT_3$, $DH_3$, $KR_3$ and $ACP_3$ and is responsible for the introduction of additional 2 acetic acid extension units to finally form a C11-15 carbon-chain framework of carrimycin. The Orf13 comprises a module 4 comprising $KS_4$, $AT_4$, $DH_4$, $KR_4$ and $ACP_4$ and is responsible for the extension of a third acetic acid unit to finally form a C9-10 carbon-chain framework of carrimycin. The Orf12 comprises a module 5 and a module 6, and the module 5 comprises a structural domain $KS_5$-$AT_5$-$KR_5$-$ACP_5$ and is responsible for the introduction of a propionic acid extension unit; and the module 6 comprises a structural domain $KS_6$-$AT_6$-$DH_6$-$KR_6$-$ER_6$-$KR_6$-$ACP_6$ and is responsible for the introduction of a butyric acid extension unit to finally form a C5-C8 carbon-chain framework of carrimycin. The Orf11 comprises a module 7 containing a structural domain $KS_7$-$AT_7$-$KR_7$-$ACP_7$ and is responsible for the introduction of a glycollic acid extension unit to finally form a C3-C4 carbon chain framework of carrimycin. The Orf10 comprises a module 8 containing a structural domain $KS_8$-$AT_8$-$KR_8$-$ACP_8$-TE and is responsible for the introduction of an acetic acid extension unit, and the cyclization and release of a carbon chain are completed under the participation of thioesterase (TE). A structural schematic diagram of polyketide synthase genes of carrimycin is shown in FIG. 2. All structural domains and amino acid positions thereof of the polyketide synthase genes are shown in table 1.

Nucleotide sequences or complementary sequences and corresponding amino acid sequences thereof of the polyketone synthesis extension unit and modification related genes orf1, orf4-6, 15 and 36-39 are: IA-W1, which encodes a PPT modified polyketide synthesized acyl carrier protein (ACP) to enable the protein to become an active protein; IA-W4, which encodes 3-O-acyltransferase and is responsible for the acylation of 3-position hydroxyl of carrimycin; IA-W5 and IA-W6, which separately encode O-methylase and crotonoyl coenzyme A reductase and are responsible for the supply of polyketide extension units; IA-W15, which encodes P450 cytochrome mono-oxidase and is responsible for the oxidation of a carbon chain of polyketide; and IA-W36-39, which separately encode methoxymalonylsynthetase, dehydrogenase, acyl carrying protein and methoxymalonyl dehydrogenase. And all the genes participate in the synthesis and modification of the polyketide extension units.

Table 1 All structural domains and amino acid positions thereof of polyketide synthase genes:

TABLE 1

| Module | Structural domain | Amino acid position |
|---|---|---|
| 1 All structural domains and amino acid positions thereof of polyketide synthase gene IA-W14 | | |
| Loading module-module 1 | $KS_1$ | 1-400 |
| | $AT_1$ | 511-814 |
| | $ACP_1$ | 918-989 |
| Module 2 | $KS_2$ | 1018-1444 |
| | $AT_2$ | 1551-1854 |
| | $KR_2$ | 2160-2338 |
| | $ACP_2$ | 2473-2546 |
| Module 3 | $KS_3$ | 2570-2995 |
| | $AT_3$ | 3109-3412 |
| | $DH_3$ | 3483-3653 |
| | $KR_3$ | 4068-4248 |
| | $ACP_3$ | 4369-4441 |
| 2 All structural domains and amino acid positions thereof of polyketide synthase gene IA-W13 | | |
| Module 4 | $KS_4$ | 36-461 |
| | $AT_4$ | 575-878 |
| | $DH_4$ | 945-1158 |
| | $KR_4$ | 1532-1711 |
| | $ACP_4$ | 1831-1904 |
| 3 All structural domains and amino acid positions thereof of polyketide synthase gene IA-W12 | | |
| Module 5 | $KS_5$ | 37-463 |
| | $AT_5$ | 662-957 |
| | $KR_5$ | 1245-1413 |
| | $ACP_5$ | 1519-1592 |
| Module 6 | $KS_6$ | 1613-2039 |
| | $AT_6$ | 2157-2458 |
| | $DH_6$ | 2524-2686 |
| | $ER_6$ | 3025-3329 |
| | $KR_6$ | 3338-3518 |
| | $ACP_6$ | 3632-3702 |
| 4 All structural domains and amino acid positions thereof of polyketidesynthase gene IA-W11 | | |
| Module 7 | $KS_7$ | 35-460 |
| | $AT_7$ | 566-864 |
| | $KR_7$ | 1149-1328 |
| | $ACP_7$ | 1433-1505 |
| 5 All structural domains and amino acid positions thereof of polyketide synthase gene IA-W10 | | |
| Module 8 | $KS_8$ | 36-461 |
| | $AT_8$ | 579-878 |
| | $DH_8$ | 831-993 |
| | $KR_8$ | 1232-1411 |
| | $ACP_8$ | 1513-1584 |
| | $TE_8$ | 1659-1872 |

The quantity of genes related to glycosyl synthesis of carrimycin is 12 in all, including orf9, 16-22, 24, 26, 28, 29, 33-35 and 41, wherein orf18, 19 and 28 encode synthesis, dehydration and isomerization enzymes of basic glycosyl units of carrimycin; orf9, 20, 21, 24, 26 and 29 encode N-dimethylation, 2,3 dehydration, amination, isomerization, dehydration and keto reduction enzymes of NDP-hexosamine in forosamine synthesis; orf16, 17 and 22 encode isomerization, amination and N-dimethylation enzymes of NDP-hexosamine of mycaminose; and orf33, 34, 35 and 41 encode keto reduction, methylation and isomerization enzymes of NDP-hexosamine of mycarose.

The quantity of genes related to glycosyl transfer of carrimycin is 6 in all, including orf7, 8, 30-32 and 40, wherein orf7 encodes glycosylase of mycaminose; orf8 encodes a glycosylation accessory protein of mycaminose; orf31 and 32 encode glycosylase of forosamine; orf30 encodes a glycosylation accessory protein of forosamine; and orf40 encodes a glycosylation enzyme of mycarose.

The quantity genes related to resistance of carrimycinis 2 in all, including orf3 and 25, wherein orf3 encodes a 23S rRNAmethylase; and orf25 encodes an ABC transport protein, the orf3 and the orf25 endow carrimycin producing bacteria with self-antibiotic producing resistance through a methylation and pumping mechanism for ribosome RNA.

The quantity genes of carrimycin related to biosynthesis regulation and control is 4 in all, including orf2, 23, 27 and 42, wherein orf2 encodes a TetR family transcription regulation and control inhibiting factor and possibly participate in negative regulation and control on biosynthesis of carrimycin; orf23 and orf42 separately encode two positive-regulation-and-control transcription factors, and the latter positive-regulation-and-control transcription factor serves as a pathway special positive-regulation-and-control factor and is used for directly regulating and controlling the biosynthesis of carrimycin; and orf27 encodes a GTP enzyme and possibly regulate and control the biosynthesis of carrimycin through regulating and controlling functions of cells.

Exogenous orf43 and orf44 are related to the biosynthesis of carrimycin, wherein the orf43 encodes a 23S rRNAmethylase gene related to thiostrepton resistance, the gene is linked to a mycarose 4"-O-hydroxyl isovaleryl transferase gene orf44, and resistance expression of the orf43 can provide an identifying marker for gene engineering bacteria of carrimycin.

Complementary sequences of Seq. 1 and Seq. 2 of the present disclosure can be obtained anytime according to the principle of complementary base pairing. Nucleotide sequences or part of the nucleotide sequences of Seq. 1 and Seq. 2 can be obtained through a polymerase chain reaction (PCR), or enzyme digestion of corresponding DNA by using an appropriate restriction endonuclease or using other appropriate technologies. Genes similar to biosynthesis genes of carrimycin can be obtained from other organisms through the nucleotide sequences or part of the nucleotide sequences provided by the present disclosure by using a polymerase chain reaction (PCR) method or a method for carrying out Southern hybridization by using DNA containing the sequences of the present disclosure as a probe.

The present disclosure further provides a way to obtain at least part of DNA sequence in Seq. 1 and Seq. 2 to construct a recombined vector.

The present disclosure further provides a way to block biosynthesis genes of carrimycin, wherein at least one of the genes comprises nucleotide sequences in Seq. 1.

New carrimycin derivatives can be obtained through blocking one or more steps of biosynthesis of carrimycin by using the clone genes or DNA fragments of nucleotide sequences or at least part of the nucleotide sequences provided by the present disclosure. The nucleotide sequences comprise the DNA fragments or genes and can be used for increasing the yield of carrimycin or derivatives thereof.

Clone DNA of nucleotide sequences or at least part of the nucleotide sequences provided by the present disclosure can be used for locating more library plasmids from a genome library. These library plasmids at least comprise part of the sequences of the present disclosure and also contain DNA of regions, adjacent to the library plasmids, in a genome of carrimycin producing bacteria.

The nucleotide sequences provided by the present disclosure can be modified or mutated. Ways of modification or mutation comprise insertion or replacement, a polymerase chain reaction, a mistake-mediated polymerase chain reaction, site specific mutation, reconnection of different sequences and ultraviolet or chemical reagent caused mutation.

The nucleotide sequences provided by the present disclosure can be directly evolved (DNA shuffling) through different parts of the sequences or homologous sequences of other sources.

Fragments or structural domains or modules or genes of nucleotide sequences or at least part of the nucleotide sequences provided by the present disclosure can be used for constructing a polyketide synthase library or a polyketide synthase derivative library or a package library. New polyketone compounds are produced through deleting or deactivating one or more polyketide synthase structural domains, modules or genes of the same or different polyketide synthase systems or increasing one or more polyketide synthase structural domains, modules or genes.

Nucleotide sequences of biosynthesis modifier genes and glycosyl synthesis and glycosyltransferase genes of the present disclosure provide a way to obtain derivatives of carrimycin through deleting, replacing or reforming these glycosyl synthesis and transfer and modifier genes.

Fragments or structural domains or modules or genes of nucleotide sequences or at least part of the nucleotide sequences provided by the present disclosure can be used for increasing the yield of carrimycin or derivatives thereof through quantity doubling.

Clone genes of nucleotide sequences or at least part of the nucleotide sequences provided by the present disclosure can be expressed in exogenous hosts through appropriate expression systems to obtain modified carrimycin or carrimycin with higher bioactivity or higher yield. These exogenous hosts comprise *Streptomyces, Escherichia coli, Bacillus*, yeast, plants, animals, etc.

Genes or gene clusters of nucleotide sequences or at least part of the nucleotide sequences provided by the present disclosure can be expressed in heterologous hosts, and functions of the genes or gene clusters in metabolism chains of the hosts are understood through a DNA chip technology.

Polypeptides of amino acid sequences or at least part of the amino acid sequences provided by the present disclosure may still have bioactivity even new biological activity after one or some amino acids are removed or replaced, or the yield is increased, or dynamic characteristics or other striven properties of proteins are optimized. New proteins or enzymes can be obtained through connecting the amino acid sequences of the present disclosure by appropriate technology deletion, and then, new or associated products are produced.

The amino acid sequences provided by the present disclosure can be used for separating required proteins and can be applied to antibody preparation.

The amino acid sequences provided by the present disclosure provide possibility for predicting a three-dimensional structure of polyketide synthase.

Genes provided by the present disclosure and proteins and antibodies thereof can also be used for screening and developing compounds or proteins for medicines, industry and agriculture.

BRIEF DESCRIPTION OF THE DRAWINGS

FIG. 3: A schematic diagram of the construction of blocking recombinant plasmids of IA-W4, 3-O-acyltransferase gene and double exchange. by FIG. 4: A schematic diagram of construction of blocking recombinant plasmids of IA-W42 transcription regulation and control gene and so on.

In which: 1: original strain; 2, 3, 4: gene blocked mutant; and 5: DNA marker III.

Figure 5:
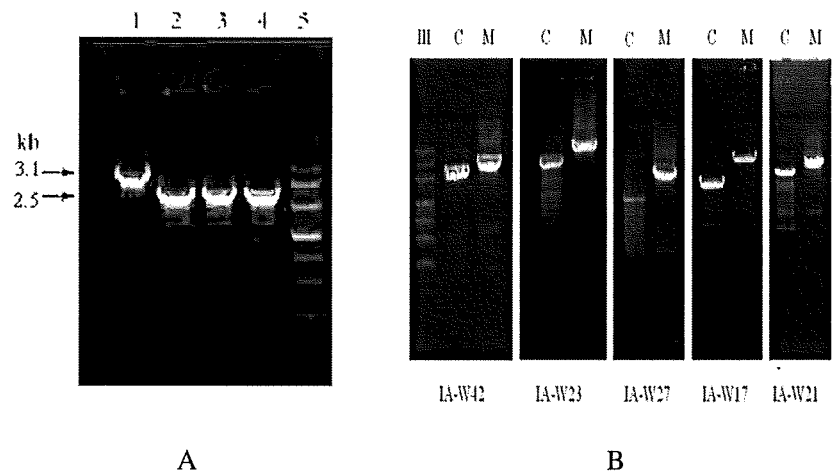
FIG. 5A: Verification of blocking of an IA-W4 3-O-acyltransferase gene by PCR.

FIG. 5B: Verification of blocking of other genes by PCR,

In which: III: DNA marker III; C: original strain; and M: gene blocked mutant.

Figure 6:
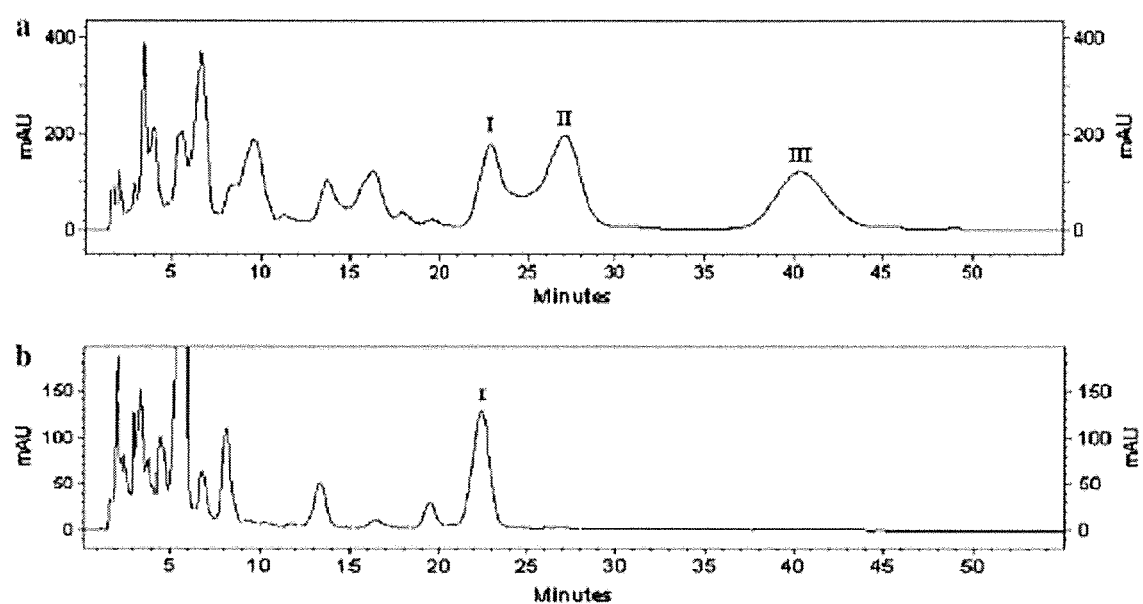

FIG. 6: HPLC analysis of fermented products of an IA-W4 3-O-acyltransferase gene blocked mutants, In which: a: a carrimycin control; and b: fermented extract of gene blocked mutant, I, II and III are absorption peaks of three main ingredients, i.e., isovaleryl spiramycin I, isovaleryl spiramycin II and isovaleryl spiramycin III of carrimycin, respectively.

According to the present disclosure, mutant strains are obtained through gene blocking experiments; and it is proven by the experiments that carrimycin ingredient change of the mutant strains is caused by gene blocking, or carrimycin is not produced any more. And thus, it is prompted that obtained gene cluster information is related to biosynthesis of carrimycin. According to the present disclosure, an exogenous thiostrepton resistance marker gene (orf43) and a mycarose 4"-O-hydroxyl isovaleryl transferase gene (orf44) linked to the orf43 are integrated to chromosomes of the carrimycin producing bacteria through genic homologous recombination. Our laboratory has proven that the orf43 and the orf44 are essential to the biosynthesis of carrimycin through researches (Chinese Journal of Biotechnology, volume 15, issue 2, 1999, 171-176).

DETAILED DESCRIPTION

Embodiments provided below are only used for helping those skilled in the art to better comprehend the present disclosure, rather than limiting the present disclosure in any way.

<Embodiment 1> Extraction of Total DNA of Carrimycin Producing Bacteria (*S. spiramyceticus*)

Formula of $R_2YE$ culture medium (g/100 ml):

| Saccharose | 10.3 | Glucose | 1.0 |
| Yeast extract | 0.4 | Tryptone | 0.2 |
| Peptone | 0.4 | Casein hydrolyzate | 0.1 |
| $K_2SO_4$ | 0.025 | $CaCl_2$ | 0.216 |
| $KH_2PO_4$ | 0.005 | $MgCl_2 \cdot 6H_2O$ | 1.012 |
| NaOH(1M) | 0.5 ml | Tris-HCl(0.25 mol/L pH 7.2) | 10 ml |

0.2 ml of trace element solution is added, and distilled water is added until the volume is 100 ml and the pH is 6.5

Trace element solution (g/100 ml):

| $ZnCl_2$ | 0.004 | $FeCl_3 \cdot 6H_2O$ | 0.02 |
| $CuCl_2 \cdot 2H_2O$ | 0.001 | $MnCl_2 \cdot 4H_2O$ | 0.001 |
| $Na_2B_4O_7 \cdot 10H_2O$ | 0.001 | $(NH_4)_6Mo_7O_2 \cdot 4H_2O$ | 0.001 |

15-pound sterilization is performed for 20 min at a temperature of 121 DEG C.

S. spiramyceticus was inoculated into 25 ml of R₂YE culture medium, shaking-table culture was performed for 48 h at a temperature of 28 DEG C. Then sub-cultivating was performed in 100 ml R₂YE culture medium, shaking-table culture was performed for 24 h at a temperature of 28 DEG C. Then the thalli (about 10 g) were collected after centrifuging for 10-15 min at a rate of 5,000 rpm. The operation was performed mainly according to product specification of UPTECH™ life science company. 50 ml of 25 mM EDTA solution was added into the thalli for washing under vibrating, and then the solution was centrifuged, and the supernatant was discarded. Themycelia were suspended with 25 ml of lysozyme solution (10 mg/ml, prepared from 10 mM Tris-HCl with pH of 8.0, 2 mM EDTA and 1.2% TritonX-100 through adding 0.5 ml of 100 mg/ml RNase), and cultured for about 1-2 h at a temperature of 37 DEG C. until cells were translucent. Then 2.5 ml of protease K solution was added, and culturing was performed for 30 min at a temperature of 55 DEG C. Then 20 ml of 10% SDS solution was added, and culturing was performed for 10 min at a temperature of 70 DEG C. An equal volume of anhydrous ethanol was added, and full vibrating was performed. Then the solution was transferred to a DNA purification column, centrifuging for 1 min at a rate of 12,000 rpm. Then 50 ml of protease-containing solution was added to wash the column, and centrifuging was performed for 1 min at a rate of 12,000 rpm at room temperature. Then, the column was washed twice with 50 ml of rinsing solution, and centrifuging was performed for 1 min at a rate of 12,000 rpm at a time. Then 5-10 ml of TE eluent was added, and was placed was for 2-5 min at room temperature, and centrifuging was performed for 1 min at a rate of 12,000 rpm. The solution was collected, and the total DNA was saved at a temperature of −20 DEG C.

<Embodiment 2> Verification of Functions of Information of Genes in Seq. 1 Through Blocking Gene It is carried out blocking genes such as IA-W1, IA-W42 at two ends of gene clusters, and IA-W4, 17, 21, 23 and 27 selected for to obtain mutant strains. It is proven by experiments, the capability of these blocked strains for producing carrimycin has changed carrimycin or is disappear. Thus, the obtained gene cluster information is essential to carrimycin production. Primers are designed according to the above-mentioned encoding genes and upstream and downstream sequences thereof and are inserted into appropriate enzyme digestion sites, and primer sequences are shown in table 2.

TABLE 2

Primer sequences designed for gene blocking experiment

| Gene | Primer sequence | Gene | Primer sequence |
|---|---|---|---|
| IA-W1 | CCGGAATTCGCCCTTGAACGCTTGTCCG EcoRI<br>CGCGGATCCGCTCACTCGGCAGGATGGG BamHI<br>AACTGCAG TCCGTCTACAAGGCGTGGTT PstI<br>CTAGTCTAGACGTATCGGTTCGTCGAGG TCT XbaI | IA-W42 | CTAGTCTAGACCGCCGACCGCAAAC TCTC XbaI<br>AACTGCAGCGACGTTCTCCTCCTCA CCG PstI<br>CGGGGTACCCGACCTGTGGCTGACC GAC KpnI<br>CCGGAATTCGTGGACGACACCTGTA TGAAC EcoRI |
| IA-W4 | AGTGTCTAGACGGCGCGCGGCACGGGGT TGAACTC XbaI<br>GACAAGCTTTGGATTCTCGCTCCTCTITC GGGATGG Hind III<br>GACAAGCTTTGAGCGTGGCAGACCAGAC CGCTCT Hind III<br>AGTGGAATTCCACCAGGGCAAGGTCGGC GTGCTCTGEcoRI | IA-W17 | CCGGAATTCATCCCCTTCCTCGACGC AG EcoRI<br>AACTGCAGGGCGGTACGGGGTAGTG GAT PstI<br>CGCGGATCCGCAGAGCCTCAGCCTT CCC BamHI<br>CTAGTCTAGACCGTACTCCCTGGCG TTGTT XbaI |
| IA-W21 | CCGGAATTCGACCGCATCCGCTACGACG EcoRI<br>CGCGGATCCGAGCCATTGGTCGTCGAAG A BamHI<br>AACTGCAGACCGACGGCATCTACACCAC PstI<br>CTAGTCTAGACCAGGACCGCAAGGACTA CG XbaI | IA-W23 | CCGGAATTCTTACCTGGATTATGGTG AAG EcoRI<br>CGGCCGAGCGGGCTGCAGA PstI<br>CGGGGTACCGGAGTACAACGCCGG CTTC KpnI<br>CTAGTCTAGACCGAGCACGGTCCGG GAGG XbaI |
| IA-W27 | CCGGAATTCGCGTGCTCACCGACAACCT G EcoRI<br>CGCGGATCCGGGAAGTCCTCACTGCTCA AC BamHI | | AACTGCAG TCGGGCCATCTTGTCGTTG PstI<br>CTAGTCTAGACCTTCAGGGTGCCGTAGTC XbaI |

Figure 1:
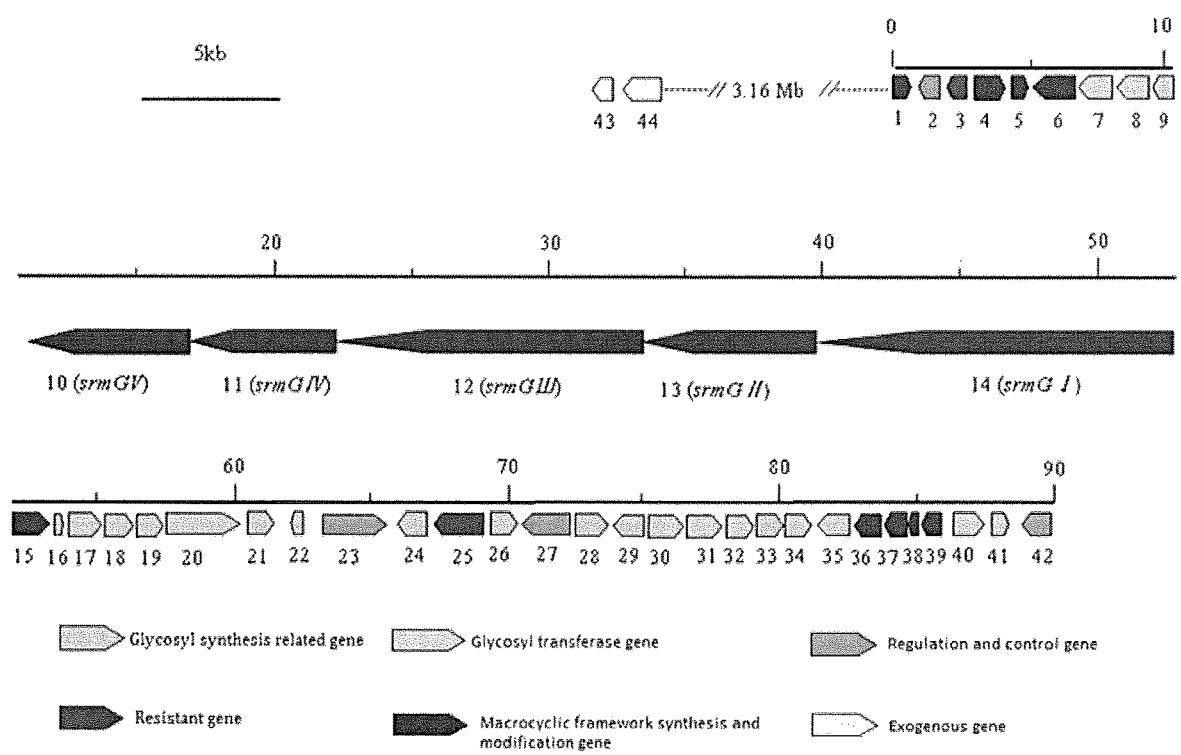
FIG. 1: A structure of a biosynthetic gene cluster of carrimycin.
Figure 2:
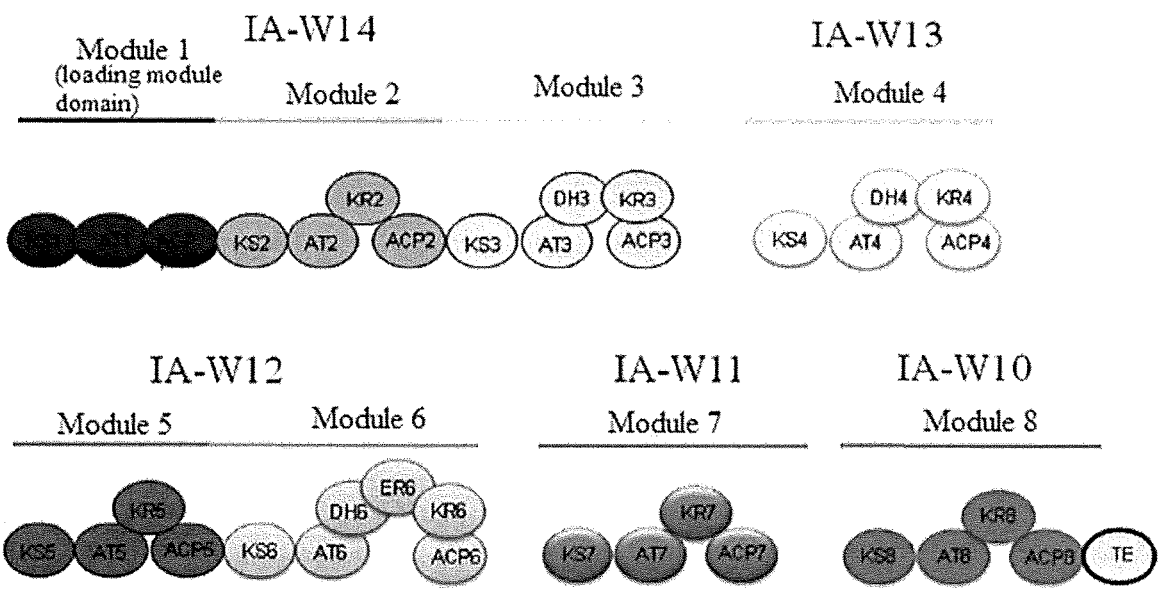
FIG. 2: A structure of a polyketide synthase gene of carrimycin.
Figure 3:
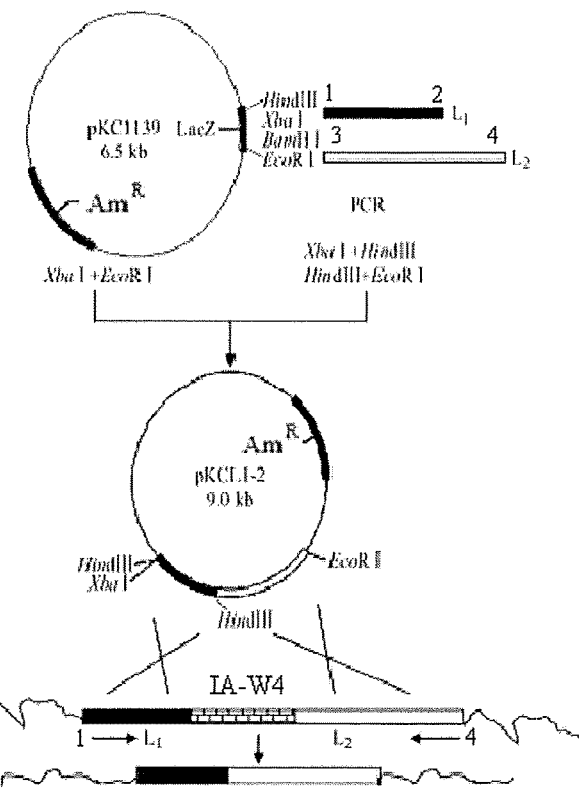
Figure 4:
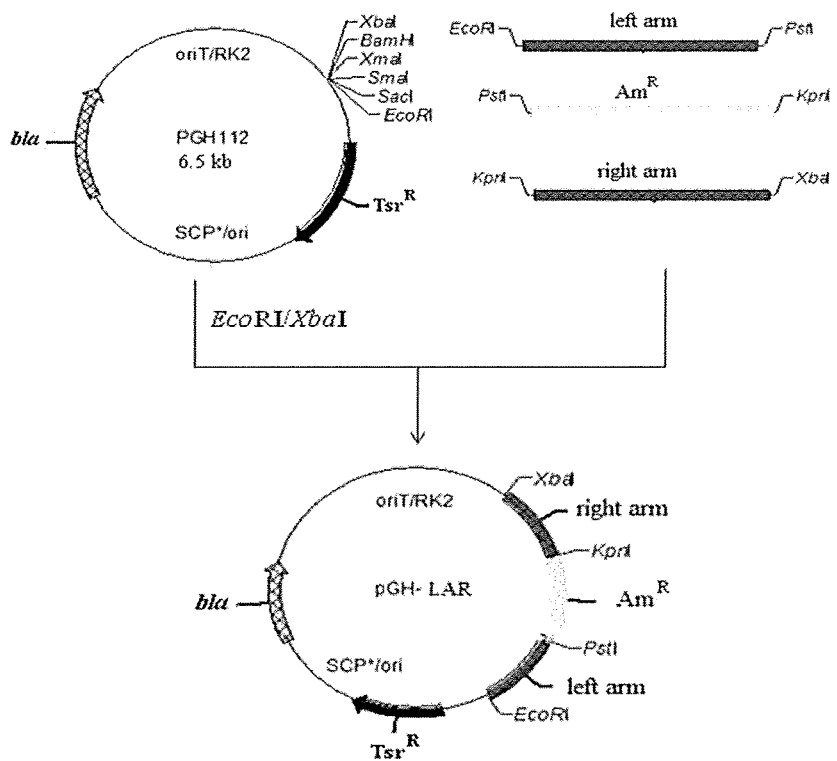

Corresponding homologous gene fragments are separately obtained through PCR amplification, and recombinant plasmid containing homologous genes was obtained through adopting corresponding enzyme digestion sites, inserting screened marked resistant genes (Apramycin-Am) and connecting the genes to a temperature-sensitive vector pKC1139 [Bierman M. et al., Gene, 1992; 116(1): 43-9] or Escherichia coli/Streptomyces vector pGH112 [Youbao Biology Company]. Recombinant plasmid was transformed with protoplasts and transferred into the carrimycin producing bacteria. After cultivation, single colonies were isolated to obtain the homologous fragment double exchange gene blocking strain. A schematic diagram of the construction of blocking recombinant plasmids of an IA-W4 3-O-acyltransferase gene and double exchange was shown in FIG. 3. A schematic diagram of construction of blocking recombinant plasmids of genes such as an IA-W42 transcription regulation and control gene were shown in FIG. 4.

Total DNA of blocked strains and total DNA of original strains were subjected to PCR verification by separately adopting corresponding primers, as shown in FIG. 5A and FIG. 5B. Shown by a result of FIG. 5A, 613 bp was deleted in the encoding gene orf4 of a mutant strain with IA-W4 gene blocked. A PCR verification result is illustrated in FIG. 5B, compared with the original strains, length of PCR products increases as the screened marked resistant genes were inserted into mutant strain with related encoding genes blocked.

Proven by fermentation experiments and HPLC detection of products, IA-W4 blocked mutant strains do not produce 4″-isovaleryl spiramycin III and II any more and are dominated with 4″-isovaleryl spiramycin I as a major ingredient (FIG. 6). It is proven that an IA-W4 3-O-acyltransferase gene in gene information in Seq. 1 provided by the present disclosure participates in the biosynthesis of carrimycin. Due to the blocking of the gene, mutant strains lose the function of acylating 3-position hydroxyl of a lactone ring of carrimycin.

Proven by fermentation experiments on other gene blocked strains and antibacterial activity and HPLC detection on products, the blocked strains do not produce activated carrimycin any more. It is proven that the gene cluster in Seq. 1 provided by the present disclosure participates in the biosynthesis of carrimycin.

<Embodiment 3> Screening of Gene Transfer and Block Strains of Carrimycin Producing Bacteria 3.1 Preparation of Protoplast:

Fresh slant spores of carrimycin producing bacteria was inoculated in $R_2YE$ liquid culture medium and shaken for 48 h at a temperature of 28 DEG C. at a rate of 220 rpm. The culture fluid was inoculated at an inoculation rate of 10% in fresh $R_2YE$ liquid culture medium containing 0.5% glycine and shaken for 20 h at a temperature of 28 DEG C. 10 ml of bacterium solution was taken into a centrifuge tube, and centrifuged at a rate of 3,000 rpm to collected mycelium. The mycelium was washed with P-buffer.

| Tris-HCl (pH 8.0) 1 mol/L | 3.1 ml | $CaCl_2 \cdot 2H_2O$ | 3.68 |
|---|---|---|---|
| $MgCl_2 \cdot 6H_2O$ | 2.04 | Saccharose | 103 |
| Glucose | 1.0 | Trace element solution | 2.0 ml |
| PH | 7.6 | | |

15-pound sterilization is performed for 30 min at a temperature of 121 DEG C.

After washing twice, the mycelium was suspended with a proper volume of P-buffer, a P-buffer solution with lysozyme (final concentration is 2 mg/ml) was added, mixed uniform, and incubated for 30-45 min in a water bath at a temperature of 37 DEG C., and shaken once every 10-15 min. Forming conditions of protoplast were observed with a 10×40 phase-difference microscope. Enzymolysis was stopped when microscopic examination shows that the majority of mycelia have formed protoplast. After filtering through absorbent cotton, the filter liquor was subjected to centrifugal washing twice with P-buffer. Finally, the protoplast was suspended with 1 ml of P-buffer, and the suspension was separately loaded to EP tubes by 100 µl/tube, and preserved at a temperature of −70 DEG C. for later use.

3.2 Transformation of Protoplast by Plasmid DNA:

100 µl of protoplast was taken and added into 10 µl of plasmid DNA solution, a tube wall was flipped to perform uniform mix. 400 µl of P-buffer containing 25% PEG-1000 (a product of Britain Koch-light company) was rapidly added, blowing-suction and uniform mixing were performed, and placing for 5 min at room temperature. A dehydrated $R_2YE$ flat plate was coated with 200 µl of mixture, cultured for 20 h at a temperature of 28 DEG C., covered with 50 µg/ml tsr sterile water, cultured for 5-7 days at a temperature of 28 DEG C., and transformants were picked up.

3.3 Screening of Gene Blocked Mutant Strains

The transformants are picked into a culture medium containing 50 µg/ml of Tsr

| Soyabean cake powder | 20 | Glucose | 10 |
|---|---|---|---|
| Starch | 30 | $CaCO_3$ | 5.0 |
| NaCl | 4.0 | agar | 18 |

Deionized water is used for preparing, and 15-pound sterilization is performed for 30 min at a temperature of 121 DEG C. at a natural pH value.

Culturing was performed for 5-7 days at a temperature of 28 DEG C., 4-5 generation passing was carried out in an undosed culture medium. Monospores were separated. The monospores were separately and correspondingly screened in an Am-containing (Am 50 µg/ml) culture medium to screen out gene blocked strains grown in Am and not grown in Tsr. Blocked strains with stable resistance marker expression were picked, the DNA of the blocked strains was extracted from genomes, PCR amplification was performed by adopting corresponding primers in the embodiment 2, and the correctness of gene blocking was judged according to product sizes and DNA sequencing.

<Embodiment 4> Fermentation of Carrimycin Producing Bacteria and Gene Blocked Strains and Detection and Identification of Product Activity 4.1 Fermentation

| Soyabean cake powder | 20.0 | Glucose | 10.0 |
|---|---|---|---|
| Starch | 30.0 | $CaCO_3$ | 5.0 |
| NaCl | 4.0 | Agar | 18.0 |

Deionized water is used for preparing, and 15-pound sterilization was performed for 30 min at a temperature of 121 DEG C. at a natural pH value.

Strains were cultured in slant culture medium for 10-12 d at a temperature of 28 DEG C. After strains were grown, the strains was inoculated by dicing into a 100 mL triangular flask containing 30 ml of fermentation culture medium, and shaken culture for 96-120 h at a temperature of 28 DEG C.

Fermentation Culture Medium (g/L):

| Glucose | 5.0 | Sodium chloride | 10 |
|---|---|---|---|
| Starch | 60 | Magnesium sulfate | 1.0 |
| Calcium carbonate | 5.0 | Ammonium nitrate | 6.0 |
| Potassium dihydrogen phosphate | 0.5 | Yeast powder | 5.0 |
| Fish meal | 20.0 | natural pH value | |

Deionized water is used for preparing, and 15-pound sterilization was performed for 30 min at a temperature of 121 DEG C.

4.2 Detection on Activity of Fermentation Product:

Fermentation liquor was centrifuged, the supernatant was taken and diluted, and then, detection was performed by taking *Bacillus subtilis* as detection bacteria referring to an acetyispiramycin microbiological assay (II), 2005<Pharmacopoeia of People's Republic of China>. Detection is performed by adopting a cylinder plate method with a standard curve method.

4.3 Extraction and Identification of Fermentation Product:

Fermentation liquor was centrifuged for 15 min at a rate of 3000 rpm at room temperature, the pH of supernatant was adjusted to 8.5 with 1M NaOH. Then, the supernatant was extracted with ½ volume of ethyl acetate. An ethyl acetate phase was taken out, and was subjected to blow-drying in a flat dish, then the dried substance was dissolved in chromatographically-pure methanol, and then 10-20 μl of a sample was introduced after filtering. Chromatograph instruments: a Shimadzu LC-10ATvp liquid chromatograph and a diode array detector; a chromatographic column: Kromasil $C_{18}$(4.5 mm×150 mm, 5 μm); flowing phase: $CH_3OH$/1% $NaH_2PO_4$ (55:45); detection wavelength: 231 nm; flow velocity: 1 ml/min; and column temperature: 25 DEG C. Fermentation products of mutant strains are identified by taking a carrimycin standard product as a control (purchased from National Institute for the Control of Pharmaceutical and Biological Products).

Genes and proteins involved in the present disclosure are shown in a sequence table.

The invention claimed is:

1. A polynucleotide comprising a carrimycin biosynthetic gene cluster, comprising 44 genes comprising:
   1) five polyketide synthase genes, including orf10 residues 16215-10543 of SEQ ID NO:1, orf11 residues 21076-16328 of SEQ ID NO:1, orf12 residues 32511-21124 of SEQ ID NO:1, orf13 residues 38599-32585 of SEQ ID NO:1, orf14 residues 52259-38643 of SEQ ID NO:1;
   2) nine genes related to polyketone synthesis extension unit and modification, including orf1 residues 1-645 of SEQ ID NO:1, orf4 residues 3614-4840 of SEQ ID NO:1, orf5 residues 4846-5511 of SEQ ID NO:1, orf 6 residues 7150-5801of SEQ ID NO:1, orf15 residues 53099-54310 of SEQ ID NO:1, orf36 residues 83164-82052 of SEQ ID NO:1, orf37 residues 84400-83279 of SEQ ID NO:1, orf38 residues 84713-84393 of SEQ ID NO:1, orf39 residues 85576-84710 of SEQ ID NO:1;
   3) sixteen genes related to glycosyl synthesis, including orf9 residues 10543-9830 of SEQ ID NO:1, orf16 residues 54495-54845 of SEQ ID NO:1, orf17 residues 54842-56041 of SEQ ID NO:1, orf18 residues 56038-56946 of SEQ ID NO:1, orf19 residues 56930-57967 of SEQ ID NO: 1, orf20 residues 57937-60174 of SEQ ID NO: 1 orf21 residues 60836-61984 of SEQ ID NO:1, orf22 residues 62796-62077 of SEQ ID NO:1, orf24 residues 67379-66318 of SEQ ID NO:1, orf26 residues 69349-70650 of SEQ ID NO:1, orf28 residues 72422-73462 of SEQ ID NO:1, orf29 residues 74601-73561 of SEQ ID NO:1, orf33 residues 78783-79775 of SEQ ID NO: 1, orf34 residues 79772-80779 of SEQ ID NO:1, orf35 residues 82055-80823 of SEQ ID NO:1 and orf41 residues 87094-87702 of SEQ ID NO:1;
   4) six genes related to glycosyl transfer, including orf7 residues 8444-7179 of SEQ ID NO:1, orf8 residues 9729-8482 of SEQ ID NO:1, orf30 residues 74913-76160 of SEQ ID NO:1, orf31 residues 76218-77486 of SEQ ID NO:1, orf32 residues 77606-78781of SEQ ID NO:1 and orf40 residues 85825-87042 of SEQ ID NO:1;
   5) two genes related to resistance, including orf3 residues 3133-2285 of SEQ ID NO:1 and 25 residues 69004-67352 of SEQ ID NO:1;
   6) four genes related to biosynthesis regulation, including orf2 residues 1810-1208 of SEQ ID NO:1, orf23 residues 63633-65645 of SEQ ID NO:1, orf27 residues 72156-70708 of SEQ ID NO:1 and orf42 residues 89315-88143 of SEQ ID NO:1;
   7) two genes, including an exogenous genetic engineering marker gene orf43 residues 866-60 SEQ ID NO:2 and a mycarose 4"-O-hydroxyl isovaleryltransferase gene orf44 residues 2337-1174 of SEQ ID NO:2 linked to the orf43.

2. The polynucleotide according to claim 1, wherein the five polyketide synthase genes are responsible for synthesis of a 16-membered lactone ring of carrimycin, and amino acid sequences of the five polyketide synthase genes orf10-14 comprise IA-W10 defined in SEQ ID NO:12, IA-W11 defined in SEQ ID NO:13, IA-W12 defined in Seq. ID NO: 14, IA-W13 defined in SEQ ID NO:15, and IA-W14 defined in SEQ ID NO: 16.

3. The polynucleotide according to claim 1, wherein amino acid sequences of the genes related to polyketone synthesis extension unit and modification including orf1, orf4-6, 15 and 36-39 comprise IA-W1 defined in SEQ ID NO:3, IA-W4 defined in SEQ ID NO:6, IA-W5 defined in SEQ ID NO:7, IA-W6 defined in SEQ ID NO:8, IA-W15 defined in SEQ ID NO:17, IA-W36 defined in SEQ ID NO:38, IA-W37 defined in SEQ ID NO:39, IA-W38 defined in SEQ ID NO:40, and IA-W39 defined in SEQ ID NO:41.

4. The polynucleotide according to claim 1, wherein amino acid sequences of the genes related to glycosyl synthesis including orf9, 16-22, 24, 26, 28, 29, 33-35 and 41 comprise IA-W9 defined in SEQ ID NO:11, IA-W16 defined in SEQ ID NO:18, IA-W17 defined in SEQ ID NO:19, IA-W18 defined in SEQ ID NO:20, IA-W19 defined in SEQ ID NO:21, IA-W20 defined in SEQ ID NO:22, IA-W21 defined in SEQ ID NO:23, IA-W22 defined in SEQ ID NO:24, IA-W24 defined in SEQ ID NO:26, IA-W26 defined in SEQ ID NO:28, IA-W28 defined in SEQ ID NO:30, IA-W29 defined in SEQ ID NO:31, IA-W33 defined in SEQ ID NO:35, IA-W34 defined in SEQ ID NO:36, IA-W35 defined in SEQ ID NO:37, and IA-W41 defined in SEQ ID NO:43.

5. The polynucleotide according to claim 1, wherein amino acid sequences of the genes related to glycosyl transfer including orf7, 8, 30-32 and 40 comprise IA-W7 defined in SEQ ID NO:9, IA-W8 defined in SEQ ID NO:10, IA-W30 defined in SEQ ID NO:32, IA-W31 defined in SEQ ID NO:33, IA-W32 defined in SEQ ID NO:34, and IA-W40 defined in SEQ ID NO:42.

6. The polynucleotide according to claim 1, wherein amino acid sequences of the genes related to resistance including orf3 and 25 comprise IA-W3 defined in SEQ ID NO:5 and IA-W25 defined in SEQ ID NO:27.

7. The polynucleotide according to claim 1, wherein amino acid sequences of the genes related to biosynthetic regulation including orf2, 23, 27 and 42 comprise IA-W2 defined in SEQ ID NO:4, IA-W23 defined in SEQ ID NO:25, IA-W27 defined in SEQ ID NO:29, and IA-W42 defined in SEQ ID NO:44.

8. The polynucleotide according to claim 1, wherein amino acid sequences of the exogenous genetic engineering marker gene orf43 and the orf44 linked to the orf43 comprise IA-W43 defined in SEQ ID NO:45 and IA-W44 defined in SEQ ID NO:46.

* * * * *

```
                        SEQUENCE LISTING

<160> NUMBER OF SEQ ID NOS: 46

<210> SEQ ID NO 1
<211> LENGTH: 89315
<212> TYPE: DNA
<213> ORGANISM: Streptomyces spiramyceticus WSJ-1

<400> SEQUENCE: 1
gtggagagcc gaggggggcga cgaggccgac tatgccgcgc tccatcccga ggaagaggcg      60
gtggtggcac aggcggtgga caaacggcgc cgcgagttca ccgcggtgcg cgcctgcgcc     120
cgccgggcca tggagaagct cggcttcccg ccgcagccca tcctgccgag tgagcgcggc     180
gccccgcgtt ggccggaggg cctgctcggc agcatgaccc actgcgacgg ttaccgcgcc     240
gccgccctcg tccgcgccac cgacctggcc tccctcggca tcgatgccga accgcacggt     300
tcgctcccgg acggcgccct gcattccgtg gcgctccccg ccgagcggga gcgcctggcc     360
ctcctcgccg ccgggcagcc cggcgtccac tgggaccggc tgctgttcag cgcgaaggag     420
tccgtctaca aggcgtggtt cccgctgacc gggaagtggc tgggcttcga ggaggcgtac     480
atcgatctcc accaggattc cggaacggcg cagcacggcc gcttccgcgc cgaactgctc     540
gtccccggac cgctggtggg gggacgaagg atcaagcatt cgaggggcg gtggatcgtc     600 cgcgagggcc tggtcaccac cgcattgacg gtccccccacc cctgatcccc ctcgcgcgcc     660
cgaaagccgc ctccgggtgg ggccagcccc gccgcccgcg gggcgtagcg ggattccggc     720
acggaccgtg cgaccgtacg ttcttccata gtggtcgggt acatccattc ccggctggca     780
gaacgacgtc gcccgcaccc agatctggca gtggctgcgc cacgggtcac cgaccgcgcg     840
acggtcctgg accttctgga cgcggaggtc gcggcgctgg gcgcggagta cccctgggcc     900
ccggtggacg aggcccgcga cctcttggaa cgtaccgctc tggcacggga cttgccggac     960
ttcttcgcct cggtcggcta cgccctcacc tggtggagca ccctaccac cggggctgag    1020 gggccccggt ggcgccgccg gggccgaggg gcgcggcggc tgtggtcgag cagggcgcgg    1080
tacgggttgg tggatccgta ccgcgcctgc ttcgccttcc ccgtacgagc cgtcaccacg    1140
agcaccaccg acgaccgcgg gcaccgtcgg cgtcggcatc ggcatcggct caaccgcgtc    1200
tccggcctca gcgcggcgcc aggccgcgga gcgcgaggtc gacgagggcg tcggtgtatt    1260
cgtgcgtgag gggcccgtcg cccatcagcc agtgctgggc gacgggcccg gccagcatca    1320
gcacagcgat ccgcggatcg acgtcctgcg cgatctgacc ggccccccgg gcagagccca    1380
agcgctccag gcagagccgt aacggggct ccaccaggcg cgccgtcagc tccttgccga    1440
gcgcagggtc ggctatgccc gcggcgacga gggcgcgggc gggcacgtcg taccccgggt    1500
cggtcatggt gtcgacagcg gaccggagaa cggccttgag atcggcctcc agatcgccgg    1560
```

```
tgtcgcggac agcgccccg gcccgcgcga tgtcctcggt cagggagacg accgcgtccc      1620
ggaggatggc cgccttggag ggccaccggc ggtagatggt ctgtttgccg acgcctgccc      1680
tggcagcgac cccttcgatg gtcactctgg gatatccgac ctcgtgaacg agttccagcg      1740
tggcgcccag gatcgcacgg tgtgcgcggc gactgcggtg ggcggtttca ggtgcgcggt      1800
gggaggacat ggtccacagc atagacctcg acgaaccgat acgtatcgtc ttgacaagac      1860
gatacgtatc gtcgaagctc atggatgtac cgagacgcaa cgcctcggct caccgacgac      1920
aggagaagcc catggccaag ggagcaaaga agatgctggg cctcggcggc acccgctcga      1980
acctctcccg cagcgcgatg cgcggcggga actcgggcgg aattcccggc ggcggcatca      2040
gcccgcagga gcagaagcgg gagctgctgc gcaaactcaa ggaagcgcgg tccaccaagc      2100
agaccccctc gtcgtgaagg cctccacctg aggggaccgg ctgcgtatgg gctttcgtac      2160
gcagccggtt cccccctccc gaggtccaca ggtccgagcg tccacaggtc cgggctgcgg      2220
gaacgccggc ccccggaata cgggctccga agtgccggaa ctcggagagc gggcccacga      2280
agcatcagca gtcggccgtc cgttggtgtg cgcggaacag cgcggtccac tccgggaccg      2340
tgaggtcctt gacccgatcg gcgggccgca ccccgcgcc cgcacgaac tgggcgtgtc       2400 cgcggcgcag cacctttcgc gcggcctcgc ctatcgtcat ctggccggtg tcgaagacct      2460
gctgggtgaa ccgctgatag gcggtgcgct cacgccaggg cacggcggc ttgcgatggg       2520 gggtcaccat caatgtctgg gtatcggcgc gcggcacggg gttgaactcc tgtcgcgaga      2580
aggccagccc tttctcaaac gcgtaccacg gctcccactg ggcgttgaag agatttccgc      2640
cccaggctcc ggtccgcttt cccacatact cgcgctgaag caggaacacg ccctggcgca      2700
tccggtccgg acccaactcc aggcaacgtc tcagtatctt ggtgccggag acaaagggca      2760
gattgccaat caaccggacc ggctgccctg gcaattgcag tgtcagaaag tcctcgttca      2820
ccaccgtgac atcgggcagc gattcggcgg ccagccgacg ggcccattgg gtgtcgattt      2880
ccaccgcgag taagggactt ccggtcgatg cgagcgcttt ggtcacccgg ccggatcccg      2940
cgcctatctc gacggtcaga aggtcattcg gcgaaccggg cgcgatggca tccgagctgt      3000
ccagctgagc ggagaacctg caggctgcag cggctgcccg gaagaaattc tgaccccatt      3060
ccctccgcgc gacgcagcgc gacgcagcgg gagcggaggc ggatcgcggc ggccgtgggg      3120
atttcgattt caccgggcg acattaccaa cccctcaccc aatgatccat caacaaccgg       3180
tatgcccaac ggaattcggc catcctcgga cccgatcacg acatcggccg acgagccctt      3240
cgggaccgac tggtgactgc cgtgcgaacc ggcattgtcg gcgaatcatc cggacgatcc      3300
acgaattccg gggcattcga gcccggcccg gcgcgttacg gcccggcgcc tgtccgggcc      3360
gtaacggtgt tccacgggc tcatggtgat tcaccacagt ctcgactgcg acggccaacg       3420
ccgtgagccg aacgggaatg aatcctggcc gacttcgtca ggttcaacgg gcgccgggcc      3480
ggcgcggccg gtgccgctg actgtgtcat ctccatgttg tcggccgaac gcaccgcgcc       3540
ccaggatgac ccagcccatt ccctgcggtc accccggcca cagtccccat cccgaaagag      3600
gagcgagaat ccagtgctcc atcgcgtcga tctgtcgtcg ctcaccgcc tccgctggta       3660 cgcggcgttg acagtattcg cctgccacat cgcccagcag ggcttcttcg ccgaccagca      3720
ggtcggcagc gcactgctgc acatcaccac gctcggctcg atggcggtct cggtcttctt      3780
catactgagt ggcttcgttc tggcgtggtc ggcccgcgac gaggactcca ccccgacttt      3840
ctggcggcgc cgcatcgcga agatctatcc gctgcacatc gtcacgttcg gcattgcggc      3900
```

```
cctgatcatc ttctccctct cggaaccggt ccttcccggt ggctccgtgt gggacggcct      3960
ggtgcccaat atcctgctgg tgcagtcctg gcttcccgac gcgtcccttg cggccagttt      4020
caacacgccg agctggtcgc tctcctgtga actcgccttc tatctgtcgt tcccgctgtg      4080
gtatcggctg gtgcggaaga ttccggtggg gcgactgtgg tggtgcgccg ccgggatcgc      4140
cacggccgtg atgtgtgtgc cgttcgtgac gggcctgctc ccggcgagcg aggaggcggc      4200
ccccgggatg ccgctcaacg aggtgtggtt cgcgtactgg ctgccgccgg tgcggatgct      4260
ggaattcgtc ctcggcatcg tgatggcgct gatcctgcgc gcaggcgtgt ggcggggccc      4320
acgggcgggg acctgcacgc tgctgctcgc cgcgagttac ggcctcaccc aggtggtgcc      4380
cccgatgttc actctcgccg cgtgctccat cgtgcccgcc gccctgctga tcaccgccct      4440
ggccgacgcc gatgtgcacg gtcggcgcac ggggctgcgc tccgcgatgc tggtgcggct      4500
gggccagtgg tccttcgcct tctatctggt ccatttcatg gtcatccgct acggacaccg      4560
actgatgggc ggcgagtcgg gatacgagcg ccagtggagc accccggccg cgatcgctct      4620
gtccctggcg atgctgatgg tcgcgatcct ggtcggcggg ctgctgcaca ccgtcgtcga      4680
gcagccctgc atgcgactgt tcggcagccg cacgccctcc gccgtcccga agcccggcac      4740
cgcccctgcg ccccgaagtt cgcccggccc cgacgtcacg ggcgtaccag tcgtcacgca      4800
cacgcccgac gtgacgaacg agctctcccc gaaaggatga tgagcgtggc agaccagacc      4860
gctctcagcc cagcgctgct ggaatacgcc cggagcgtcg cgctgcggga cgacggcctg      4920
ctgcgtgaac tgcacggggt aaccgcgggg cttcccgggg gccgggccat gcagatcatg      4980
cccgaggagg cacagttcct cgccctgctg atccggctcg tcggcgcccg gcgcgtgctg      5040
gagatcggca cgttcaccgg ctacagcacg ctgtgcatgg cgcgagcact gcccgccgac      5100
ggcagaatcg tcacctgtga catcagcgac aagtggcccg gcgtgggcgc cccgttctgg      5160
cggcgggccg gggtggactc cctgatcgac ctgcgcgtcg gcgacgccgc ccgaaccctc      5220
gccgagctgc gcgagcacga gggggacggc gtgttcgacc tggtcttcgt cgacgccgac      5280
aagaccgggt acccgcacta ctacgagcag gcgctggcgc tggtccgccc cggcgggctg      5340
gtggcgatcg acaacacgct gttcttcggc cgggtggccg atcccgccgt cgacgacgcc      5400
gacaccgtcg ccgtgcgcag gctcaacgac ctgctgcgcg acgacgaacg cgtggacatc      5460
gcgttgctga cgatcgccga cgggatcacg ctggcccgcc gacgggagtg agatcgcacg      5520
gcgtggggcg cagacgcaac gtcgtgaacg acggcggatt cgcgccaacg cccgcctgtg      5580
caaagcgact tcgcgacgtc tccgggacgc tgctggaatc ggctgccgcc gccggcctgc      5640
tacgacaggc cggcggcggc agcgtgtgcg gacctcgtgc ggtggcgccg taccgcgacg      5700 aggggccccct gcaccggaag cagcacggca agcgtccgca cgcccccga cgcatccgag      5760 ggcgtgcacc gggaacgccc cggagggccc gcccgaccgg tcagcggaac cggttgatgg      5820
cgtcgatgtg cttcgcgcgc ttctcctcgt cgcgcacgcc cagcccctcc gtcggggcca      5880
ggcacagcac gccgaccttg ccctgatgga ggttgctgtg cacgtcgtgc acggcgagcg      5940
cggtgtcggc cagcgggtag gtgcaggaga gcgtggggtg gatcttcccc ttggcgacga      6000
gtcggttcgc ctcccacgcc tcgcggtagt tggcgaagtg ggttccgacg atgcgcttga      6060
ggtgcatcca caggtagcgg ttgtcgaact cgtggcggaa gcccgaggtg gaggcgcacg      6120
tgacgatcgt gccgcccctg cgggtgacgt agacggacgc cccgaaggtc tcccggccgg      6180
ggtgttcgaa gacgatgtcg acgtcctcgc cgccggtcag ctccctgatg cggccgccga      6240
accgcttcca ctcccgcggg ttctgggtgt cctcgtcggt ccagaagcgg tagtcctcgg      6300
```

```
cggagcggtc gatgatggcc tcagcgccca tgggccggca cacctgagcc ttgcgctcgc    6360
tggagaccac gcagacggga ttggccccgc cggcgagggc gagctgggtg gcgtacgagc    6420
ccagaccacc gctggcgccc cagatcagca cgttgtcgcc ctgcttcatg ccggcgccgt    6480
tgcgggagac cagctgacgg tacgcggtgg agttgaccag accgggcgcg gccgcctcct    6540
cccaggtgag gtgggctgcc ttgggcatca gctggttgga cttgacgagg gccacctcgg    6600
ccaggccccc gaagttggtc tcgaagcccc agatccgctg ggccgggtcg agcatggtgt    6660
cgtcgtgccc gtcggcgctc tccaactcca ccgacagaca gtgcgccacg acctcgtcgc    6720
cgggcttcca gacgttcacc ccggggcccg tgcgcagcac cacgccggcc aggtcggagc    6780
cgaggatgtg gtagggcagg tcgtggcggg cggccgacgg cgatgtgcgg ccgtagcgct    6840
ccaggaagcc gaaggtcggc agcggctcga agatggacga ccagaccgtg ttgtagttga    6900
cggagctggc catcaccgcg atcagtgcct cgccgggccc cagttcgggc agcggcacct    6960
cgtcgacgcg cagcgacttg cgcgggtcct tgtccgtgct cgtcatgccg cggaacatgt    7020
cggtgtcctc tttgcggacg gtcacggccc ggaaggactc gggcaggcgc agcgccgcga    7080
tgtcctcggg ggtgcggtcc ggcgcggtga tcgcggcgag cagcgcgctc tgggcatggc    7140
tttcgggcat ggggggacgga ctccgttcga tcgtttcgtc aggtcgcccg gtgcagggcg    7200
gtgaggcgct ccagggtggg gacgatcccg gcaggcgtgg ggtcggcgag catctcctcg    7260
ctgagccgcc gcgcgcctgc tttgatcgcg gggtcgtgca cggccgtgtg caccgcgtcg    7320
gccaggccgc gtgccgtgag gtcgcggcg gcaggtcga accggcgga gaggcgctgg    7380 agttgctggg ccttgagcgg cgcgtccac agcgagggca gcaggatctg cggcactccg    7440
tggagcaggg cggtggacca ggtgcccgct ccgccgtgat ggatgatcgc ggcgcagctc    7500
ggcagcagcg cgtcgagcgg cacgaagtcc accggtacga cgttgtcggg aaggacgccg    7560
aggcgctcgc gctgggaggc gtcgagggtg gccaccacct cgatgtccag ccgtcccagc    7620
gcctccagca gttcggagta ggagaccgcg tcgcggccgt aggtctcgcg ggcagacacc    7680
ccgagggtga ggcagacgcg ggggcgatcg ggcttcttgg cgagccaggg ttcgatcacg    7740
gagcgcccgt tgtagggcac atagcacatg gcaccatgg tctgcccag gtcgagccgg    7800 gtgctgcggg gccccgggtc gatcacccag tggccgagca cgtcgcgttc gtcgaaggcg    7860
tacccgtatc ggtcgagcgt ccagccgagc cattcggcga tggggtcctc gcgcagttcc    7920
tccggtacct gctcgagcgc tgcgaggaag cgccggcggg agcgtccgat ggcatcgggg    7980
ccccagagga tgcgggcgtg gcggcgccg caggcgcggg ccgcgaccgg ccccgcgtag    8040
gtccagggtt cccagacgac caggtcgggg cgccagccac gggcgaaatc gacgatctcg    8100
tccatcgtgg cggcgccgtt gaacggggcg aagcacaggg cggccatcat gctctgctgg    8160
ccgagcagat actcccaggt ggtctcctcc tcgctctcca cctcgccgaa ctcgaagccc    8220
cgctggtagg ggacgaggtc gctgccatc tcggcgagca gctccgcggc gggtcggtcg    8280
tcgccgacgg ggacggcggt caggccggtg gaggtgatga cgtcggtgag cgagggcggg    8340
ctcgccaccc gtacctcgtg cccggctgcg cgcagcgccc aggccagggg caccaggctg    8400
tagtagtggg tgttgtgggc gagggaggtc agcaggacgc gcacggtgac tccggtctgg    8460 gacggggtg tacgggcggg gtcatcccgg gtggacccgg aggcgggcgc aggcgcctac    8520
gaccggggaa cgcggccggg tcagcggcgc gccctcggcc cgcagtccgg gcaggcggcc    8580
ggccatgacc tggaccgcgg tggtggtggc caggcggatg agcgggaggg cgagcgccag    8640
```

-continued

| | |
|---|---|
| gtgcggcccg tccgggccgc cgagcggctc cggccccggg gtctcccgtc cggcggcggc | 8700 |
| cagcaccaca atgtgctcgt cggcggcgat ccggcggccg ccgagttcga ggtcggtgtg | 8760 |
| cgcgaccctg ctctccagcc gggccggggg gcggtggcgc agcgtctgct cgacggccct | 8820 |
| cgcggcggcc ggggtccggc gggcccttc ccactccccc ggccggccca gcagccggtg | 8880 |
| caccgtgtgc gcgacggcgg tggcggccgg ctcggggggcg ccgatggcga ggaccagcgc | 8940 |
| gatgcgctcg acgtcgcggg gtgcgacgcc atcgcgcagg aggagggcga ggacgtcgtc | 9000 |
| gggccggggc ccgccgctct cgacggcccg cagcttctcc gcgacgagct ccgggaccag | 9060 |
| gtcggccagg gtccgcacgg cgtcggcgga ctcccgggcg acggccagga tctgcggggc | 9120 |
| cagccgggcg tcgagctggg gggcgcaggc ggcgagcgcc cgcgcggcgg cgtcgcggtc | 9180 |
| gcggtccggc actccgagga acccgagcac cagctcgacg gcgtacgcc gggcgacctc | 9240 |
| ggtgacgagg tcgaacccgg cgccaccggt tggcaggaga cggcggagca ctcggcgggc | 9300 |
| ggtggtgcgc ccgcgcagg gcgcctcggc cggggcgcaa cggttgagta cggggtcggc | 9360 |
| cagcgcccgc aggcgtacga gctccgcgcg ttcgtggcgg gggaacgcct cggcgagggg | 9420 |
| cagcagttcc tcgtccggac ggcggccggc ccggtccagc gtgccgaaac gtgggtcggc | 9480 |
| caggacagcc gccgccacct ctgggtccgc ggtcacccag gcgcccagca gttcgctgtg | 9540 |
| gaaccacggt ccggcggcgc agatttcccg ttcgagcggc tcggggtcgg agacggcgcg | 9600 |
| cagaatcagc gcgtacgggt cgccctgatt gcccgcgcac cagtgcgcgg cacgggtcag | 9660 |
| ctgaagccga cggccgagct cccgggtgcc cgcgctcgcg ggagccggct ccatggcaag | 9720 |
| gatgggcatg gcttcctctc gtcatctcgg atggcacgaa gtcggacggt acgaaggggg | 9780 |
| tggcgaaggc gtgtcgccac ggggaggtcc gcctcggcgg cgggcagctt cagcggcggg | 9840 |
| tgccgatgaa cagtccgcgg ccggagggggc cgccctcctg gtagaccacg tcgcagccgg | 9900 |
| cgcgctcgaa ggcggcttcg tagtcggcgc gcgggaacag ggtgatggcg tggtcctcgg | 9960 |
| tgaggtgacg gatgccgccg ccgggctcgg cgacgaggta gtgcacctcg atgcgggtgg | 10020 |
| cgttccccctc ccgcacagaa tgcgagaccc ggcagatggt gcgctcgccc gcctcggtga | 10080 |
| cgctggcgcc gacgtagccg ggggtgaagg agctggggaa ccaccagggt tcgacgacga | 10140 |
| tgacgccgcc cggttcgagg tggtcggtga aggaccgcag cgtgctgtcg agttcgtccg | 10200 |
| tggtccgcag gtggcctatg gagctgaaca tgcagatcac cgcgtcgaac cggcggccca | 10260 |
| gggcgaacga gcgcatgtct ccttcgtgga aggtgacgcc ggggttgcgg tcggtcgcga | 10320 |
| gggccagcat gtcgtgggag agctccaggc cctcgacgtg gtcgaagagg ccgtcgaggt | 10380 |
| ggcgcaggtg ctggccggtg ccgcaggcga cgtcgagcag tgaccgggtg tccgggcggt | 10440 |
| ggacgcgcac cagtgcggcg atctcctcgg cctcctgccg gtagtccttg cccttccct | 10500 |
| cgtggaccag gtcgtagacg gccgcgatgt cgttggcgta catcagtgtt ctcctccggt | 10560 |
| gagcagggcg ggcggcccgg ccgggtgcgg gacggcctcc agccagtcgt gcaccacgga | 10620 |
| cgcggtgtgc cgcgcgtgtt cggtgagcat ggtgaagtgg ttgccgggca cgtcggcgac | 10680 |
| ggtccgggcg aacgggaccc gggagcgcca gtcgccctgt gcctcgccga cgggccactc | 10740 |
| gcgcaggggt tcgacgcccc ggacgagcag gacgggggcg ttcagggcgg tgagccgggc | 10800 |
| gccgagcagc agccggtggt agccggccat ggcggtgagc cggtggtcct ccaggggggac | 10860 |
| ggtgctgcgt tcgagggccc ggctgagcag gtcgtcgcgc cacacgccca tcgcgccggg | 10920 |
| gtcctcggga cggtagacgt ccatcagcac gacggccgtg gggccggtgc cgcgctcctc | 10980 |
| caggcgggcg gccagggcat gggcgacgtt cgcgccggcg gagtgaccgg cgagcgcgaa | 11040 |

```
cggcttgccc gcggcgtgct ccaggaggac gtcggcctgg acgtcgagca gggcgtcgag    11100
ggatgcgggc agcggctccg cggggccgcc gaaaccggac aggggagaa cgaccgtctc     11160 ccggctgtcg cgcagccctt cggcgaaggg gacgtactcg ccggggccgg agccgaccgc    11220
ggtgccggcg cagcagtaca gcgtggggtg cgtcgtcggg ccggtcgcga ggagcaccgg    11280
cgcggggcgg gcggagccgg gctgttcccg ggagtaggcg ggccggaacg cggccaggga    11340
ggccatcagc tccacggcct cgcccgacct gctctgttcg acggcggcgc ggaaggaggc    11400
gagcagcccg ctctcggccg gtacggcgct ctcgtgacgg ccggtggccc cggcgtcagc    11460
gaggccggcc aggtggtgtg ccagtgcggt gggatcctcg tggtcgaaga cgagggtgct    11520
gggcaggtcg agcccggtgt cctcggccag tcggccgcgc agccgcaccg cggccagcga    11580
gtcgaagccg atgtcccgga aggggccctg tgcgtcgccc cggttctcct cggtgtggcc    11640
gaggaccgct gcgatgtggc ggagcaccag ttccagggcg agccgcggcc ggtcctcggg    11700
ccgcgcccgt acgaggtcgg gtgcggtggg ggtgtcgtcg gcgggctgcc cggcggcggc    11760
gagcgccgta cgggcgacgg ggatgccgga gatcaggggg ctgggcgga aggcggtgaa     11820 gccggggggcg aaccgttccc agtcgaggtc ggccacggtc accgtggcgt cgccgctgtc    11880
gacggcctgg tgcagggcgg tgagcgccgt ctccgggcgg aggggaacaa ggccatggcg    11940
ggcgaggtat ccctcggggg ccatctcgcc catgccgccg ccgtcccaga cgccccaggc    12000
gacggaggtg gcgggacggc cctgcgcacg acgccgctcc gccaacgcgt ccaaatgcgc    12060
attggccgcc gcatacaccg actgcccccc actcccccac accgccgcac ccgacgagaa    12120
caacacgaac acatccagat ccacacccgc cgtcaactcg tccagcaact cagcccccac    12180
cgccttaccc gccaacaccc ccgcagcctc cgccaacgac acctcaccca acgccgacac    12240
ctgagccaca cccgccgcat gaaacacccc acacaacggc cccccaacc cctccaccac     12300 acccaacaac cccaccaccg acgcacgatc cgccacatca cacgcaacga acgtcacctt    12360
cgcccccaac cccaccaact cccgctccaa ctccaccgcc cccggcgccc caccaccacg    12420
ccgacccgcc agcaccacat gctccgcacc cccacgcgcc aaccaccgcg ccacatgacc    12480
acccacacca cccaacccac ccgtcaccaa cacacacccc cgcggccgcc acgacctcga    12540
ggccgagggc acagcggcag gcagcaggcg gcggccgaac aaccccgacc cgcgaatcgc    12600
cacctggtcc tcaccgccgc ggccggagac gacagcggcc agacgccgcc agtcacgccc    12660
gcccggctcg gccggcagat ccaccagacc gccccactgc acaggcgcct ccaacgccgc    12720
cacccgccca agccccccaca cacgcgcacc catcgcacac ggcacctcac ccggcccgac    12780
cgccaccgca ccccgagtgg ccacccacag cggtgtctcc accgcggcat ccgccatcgc    12840
ctgcaccatc agcagcaccg ccgtcgtccc ctcgtccagc cccgggtgcc cggcgagcgt    12900
ggctccgccc gtgtcgggga gcagcagcac gccggccaag ctctccgggc tccgcgcgag    12960
ttcggccagc cgagcagcca gggcgtcccg gtccagtgcg tccgtccgcg gcgctccggc    13020
ggcctgcccg agcggccgca ccaggcggat cacttccgcg ccggccgcgc gcagcgcccg    13080
ctccgcggcg tccgcggagt ccgtgcactg cccatgctcg accatcagcc agcgatccga    13140
ggggctgaac ctgacagcgt ctggggcgat cgcctgccag gcgacgcggt agcgcagccc    13200 tgccggtctgc gcggtcgtgc ggcgccggtc gtgccaggcg gctaagtgcg gtaggacggc    13260
ctgcagttgg ctttcgattc ccgcaccgtc ggcgcccagt cgcgccgcgg ccgaggcagc    13320
gtcgcccgcg tgcaccgcgg cccacagggc gtcgtcctgc tctgcttccg cgacgggccc    13380
```

```
tgcggagggg gcggaggtcg cggggcgac  cgtgggcgag gcggcggtgg gggcgagcca  13440
gtagcggctg tgctggaagg cgtaggtggg caggtcggtc cggcgtgcgc ccgtaccgct  13500
gtagagcgcg gaccagtcga ggtccgcgcc gcgaacgaac gccctcgcag cggcccggag  13560
cgcggtgtcg ccctccggtc gcccgcggcg cagcgcgggg gcgaacacgg tgtcggcctc  13620
gtcggccagt gactcctccg ccatgccgga gaggactgcg tcggggccga gctcgatgaa  13680
ggtcgtggcg tcacgggccc gcgcggtgcg cactgcgtcg gcgaaacgca ccggctcccg  13740
cacctggcgg gtccagtagc cagggtccct cagctgggcg gcggtggcga gttcgccggt  13800
cacttcggag acgaccggca gccggggagc gtggtagtcg accgtttcgg cgatcacgcg  13860
gaagtcggcg agcatggcgt ccatgcgcgg cgagtggaag gcgtggctca cccgcaggcg  13920
cttggtacgg cggccccggg cggccagttc accggccgcc gccagtacgg ccgcttcgtc  13980
cccggaaagc acgagggcct gcggtccgtt gaccgcagcg atgaccgcgc caccggcgac  14040
gacgggctcc agcgcggcga cctcccgctc ggtggcctgc acggcggcca tcgcgccgcc  14100
ctcgggcagg gcccgcatca gccggccgcg tgccgcgacc agccgggcgg cgtcggccgc  14160
cgagaacact cccgccgcgt gagccgccac caggccgccg atcgagtgcc cacgaggac  14220
gtccggcacc aggccccagc tctcgaagag ccggaacagt gcggtctcga ccgcgaacag  14280
ggcgggctgg gtgtagtcgg tacggtcgag cagtgtggcg tccggcgcgg agggttcggc  14340
gaacatcacc gacagcaaag ggcgttcgag gtgggcgtcg aactccgccg cgatctcgtc  14400
gagggcgtcg gcgaagacgg ggaacctcct gcggagctcc tgaccggcgc cgagccgctg  14460
ggcgccctga ccgaacagga ggaaggcgat cccgcgccg cgccgcgcga cgcctgtgac  14520
catgttctcc ggcgtccggc cggcggccag cgcggcgagg tcctcccggg ccgcccgggc  14580
gtcgtgcacc agcgcaaccg cccggtgttc cagggcttcc ctggtggtgg ccagggagta  14640
tccgaggtcg acggcagtgg tgagatcggc gtcggtgtcc tccgtgggcc cccggcgggc  14700
gagggcggcg agccggtcgg cctggccacg cagtgcctcc tccgagcggg cggagatcac  14760
ccagggaagg ggggtcgcgg ccgtgatgcg ggggtcaggg gcgggcccgt cgctgccgtc  14820
ggcctcactc ggaggttcct cgatgacgac atgggcgttc gtcccactga cgccgaaggc  14880
agagacagcc gcccgacgca cccggcccgc ccgccggggc caggaccggg cctcggtcag  14940
caactccacc gaccccgaac cccactcgac cttcgacgac ggagcatcca catgaagagt  15000
gcgaggcaac gacgaatgcc gcatcgcctc caccatcttg atcacaccac ccacacccgc  15060
agcggcctga gcatgcccga tgttcgactt caacgacccc aaccacaacg gatcacccac  15120
ccgctcacgc ccatacgtcg ccagcaacgc acccgcctcg atcggatccc ccaacgccgt  15180
acccgtgcca tgcgcctcca ccgcatccac atccccggc gccagcccgg catcagccaa  15240
cgcctcacgg atcaccctcc gctgggccgg accactgggc gccgtcagac cgttactcgc  15300
accatcctga ttgaccgcac tccccgcac caccgccagc acccgatgcc cataccgacg  15360
agcatccgac aaccgctcca ccaacaacac accaacaccc tcggcccaca cagtgccgtc  15420
cgcaccctcc gcaaacgcct tgcaccgccc gtccgacgcc agcccacgct gccgggagaa  15480
ctccacgaac accgtcgggt cgggcatgac cgctacgccc ccggccagcg cgagatcgca  15540
ctcgccccgc cgcagcgact gcaccgccag atgcaatgcc accaacgacg acgagcaggc  15600
cgtctcgatc gtcagcgccg ggccctccag gcccagggtg taggcgatac ggcccgacat  15660
caccgcgtcg gcgttgcccg tcagcagata gccctcggtg ccctcgggcg cccgcgcggt  15720
gtcggcgacg tatccggtgt gtgcggctcc gacgaacaca ccggtacggc tgccgcgcag  15780
```

```
cgacgcgggg acgaccccgg cccgctccag cgcctcccag gacgtctcca acagcagtcg   15840
ctgctgcggg tccatcacca gcgcctcgtt cggcgagacg ccgaagaagg cggcgtcgaa   15900
gtcgccgacg ccggtgagga agccgccctc gcggcagtag gtagtgccgg gcgtgtcggg   15960
gtcgggcgag tagacggcgg cttcgtccca gccgcggtcg gcggggaagc gggtgatcgc   16020
gtcgacgccg tccgcggcga gctcccacag gtcgtcgggg gtggtcacgc cgccggggta   16080
gcggcatgcc atgcccacga tcgcgacggg ctcgtgcgcg gcggccagga gctctcggtt   16140
gtgtcgacgc agccgctcgg tctccttgac cgaggtgcgc agcgcaccca gcacttcgtc   16200 catgacggt gacatcttcg gcttcctcgt ctgctcgctg tgggggggcgt cggtggtacg   16260 gcgcactgcc ggtccgcacg cacccggtac gggccgctac cggcggcac acaccggtac   16320 gggggggtta ctgctctggt gctccgccgc gggtggtccc cgcttcggtg gacccgtcgt   16380
tcgccggcgc gccgtcggcc ggtccggtgc cgcccgtcgc cagccggacg agggcatccg   16440
cgtcgagctc gtcgatctcg gcgtcgtggg cagccggctc cggtgcgggt ggcgacgcgt   16500
cgttcccgcc tgtgccggcc gggcccggcg cgccgccccg ttcggggtcg ctcgcgccgg   16560
tcagctcctc cagcagcgcg ttgccgagcc ggtcaacggt ggggtggtcg aagatgatcg   16620
tcgcgggcag cacgagcccg gtcgcctcgg ccagccggcc gcgcaccgc accgcggcca   16680 gcgagtcgaa gccgagttcc ttgaaggcga cgtcgtggcc gatacggccg atccgtcgt   16740 ggcccaggac ctctgccgcc accgtgcgga ccaggtcgac cagcaccttc gtgcgctcgc   16800
gcggggtgag tgcggcgtcg atgcggcggc gcagatcgtc cgacgcgccg acggtgggct   16860
gggccgcccg cagcgcgcgg acctggggga tgccggagat caggggcgctg ggccggaagg   16920 cggtgaaccc ggtgacgaag tgctcccagt cgatgtcggc gaccgtgaca caggtgtcgt   16980
cctggttcag cgccgtgtgc agggcctcaa tgcccgactc cggtcgcatc ggggcgagtc   17040
cgcgctcggt gtagaagtcc ctgacgccgt cgcccgcgcc catgccgccg ccgtcccaca   17100
ggccccaggc gacggaggtg gcgggacggc cctgcgcacg acgccgctcc gccaacgcgt   17160
ccaaatgcgc attggccgcc gcatacaccg actgccccccc actccccac accgccgcac   17220 ccgacgagaa caacacgaac acatccagat ccacacccgc cgtcaactcg tccagcaact   17280
cagcccccac cgccttaccc gccaacaccc ccgcagcctc cgccaacgac acctcaccca   17340
acgccgacac ctgagccaca cccgccgcat gaaacacccc acacaacggc accccccaacc   17400 cctccaccac acccaacaac cccaccaccg acgcacgatc cgccacatca cacgcaacga   17460
acgtcacctt cgccccccaaa cccaccaact cccgctccaa ctccaccgcc cccggcgccc   17520
caccaccacg ccgccccgcc agcaccacat gctccgcacc cccacgcgcc aaccaccgcg   17580
ccacatgacc acccacacca cccaacccac ccgtcaccaa cacacaccccc cgcggccgcc   17640 acgaacgccg cctcacacca ggcgcagccg gcagcatgcg gcggccgaac agcccggatc   17700
cgcgaatcgc cacctggtcc tcaccgccgc ggccggagac gacagcggcc agacgccgcc   17760
agtcacgccc gcccggctcg gccggcagat ccaccagacc gccccactgc acaggcgcct   17820
ccaacgccgc cacccgccca agcccccaca cacgcgcacc catcgcacac ggcacctcac   17880
ccggcccgac cgccaccgca cccgagtgg ccacccagac ccgggctttc ggtgcgccgt   17940
ccgtcacggc ctgggtcacg agcagcacgg cggccgtgcc cggtcgagc gggaaggcat   18000 cggcggtgc ggcgtccgct gccggccgg gtagcaccag tacgcccgcc aaccctgcg   18060 ggcccgcggc gagttcggcc agccgctcgg tgagggcgac gcgcgcgacc tcggccggat   18120
```

```
ccagcggaca acgctccacc accgcgccgg ccgtgccgag tgccgttgcc gcggcgtcgg    18180
cctcgtccgg cgcagcgccg gggagctcca ccagcagcca gcgcccggac ggcgcaccgg    18240
aaccgccggt ctccagggcg gtccaggtga cccggtagcg ccaggcggcg gactcgtcgg    18300
cgggggcctt ggcggtgcgc cggccgacgg cggtcggcag ccagaaccgg tcacgccgga    18360
aggcgtacgt gggcaggggt acacggcggg cgccggcgcc ttcgaagagg gggctccagt    18420
cgacccgtac tccatgggcg aacgcggcgc ccaccgaggc gcggaaccgg tccaggccgc    18480
cggagccgcg gtggagggtg gacagcgcgg tggcgtgcac gccctcggcc tcggcgatct    18540
cgtcgatcga ggagcccagc aggggtgcg ggcccatctc gacgaaggtg cggtggccct    18600
ggcgcagcag cgcccgcagg gtggactcga actccaccgg ttcgcgcgtg ttccggtacc    18660
agtacgcggc gtccagaccc tcagggtcgt gtgctccggc ggtcacggtg gagaagaacg    18720
gcagccgggc ggcggtcggc cggacgtcgg cgagcgtgcc gaggagctcg gtgcggaact    18780
gctccacctg cggcgagtgg ccggcgaagt cgacgccggc gaggggccag cgcagtaccc    18840
cgtcggcgga caaccggacg ccgaactcct ccagcgcctg cgcgtcaccg gccacggtga    18900
ccgaggcggg gccgttgacc gcggcgacag agatccgctc cgcccagggc tccagcagct    18960
gcggacccg gtcggccggg gccatcacgg agaccatgcc gccgtttccg gccagtcgcc    19020
cccacaacct gctgcgctcg gcgatcaccc gggccgcgtc gtcgagggac agggcgcctg    19080
ccgcgtaggc ggcggcgacc tctccctggg agtggccgac gacggcggcg ggccgtacgc    19140
catgggcctc ccacagcgcc gcgagggaga ccatcatggt gaacagcgtc ggctggacca    19200
cgtccgcgcg gtcgatcggc ggggcgtcgg ggccgccgcg cagtacgtcg agcaccgacc    19260
agtcgagatg tgctgcgagc gcccgcgcgc actcctcggc cttgacgcgg aaggccgggg    19320
ccgactccag cagttcggcg cccatgccgg tccactggga gccctgcccc gggaagacga    19380
agacgggggg ccggccgctg cccgcctcgc cgacggcgac gtcgacgtcc ctcctgccct    19440
ccgccagcgc ggtcagccgg gcgatcagcg actcccggtc gtcggcgagg accgaggccc    19500
ggttcgagag tgcggcacga gtggtggcgg cggagtaggc ggcgtcggcg cggtgatct    19560
cctcgtggtc ggccaggtgt gcggcagacc tgcgggcctg ctcgcgcagg ggttgcgcac    19620
cggcggccga cagcgggagg acggtggtgg gggagacggg cggctcctcg ggttcctcgg    19680
gttcggcccg ggcggtcggc gcctcctcga caacgatgtg ggcgttggtg ccgctgatgc    19740
cgaacgagga gatcgcggcc cggcgcgggc cgtcggcccg ctgcggccag ggcctggcct    19800
ccgcgagcag ctcacacggct cccgcacccc attcgatctt ggacgaggcg gtggtggcgt    19860
gcagggtgcg gggcagcgtg ccgtgccgca tcgcctccac catcttgatg acaccagcca    19920
caccggcggc ggcctgcgtg tgcccgatgt tggacttcag cgaccccaac cacagcgggt    19980
cgcccgcccg ttcgcgcccg taggtggcca tcagcgcact ggcttcgatc ggatcgccca    20040
gcggtgtgcc cgtgccgtgc gcctcgaccg cgtccacgtc ggcgggagtc agcccggcat    20100
cggccaacgc gtcgcggatc accttctgct gggccggacc gctgggcgcg gtcaggccgt    20160
tgctggcgcc gtcctggttg acggcgctgc cccgcaccac cgccagtacc gggtggccct    20220
tcttctgagc ctccgacagc cgctccacca gcagcattcc ggctccctcg gcggggccga    20280
agccgtcggc cgcctccgcg aaggccttgc agcggccgtc ggggcgagc ccgcgctgcc    20340
gggagaactg agtgaagagg gcgaagtcgg cgatgaccgt ggcgccgccg gccagtgcga    20400
ggtcgcactc gccccggcgc agcgactgca ctgccaggtg cagtgccacc agcgacgagg    20460
agcaggccgt gtcgatcgtc agcgccgggc cctccaggcc cagggcgtag gcgacccggc    20520
```

```
ccgcggtgaa gctgacgatt ccggccagga gctgggcctc cagctcggct tcgagcccct    20580
cgacgccctt ctggtagccg ctctcccacg ccccggcgaa cacgccggtg cggctgccgg    20640
ccagggactg ggggtcgagg ccggcccgct ccagtgcctc ccaggacgtc tccagcagca    20700
gccgctgctg gggatccatg tgagcgcct cgttggggga gatcccgaag aggccggggt     20760
cgaaccggtc ggccccctgc acgaagcccc cctcgcggca gtacgtggtg ccgggcgtgt    20820
cggggtcggg cgagtacatc gcctccacgt cccagccgcg gtcggccggg ccaggctga     20880 cggcgtcggt cccggcgagc agcaggtccc acagttcgtc cgggctgcgg acgccgccgg    20940
gcagccggca ggccgccccg acgatcgcga tcggctcgtg ggcccgctcg tccagggtgc    21000
gcagctgctc ggtggcccgg tgcagctcgc ccgtcacgcg cttgaggtag gcgcgcagct    21060
tctcttcgtt cgccatggtg gtacttccct tcgaggactg gcgacggggc gccgaaccag    21120
tggtcacgac gcgccgtacc gctcgtcgat gaacgcgaag atctcgtcgt cgtcggcggt    21180
gctcaggacg tcggcgatgt cgtcgtcgac gccggccgcg ccgtcgtgca gggcgcgcca    21240
gcggtcggcg agtgcgtcca ggcgcagggc gacctcggcg cgggcgtcgg gggcgggtgc    21300
gaccgccgcg agaccttcgg gggtgagggc ggccagggcc tcctcgatcc ggtcgagttc    21360
ggacagcagc ggtgcggtgg tgggcggccg ctggggcgcc agcaggccgt cgaggtgcgc    21420
ggccagcgca gccggggtgg ggtggtcgaa caccaggggtg gcggggagcc tgaccccggt    21480
gaccgcgccc atccggttgc gcagttccac ggccgtgagc gagtcgaatc cgacctcgcg    21540
gaacggccgg tcggagcgga cctccgcggc ggagccgtgg cccagcaccg cggccacgtg    21600
ttcgcttacc aagctgagca gctggtcgtg gcgttcttcg gcggagagcc tggccagccg    21660
ttcggcgagc ggctcgccgg tgtgcccgc gtccggtgtc gggtacgggc cggcggccgg    21720
ggttgcggac ccggcggccg gggcgggtcc gacgaggtcc gacagcagag cggggactgt    21780
tccggtggcg cgcagcgcgg ccgggtcgaa ccgcatgggg atctgcacgg cctcgtccac    21840
tcgcagggct gcgtcgaaca gtgcggcgcc cagggtcgct gacaggggag ggaagccgtt    21900
gcgggcgaag cgccgctgga ggctctcctg gtccagtccg ccggccatcc ggctggtgtc    21960
ggaccacagt ccccaggcca gcgacaccgc ggggaggccg agggcccgcc gccggacggc    22020
gagggcatcg agcgtggcgt tggccgctgc gtaattgccc tgcgccgggc tgcccagcag    22080
accggcgctg gaggagaaga ggacgaatgc cgacaggtcg aggtcgcggg tgagttcgtc    22140
caggtggacg gcggcctcca ccttgggacg cagcacgcgc cgcatccgct cggggggtgag   22200 cgtgggcagc acgccgtcgt cgaggacgcc ggcgctgtgc accaccgccg tcagcggggtg   22260 ctcggccggt acgccggcga gcagccggcg gaccgcgtcc gcgtcggaga cgtcgcaggc    22320
gacgacggtg gccgaggcgc ccagggcggt gaggtcggca accagttccg cggcgccctc    22380
gccgtccggg ccgcggcgtg cggcgatcag cagctggcgt acgccgtgat gggtcgccag    22440
gtggcgggca atgcggccgc cgagggcccc ggtgccgccg gtgatgagca ccgtgccgta    22500
cgggtgccag gcgggcggca tggtcaggac gagctttccg gtgtgcctgg cctggctgat    22560
ggtgcgcagg gcgtccgcgg cccggcgcac gtcgtgggtg acgacgggca gtgggtgcag    22620
cactccggcg gcgaacagtt ccatcagttt ccgcagcagt cggccgagtt cgtcgggtcc    22680
ggcctcgttg aggtcgaacg cccggtagcg gactccgggg tggtcggcgc cgacctgctc    22740
ggggtcccgt acgtcggtct tccccagctc caggaaccgg ccgccggcc ggagcagccc     22800 gagggaggcg tccacgaact ccttggtgag cgagttcaga acgacgtcgg cgcgggacgt    22860
```

```
gccgtccgta ccggcgaagg cggtggcgaa gtcgagggtg cgggaggagg cgaggtgttc    22920
gtcggtgatt cccatggcgc gcaggacgtc ccacttgccg gtgctcgcgg tggccagcac    22980
ctcggcgccg aggtggcggg cgatctgcac cgcggccatg ccgacgcctc cggcggcggc    23040
gtgcacgagc accttctccc ccggtcgcag gtccgccagg gtgaccagcc cgtagtaggc    23100
gctgaggaac accgcgggga ccgaggcggc ccgggcgtag gaccagccgt ccgggatcgg    23160
gacgagcagc cggtggtcgg ccacgcacac cgggcccagg ccgccgttcc acaggccgag    23220 caccccggtcg ccggggggcga cgccggtgac gccggggccg acctcgacga cggtgccggc    23280
gccctcggtg cccatttccg cctcgcacgg atacatgccg agggcgatga gggcatcgcg    23340
gaagttcacg cctgcggcgc gtacggcgac gcgcacttgg ccgtgctcca gcggggcctc    23400
cgcgtccggg gcgggcacca gcgcgaggcc gtcgagggtg aggtcggcgc ctcggccgag    23460
ccgccaggcg cccttctccg gcggggtgag cggcccgtcc gtgctgtcgg cggcccgctc    23520
cagccggggt acgtacaccc tcccggcacg caccgcggtc tgcggttcgc cggaggcgag    23580
ggcggtgggc agcgccctcg cggacgccgg gtcgtcgtcc aggtccacca gcaggaaccg    23640
gtcgggctcc tcggcctgcg cggagcgcag caggccccat gcggcggccg cggccgggtc    23700
gctcacctcg gcgtcgccgc gtacggcgac cgcgccgcgg gtggccacga ccaggcgggc    23760
gccttccggg gcgtccgggg ctgcgagccg gcgctggaca aggtccagca cctggcaggc    23820
gacggcgtgg gcgtcggcgg cgacatcgcc ggttccggtc ggcactccga acacgaaggc    23880
gtccggcgcc gcttcgccgg ccgcggtcgg cagcgggccg tccgggccga gtgcgtcggg    23940
caggtgtgcg tcggcggcct cggccaggcc cagcacgtcg ggccccgcga ccacccagcg    24000
caccgaggaa gcggcgccgg cgccgttgcc ggtacggagg ccggtgcccg agccgctggt    24060
gagctcccgc caggcgatgc ggaagagcgc gtcggcgccg accgggcggc cgcccaggag    24120
ctgctcgggg tcgaccggcc gcatgaggaa cgagtcgatc tcggcgaccg cccgtccctc    24180
ggtgtcggcg caccggatgc ggacggcgtc ctggagacg ggcgagatgc gcacgtgcag    24240
ccgctcggct ccggtgcggt acagccggac gccgcgcagc gcgaagggca tccggatgcg    24300
gccgtcctca gggaagaagc cgcccaggct catggtctgc agcgccgcgt ccaacagcgc    24360
ggggtggatt ccgaaccgtg ccgcgtcgcc ctgggcctgg acgggcagcg cgacctccgc    24420
gtggatgtcg gagccggagc ggtgcgcgct caccagtccg cggaagaacg gcccgtagcc    24480
gtagccgagt tcggcgaaac gctcgtagaa gtcgccggtg tccagttgtt cggcgccggg    24540
cggcggggct gtcgccgagg cgtccggcac gtcggcggcg tcctccgcgg tgagcagccc    24600
ctcggcgtgc agggtccagt ctgcggcgcc ctcgcgcgg gcgtgcacgg cgaagcggcg    24660
ggcgtcgtct gcgcccgggg cgccgacgtt cagccgcagc cggacaccgc cggactcggg    24720
cagcgccagg ggtgcggcca gggtgagttc ctcgatccgg ccggtgccgg cctggcggcc    24780
ggcccagagg gccaggtcgg cgaacgcggc gcccggcagc agcgccgccc ccatcagtgc    24840
gtggtcggcc agccacgggg tggcgtcggt gcccaggcgc gcggtgtaca tctgagcgcc    24900
ggagtcgggc agttccacgc cgccgccgag cagcgggtgg tcggcggcgt ccaggccgag    24960
ggaggcgggg tcgtcgccac ggctggtggg gctgtaccag tagcgctcgc gctggaaggg    25020
gtaggtgggc agttccacat gacgcgagtc ggggccgaag atggcctccg cgtcgatctc    25080
cacgccgtgg gtgtaggcgc ggcagacggc gacggccagg cagcggggc cgccctgacc    25140 gcgacgcagg gtgccgagaa ccgccgcgga ggcgccggcc tcgctgatcg tctcctggag    25200
ggagacggcc agcatggggt gcgggctcga ctccaggaac acgtcgtggc cgtcggcgat    25260
```

```
cagggcgcgg gtggccttct cgaactccac cggctcgcgc atgttgcggt accagtagtc    25320
ggcgttcagc tcggcggtgt cgagcagccc accggtgacc gtcgagtaga acgggatgtc    25380
ggaggatcgc ggcgcgaccg gggcgagcac ctcccgcaga tgctcctcca gcatgtcgac    25440
ctgcggcgag tgcccggcgg tgtcgacgcc gggatcgggc cggcgtgca ccccctccgc    25500 gctgagttcg gcgaccagct ctgccagggc gtccgggtct ccggagacgg cgcaggtctc    25560
ggggccgttg acggcggcga cggcgagccg gtcgctccag ggctccagcc ggggacgcag    25620
gtcgcgctcg gacatggtca ccgcgaccat gccgcccttg ccggccagcc gcagccatgc    25680
ctggctgcgc agggcgacga tgcgcgccgc gtcgtccagc gagagggcgc cggcgacgtg    25740
ggcggcggcg atctctccct gggaatgccc gacgaccgcg gccggttcga cgcccagcga    25800
acgccaggtc tcggcgagcg agaccatcat ggtgaacaac acgggctgca ccacgtcgac    25860
ccggtcgagc gagggcgcgc cgggttcccg gcacagcacg tccagtacgg accagccgag    25920
gtggggccgg agcgcggcgt cgcaggcgcg tgcggtctcc aggaaggagc tggagtcgct    25980
ggagcggtcg aacagcccgt cggccatctc gggccattgc gagccctggc cggggaagac    26040
gaacaccacc tggtcggcgg tgccggcggt gccccgcagc acgagcgggt gcggccggcc    26100
ttcgacgagg tcgtcgaggg ccgcgatcag ctccgtgaag ttctcgccga ccacggcggc    26160
ccgctgctcg aagcgggtgc gggtggtgat gagggtgtag ccgacgtcgg ccgggtgcag    26220
ctcggggtgg gcgagcaggt ccgcgcgcag ccggcgcgcc tggtcgcgca gggcggcgtc    26280
gttgtgcgcg acatcatca acggcacggt cacctcgtgc caccactcct cggaccagac    26340
gtcgccgtcg gcggccggtt cgggcgcgag cagctcgggc gcggtgggct ccggcggctc    26400
ctcgacgacg acgtgggcgt tggtgccgct gatgccgaag gaggagattc cggcccggcg    26460
cagtccgtcg gcccgctggg gccagggcct ggcctcgtcg agcagttcca cggctcccgc    26520
atcccattcg atcttggacg aggcggtggt ggcgtgcagg gtgcggggca gcgtgccgtg    26580
ccgcagggcc agcaccatct tgatgacacc ggccacaccg gcggcggcct gggtgtgtcc    26640
gatgttggac ttcagcgagc ccagccagag cgggtcgtcg cgccggtccc ggccgtaggt    26700
ggcgagcagt gcgcctgctt cgatcgggtc gcccagcggt gtgccggtgc cgtgcgcctc    26760
gaccgcgtcg acgtcggcgg gggtgagccc ggcatcggcg agcgcctcgc ggatcaccct    26820
ctgctgggcc ggaccgctgg gcgccgtcag gccgttgctg gcgccgtcct ggttgacggc    26880
gctgccccgc accaccgcca gtaccgggtg gcccttcttc tgagcctccg acagccgctc    26940
caccagcagc attccggctc cctcggcgag gccgacgccc tcggccgtct cggcgaacgc    27000
cttgctgcgg ccgtccggcg agaccgctcg ctggcgggcg aactccacca gcatctcggg    27060
ggtggacatc accgtggcgc cgccggccag ggcgtagtcg cactcgcccc ggcgcagtga    27120
ctgcaccgcc aggtgcaggg cggcgaggga ggccgagcag gcggtgtcga cggtgacggc    27180
ggggccctcc aggccgaaga cgtaggagag ccggccggac atcacgctgg cggaattgcc    27240
ggttgcgatg taaccgtcga agctctcgtc gccgtcctgg agcagcggca cgtagtgctg    27300
cccgttggtg ccgacgaaga ctccggtgcg gctgccgcgc agctccaccg ggtcgatgcc    27360
ggcccgttcg aaggattccc aggaggtttc caggatcagc cgctgctgcg gtccatggc    27420 cagggcctcg cggggctga tgccgaagaa gccggggtcg aactcggccg cgtcgtgcag    27480
gaatccgcct tcgcgcacgt aggtgtggtg tccgggtgag ccggggtcgg ggtcgtagag    27540
ggcttcgttg ttccatcccc ggtcggtcgg gaacggggtg atggcgtcga cctcgccggt    27600
```

-continued

| | | | | | |
|---|---|---|---|---|---|
| cagcaggtcc | cacaggtcct | cgggggactg | gaccccgccg | ggcagccggc | aggccatgcc | 27660 |
| gatgatggcg | atgggctcgt | ccgtctgtgt | cggggtctcg | gggccggtcc | ggtcggcggt | 27720 |
| gtcgccccgg | ccgaggagtt | cctcgccgag | gtggcgggcg | agcgcggccg | ggttggagtg | 27780 |
| gtcgaagacc | agggaggtgg | gcagcttgag | gccggtggcg | gtgctgagcc | ggtcgcgcag | 27840 |
| ctccagggcg | gtcagcgagt | cgaagccgag | gtcgcggaag | gcgcgggcgc | tgttcaccgc | 27900 |
| gtcgccggag | gactgcccga | ggacggcggc | ggcgtgggcg | cggaccagcc | gcagcagggt | 27960 |
| gacgtgccgc | ttgtggccgg | actgcgcggt | cagttcgcgg | acgagttcgg | aggtggtcga | 28020 |
| gtcgccgttg | ctcggggcga | gttcgaccgc | gcgcagccgc | tgcacgtccg | ggatgtcgtc | 28080 |
| gaacagtacg | gcgggcgca | cccaggtgta | ggaggcggcg | aatcggttcc | actcgacgtc | 28140 |
| ggcgaccgca | ccgcaggcgc | tgccgcgctc | cagcatgcgg | cgcagggtcc | gcactgcctc | 28200 |
| gtccgggtcg | agggggcca | ggccacgccg | gttgaggaac | tccgcttcgg | cgccgtcggc | 28260 |
| gggcgtgccg | ccggcccagg | ggctccaggc | cacggagagt | gcgggcactc | cggcggcgcg | 28320 |
| ggcgcgttcg | gccagcgcgt | cgaggtgcgc | ggtggcggcc | gcgtagcagc | cctgggccgc | 28380 |
| gccgccccac | acgccggaga | ccgaggagaa | cagcaccagc | gcatcgaggc | cggcggcggg | 28440 |
| cgccaggtcg | accaggtggc | cggcggccgt | ggtcttggcg | gcgagggcgg | tggcgatgtc | 28500 |
| gccgggcgcc | gtctcgttca | gcggggccag | cggtacgagc | ggcggggcgt | gcacgacgac | 28560 |
| ggagggcgcg | tgctcgccga | gcaggccggc | cagggtggtg | cggtcggtga | cgtcgcagcg | 28620 |
| tacggggacg | acggaggctc | cggtgagtcc | ggcggcggcg | gcctgtgcgg | gggcgtcggg | 28680 |
| cccggccagc | accacgcggt | ccgcgccgtc | ctccaggagg | gagcggatca | gccgaccggg | 28740 |
| caccgtcgtg | atgtcgccgg | cgatgaggac | ggtgccccgg | gcgcgccagg | ccggggagcc | 28800 |
| ggcgtcggcc | gggttccgca | ggacgcggcg | gccgaagacg | cccgccatcc | ggatggcgat | 28860 |
| ctggtcctcg | ccgccgggtt | cggcgaggac | gccggcgagg | cggtcgagga | cccgggcgtc | 28920 |
| gggctgcgcg | gcaggtcga | tgaggccgcc | ccacacctcg | gcagctcca | gcgcggccac | 28980 |
| ccgtcccagg | ccccacagtt | gggctccggc | ggtgcacggc | agttcgtcgg | gggcggtggc | 29040 |
| gaccgcgccg | caggtgacgg | tccacagcgg | tgcggtgctg | ccgaggtcgg | ccagggcctg | 29100 |
| gaccagggcg | agtgtggcgg | tgactgcggt | gggcacggcg | gggtggtcgg | gccggccgtc | 29160 |
| ggtgcacagt | ccgagcagcg | aaacggcgcc | ggtgacggcg | gtgtcgccgt | tgattgccga | 29220 |
| ttcgagcagg | ccgagcagtt | cggcgcgtcc | ggtgcgggcc | gggtcgacgg | cgatgcggcg | 29280 |
| gaccgttccg | ccgaaggagg | cgatcgcctg | ttccacggtg | tcggcgaggg | cggcgtgctg | 29340 |
| ttccccggtg | ggcacgatca | gcaggcgcag | gcccgggcgc | cagccgccgg | tggcggagcg | 29400 |
| cagccccttc | cactcgacgt | ggtagccgag | ccggtcgccg | gactccgggg | cgccttcgcc | 29460 |
| ggtttcggcg | gtcttcgccc | ggtcgggccg | ggcggagccg | acccagtagc | gttcgcgctg | 29520 |
| gaaggcgtag | gtcggcaggt | tcacccgcc | ggccccgggg | tggagcgtgg | cccagtccac | 29580 |
| cggtacgccg | acgacctggg | cctccgccgc | ggaggtgagg | aagcgccgca | gaccgccctc | 29640 |
| gtcgcgccgc | agcgagccga | cggccggtac | cgcggtgccg | acgctttcca | cggtctggcg | 29700 |
| tacgccgacg | gtgaggacgg | ggtgcgcgga | gcactccacg | aacgcgtcga | tgccgtcggc | 29760 |
| gagcatggcg | cgcacggtcg | gctcgaagcg | caccgggagc | cgcaggttgc | ggtaccagta | 29820 |
| gtcggcgtcg | agggcggccg | tgtcgaggag | cgccgcctcg | acggtggagt | agaagggcac | 29880 |
| gtcgcctctg | tacggccgga | ccggggcgag | gacggtggcg | agctcctccc | ggatgctctc | 29940 |
| gacgtagtgg | gagtgggagg | cgtagtcgac | gtcgatgcgg | cggactcggg | agccctcggc | 30000 |

```
ctccagggcg accagcagcg cctccagggc gccgggctct ccgcagacga cggtcgaccc    30060
ggggccgttg acggcggcga tctccacgcc gccggcgagc cgtgcctcga catcggtcgc    30120
gggcagggcc accgaggcca tgccgcctcg cccggccagt tcgcgggcga tgacctggga    30180
gcgcagggcc acgatccggg cggcgtcgtc cagggagagc gcgcccgcca cgcaggccgc    30240
ggcgatctcg ccctgggagt ggccgatgac ggcggcgggt tcgacaccga gggatcgcca    30300
cagcgccgcg agtcccacca tgacggcgaa ggtggccggc tggacgacgt cgacgcggtc    30360
gaggccgggc gccccgggcg cgccgcgcag tacgtcgctg agggtccagt ccacgtacgg    30420
ggagagcgcg ctctggcaga gctccagttc ggcggcgaag gccggggccg tgtccagcag    30480
ttcggcgccc atcccggccc actgggagcc ctggccgggg aagacgaagg cgacccggcg    30540
gatgtccgcc gcggtgccgt gtacggcgtc cggggtggtc tcgccggcgg cgagggcggc    30600
gagggcgtcg accggggcgc cgttgtctcc gagcagcacg gcgcgttggg tgagggcggc    30660
gcggtcggcg gccagcgcat ggccgatgtc ggtcggcgag gtgtcgggga ggcgctcaag    30720
gtgcgcgcgc aggcgtgcgg cctgggcgcg cagggcggga gcggtctcgg cggacagcgg    30780
ccagaccacg gtggagggg tcgcgggcgt gtcgccggtc atggacgctt cgtccggtgc    30840
ggacgcgggg cgaggagcgg acgcgtcgcg tggtgcggac gcgtggcctg gcgcggacgc    30900
gacgcgtggt gcggacgcat ggcccggcac ggacgcgacg cgtggtgcgg acgcatggcc    30960
cggcacggac gcatggcccg gcacggacga gacactggtt ccagccgccg cgcctgccgc    31020
gggtacctca cctgtcacag gcgcgtcgcc ggtcacgggc tcctcgcctg ccacaggtgc    31080
gtcaccggct gcggctgcgc cgcctgttgc ggtctcggcg ggcggttcct cgatgatgac    31140
gtgggcgttg gtgccgctga cgccgaaggc ggagatcgca gcccgccggg acggtgctc    31200 gcgctgcggc cagggccggg cgtcggtgag caactccacg gcgctcgggt cccattcgac    31260
cttggccgag ggtgcgtcga cgtggagggt gcggggcagc gtggagtgcc gtatcgcctc    31320
caccatcttg atgacgccgg cggctccggc ggcggcctgg gtgtgcccga tgttggactt    31380
cagcgagccc agccacagcg ggtcccggcc ctggcgctca cttccgtagg tggccatcag    31440
cgcaccggcc tcgatggggt cgcccagagg ggtgccggtg ccatgcgcct ccaccgcgtc    31500
cacgtccccc ggggccagtc cggcatcagc caacgcctcg cggatcacct tccgctgggc    31560
cggaccactg ggcgcggtca ggccgttgct cgcgccatcc tgattgaccg cactcccccg    31620
caccaccgcc agcacccgat gcccataccg acgagcatcc gacaaccgct ccaccaacaa    31680
cacaccaaca ccctcggccc acacagtgcc gtccgcaccc tccgcaaacg ccttgcaccg    31740
cccgtccgac gccagcccac gctgccgcga gaactccacg aacaccgtcg gcgtcgccat    31800
caccgtcacc ccaccggcca acgccatgtc acactcaccc cgccgcaacg actgcaccgc    31860
cagatgcaac gccaccaacg acgacgaaca cgccgtgtcc atggtcacag cggggccctg    31920
caggccgagc gtgtaggcca cccggccgga tgcgacgctg cccgcggtgc cgaggccgag    31980
ctgtccgctg ggatcggcgg cggtgccgac ctggtggctg ccgtagtcgt ggtacatcac    32040
gccggtgaag actccggtac gggtgccgcg cagcgagtcc ggcacgatcc cggcccgctc    32100
caacgcctcc cacgacgtct ccagcaacaa ccgctgctgc ggatccatcg ccgccgcctc    32160
acgcggcgaa ataccgaaga actccgcatc gaactcggcc gcctcgtgca ggaagccgcc    32220
ctcccgcacg taactcttgc ccggcacgcc cggctccggg tcgtacagcc cctcggcgtc    32280
ccagccgcgg tccgcgggga acggggagat cgcgtccgta ccggcggcca cgaggtccca    32340
```

```
gaggtcctcc ggcgacgcca caccgcccgg gtagcggcac gccatgccca caatcgcgat    32400
cggctcacga ctcgccgact cgacttcgcg cagccgctcg cgcgcgctgt gcaggtcggc    32460
catcgcgcgc cgcaggtact cccgcaactt ctcctcgttc gttgcagaca cggttctcct    32520
catgcgtcat gtcatgggtc agggtgcgga gcggttcagc agccggcgcg cggcgcggtc    32580
cggctcactg gaaatcgctg tcgagcaggt cgaacaagtc gtcgtcggag gccgacctga    32640
gccggtcgat caccacatcg ccgggccgt gggggctttc tccggcgccc ggtccggatt    32700
gctcgccgga gccgacggtg agcgcggcca gcaggccgcg cagccgctgt gcggcgcgga    32760
cacgggcatc gccgtcgtcg gtcgcggcga ggctgcgctc cagccggtcg aatgcgctgg    32820
acaggtcttc ggcaccggcc ggttcgtccg ggaccgggcc ggccggttcc gctcggcctg    32880
ccgccgtcaa ctcgccgagc aggagttcgg cgagggacag cggtgtgggg tggtcgaaca    32940
cgagggtcgc gggcaaccgc agcccggtgc gcgcgttcag ccggttgcgg agatcgacag    33000
ccgtgaggga gtcgaatccg cgtccttga aggaacgggc ggcgcccacc gcggcggtgt    33060
cgccgtgtcc cagcaccgcc gcgacctcgg tccgcaccag gtcgagcagg agggccgtcc    33120
gctcgggcgc ggagcgcccc gcgagccggg tcgccagtgc cgcggcggcg tcggccgggg    33180
cgggaggccg gtggccggta ccggcctcgc ccccggcgcc cgccacggct ccgggcgcgc    33240
tcccgccgtc tgccgggacg ccgaccaggt cacgcagtac ctccggcaga acggtggcac    33300
gggccgcggc gcgcaggtcg aggcgcacg gcagcagtgc gggctcgggc ctgaccaggg    33360
cccggtcgaa cagctccagc gcggcccggg ggtcgagcgg ggcgacgccg gagcgccgga    33420
tacgcgcggc gtccgctctc tccagcccgg tggccaggcc caggccggac caccagcccc    33480
agccgagcga cagcgcgggg tgccggcgg cgcgccgccg ggcggccagg gcgtccagga    33540
acgcgttggc cgcggcgtac ccggcctggc ccgcactgcc cagggcggcc gagaccgagg    33600
agtacaacac cagtggaacc ggcccgagtt cacgggtcag ctcgtccagg tggacggcgg    33660
cgtccgcctt gggccgcagt accgcgtcga tccgctcggc agtctggacg gagagcacac    33720
cgtcgtcgag cacccccggcg gtgtgcacga cgcaggtcag cggatgttcg gcggggagct    33780
cgccgagcag gcggcggagg gcgtcgcggt cggcgacgtc acaggcccgg acggtgacct    33840
cggcgcccag attcgtgagt tccgcggcca gttcggcggc gccgggtgcg tcggggccgc    33900
gcctgctgac gagcaggagg tggcgcgcct tgtgccgttc cacaaggtgc cgggcggttt    33960
ctgcggccag tgctccggtg ccaccggtga tcagcacggt gccgttgggg tccagcgtct    34020
cggccggctc cccggcaccg gtctcgtcgg ccgctgtgtc gctgccggtg tccaggtcgg    34080
ccacgtcggc cacgtcggcc accgtacga ggcgcgggac ggcggcgcgt ccatcgcgca    34140
cggccaactg agcggtgtcc gtggccagca ggccgggcaa ggcccgcagc gacgcctgcg    34200
cgccgtcgac gtccaccaga gtgaagcggc cgggctgttc ggcctgggcg accgggacga    34260
gcccccagac agcggcaccc gcgggatcgg ccgcgcctcc ctcggaccg gccgcacccc    34320 gggtcaggac cacgagccgc gggcggccgc cgggacgggt ggctgtacgg cgtccgtac    34380 ggacgccgga gtctgcaccg gcatccgcgt tggtgtcgt gtcggtgtcg gtgtcggcga    34440
gtcgggcctg tacggcttcg agagtccggc gcaccgtcgc acgcagctcg tcgaggaggc    34500
cgaggagcct gccgtggggc gccgtacgac tggcggtggc ggtggcggtg gcggtggcgg    34560
tggtcaagtc gaggaggatc acttcggcgt ccgccgac ctgcggcggc agcggctcgt    34620 cgaagggag cacgtgggta cgggcgtcga tgccgacgc acgcagcccg gccgcggtgg    34680
cttcggcctc cggtccgacg accgcccagc gcgtgactgc ggcgacggac actcgcccgg    34740
```

```
gaagcggcac ccagtccacg cggtagagag gggcggcggg tgcggcggga agccggtccg    34800
cgggtatgcg acgcagtgcc agggagcggg cggaaagcac tggggagccc tcgcggtcga    34860
ccgcggcgat cgacaccgcg ccgccgtcga cggccgccac ccgtacccgg agcgcatgtc    34920
cggcggcatc gtggcgccgt acgtcggtcc aggagaacgg cagcaagccg tgtccgccgt    34980
cgcccaacgg gtcgagcagc gcgatcgggt ggagagccgc gtcgagcagg cgggggtgca    35040
ccccgtaacg ggcggcatcg gcggcgtgcg cgtcgggcag ccgcacttcg gcgaagatct    35100
cgtcgccgcg acgccatgcc gcgcgcagcc ctcggaaggc cccttcgtag cgcactccgg    35160
cggctgcgaa gagcgggtac tgaccggcga tgtcgagcgg ctcggcgccg gcaggggggcc   35220 aggcgccggt gagttcggcg aaggcgtcgg caccggttcg gtcggcaccg tgggggtggc    35280
cgctctcgtg gggggtgggga gcccgtggg ggtggccggc ctcgtgcgtg tggtcggcat     35340
ggtcggcagc cggggcgagc agcccggagg cgtgccgggt ccagccgttg tcacgatcct    35400
gcgccgcgag gtgcggggaa cgggtggaat gcgaggggtc ggcgacgggt tcgggccgtg    35460
agtggagact cacctcacgg gcaccccgg ggccggaggc aggagcggcc acgacgaccc     35520
ggatctggac cgggttgtcc gcagcccagg tcagcgcggt ctcgaaggcc agttcggcga    35580
cgcgcggcag accgatccgg cttcctacct ggagcagcat ctccagcagt gcggatcccg    35640
gcaccacgcc gcggtccac accaagtggt cggcgagcca cggaggtcc gcagcggaga      35700 tccggccggt ccacacctcg gtttcggcgc cgggcagttc cacggcggcg gcaagcagcg    35760
ggtgttccac cccatgcagg cctgccgccg cacccccgcc ggtcgtgagc cggggcagag    35820
ccgccagcca gtagcggtcc cgatggaagg cgtacgtggg caggtcgacc cgccggccgg    35880
caggctcgga gggagccggc ggcaccggaa ggccccgggc gtagagggtg gcgagtgcgg    35940
tggtgaaggt ctccagctcc ggccggtcac gccgcagtac cggcacgaaa gcaagatcac    36000
cctcgtcccc gtcgagacac tgccccgcca tcaccgtcag aacagcatgc ggacccacct    36060
ccacaaacgt atccacaccc acatcacgag cagcccccac accatccgcg aaccgcaccg    36120
cctcccgaac atgccgcacc cagtactccg gatcccccaa ctcatccaaa cccgcaaccg    36180
cacccgtcac actcgacacc accgccacac cagaacgagg ccggtgaaac tccaccgaag    36240
cagcaacccg acgaaactcc tccaacatcg gatccatcaa caccgaatga aacgcatgcg    36300
aaacctccaa ccacctgcac tccacaccac gacccaccaa acccgccacc acaccatcca    36360 gcaccccgc ctcacccgac agcaccaccg acgccggacc attcaccgcc gcaaccgaca     36420
cccgaccacc caacccagcc accaaacccg ccagctcggc ctcagacgcc ccaccgaca    36480 ccatcgcccc acccacaggc aacgcaccca tcaaccgacc acgcgccacc accaaccgca    36540
ccgcatcagc caacgaaaac acaccgcca catacgccgc agccacctcc cccaccgaat    36600
gacccaacac caccgacaca cccacacccc gagcctccaa cgcccggaac aacgccacct    36660
ccaacgcaaa caacgccggc tgagcaaact ccgtacaccc caacaacccc gcatccacac    36720
tccccgcctc cgcaaacatc acctcacgca gagaccgacc ccccacctcc cccacaaccc    36780
ccaacacctc atccaacaca cccgcaaaca ccccacccgc cccatacaac tcacgcccca    36840
taccaaccca ctgcgcaccc tgacccgtaa acaacacccc cacccgacgc ccccgcaccg    36900
ccgaaccccg caccacaccc gacgcggcac ccccgcagc aaccacaccc gccgccacag     36960
catccagacc ggccagcagc tccccacgct ccgaccgac aaccaccgca cgctcaccga     37020
acgacgcacg cgacaccaca agcgaatgcg caacatccac cggatcagca cccacacgct    37080
```

```
ccacgtgctc ccgcaaccgc accgcctgcc cccgcaacgc ctcctccgaa cgggccgaca   37140
ccggccacgc cagaaccgaa gaggactcag ccgcagcagt gacaacagcc tcggcttcgg   37200
ccgactcctc gaccgacggt tcctcgatga cgacatgggc gttcgtcccg ctcacgccga   37260
aggcagaaac agccgcccga cgcacccggc ccgcccgccg gggccaggac ctggcctcgg   37320
tcagcaactc caccgcccce gaaccccact cgaccctcga cgacggagca tccacatgaa   37380
gagtgcgagg caacgacgaa tgccgcatcg cctccaccat cttgatcaca ccacccacac   37440
ccgcagcagc ctgagcatgc ccgatgttcg acttcaacga ccccaaccac aacggatcac   37500
ccacccgctc acgcccatac gtcgccagca acgcacccgc ctcgatcgga tcccccaacg   37560
ccgtacccgt accatgcgcc tccaccgcat ccacatcccc cggagccagc ccggcatcag   37620
ccaacgcctc acggatcacc ctccgctggg ccgcaccact gggcgccgtc agaccgttac   37680
tcgcaccatc ctgattgacc gcactccccc gcaccaccgc cagcacccga tgcccatacc   37740
gacgagcatc cgacaaccgc tccaccaaca acacaccaac accctcggcc cacacagtgc   37800
cgtccgcacc ctccgcaaac gccttgcacc gcccgtccga cgccagccca cgctgccgcg   37860
agaactccac gaacaccgtc ggcgtcgcca tcaccgtcac cccaccggcc aacgccatgt   37920
cacactcacc ccgccgcaac gactgcaccg ccagatgcaa cgccaccaac gacgacgaac   37980
acgccgtgtc caccgtcaac gccggcccct ccaacccccaa cacataagca acccggccgg   38040
atgcgatgct gccggcgctg ccgttcacga ggtagccctc gtactccggc ggggccgagt   38100
cgaactgcga tccgtagtcg tcgtacatca cgccggtgaa gactccggta cgggtgccgc   38160
gcagcgagtc cggcacgatc ccggcccgct ccaacgcctc ccacgacgtc tccagcaaca   38220
accgctgctg cggatccatc gccgccgcct cacgcggcga aataccgaag aactccgcat   38280
cgaactcggc cgccccgtgc agaaacccgc cctcccgcac ataactacga cccaccgcct   38340
ccggatcggg gtcgtacaac ccctcgacgt cccagccacg gtcgacaggg aacggagaga   38400
tcgcgtccgc accggcggcc gccaggtccc acaggtcctc cggcgacgcc acaccgcccg   38460
ggtagcggca cgccatgccc acaatcgcga tcggctcacg actcgccgac tcgacttcgg   38520
ccaggcggga cttggtcttg tggagttcgg cggtggcacg cttcaggtag ctgcggatct   38580
tgtcgttctc ggcggtcatt gctgccacca actcctcggc atgcggtcgg tccacggtgc   38640
ggtcacagct gctcgtccag gaaggcaaag atctcgtcgt cggtcgcctc gtcgagccgg   38700
tccgttacgg tcgccccggc gccgtcggca gcggcgggcg cggcgggcgc ggtgcggccc   38760
tggggtccga cgacgccgcg cccaggggtg tcgagcgcgg tcagaagccc gacgagccgc   38820
tgtcgtacct cgactcgacg ggcgtcgtcc gagcccagca gggcgaccgc ccgcgcaagt   38880
tcgccgatcc cctccagcgc ggcgtccacg accggggctc cggcgggggcg gggcagctcc   38940 ccgtcgatcc actcggccat gtccttgggc gtggggtggt cgaaggccag cgtggtcggc   39000
agccgcaggc cgaccaggcg gctgagccgg ttgcgcagct ccaccgccgc cagggagtcg   39060
acgccgatct cccggaaggg gcgttcgggc tcgatctcgg cggccgacgc gtgcccgagg   39120
acctcggcga cctgttcggt gaccaggtcc agcacggccg tggaccgctc cgctgcgtcg   39180
agcgccacga tccgggcgat gcgtccggtg ccggactccg cccccttgcc gtgccggtcg   39240
gcagccgcag gggtgccggt actgctatgg cgcagggctg cgggaagcag gccgcgcagc   39300
aacggaggca ccgcggccgc gccgcgctcc ttggccgtgc gccgcagagc ggcgccgtcg   39360
aggaggagcg ggacgaggac ggcgggcccg tcccggtgcg cggtcagagc ctggtcgagc   39420
agcccgagcc cttgctcggg cggcatcgcc gcgatgccct cgcggcgcag ccgatggagc   39480
```

```
gccacgtcgt ccagacccc ggccatgccc gccctctcgt cccacaggcc ccaggccagg    39540
gacaccgcgg gcagcccggc tgcgcgacgg gctcccgcga gcgcgtcgag gaccgcgttg    39600
gcggccgcgt aggagccctg ccccggacgg ccgaggagtc cggcggcagc ggagaacagg    39660
acgaacgcgc gcagcggtcg gtcgagggtg gcctcgtgca ggttccgtac ggcgtcggcc    39720
ttcgaccgca ggacggtgtc gagccgttcc tgagtcaggc cggtcagggc gccgtcgtcc    39780
agcacgccgg cggtgtgcac cacaccggtc agcgggtgtt ccggcgacac tgcgacaacg    39840
gccttccgca cggccgcggg gtcggcgaga tcgcatgcca ggaaggtggc ggtgacgccg    39900
aggccgacga gctcccgttc caggagggcg gcttcgggag catccggccc gcgcctgctg    39960
accaggagca tgtggcgcac gccgtgccga cgcgccaggt gcggggcgac gcgccgcccc    40020
agggcgccgg tgcagccggt gatcagtacc gtgcccgcag ggtcgaacac ggcgtccacg    40080
gcggaaccat cgggatcgaa cgcgccgtct gaggcgggc gccggtcgc cgcgccgccc    40140 ctctcggccg gccggccgc ttccggcgcg acgctctgtg ccgcgaccgc tgccgctgcg    40200
gagtccactg ccgtcgccgg ggttgctgcc gtcgccgggg tggtgatcgg aacgagggcc    40260
ggtgcgagca acgccccggc gcgcagggcg agttgcggct cgcccgattc cagagcccgc    40320
ggtagggccg cacgggattc cggggagtcg tccacatcga cgagggtgaa gcggtcgggg    40380
tactccgact gggcggagcg gagtagcccc cacagtgccg cacccgccag gtccggcact    40440
tcgccggaac cggcctcgac cgcgcccccgg gtgaggacga cgagccggga atccgccaga    40500
cgttcgtcct cggtccactc ccgcaccaag gccaggccac ggccgagggc gacgcgtacg    40560
gggtcgtcgc cccagtccgt acccgtacgg gcatgagccg tagccgtacg gacatgggcc    40620 ttaccctac ggacacgagc atccgcaccc gcgtccacgc ccgcacccgc acccgccgac    40680
gactcggcgg gccgaatgtc ggtggccggc acaaccacca gtccgggtac gggcgttccc    40740
gcagtcaggg cagtgcgcag ggcggcgagg tcggcatggg cggcgggctc cgcgccgggc    40800
agggcgcgca aggtcgcgca ctcctccgtc gcagcctgtt ccgcagctgt ttcgcccgcg    40860
gcgggtccga gcaccgtcca gccatgggcg ccggggtgt cggacctctg cggtactggc    40920
tgccagtcga cgcggtacag cggttccggc gcgccggcc tgcccagggc caccgggcgc    40980
agcagcagtg cgtccagggt gaggacgggg gcgcctgccg gatcggcggc ccgcaccgag    41040
aaggctgatt cggcgccgct gcccgccggt gccagcctga cgcggagcgt ctcggctcct    41100
gtggcgtgga gcgcgatgcc ctgccaggag aacggtgcca acgtggtgcc gcccgtgtcg    41160
ggcagcaacc caccggcccg ccatgggtgg agggccgcgt cgaagagtgc gggatggata    41220
ccgaaaccgt caccggccgt gcccgtcgcg gacagccgca cctcggcgaa gagctcgttg    41280
ccgaggcgcc atgccccgga cagtccgctg aaggccgggc cgtagtcgta gccgtccgcg    41340
gcgaacccct catacaactc cccgacgtct accggttcgg cccccggcgg cggccaggcc    41400
ccggcggccc aggccgtgtc cggaacggcc ggctccgcgg gcgcgagcac gccttccgcg    41460
tgtttggtcc actccggttc ctcgccgtcc caccccggtg tctcggggcg tgcggcaagt    41520
gcgacagcgc gccggccctg cccgtcggct gcctcgacca gcacctggag tcgcagtccg    41580
ccctgttcgg ggaggagcag gggcgcatgg agcgtcagct cctcgacgcc tcccgcgccc    41640
acctcttcgg cggcccgcag caacaggtcg gcgatcgccg tcccggggag cagcaccgtg    41700
ccggagatgg cgtggtcggc cagccacggg tgggtggaga gcgccacccct gccggtgagg    41760 agcaacgcgc cggagccgac tatcggcgtg gcgccgctga ggaacgggtg gtccttccat    41820
```

```
tccagcccga agcgggcagc ggccgaggag ccggtggagc cggacaccga gcccgtcgcc   41880
cagtagccac ggcgttggaa ggggtaggtg ggcaggtcga cccgccggcc gccgaaaccc   41940
gaatggaggg cagcgacgtc gagttcggca tcccgcgtat acagcgtggc gagtgcggtg   42000
gtgaaggtct ccagctccgg ccggtcacgc cgcagtaccg gcacgaaagc aagatcaccc   42060
tcgtccccgt cgagacactg ccccgccatc accgtcagaa cagcatgcgg acccacctcc   42120
acaaacgtat ccacacccac atcacgagca gcccccacac catccgcgaa ccgcaccgcc   42180
tcccgaacat gccgcaccca gtactccgga tcccccaact catccaaacc cgcaaccgca   42240
cccgtcacac tcgacaccac cgccacacca gaacgaggcc ggtgaaactc caccgaagca   42300
gcaacccgac gaaactcctc caacatcgga tccatcaaca ccgaatgaaa cgcatgcgaa   42360
acctccaacc acctgcactc cacaccacga cccaccaaac ccgccaccac accatccagc   42420 accccgcct cacccgacag caccaccgac gccggaccat tcaccgccgc aaccgacacc   42480
cgaccaccca acccagccac caaacccgcc agctcggcct cagacgcccc caccgacacc   42540 atcgcccac ccacaggcaa cgcacccatc aaccgaccac cgccaccac caaccgcacc   42600 gcatcagcca acgaaaacac acccgccaca tacgccgcag ccacctcccc caccgaatga   42660
cccaacacca ccgacacacc cacaccccga gcctccaacg cccggaacaa cgccacctcc   42720
aacgcaaaca acgccggctg agcaaactcc gtacacccca caacccgc atccacactc    42780 cccgcctccg caaacatcac ctcacgcaga gaccgacccc ccacctcccc cacaaccccc   42840
aacacctcat ccaacacacc cgcaaacacc ccaccgccc catacaactc acgcccata     42900 ccaacccact cgcacccctg acccgtaaac aacacccca cccgacgccc ccgcaccgcc   42960
gaaccccgca ccacacccga cgcggcaccc cccgcagcaa ccacacccgc cgccacagca   43020
tccagaccgg ccagcagctc cccacgctcc cgaccgacaa ccaccgcacg ctcaccgaac   43080
gacgcacgcg acaccacaag cgaatgcgca acatccaccg gatcagcacc cacacgctcc   43140
acgtgctccc gcaaccgcac cgcctgcccc cgcaacgcct cctccgaacg ggccgacacc   43200
ggccacgcca gaaccgaaga ggactcagcc gcagcagtga caacagcctc ggcttcggcc   43260
gactcctcga ccgacggttc ctcgatgacg acatgggcgt tcgtcccgct cacgccgaag   43320
gcagaaacag ccgcccgacg caccggccc gccgccggg gccaggacct ggcctcggtc    43380
agcaactcca ccgcccccga accccactcg accctcgacg acggagcatc cacatgaaga   43440
gtgcgaggca acgacgaatg ccgcatcgcc tccaccatct tgatcacacc cccacaccc    43500 gcagcagcct gagcatgccc gatgttcgac ttcaacgacc caaccacaa cggatcaccc   43560 acccgctcac gcccatacgt cgccagcaac gcacccgcct cgatcggatc ccccaacgcc   43620
gtacccgtac catgcgcctc caccgcatcc acatcccccg gagccagccc ggcatcagcc   43680
aacgcctcac ggatcaccct ccgctgggcc gcaccactgg gcgccgtcag accgttactc   43740
gcaccatcct gattgaccgc actccccgc accaccgcca gcaccgatg cccataccga    43800 cgagcatccg acaaccgctc caccaacaac acaccaacac cctcggccca cacagtgccg   43860
tccgcaccct ccgcaaacgc cttgcaccgc ccgtccgacg ccagcccacg ctgccgcgag   43920
aactccacga acaccgtcgg cgtcgccatc accgtcaccc caccgccaa cgccatgtca    43980 cactcacccc gccgcaacga ctgcaccgcc agatgcaacg ccaccaacga cgacgaacac   44040
gccgtgtcca ccgtcaacgc cggcccctcc aaccccaaca cataagcaac ccggccggag   44100
atcacgcttc cgagcgtccc cgtgagcaca tgcccgccgt aggtttcggc ggcgtccccc   44160
aactggcttg cgtagtcctg ctgggagatg ccggtgaaga ctccggtacg ggtgccgcgc   44220
```

-continued

```
agcgcgtccg gcacgatccc ggcccgttcc aacgcctccc acgacgtctc cagcaacaac    44280
cgctgctgcg gatccatcgc cgccgcctca cgcggcgaaa taccgaagaa ctccgcatcg    44340
aactcggccg ccccgtgcag aaacccgccc tcccgcacat aactacgacc caccgcctcc    44400
ggatcggggt cgtacaaccc ctcgacgtcc cagccacggt cgacaggaaa cggagagagg    44460
gtgtgcccgt cttcggccac caggcgccac aggtcctccg gcgacgacac gccgcccggg    44520
tagcggcacg ccatgcccac gatcgcgatc ggctcgcgct cgtcggccgt ggcccggggc    44580
cgggtgtccg cgacaggctc cgcttcgctg tcggtaccga acagttcgtc gtgcagatgg    44640
gcggccaggg aggtcgggtt ggggtggtcg aagagcaggg tgctcggcag gttcagcccg    44700
gtggcagcgg tcaggcggtt gcgcagttcg agaacggtga gcgagtcgaa cccggcggac    44760
cggaacgcga tctccgggtc gaccgcgtcg gccgaggcgt ggcgcaggat ctcggcggcc    44820
tcggagcaca ccaggtcgag cagggcccgt cgccgttccg tcgacgaggg gccgacggag    44880
agccagggtc ggccttcgtc cgctccggct ccgcttccgc ccgcccaccc gtggcccggc    44940
cgcgtccccc gggggagagt ggcacggcct tgcgcggcac gggcggaacg cgctgagcgg    45000
gcggcgggaa caccgtcgaa aagtgcccag gtgcggcggg tgacgaacg cccgacgaag     45060 gtttcccagt ccacatcggc gacgatcagc gaggtcgcga cggccgcaga ggccccggcg    45120
gcagcggagg tccaccggc gccgaccgcg tcgtccagta cgtcgagcgc gtgctcggga     45180
tccagggccg cgacgccgtc ccgctcgaag gacttcgtcg ccgttccgga cgccatcccg    45240
gctccggccc acgggcccca ggcgatcgag gtggcacgcc ctccccgggc ccggcgccgg    45300
tgcgccaggg cgtcgagcgc ggcattggcc gccgcgtagg cggcctgccc cccgttgccc    45360
cacactccga cgatggagga gaagagaacg aaggcgtcca gcgggaggtc ggcggtgagc    45420
tcgtccaggt ggcgggccgc agtgaccttg gcacgcagta cggcgtctat ccggtcggag    45480
gtgagcgagt cgagcacacc gtcgtcgagc acgcctgccg cgtgcagtac ggcggcgagg    45540
ggccggtctt cgggaatgcc cgcgagcagc gcggcaagcg cgtcccggtc ggcgacgtcg    45600
caggctgcga cggtcacttc ggtaccgagg gctgtcagct cctcgacaag ttcgcccgct    45660
ccggggccgg ccgcccgcg ccggccgacc aggagcagat gcggggcgcc cgcccgggcg     45720
agcctgcggg cgacctgcgc gcccagggcg ccggtgcccc cggtgatcag tacggtgcct    45780
gaggaccgcc ggtttcccgg cacgactccg tcgggcgtgt cgccctgcgc gtccggggcg    45840
gcggcggtgg tggcggcgcg gacggggacg gggaccacgc ggcggacatg gactccggag    45900
ggccgtaccg cgaactggtt gtcctcgccc tcggcgagca gcgtcccgac gaacgcacgg    45960
agcgcggcag gcgacggctc cccgggcagg tccgccaaac cgccccagcg ctgggcaagt    46020
tcgagtgcgg cgacctgccc cagccccag agctgagcgc ctgcgacgga aggggcctcg     46080
cccggctgag cagccaccgc gtcgcgcgta gtgatccaga gcggggcgtc gggtcccgcc    46140
tcgcccaggg cctggatcag cgcgacggcg tcggccgtgt ccggctcggc cggggcgagc    46200
cacaggacgt gcgtgctgcg tgcggcaccg tcaccggcgg cccgcagcag gtctgcggcc    46260
gcctcccgac cggtaccgac cggcacgaca gcggtgtgga cctcggtgcc gcgcacggcg    46320
agttcacgcg cgatcgcggt ggcgagcccg gagtccgtcg tgtcgtcgtc cgaggccagc    46380
agcagcatac gacccgccgg ccgggggact ccgcagccga cggcggcggg ctgccaggtg    46440
acgcggtagc ggagcccggc cgtcgccgaa gtcaccccctt gagcagcggt cggaacgtcc    46500
tcggacgaac cggcggccat ggcggtgggc actgcggcgg gggcggggtc cagccagaaa    46560
```

-continued

```
cgggcgcgct ggaaagggta tgtgggcaga tcgatgcgtc gtgcgtccct cttccgattc   46620
ggcgcgtccc agtcgatctg ggcgccccgg gcgtagaggg tggcgagtgc ggtggtgaag   46680
gtctccagct ccggccggtc acgccgcagt accggcacga aagcaagatc accctcgtcc   46740
ccgtcgagac actgccccgc catcaccgtc agaacagcat gcggacccac ctccacaaac   46800
gtatccacac ccacatcacg agcagccccc acaccatccg cgaaccgcac cgcctcccga   46860
acatgccgca cccagtactc cggatccccc aactcatcca aacccgcaac cgcacccgtc   46920
acactcgaca ccaccgccac accagaacga ggccggtgaa actccaccga agcagcaacc   46980
cgacgaaact cctccaacat cggatccatc aacaccgaat gaaacgcatg cgaaacctcc   47040
aaccacctgc actccacacc acgacccacc aaacccgcca ccacaccatc cagcaccccc   47100
gcctcacccg acagcaccac cgacgccgga ccattcaccg ccgcaaccga cacccgacca   47160
cccaacccag ccaccaaacc cgccagctcg gcctcagacg ccccaccga caccatcgcc   47220 ccacccacag gcaacgcacc catcaaccga ccacgcgcca ccaccaaccg caccgcatca   47280
gccaacgaaa acacacccgc cacatacgcc gcagccacct cccccaccga atgacccaac   47340
accaccgaca cacccacacc ccgagcctcc aacgcccgga acaacgccac ctccaacgca   47400
aacaacgccg gctgagcaaa ctccgtacac cccaacaacc ccgcatccac actccccgcc   47460
tccgcaaaca tcacctcacg cagagaccga ccccccacct ccccacaac ccccaacacc   47520 tcatccaaca cacccgcaaa caccccaccc gccccataca actcacgccc cataccaacc   47580
cactgcgcac cctgacccgt aaacaacacc gccgtcccac ccgaaacagc cgtgccccgg   47640
acggtcttcg gcctcgtgtg tcccgcgcg agcgcgtcca ggcctgccat cagctccgca   47700
cggtcgccac cgacgaccac cgcacgctca ccgaacgact cacgcgtcac cgcaagcgaa   47760
tgcgcgacgt ccaccggatc ggcgcccaca cgctccacgt gctcccgcaa ccgcgccgcc   47820
tgcgcccgca acgcctcctc cgagcgggcc gacaccggcc atgccagagt cggtgcgagt   47880
tcggctgtgg gagcggtgac agtcggcggc tcggtgggcg tctctgccgg cgcctcctca   47940
atgaccaggt gggcgttggt gccgctgatc ccgaaggagg acaccgcggc ccgccgcggg   48000
cggcccgcgc gctccggcca ccggcgcgcc tcggccagca gttccaccgt gcccgacgac   48060
cagtcgacat gtgtgctggg ccggtccgcg tgaagcgtcc gcggcagcgt gccgtgtcgc   48120
atggccagca gcatcttgat gacgcctgcg gccccggcgg cggcctgggt gtgcccgacg   48180
tttgacttca gcgaccccag ccacagcggt tctcccaccc gctcacgccc gtacgtggcc   48240
agcagcgcgc ccgcctctat cgggtcgccc agcgccgtac ccgtgccgtg cgcctcgacg   48300
gcgtccacat cgcccggggc gagtccggcg tcggccaggg ccgcccggat gacgccttcc   48360
tgcgcggaac cattgggcgc ggtgaggccg ttgctggcgc cgtcctgatt gaccgcactg   48420
ccccggacga ccgccagcac ccggtgacct gcgcgccggg cgtcggagag ccgctccagt   48480
gccagtacgg caacgccctc ggaccaggcc gtaccgtcgg catcggcgga gaacggcatg   48540
cagcggccgt cggggggccag cccgcgctgc cgggagaact ccacgaacat gccgggcccg   48600
gacatcaccg tggcgccgcc cgccagagcc agtccgcact cgccccggcg cagcgcctgc   48660
acggccaggt gcagcgccac cagagacgag gaacatgcgg tgtcgacggt gagcgccggt   48720
ccgcgcgtgc cgagggtgta ggcgatccgg ccggaggcca cgctcgccgt ggtgccggtg   48780
agcagatacc cctcgtatcc gtccgctcct tcgtgaagcc tcggcccgta ctccggtgcg   48840
acggcgccga tgaacacgcc ggtgtcgccg ccgcgcagcg actcggggag cactccggcg   48900
tcttcgagcg cctcccacga ggtttccagc agcagccgct gctgcgggtc catggcggtc   48960
```

```
gcctcacgcg gcgagatgcc gaagaactct gcgtcgaact cggccgcctg gtgcaggaag   49020
ccgccctgtc gcacgtaggt cttgccgggg acgcccggtt cggcgtcgta cagcccgtcg   49080
aggtcccagc cgcggtcggc ggggaaggac gagatcgcgt cggtgccgga cgccagcagg   49140
tcccagaggg cggcccgcga gtcgacgccg ccggggaggc ggcaaccgac gccgacgatg   49200
gcgatcgggt cgtcgtcccg tgtgccgccc cgggcggccg ccgccccgac cgcctcgtgc   49260
tcgccggggt gcgcgctctt tgtcccgtgc agtgcggcca ccaggtgttc ggcgacggca   49320
cgcggggtgg gcaggtcgta cgagcgtg gcggcgaggg tgagcccgt ggcccggttc    49380 agcaggtcat ggagctcgac cgcggtggct gattccaggc cctgggaggt gaaggtgcgg   49440
tcgagcgcga tctcgtcggg gtcgtcgtgg cccaggacgg tcgcggtggt ctcgcgtacc   49500
agacggacga gctgctcggg agacatcggc tccggggacg ccgtgagcgg ttcgtcgtcc   49560
gggtccctga ggggcgcctc ggtgctctcc gggggcgcgg tgttcccgc ggcgtcggtg    49620 gtggtcaggc ccgccccggc gtcggccgcg attccacggc tcagcgccgg cgaccagtga   49680
gtacggcgtt ggaagggta ggtgggcagg tcgacccgcc ggccgccgaa acccgaatgg    49740
agggcagcga cgtcgagttc ggcatcccgc gtatacagcg tggcgagtgc ggtggtgaag   49800
gtctccagct ccggccggtc acgccgcagt accggcacga aagcaagatc accctcgtcc   49860
ccgtcgagac actgccccgc catcaccgtc agaacagcat gcggaccac ctccacaaac    49920 gtatccacac ccacatcacg agcagccccc acaccatccg cgaaccgcac cgcctcccga   49980
acatgccgca cccagtactc cggatccccc aactcatcca aacccgcaac cgcacccgtc   50040
acactcgaca ccaccgccac accagaacga ggccggtgaa actccaccga agcagcaacc   50100
cgacgaaact cctccaacat cggatccatc aacaccgaat gaaacgcatg cgaaacctcc   50160
aaccacctgc actccacacc acgacccacc aaacccgcca ccacaccatc cagcaccccc   50220
gcctcacccg acagcaccac cgacgccgga ccattcaccg ccgcaaccga cacccgacca   50280
cccaacccag ccaccaaacc cgccagctcg gcctcagacg cccccaccga caccatcgcc   50340 cacccacag gcaacgcacc catcaaccga ccacgcgcca ccaccaaccg caccgcatca    50400
gccaacgaaa acacacccgc cacatacgcc gcagccacct cccccaccga atgacccaac   50460
accaccgaca cacccacacc ccgagcctcc aacgcccgga acaacgccac ctccaacgca   50520
aacaacgccg gctgagcaaa ctccgtacac cccaacaacc ccgcacccac actccccgcc   50580
tccgcaaaca tcacctcacg cagagaccga cccccacct ccccacaac ccccaacacc     50640 tcatccaaca cacccgcaaa caccccaccc gcccatacaa actcacgccc cataccaacc   50700
cactgcgcac cctgacccgt aaacaacacc gccgtccac ccgaaacagc cgtgccggtc    50760
cgcactcccg cagaggtctt accgcgagcg aacgcgtcga gggaggcggc gagttcctct   50820
cggtcgccgc agcgcagtgc ggcgcggtgc tcgaagagag tgcgcgtggt ggccagggag   50880
taagcgatgt cccgcgggtc cgcgccggtc cggcccaggt ggtcgtgaag ccgcgcggcc   50940
tgcgcccgca gcgccgcgcg ggagcgggcc gacagcagca ggggcggggc cgggtgcggg   51000
gcggcggctt cggaggccga cgacgggatg gcgtccggtc cggccggggc cggctggggc   51060
aggtgctcca gcaccacatg gcagttggtg ccgccgatac cgaacgagct gacgcccgcc   51120
agcaggggtg cgccgctcgg gccggggtgc agttcggtcg gggccgtctg caccttcagc   51180
cggagccggt ccaaggggat ggcgggattg ggggtgtcga agttgagcga gccgggcagg   51240
gtgcgttccc gcaggcagag cacggccttg accagtcccg cgatgcccgc ggcgccctcc   51300
```

```
aggtggccga tgttggtctt caccgacccc accaacaagg gagtgtccgc cgaccgtccg   51360
gagccgtgga ccgcgccgag ggcgtgcgcc tcgaccgggt cgcccacggg ggtgcccgta   51420
ccgtgcagtt cgacgaagtg cacctcagcg gggtcgaccc cagcctgggc gcaggcggac   51480
cggagcaccg cttcctggcc ctcacggtca ggggcggtca gcccggggcc gccgccgtcg   51540
ttgccgatgg cgacgccgcg caccacgcag tacacggggt cgccgtcggc cagggcgtcg   51600 gcgagggggtt tgagtacgac ggcggcgccg ccctcaccgc gcacatagcc gttgcgcgg   51660 gcgtcgaagg tgtggcagcg gccgtcggga cagcgcgc cgagccgttc catggcggcc   51720
gaaccctcgt cggcgaggat caggttgacg ccccggcga cggcgatgcg ggaggtgccg   51780
gctcgcaggc tctcgacggc gagggccacg gcgaccagtg acgacgactg cgcggtgtcg   51840
accgcaaggc tggggccgcg cgttcccagg acgtaggaga ccggttggc gagcatggcc   51900 cgctggaggc cggtggcggt gtgggcgcca atcggcgcgc cggcccggtg gagcagcgtg   51960
gcgtagtcgt cgttcatggc ccccacgaag acgcccaccg cctcgcctcg cagcgaaccc   52020
gggacgattc cggcgtcctc cagtgcttcc cagccgagtt cgagcatcag gcgctgttgc   52080
gggtcggtct cggcggcctc gcgcggtgac atgccgaaga acgcggcgtc gaagtcgccg   52140
accgcctcga tcatgccgcg ccgacgaccg tctgcgcac ggcctatcgc ttccgttccg   52200
tcggtcagca gtttccagaa ttcctggatt cccggtgcgc tgggaaatcg gcacgacatt   52260
ccaacaacgg caacggcatt ggaccggtcg tcacttcggg aaatcacgag atcttcagac   52320
acctgcatcc ctcatatgct cgccatgcca tgtcgcggaa tgttctgccg tttctggatc   52380
ttcacgagcg tacagcggac gaacagttgg gcgacaggaa cgaccaacga acggcaatca   52440
attgtgtcaa gttccgcgga ttcgccgcgg attctcatga cacgggtcgc cgacgactgt   52500
ggactgggat cttccggaag gctttccggc gaaaagggag cggcattgtg tcaggtctgt   52560
attgccgagc tgcggcgact gcgcgcaagc accccgcccg ccggggccgg agtcggcgcc   52620 ggcgccggt cgggtgcagt gactcacggc ctgcgcccca agggccgacg gcccgctcac   52680
gcggtcaccc ggcatttccc cgacctggcc cctgccttgc ccagccccc tgcccctggc   52740 tgggcctcgg tgcggaattc cgcgaactcc ttcgcgaatc ctctgacaca tgaactcgca   52800
catgaacgtg cacgcgaact cctgggtgaa cgcgcacgtg atctcccagg tgaaccgcga   52860
agctttcagc accgggtcgg ctcggcacaa ccgccccgcg gtgaatatgt caggttcccc   52920
gcgccgctcc gtccgctccc gagcggcatc tcgacaaggt tccccggacg gggagtcatt   52980
gtgtcaggtc cgccttgctg gcgttcttca ccgattcata agctctgccg ggatcgaggg   53040
accgatactg ccgtgtcgcg cgttcggtcc gcacaccgat tttcaaggag ttcgactgat   53100
gggtgaggct gtgtcgggac cgatggagtt gagcaaggat gcggatgccc ggggctgct   53160 ggactggttc gctttcaaca ggacacgtca tccggtgttc tgggacgagg gccggcaggc   53220
gtggcaggtc ttcggttacg acgactacgt gacggtgtcg aacaacccgc agttcttctc   53280
gtcggacttc aacatggtga tgccgacgcc gcccgagctg gaaatgatca tcgggccggg   53340
cacgatcggc gcgctggacc cgccgcgca cggaccgatg cgcaagctcg tgagccaggc   53400
cttcactccc cggcggatcg cccggctgga acccagggtg cgcgcgatca ccgaggaact   53460
cctggacaag gtacgggaac agaacgtcat cgatgccgtc ggcgacctct cctacgcact   53520
gccggtcatc gtgatcgccg aactgctggg cgtacccacc ggcgaccggg acctgttccg   53580
ggagtgggtc gacaccctgc tgacgaacga ggggcctggag tacccgaacc tcccggacaa   53640
cttcaccgag acgatcgcgc ccgcgctcaa ggagatgacc gactacctcc tggaacagat   53700
```

```
ccacgccaag cgggaagccc cggccgacga cttgatcagc ggtctggtcc aggccgagca   53760
ggacggccgc cggctgaccg atgtcgagat cgtcaacatc gtcgcgctgc tgctgaccgc   53820
cgggcacgtc tcctccagca ccctgctcag caacctcttc ctcgtcctgg aggagaaccc   53880
gcaggcactg gaagacctgc gggccgatcg cacgctggtg cccggcgcga tcgaggagac   53940
actgcgctac cgcagcccct tcaacaacat cttccgcttc gtcaagcagg acaccaccat   54000
cctcggcccg ctcatggaga agggccagat ggtgatcgcg tggagccagt ccgccaaccg   54060
ggacccccgg cacttccccg acccggacac cttcgacatc cgccgctcgg acggcacccg   54120
gcacatggcc ttcggccacg gcatccacca ctgcctgggc gccgcctggg cccgcctaga   54180
gggcaaggtc atgctcgaac tcctcctgga gcgggtcgac ggcttccgca tcgaccacga   54240
aaacacgctg ttctacgagg ccgaccagct cactccgaag tacctgcccg tccgcgtcga   54300
ctggaactga acccgagggt tccgtccccg ggccagggcc gtcccgagcc ggccgtggac   54360
ctcacgaccg cccgataagg agcgccgcca tcgccgagaa cacagccgag cctcccgccc   54420
ggcgggtcgg caggatcaag ccgtgccggc tgatcaggct cgagcagcac atcgacccgc   54480
gcggcagcct gtccgtggtc gagtccgcg tgaccgtgga cttccccgtc caacgcgtct   54540
actacatgca cggccagacc cagtcctcac ccccacgcgg cctgcacgca caccgcaccc   54600
tggaacaact cgtcatcgcc gtccacggcg ccttctccat cacccctcgac gacggcttcc   54660 agcacgccac ctaccgcctc gacgaacccg gagccggact ctgcatcggc cccatggtct   54720
ggcgcgtcct caaagacttc gccccccgaca ccgtcgccct cgtcctcgcc tcacagcact   54780
acgaagaatc cgactactac cgcgactacg acaccttcct gcacgacgca cggagcctca   54840
catgacaatc cccttcctcg acgcaggcgc cggctaccgg gagttgcggg ccgacatcga   54900
cgcggccctc cagcgggtgt ccgcctccgg ccgctatctg ctcggcgctg aactggaggg   54960
tttcgaggag gagttcgccg cgtactgcga caacggccac tgcgtggcgg tcggcagtgg   55020
ctgcgacgcg ctggagctgt ccctgcgcgc gctggacatc ggtcccgggg acgaggtggt   55080
ggtgcccgca cacaccttca tcgggacctg gctggccgtg tccgccaccg ggcgcagcc   55140 ggtggccgtc gatccgacgc cggacgggct ttccctggac ccggcgctgg tggaggcggc   55200
cgtcaccctt cgcaccaagg ccctgatgcc cgtacatctg cacggacacc cggccgatct   55260
ggacccgctg ctggcggtcg ccgaacggca cggcctggcc gtggtcgagg acgccgcgca   55320
ggcgcacggc gcccgttacc ggggccgccg gatcggctcg ggccacgtgg tcgcgttcag   55380
cttctacccc ggcaagaacc tcggcgccat gggcgacggc ggcgcggtgg tcacccggga   55440
cgccggagtg gccgatcgga tccggctgct gcgcaactgc ggctcccggg agaagtaccg   55500
gcacgaggtg cgggcgacca actcccggct cgacgagctc caggccgccg tgctgcgcgc   55560
caagctgccg cggctcgacg cgtggaacgc ccgccgggcg cgcacggccg aacgctacac   55620
ccgggccctg ggttcccttc cgcagatcgc cgtcccgtc accgctcgct gggccgaccc   55680
ggcgtggcac ctgtacgtga tccgctgcgc ggaacgcgac gagctgcgcc gccggctcga   55740
gcgggccggg gttcagaccc tgatccacta ccccgtaccg ccgcaccggt ccccggccta   55800
cgccgacgcc ccgccggggg ctccggccgg ggcccacccg cgcagtgaac gcctggcggc   55860
gcagagcctc agccttcccc tgggaccgca cctcggggac gacgagtccc gtgccgtcgt   55920
ggcggcggtc cgggcggcgg ccgcggggct ggcggcgtac ccgacgccgg acggcacgcc   55980
gcgcacgccg cgcacgacgc cggacggcca gcgttttcct ctagcgacgg agaaacgatg   56040
```

```
accgaggtca tgtcagggcg ttccggaatg aaagggatca tcctcgcggg cggcggaggc   56100
acccgcctgc gccccttgac cggcacgctg tccaagcaac tgctgcccgt ctacgacaag   56160
ccgatgatct actacccgct gtccgtcctg atgctgggcg gcatccgcga gatcctcgtc   56220
atctcctcca cccagcacat cgaactcttc cagcaactgc tgggcgacgg ctcccggctc   56280
ggcctggaca tcacctacgc cgaacagccc gagcccagg gcatagccca ggccctcacc   56340
atcggcaccg accacatcgg tgactccccg gtcgcgctca tcctgggcga caacatcttc   56400
cacggccccg gcttctcctc cgtactccgg ggcagcatcc gccacctcga cggctgtgta   56460
ctgttcggct acccggtcag cgacccgcag cgctacggcg tcggcgagat cgacgaccag   56520
ggcatgctgc tgtccctgga ggagaaaccc gcccggcccc gctccaacct cgccgtcacc   56580
ggcctctacc tctacgacaa cgacgtcgtc gacatcgcca agaacatccg gcctccgca    56640 cgcggcgaac tcgaaatcac cgacgtcaac caggtctacc tggagcagaa acgcgcccgg   56700
ctgatcgaac tgggccacgg cttcgcctgg ctcgacatgg gcacccacga ctccctcctc   56760
cagggcggcc agtacgtcca actcctcgaa caacgccagg gagtacggat cgcctgcatc   56820
gaggagatcg ccctgcgcat gggcttcatc gacgccgaca ccctctactg gctcggccgc   56880
gagctgggca cctccggata cggcgcctac ctgatggagg tggccaccca tgcaggcgcc   56940
gcatgagtcc ccgcaccggc ccacccgctt cgccgacggt cggcagccgg cccgtatcct   57000
cgtcaccgga ggcgccggct tcatcggctc gcgcttcgtg aacgccctgc tggacgcgtc   57060
gctgccggag ttcggcaagc cgaggtgag ggtgctcgac gcgctcacct acgcgggcaa     57120
cctggccaat ctggccccgg tgggcgactg tccccggctg cggatcttcc agggggacat   57180
ctgcgaccgc agcgcagtcg cccaggccat ggcgggggtc gatctggtgg tgcacttcgc   57240
ggccgagtcg cacgtggacc ggtcgatcga cgacgccgac gccttcgtgc gcaccaatgt   57300
gctgggcacc caggtcctcc tccaggaggc gctggccata cgccccggcc tgttcgtgca   57360
cgtttccacg gacgaggtct acggctcgat cccggtgggg tcgtggcccg aggaccaccc   57420
gctgagcccc aactccccct atgcggcctc caaggcgtcc tccgacctgc tggcactggc   57480
ctaccaccgc acgcacgggc tgccggtgtg cgtcacccgt tgttccaaca actacgggcc   57540
gtaccagtac ccggaaaaga tcatcccgct gttcaccagc aacctgctcg acggcaggac   57600
cgtcccgctg tacggggacg gcggcaaccg gcgcgactgg ctgacgtga acgaccactg     57660 ccggggcatc gccctggtgg cccggggcgg tcgccccggc gaggtctaca catcggcgg    57720 cggcgccgag ctgaccaacg tcgagctcac cgaacgtctg ctgaagctgt gcggagccga   57780
ctggtcggcg gtgcggcagg tgccggaccg caagggccac gaccagcgct actccgtcga   57840
ctacaccaag atcgccaccg agttgggata cgcgccgcgg atcaccatcg acgagggact   57900
ggagcagacc gtgcgctggt accggagaa ccacgcgtgg tggacgcctg tgaagagggg     57960
acgatgacgt tgatgtccgc atccgtggac ccgcgtgacc tttggctccg ccggtaccag   58020
ccttccgcgt cgcccgccgt gcggctggtg tgcttcccac acgcgggcgg ctcggcgagt   58080
tccttcctgc cgttcacccg gcaactgccc gacagaatcg aggtgtctgc cgtccagtac   58140 cccgacgcc aggaccgcag gagcgagcct ctgatcgaca ccatcgaggg cctggccaag    58200
cccctggccg acatgctgga gacacgggcc gggcccctg tggtgctgtt cgggcacagc     58260
atgggcgcgc tggtgcgta cgaggtcgcc cgcgtgctcc agcagcgggg agcggccccg    58320
gtgcgcctgg tggtctccgg acgccggggcc cccgcctcgg accgaccgat gaccgtgcac   58380
ctctacgacg acgaccggct ggtcgaggaa ctccgcacgc tcgacggcac cgacagccaa   58440
```

```
gtgttcgccg atccggagct gctccagctg gtgctgcccg cgatccgcaa cgactaccgg    58500
gccgtgggga cctacaccca ccgtccgggg gcgcccctgg actgcccct caccgtgttc      58560 accggtgccg acgacccac tgtgaccgcg gccgaggcgg cggcctggca cgaggtggcg      58620
gcggccggcg ccgagatgcg gaccttcccc ggcggccact tcttcccgta ccagcggacc    58680
gcggaggtgt gcggagccct ggtggacacg ctcgcgccgc tgctctcgac cgggacgcgc    58740
ggcgtccggc gggtccgccc cggggacgtc ggcacggtcg aatacgccgg ccaccggcgc    58800
accgcggaac gggtgctgct ctccgccgac acgctcgaca gtccggtcac ctcgctggcg    58860
gacgtgcccc gctggctgga ggcgtaccgc cgggcgcacc gcttccacgt cgagccgatc    58920
ccgttcgacc ggctccggcg gtggtccttc gagccgggca ccggcgacct gcggcacgag    58980
acgggtcgct tcttctccgt ggaagggctg cgcaccagct cggacgccga cccggtcgcc    59040
cgcgtccagc cgatcatcgt gcagcccgag gtggggctgc tcggcatcct ggcgcgggag    59100
ttcgacgggg tcctgcactt tctgatgcag gccaaaccgg agcccggcaa cgtcaacggg    59160
ctgcagctct cccccacggt gcaggccacc cgcagcaact tcgacgaggt gcaccacggc    59220
cggtccaccc cgttcctcga ccacttcatc caccgtcccg gccgacgggt cctgatcgac    59280
accatccagt ccgaacaggg cgactggttc ctgcacaagc gcaaccgcaa catggtcgtc    59340
gagatcgaca cggacatcga ggccgatgcc accttccgct ggctgaccct gggtcagatc    59400
cgcaggctga tgctccagga cgacctcgtc aacatggaca cccgcagcgt gctggcctgt    59460
ctgccgaccg cgcacggcgc gcccgacgac gacgaggact cccggcggc gctccggcgc    59520 tccttctacg gggaggccgc accgctgcac gacctgcacg ccatcaccag ctgcctcacc    59580
gacgtccggg cactgcgggt gctgcgccag cagagcgtgc cgctcgacga cgcccgtcgg    59640
gacggctggg agcggaccga gagcacgatc cggcaccgca gcggtaagca cttcgagatc    59700
atggcggtgg aggtgacggc ggagcggcgc gaggtggcgt cgtggaccca gccgctgctc    59760
cgcccgtgct cccagggct cgtggctctg atcaccggc ggatcaacgg ggtgctgcac      59820
gccctggtgg aggcgcggtc ggacgtaggc accctgaacg tcgccgagtt cgggccgacc    59880
gtccagtgcc ggccagccga atcggacggc atgtcgcccc cgtacctgga ccaggtcctg    59940
acggccggag ccgaccgcat ccgctacgac gtggtgcagt ccgaggaggg cgggcgcttc    60000
taccacgcgc gcaatcgcta catggtggtc gaggcgggc cggagctcga cacgggctgc      60060
ccgcccggct tctgctgggc gaccttcggc cagctcaccg aactgctcgc gcacggcaac    60120
tacctcaacg tcgaactccg caccctcgtc gcgtgcgcac acgcctccta ctgaatgcct    60180
acgaaaacta caccgcgggg gaatcggcac cacgcccgcc ggtcaaccat cggcaaagaa    60240
ggcagaggac cgttctcgca catcagcgac gtgcgggaag cgacggaacg cccggcacgg    60300
accgcgcaca attacgggag agaacctccg ggtatccgcg gataaccgct tcctcccaag    60360
ccttcctcac cccccgaagg accgtgcaag aaatcccgat ggccgacgac attccttttcg    60420 atcctccccg gatatggaga tcccgtgggc gagcgtgcga atatcgtgca cggcacgta      60480 catcgccctg ctcgattcca gccaattcct gccatcggtc ccgcattccc actcctgcgg    60540
cgcgctcggt gccgtaggtc ccgcgccggt ggacacgcgc cttccgagac cgggcacatg    60600
ccggtggatg cgcgacttcc accaccggcc acacccggcg gatgcgcgat ttccacgagg    60660
tgaccgacag cgacttcacc ggaatggcgg cccgccgggc atcgccgcgc caccgctttc    60720
cggccgctcg ccccgccgcc gcccgggaca ccgcacggga cgggaagcga ccgcggcccg    60780
```

```
gcgtcgagcg aacctgccca agcccggacg agacagcgcg acgcgagagg tgaccatgat   60840
caatctcttt caaccccaga tgggtgccga ggaactggcg gcgatcgccg gggtcttcga   60900
cgaccaatgg ctcggtcacg gaccacggac caaagcattc gagtccgcgt tcgccgacca   60960
cctcggggtc ggccccgagc acgtcgtctt cctcaactcg ggtacggcgg gcctcttcct   61020
ggccctggaa tcgctcggac tgcagcccga cgacgaggtc gtgctcccct cgcccagctt   61080
cctcgccgca gcgaacgccg ttcagctgac gggagcgcgc ccggtcttct gcgacgtcga   61140
cccccggacg ctgaacccgg ccctggagca catcgagcag gccgtcaccg cgcgcaccag   61200
ggccgtcatc gcactccact acggcggata ccccggcgac atcgtccgca tcgccgagca   61260
ctgccggaac cagggcatca ccctgatcga ggacgccgcg tgttcggtgg cctcccgcat   61320
cgacggccga gtggtcggca ccttcgggga cctcgccatg tggagcttcg acgcgatgaa   61380
ggtcctcgtc accggcgacg gcgggatgat ctacgtcaag gatcccgggg cggccgcccg   61440
catccggcgc ctcgcctatc acggcctcac ccagtccagc ggcctgggat acgccagggt   61500
ctcggcgcgc tggtgggaga tggacgtccc cgagccgggc cgacgcgtca tcggaaacga   61560
cctcaccgcg gccatcggcg cggtgcagtt gcggcggctc cccgatttcg tggcccgccg   61620
caaggagatc gtcgccctct acgaaagcga actgcgcaca atggagggcg tgtcgacgcc   61680
gcccgcgctc ccggaaggac acgagtccac gcactacttc tactggatcc agctgccccc   61740
cggcgtccgg gaccgggtgg cgcgcgacct gctcaccgac ggcatctaca ccaccttccg   61800
ctacgccccc ctgcacaagg tgcccgccta cggtcacgcc ggacgcgaac tgcccggcgt   61860
ggagtgggcg tccgagcgga ccctgtgcct gccccctgcac ccgggcctgt cggacgccga   61920
cgtcctcacc gtcgtgtcct ccttgcgcaa agctctgaac gccggggcgc aggctcccgc   61980
ataacaggcg catacggtac ggcccctgcc cggcggttct ccgccgggca ggggccgttt   62040
cgcgtccggg acgtctccg tcgtcccgtc ggctcgctag gcgcgcgtgc cgaggaaaaa   62100
gccgggggag ccgttgcccg tctcgacgta ctcgacgtgc aggccggcct tgcggtacgc   62160
ggtctcgtac tccgcacggg agaacagcgt gaggtagtcc acctcgctgc ggtgccggat   62220
gccgtcggtg gtgtgcgcga tcaggtagtg gatttccatc cggtcttcct tgccctccct   62280
ggtcgagtgg gcgacgcggg cgacgccctg gtctcccgac tccgtcctga gggcgtgggt   62340
ggagacgtag ccgtccagga aggtgtcggg gaagtaccac ggttcgacgg ccaggacgcc   62400
gtccgcggag aggtgccggg acatggcggc gatcgcgtcc tccaggtcgg ccgcggtctc   62460
cagatacccg atcgaactga acatgcagac cacggcgtcg aacgtctcgc cgaggttgaa   62520
cgagcgcatg tcgccgcggt ggagggtcac atcggagagc cgctcctcgg cgcgggccgc   62580
catccattcg gagagctcca ggccgctcac acggtcgtag agcttggcga aggcctccag   62640
gtgcgtgccg gtgccgcagg cgatgtcgag caggctggag gcgttcggcg tgcgttcccg   62700
gatcaggccg gtgacccggg cggcctcgcc ggcgtagtcc ttgcggtcct ggtacagcag   62760
gtcgtagacc tcggccgcac tgtcgttctc gtacatggga atcctccggg ccgtgttggg   62820
gggggaaccg ttggtgtgtc gaagaggagt gcgccgtgcg gtcggggggca cgggcggcat   62880
tccgctgcgg aggccgtcgt tcggacgcgt cgtgcgcacg ccgaacccgc tatgcgcgta   62940
cgggagttcc atcgaccgaa gccgtgcggg tatccgaccc gcaccggtcc ttcgcggtga   63000
tctccgtacg gacacccaac agttcacgcc gagtcgaggt caaggaacgg cagcctggtc   63060
agtcaagtcc ggcggtccgc acttgggggca gtggcgccg acgcgccccg ggccccgggg   63120
cgggcgccgg tcgggccgtc ccgcggagcc ccattcccgt cctcccgcag aagggatgca   63180
```

```
gaatcggaca gccgacggct tgtttcaccg gaaaacgcgt ggtgcgcccc gagtcgccgg   63240
tagcttatcc accgttcgcc gaggcggttc aagtggcagc gttcaaccgc gatccggtct   63300
ttatggaatt catatctgcc cgctggcttg atgagtcggg cctcatgtcc ggaagtcgat   63360
cccggccggg agtgcgcggc gatccgcccg gacgccgaat gccgtggccg cacccgtcc    63420 ggtaacgtcc tgcggggtac ggacggcggt ccggccgtcc atcagaatcg gacgaacggg   63480
atgaaatgtt atggcgaggg agcgaaagga agcgggtgcg gaggatttac cgcagcccgt   63540
tccaggaccc tcggcgatct agatcgggta ccctgatagc gtaataacct gtcattgtat   63600
tcgtaaagca cagggatggg ggcgcctgcg gcatgagtta cctggattat ggtgaagaag   63660
cgtctgaaga agacgagtcg gacgacgcac tcaccttcct cgaatttgtt gcccggtcgg   63720
ccccgcggag cgaatacgac cggctcatgg cgcgcgcgga acgcgcgggc gccgacgagg   63780
aacggatgcg tcggctggag cgcttcaacc ggctcgccct caccgcgcag tcgatgatcg   63840
agtaccgccg cgaccgggag gcggagctcg cggcgctggt cgacgccgcg cacgagttcg   63900
tcgccgccca gcagtacaag gacctgctcg aatccgtcgc ccgcagagca cggctgctgc   63960
tcaagctgga tgtcgcctac gtcagtctgc accaggagga cctgcaccac gaggaccggc   64020
ccggcacggt ggtgctgagc gccgacggca acgcggtcaa ggtcgccgac agctaccggc   64080
tgccggccga cggcgggctg gcggcatgg tgcgcacctg ccacgctccc ttctggaccc    64140
ccgactacct cggggacagc agcttcgtgc acgtcgagac cgtcgacgac atcgtccgcg   64200
cggaagggct gcgcgcggtc ctggccgttc cgctgtgcgt cggcgacgac tcggtggggg   64260
tgctctacgt cgccgatcgc caggtccggc acctgacccc caacgaggtc accctgctgt   64320
gttcgctcgc cgatctggcc gccgtcgcga tcgagcgtat ccggctggtc gaggagctcc   64380
gcgacaccat cgggcggctg cgcgaggacg tcggtgaggc ccgcgccgcc ctcgcgggca   64440
cccgcaggtc cgccgacctc cagtcgcacc tgatcactca ggtcctcgaa aggcgcgggg   64500
ccgacgcctt actcgccgcc gccgccgaat ccctgggcgg cggcaccagc ctctgcagcc   64560
cgctcggccg gccgctcgcc gagtacggga acctgcgccc cgtcgccccc gccgacctgc   64620
gcgccgcctg ccgcagggcc gccgaaaccg gccgacccac ccccgtcgca ccggggtact   64680
ggacggtccc cctgtacccc ggggagtaca cgccggcctt cctgctgacc gacgtcggac   64740
ccgaggcgga ccacacggtc gtaccgctgc ttcccatggt cgcccgtacg ctcgcgctgc   64800
atctgcgcat ccagcgcaac gactccacca aggcccagag ccaccaggac ttcttcgacg   64860
atctggtcga ggcgccgcgc tcgcccgccc tcctcaggga gcgcgccctg ctgttctccc   64920
tcagcttccg ccgcccgcat gtcgtgctgg tggcgagcgg accccacgga gcctcggcgc   64980
ggctggagtc ctccggcgcc gactacgcga aggaactcgg cgggctgtgc agcgtacggg   65040
acggcgccgt cgtcctgctg ctgccccggcg acgacccgt ggccgtggcg cagaccgccg    65100
ccccggaact caccgatcgg gtggggcacc cggtcaccgt gggggccgcg ggccccgcct   65160
cgaccgtcga cggcatcagc gacgcccacc gcgaggccgc gcagtgcctg agacccttc    65220 gcgcgctcgg cggtgacggt ggcaccgcct gcgcctccga cctggggttt ctcggaatgc   65280
tcctggccga ggaaaacgat gtccccggct acatcaagac gaccatcggc cccgtgatcg   65340
actacgacac ccaccgcttc acggatctca tccccacgct gagggtgtat ctggagtcgg   65400
gcaggagccc cacccgcgcc gcggagacgc tgcgcgtgca cccaacacc gtctcgcggc    65460 ggctggagcg catcggccaa ctgctgggag aggactggca ggggccggag cgggtgctgg   65520
```

```
acatccaact ggccctgcgg ctgtaccagg tgcgttcggc gctctcctcg cgctccgcgt   65580
ccgcctcgct ccccccgcgc ccggcgcccg cctcccggac cgtgctcgga tcgcagcgcg   65640
agtgagcgcg ggcggccagg cgatgcgcgg ccggacggcg cccggtggcc gcgccaccgc   65700
cgtggtcacc cggtgacgga ctcctggtgg ccgcgccacc gcccgtcctg cgacagccgc   65760
agcgcatggg cgatcgaggc cggcgtcacg tgccggtgcc ggccctggaa cgagcgcccc   65820
tcgaagtcac ggatgccgac gtccacgccg acccgggcga agtcggcgtc caccggtcg    65880 gtcagcgccg ccagcggcag cagcgcccgg tgcccaacg gccgaggtc ggtcagccac     65940 aggcttcggg tccggcttcg ggccccgatc gggtttcggc ttcggcgtcc gtttcgggtc   66000
ccggtgggga ttcggcttcg ggtcaagcgg agtagtgatc atcacgccct cgcagggcg    66060 ctcgaattcc ggtgactgcg tgcgccacag ccttacggaa ttctccgggc cctcgcagac   66120
acaccgggca caccctttca gcgccgcccc ggctcccgcg attcactccg ggcccacggc   66180
ccgtctcgcc ctgaaaaccg gtggtcaact caccgtggcg accctctcga cggtggcggg   66240
acattccacc gaatggcacc gagaaacgac gccactgcac ccgtgctgcg gcattccctt   66300
ttccgtcgct ttggtcatgt gaggctccgt gcgtcgtgca ggaaggtgtc gtagtcgcgg   66360
tagtagtcgg attcttcgta gtgctgtgag gcgaggacga gggcgacggt gtcggggcg    66420 aagtctttga ggacgcgcca gaccatgggg ccgatgcaga gtccggctcc gggttcgtcg   66480
aggcggtagg tggcgtgctg gaagccgtcg tcgagggtga tggagaaggc gccgtggacg   66540
gcgatgacga gttgttccag ggtgcggtgt gcgtgcaggc cgcgtggggg tgaggactgg   66600
gtctggccgt gcatgtagta gacgcgttgg acggggaagt ccacggtcac gccggactcg   66660
accacggaca ggctgccgcg cgggtcgatg tgctgctcga gcctgatcag ccggcacggc   66720
ttgatcctgc cgacccgccg ggcgggaggc tcggctgtgt tctcggcgat ggcggcgctc   66780
cttatcgggc ggtcgtgagg tccacggccg gctcgggacg gccctggccc ggggacggaa   66840
ccctcgggtt cagttccagt cgacgcggac gggcaggtac ttcggagtga gctggtcgcc   66900
ctcgtagaac ggtgaactcg atccggcgtt cggcttccgg catccgagcc gtcgacgtc    66960 agcggaacat acgaagcacc gaggcagtcg gcaagacgga cgtgacacag tgggcgcctc   67020
tgtcggaagc ggcgcccgga cccggcgcac cgcaccggtg gacacgaatt tccgtaccgt   67080
cggcggaagt tgacggacgc ctcgcctttt ccgcacgaag gcgcgcgaag gcgcgcgaag   67140
ttccttggcc ggacgacagc gccgaccgcg acctgacatc cgttcatcgg caagtcctgc   67200
cgcttccgca ggcgcccggg ctcagggaac agcggtgcag ccagagcacc ggcccccgcc   67260
cgtcggcgcg gatcgccgtc gggcgggcgg gttttgagcc ttgaccgcgg ccccttcgga   67320
acgaggtccc gggcccgcgt gagggcgtgg ctcagcctgc gctgaactcg gcgatgcacc   67380
cgtggtccat ggcaagccgg gccccggtga accgggaccg catccggcgg tcgtgggtga   67440
cgacgaccac ggcgccccgg tagtccacga gtgcctgctc cagttcctcg accagcaccg   67500
gggtgaggtg gttggtgggt tcgtccagta gcagcaggtc catcggtcg ctcaccagcc     67560 gggcgatctc gatccggcgg cgctgcccgt acgacaggtc cttcacccgt cgccgcaggt   67620
cggacgggct gaacaggccc aacgagagca gtttctccgc gtggtcctcc aggtagccct   67680
cccggccgtg ggcgaaggcc cgcagcaccg tgagctcggg cgaccagggc gtctcgtcct   67740
gccgcaggtg cccgactcgg cagccgacgc gcaccgagcc gctgtccggc gccagttccc   67800
cggagagcac ccgcagcaag gtggacttgc ccgcaccgtt gggtccggtg atcagcagcc   67860
gctcgccggg ccggatcttc agggagtcga cgtcgagccg gtccgcgacc cgcacgtcgg   67920
```

```
tgagttcggc caccgcctcc tccgcctccg ggcccgcggt gtcgatgcgg gcggcgaagg   67980
acagcgggtc cgcggggggcc agggccgggt tctcggtcag ctgcgccacg cgttgcttgg   68040
cgttgcggat ccgcaccatc gcgccgtggt cgcgtccgcg cctgcggtag gcgccgtggc   68100
cgaacacgga gagggacatc ttgcgcggga tgttgtccat ccgcgccacg ttggaggtga   68160
tcagcccctg gttgcgctca agttcggcac gccattcctc gtactcccgc agccgccgct   68220
cgcgttccac ggccttggcc gtcagataac cctcgtaacc gttgccgtag cgggtgacgc   68280
ggccggagtc gacctccagg atcgtggtgg tgagccggtc caggaacacc cggtcgtggg   68340
tgaccgcgat caccgtgccg cggtggccct gcaggtggtt ctccagccat tccatcgccc   68400
ggtcgtcgag gtcgttggtc ggctcgtcca gcagcaacag ttcgggcgcc gaggccaggg   68460
tcgccgcgag ggcgaggcgg gagcgctcgc cgccggagag ggttccgagc ttccggtcgc   68520
ggtccaggct cggcagtccg aggccgtgca gcgcgacctc cacgcgtacg tcggcctcgt   68580
aaccgccacg ggcctggtac tgctcgacca gaccggcgta gcgctggagg agggcggaca   68640
gctcccgttc ggaaccgtcc tcgtcgcgct cggtcagttc cgcctcgacc tcgtgcatcg   68700
acgcttcgag ctcgcgcagg tcggacaggg ccagatcgac ggcgtcttgg acggtggcgt   68760
cgagcggcag ttccaacgtc tgtgccagat agccgatgcc gccggggcg accacggtga   68820 gcatgccgtt gtcgggctgc tcgcgcccgg cgaggacctt gagcagtgtg acttgccgg   68880 aaccgttgtc gccgatcacg ccgaccttct cgcccggctt gatgctgaag ccgacccggt   68940
cgagtacgac acagtcgtgg tagcgcttga tgacgtcatg cagggcgaat tgcgcaatcg   69000
acacgtgtgt gtctcctgtt tcacgatgag gatgagtgaa tgcgtgagcg cgctcggcga   69060
aacggccgga agaaagcgac acaaacgcca ccacagcgga ctgaccgatg cagtggtgtg   69120
tcagcagcac gctgctggat gcggcaacgg agtccagctc aacgccgcgc atcctcatct   69180
atcacagaga tccatgcgca tgaactataa acgggccacc cgatgccggg caagggggatt   69240 cgggttcccc ggcccgacgt gatgcagtcg gaacgggatg atcgcccgtc cggcggtcgg   69300
gtgcctagcc tcgggaacaa ccacagcggt ctttcaggag ggctggccat gggcgagacc   69360
aagaaccgga tcaccgaact ggtccgcgcg taccaccggg aacaggcgac cgggaatttc   69420
gttcccggga cgacgcacgt accggtctcg ggcgcggtac tgagcgagga cgaccggttg   69480
gcgctggtgg agacggcact ggagatgcgg atcgcggccg gcccggcctc ccggagcttc   69540
gagcggcagt tcgcccggta cctcgggcta cggaaggcgc atctgaccaa ctccggctcc   69600
tccgccaacc tcctcgccct cagcgcgctc acctcaccgc agctggagga caggcggctg   69660
aaaccgggtg acgaggtcgt caccggtcgcc gccgggttcc cgacgacggt caacccgatc   69720
ttccacaacg agctggtgcc ggtcttcgtg gacgtcgaac tcggcacgta caacaccacg   69780
cccgagcgca tcgagcgggc catcggcccc cggaccaggg cgatcatgat cgcgcacgcc   69840
ctcggcaacc ccttcgaggc cgaagaggtg gcccgactcg ccgacgagcg cggcctgttc   69900
ctcgtcgagg acaactgcga cgcggtgggc tcccgctacc ggggcagact cacgggctcc   69960
ttcggcgacc tgtcgaccgt cagcttctac cccgcgcacc acatcgcgat gggcgaggga   70020
ggctgcgtgc tcaccgacaa cctggccctc gcgcggatcg tggagtcact gcgcgactgg   70080
gggcgcgact gctggtgcga acccggcgag gacaaccgtt gcctcaagcg gttcgaccag   70140
aaaatggggg acctgccgcc cggctacgac cacaagtaca tcttctcgca tgtcggttac   70200
aacctgaagt ccaccgatct gcaggcggca ctcgggctgt cccagctgac gcggatcgag   70260
```

| | |
|---|---|
| gagttcaccg acgcccggcg cgccaactgg cgccggatgc gggagacgtt ggacgggttg | 70320 |
| cccggcctgc tgctgccgga ggcgacaccg ggcagcgacc cgagctggtt cgggttcctc | 70380 |
| atcaccgtgg acccggacgc cacgtacagc cgggcggccc tggtcgacca cctggagtca | 70440 |
| cgccggatca gcacccgccg cctgttcggc ggcaatctcg tccgccaccc cgcctacacc | 70500 |
| ggccgtcagt accgggtgtc gggcgccctg gagaacagcg acctgatcac cgatcagacc | 70560 |
| ttctggatcg gggtcttccc cggcatcacc acggagatgg tcgactacgt caccgacacc | 70620 |
| gtccgggagt tcgtgctcaa gcactcctga cacgtccgcg gaacgtcggg gtggggaggg | 70680 |
| ccctgtcggc cctccccacc ccgacgttca cggccgcggg tgcgcctgca actccgaggc | 70740 |
| gaggtcgggg tggaccagcg ccgtgagcag ggtgccctcc ggcgtgtgct cggcactgag | 70800 |
| cacctcgccc tcgtcgtgcg cccgcgccac caggcccccc tcgtcgtagg ggatcacgac | 70860 |
| ctcgacctcc acggcggggt gcggcagcag gcggtcgatc agctcctgca actcgtcgat | 70920 |
| gccctgcccc gacctggcgg agacaacgat cgccgtccggc tcctgctcca gcaggcgggc | 70980 |
| gagtacgtcc gggtccgcga cgtcggcctt gttgacgacc acgatctcgg tggactcggc | 71040 |
| ggcgcccacg tcccgcagca cctcgcgtac ggaggccagc tgcgcgccgg ggtccgggtg | 71100 |
| cgacccgtcg accacgtgca gcaccaggtg cgcgtccgcg acctcttcga tcgtggagcg | 71160 |
| gaacgcctcc accaggtgat gcgggagatg ccgtacgaag cccacggtgt cggcgatggt | 71220 |
| gtacgtcgcg ccgctgggcg tggtcgcccg ccgcacggtc gtgtccaggg tggcgaacaa | 71280 |
| ggcgttctcc accaggacac cggcgccggt gaggcggttg agcagtgagg acttcccggc | 71340 |
| gttggtgtag ccggcgagag cgaccgacag caccttgttg cgccgtcgtt cctcccgctt | 71400 |
| cacgtcccgg cccgtctttta actgctccag ttcccggcgc agtcgggcca tcttgtcgtt | 71460 |
| gatccgccgc cggtccgtct cgatcttcgt ctcaccgggg ccgcgcgtgg ccatgccgcc | 71520 |
| gccaccgccg ccgcccatct gccgggacag cgactggccc cagccgcgca gccgcggcag | 71580 |
| catgtactgc atctgcgcca gcgccacttg cgccttgccc tcccgggact gggcgtgctg | 71640 |
| cgcgaagatg tccaggatca gcgccgtgcg gtccacgacc ttgacgccca cgacctcctc | 71700 |
| gaggtgcatc agctggctgg ggctcagctc tccgtcgcac accacggtgt cggcgccggt | 71760 |
| ctcctcgacg atgtcgcgca gctgcgacgc cttgcccgag ccgatgtacg tcgccgggtc | 71820 |
| gggcttctgc cggcgctgca cgaccccgtc cagcacgagg gcgccgcgg tctcggccag | 71880 |
| cgccgccagc tcggcgagcg agctctcggc ctcggcggcc gttcccgagg tccagatgcc | 71940 |
| gacgagcacc acccgctcca gtcgcagctt gcggtactcg acctcggaga cgtcggtcaa | 72000 |
| ttcggtggac agccccgcga cgcggcggag ggaggcccgg tcctcgcggt cgaactgctc | 72060 |
| gccgtcccac ccttcggcgt cggccgcggc caatgtgtcg ttcatcagtg cgtcggctcg | 72120 |
| ctgggaggtg ccggcggagt cttcgggatg tgtcaaagta cgtcccttct gggggctcag | 72180 |
| gagcgttccg gggtggtgtg cggtcggctc ggcgggatgc gcacgggtcg ggaaatgggc | 72240 |
| cgacgtgccc gcaccgcgcc ccacaggccg gtgccgctga agtcgctgcc ggaactcacg | 72300 |
| tgttgaccac cctagccatc ccgccgaggt gcgcaaacaa gtatcggtga tcacgtctcc | 72360 |
| agctgacaga gtctgcaccg ggtactgcgc acgcgggcgt ggagcgggca agtgtgatgt | 72420 |
| catgcgagta ctcattatcg gaggttcaca gttcgtgggc cgggcctacg ccgccgaggc | 72480 |
| gctggccgcc gggcacgagg tcaccacgtt caaccggggc gtcagcggca cggacctgcc | 72540 |
| cggcgtcgag gcggtcaggg gtgatcgcga ggcggccggc gacctggagc ggctggtgtc | 72600 |
| cggaaggcgc tgggacgcgg tcgtggacac ctgcggctac gtgccccgta cggtgggcgc | 72660 |

```
ctcggccgcg gcgctgtccg ggcacgcgga cgcctacctc tacgtctcca gcatcgcctg   72720
cctgcccgac tggacgcagg cggtccgccc ggtcgacgac gactcaccgg cctacgactg   72780
cccgccggac gcaggcccgg accacgccga cggcgactac ggcaccctga aggccggctg   72840
cgagcgcgcc gtggaccagc acttcgtggg ccgcaccctg cacctgcggg ccggcgtcat   72900
cctcgggccg cacgacaaca tgcgcatgct cgacgcctgg ctgtggcgca tgcgcgccgc   72960 cgaggggag caccgccggg ttctggcccc gggcggcccc gaggtcggca tgcgcctgat   73020
cgacgtgcgc gatgtcgccg ccttcggcct cgactgcctc gccgagggcc gcaccggcgc   73080
gtacatcgtc aacccgccgg agaagaacac cacgttcggg aatctgctca cggagtgcgt   73140
caaggccacc gggtccgccg ccgagccggt atgggtcgac gaccggtttt cgccgacca   73200 cggcgtgagc ccgtggacgg acctgccgct gtgggttccc gacaccgcgc aggacaccct   73260
ggtctgggcg gccggggcgc cgcgcgcacg ggccgcggga ctggcctgcc gcccgatctc   73320
cgagacggtg cgtgacgcct gggaggtcat ccgggaccag cccgtccctg agcttccgct   73380
cgctgccggc tgcggccttt ccctggcccg ggaaagggag ttgctcgccg cctgggacgc   73440
gcgcggcggt gcggccggct gacgcggccc cggggagtgc ggcgccgttt cccgttcgcg   73500
gggagcggcg tcttccgttt ccgacccatg gggcggcgct ttccggctct tcgcgcggag   73560
ctacaccgtg acggtctcgg cgcgggcgac gatctcgtcg accaacgccg cctgacgcag   73620
ggcggcatac gactcggcgg agatgttctc ggcccgggtc accgcgcggc ggaagaccga   73680
caggatgttc acgaagtgcc ggtccacggg cagcactcgc tcttcgcggt ggtcctggcg   73740
ggacagccgc agtacggggt ggtggctgtc cggagtcgtg aagacgtggt tcagggcgag   73800
cgagccggtg ctgccgtgca gttcgtacgc cgagcggtag ccgtgttcca tgccgaaggc   73860
gaggtgggcg gccacccccg tcggcgcggc cagcaggacg ctgccggaga ccaccacgcc   73920
ccggcgccgc tcgcggcgca gcaccgctcc catcaggcgc agctcgggcc cgaggaagtg   73980
gatcgcggcg cgcagcgggt agacgccgtt gtcgaggagt gcgccgccgc cgatgtcggg   74040
gcggtagcgc atgtcgtcgt cggggcgcgg cgggatggtg aaggcggcgg agaaggtgcg   74100
caggtctccg atggccccgg tctccaacag cactttgacg gtggcgtgtt gcgagtggtg   74160
gaggaacatg aagttctcca tcagcaccag tccgcgctcc cgcgccatgg cgaaaagccg   74220
tgccgcgtcg gcgtggttgg cggcggcggg cttctccacc agtacgtgtt tgcccgcccg   74280
cagcgcggcg gcgcccatt tggcgtgcag catgctgggc acggcgatgt agacggcgtc   74340
cacgtcgggg cgttccagca gtgcctcgta gggcgcgacc gctcgcagc cgaagtctc   74400 ccccagggcc ttggcccgtt ccggttcacg gctgccgacg caggtcagca cggtgccggg   74460
ggtggagagc agggcgggca gggtgcgcg gcctgcgatg tcgccgcaac ctatcgctcc   74520
gaagcgcagc accggggacg cttcgggcca cggcgggccg ggtgcggcgg acggttcggc   74580
tggagtaccc agggcggtca tggatggttc cgtcaatcgg tccggatggt cacggcacag   74640
cgtggtgaac ggccggcgcg cacccacgag tcgcttccga caatgggcgg ccctgaagct   74700
acccggccgt ggggcgcgac gacaaggccg atctgacaca gtgccgcgcc aaggggccgc   74760
cgccgccctg cggacccgtt gacctgacac ttcgccaccc aatctgtgga cgggacggtc   74820
gcggtccggg ttaggtgagc gcggcgcccg cggccacgcg acgcctgtcc gaagcggccc   74880
tcggggcacg ccatttgaga gaggagacgc gggtggcaga cgccgatcacg accgagctgg   74940 cggaccgcga actgggccgc agactgcacc ggatacgggg cgcccactgg tacttcggca   75000
```

```
accacggcga tccgtatgcg ctcatcctgc gcggccaggc ggacgacccg tcggcgtacg    75060
aggagcgggt acgggacggc ggaccgctgt tccgcagcca catcgggacc tgggtgaccg    75120
cggacccgga ggtgggcgcg gccgtgctgg gcgatcccg gttcggcgcg ctggatcgcg     75180
ccgggcggcg ccccgaggag tacctgcagc cgtcgcccgc ctcgtgcctc gggctggacc    75240
gtgccgcgta cctgcgtctg cggcgggtgg ccgaaccggt gttgggggcg ggcgccgccg    75300
acgagtggcg ccggctcgcc gaggacctcg gtcgtcggct gctcgacggc cgtggttccg    75360
gcttcgacct gacggcggac ttcgcccgcc gactgcccgc gctggtcctg gccgcgtggc    75420
tcggggtgcc ggacgaacgg cgggaggagt gggaggagtt gctgcgggag gcggggccac    75480
tgctcgacag cctgctgtgt ccgcagacgc tggcggccac ccgcgcggcg gactcggccg    75540
ccgaggggct gcgcacgctg ctgggcaagg tggccgtcgc gcgctccgac ggggccggcg    75600
acggcgcgct gggccgcatg gtcgccgccg gggccgcccc ggacgacgcg gtggccgccg    75660
ccatgtgcct ggtgctctcg gccgccgaga cgaccacgac cctggtgtgc gatgcggtcc    75720
gcctgctgct cgaccgcccg cgatggtggc gggcgctgtg cgactccccc gctctggcgc    75780
cggccgcagt ccggcacacc ctgcggtacg tgccccccggt gcggctggag agccgggtgg   75840
cccacgagga cgtggcgccg acggggcacc cattgcccgc cggagccat gtggtggtgc     75900 tcgtgagcgc cgcgcggcgc ggggccgccc cggacgccgg accggcggac ctgacgaacg    75960
tgcccacggc ggccggggcg ggcctgccgg acgacctgta cttcgcactt tccggggagt    76020
tcgtcgggcg aaccgccgag accgcgttgg gcgtgctggc cgaggtagcc ccccggctgc    76080
ggcgggaggg cgacatcgtc cggcggcgcc gctcccccgt cctcggcagg tatgcgcggt    76140
tccccgtcgc gtactcctga caggcccccg ccggtatcc ccctcagaac ccctcgaagt     76200
ccgatgaaag gagtcccgtg cgcgtcctcg tgacttccat tccgcaccac acgcactact    76260
accacctggt gcctctgatc tgggcgctgc gtgcctcggg gcacgaggtg gtggcggccg    76320
gccagccgtc gctgatcgac gccatcacct ccagcggcat cccggggttc ccgctcgccg    76380
aggaggagtc gctggcccag atcttcgagg aggtcgaggg cgatcttcag ccgtatcagc    76440
acgggatcga cgagttcgac ttcctcggta ccctgcagga cgccctggac tgggagaagt    76500
tgctcgccca gcaggtgatc ctctccggtc tgtggctcga accgctcaac ggcgccacga    76560
ccctcgacag catcgtcgac ttcgccaggt cgtggaagcc cgacctggtg ctctgggagc    76620
cgttcaccta tgcggggccg gtggcggccc gtgcgtgcgg ggcggcgcat gctcgcgtcc    76680
tgtggggtcc ggacacgatc gggctgatgc ggacgaagtt cctccaggcc caggcgcagc    76740
agcccgagga gcaccgggac gacccgatcg cggagtggct gacctgggcg ctggagcgct    76800
acgggtgcga cttccgggag gaggacgtgc tcggccagtg gagcgtggat cccatggcgg    76860
agggcgtcag cctcggcctg gacctgccga ccgtcccgat gcgctacacc ccgtacaacg    76920
gctcggcggt gattcccgac tggctgaccg aggagccgaa gcgcccgcgc gtctgcctga    76980
ccctgggggt gtcctcgcgg gagtacggcg aggacgaggg gccggtgcag aagttcatcg    77040
aagcgctggc cgacctggac atcgagttgg tggcgaccct ggacgacgcc cagcgggacc    77100
tgctgccgcg gatcccggac aacacccgga tcgtcgactt cgtccccatg gacgcgttgc    77160
tgccgacgtg ctcggcgatc atcaaccaca gcggctcggg cacgtgcaac accgcggcgc    77220
tgcacggggt gccgcagatc atcctcggca acatcctgga cgccgccgtg cggcagcaca    77280
tgttcgcgca gtcgtccgcc gccctcacct tcgcccggga ggaggtgacc ggcgagtcgc    77340
tgaggagcgc gctggtgcga ctgctcgggg aaccgaagtt ccgcgacggt gcgcagcggt    77400
```

-continued

```
tgaaggagcg gatgcggggcc atgcccagtc cggccgggat cgtcccgacc ctggagagcc    77460
tcacggcccg gcaccgccgt gcctgagggg ccgtcaagtg tgtgatgcag caaggctatc    77520
gcgtgacacg actcctgcgc gtaatcgatc tcgtcgactc agccgtggac cggttcgcct    77580
gtccgcgccg gacactggag tgttcatgcg ggccctttc acgaccgcgc cgctcgccgg     77640
tcacctgctt ccgctcgtgc cgacggcatg ggccctgcgg gcggccggtc acgacgtcct    77700
ggtgacgacc cggagaaact tcgtcccggt cgcgctgcgg tcggggctgc cgtcctcctc    77760
gtgcgggccc gccgtcgatt tcacgggcac ggtcgccgac ggaccgctcg cgccgtctcg    77820
ggacgaggcg gggcagcggg gcgtcctggg cggggcgttg gcgcgcgtcg ccggggcag    77880 cctggccggg gtgcggcggc tggcggacgt ctggcggccg gacttgatcg tcagcgaacg    77940
ggccgagttc gccggaccgc tggtcgcggc ggccctcggc atcccgtggg tccgctacca    78000
ctggtcggtc tcctgtctgg aggagtaccg gcgcgcggcc gaggaggagt tcgcgccgga    78060
gctgaccgcg ctcggcctcg accggttccc ggatcccgcg cgcgtgctcg atccgtggcc    78120
ggtgtccctg cgccggccgg acgcggtcgc ccacgacggc atccggcacg taccggccca    78180
cggggacgcc cccgtgccgg agtgggcgtt cacgcgcggc cgcaggcccc ggatctgcgt    78240
gacgctcggc accatgctgc cccggtacgg cgcgttcggg gtgcgcgact tcctggcgga    78300
gctggtggag gagacgcgcg gatcggactg cgagctgctg atcgcggtcg acgacgacat    78360
cgtcgcgcgg tggccgccgc tgcccgccgc ggtgcggcac gccggccggc tgccgttggc    78420
cgaggtgctg cccgcctgcg acgtggtggt gcaccacggc ggtcagggca cgtccctgac    78480
cgccctggcc gcgggccggc cacaggtcgt catgccgcgg ctcgacgacc agttcgacaa    78540
cgcgcaggca ctggcggcgg cggatgcggc cctgctcgtg ccaccgtccc tggccactcc    78600
cgcggccgtg gccgcggggt gcgccgaact gctggagaac gccctgtatg ccaaggcggc    78660
agccgggctc gccgagacga tggcgctgct gccgtcgccg tcggcggcgg tcggaccccc    78720
ggagcacctg gggcctgcac cgggcatgct gcggagccac gcgaacgagg atgcggtgtg    78780
acgtgatttc cgaagtactc aaccgttcga acgatccgcg cgggccgttg atcacggtgg    78840
tcggcgcgtc cggcttcatc ggatccgccc tggtcgccga gttggcgcgc acgccggtgc    78900
ggctgcgggc ggtgtcccga cgcgaggccc ccgtccccgc ggggacgccg gccgccgtcg    78960
aggtccgccg gcggacctc gcccggccgg gcgaggtccg ggacgccgtc gagggggcgg     79020
acgcggtcgt gcacctcgcc gcccacatcg gcggcgcgca gtcgtggcgc gcggccgacg    79080
agcggtcggc gcgggtgaac gtcggcctgc tgcacgacct ggtcgacgcg ttccggggcc    79140
gctcgggcac cctcccggcc gtggtcttcg ccagtaccct gcaggccggc gccgacgtcg    79200
cccggcaggg cgcgtacgcc cggcagaagt cggccgccga agaggtcctg ctgcgggccg    79260
cgtccgaggg ggtggtccgg ggcgtcgtgc tgcggctgcc gaccgtgtac ggccgcagcc    79320
cgctgaccgg gtggaccggt cgcggggtgg tcgcgtcggt ggcgcggcgg gccgtcgagg    79380
acgggccggt cacgatgtgg cacgacggca ggtcgggcg cgatctgctc cacgtggagg     79440
acgcggcccg cgccttcgtg gcggcgctcg accacgcggc gcggctcgac ggcggcacgt    79500
ggtccgtcgg caccggccgg ctggagccct tgggagaggt gttctcgacc atcgccggc     79560 tggtgtccga gcggacgggg aggccccccg tccggtggt ctccacggag ccgcccgacc     79620
atgccgaggc gggcgacttc gacagcccgg tctccgaccc ctccgcgttt cgcgcggtga    79680
ccggatggtc tccccgcgtt ccgttgcagg cggggctcag cgccgtggtg gagacgatgg    79740
```

-continued

| | |
|---|---|
| tggccgcgga atcgaggggt gggatccgag gttgagcacg gaccggaatc aggccgcgca | 79800 |
| cacgcggctc ggccgcagcg cgacgctggt gagccggctc tggctgggca ccgtgaactt | 79860 |
| cagcggccgg gtcgaggacg cggacgcgat gcacctgatg gagacggcgg tcgaccgcgg | 79920 |
| catcaactgc atcgacacgg cggacatcta cggttggcgg gtccacaagg gcacaccga | 79980 |
| ggagttggtg ggccgttggc tggccaagag cgccgcgcgg cgggaggacg tcctgctggc | 80040 |
| caccaaggtc ggcggggaca tgagcgaacg gctcaacgac ggcggcctgt cggcccggca | 80100 |
| catcatcacg gcctgcgagc agtcgctgcg gcgtctgagg gtggaccaca tcgacctgta | 80160 |
| ccagatgcac cgcatcgacc acgccgctcc ctgggacgag atctggcagg cgatggaccg | 80220 |
| tctggtggcg agcggcaagg tgacctacgt ggggtcgtcg aacttcgcgg gctggaacgt | 80280 |
| cgccgccgca caggacgccg cgcggcgcg cggtccctc gggctggtgt ccgagcagtg | 80340 |
| cctgtacaac ctggcggtac ggcacgccga gttggagttg ttgccggcgg cgcaggcgta | 80400 |
| cgggctggga gtgttcgcct ggtcgccgct gcacggcggg ctgctcagcg gggtgttgcg | 80460 |
| caagctggcg gcgggcactg cggtgaagtc ggcgcagggg cgggcccaac tgctgttgcc | 80520 |
| cgagctgcac gccacgatcg aggcgtacga ggggttctgc gaccggatcg gggcggaccc | 80580 |
| ggccgaggtc ggcctggcct gggtgctgtc ccggccgggg atcagcggtg cggtgatcgg | 80640 |
| gccgcgcacg gtggagcagc tggactcggc gctgcgggcc ctggacctgg tcctcgggga | 80700 |
| ggccgaactg gccgaactgg acgccatctt cccggccctg gcaacgcgcg gccgggcgcc | 80760 |
| ggatgcgtgg atcagctgaa gggcggtgca tcggccgacg tcacgccggc cgatgccgcc | 80820 |
| ggtcatacga cgtcgagcgc gggcagcggg aagatcagtc ggccgccgcc gtcgaggaag | 80880 |
| tcccgttccc gctcgacgaa tccgtcccgg tagatccagg gcaggaccag caattggtcc | 80940 |
| ggcttctgtg ccttcgcgtc ctgttcggac acgatgggga tggccgttcc cggggtgaag | 81000 |
| cggcccgcct tctcctcgct cacctcaccg atgcagggca ggtcccgctc ggtgatcccg | 81060 |
| cagtactgca ggatgacgtt gcccttggtg gaggcgccgt accccagggt cagcctgccc | 81120 |
| tcttcgcggg agcggtcgag gaagtcgcgc agggcgcccc gctggttcac gacccggcgg | 81180 |
| gcgaagccct cgaacggcgc catgccgtcc agtcccgccg cggcctcccg ggcacggatg | 81240 |
| cgggccaggc ccgcatcgtc cttccggtgc tgggagccgc tcctggccag cgtgacgcac | 81300 |
| aggctgccgc cgtacacctc ggtgagctcg gccctgatga cagtcaggcc gacccgctct | 81360 |
| gccatccact cgatctgccg gagggcgtag tactccaggt gctcgtggca gacgatgtcg | 81420 |
| tacgcgtcgg cttcgagcat ggcgggcagg tagctctgct ccatcatcca gatgccgtcc | 81480 |
| tcggtgagga cgtcgcggac gtcgctcatg aagcgcagcg ggtccggcag gtcgtagaac | 81540 |
| atggctatcg aggtgacgac cttcgcccgc cgcgcgccga accggctctc gaaggtctcg | 81600 |
| cgggtgaagt agtcgacgat caactcggcg ttccgcgggt acagttcgcg gaacttcccg | 81660 |
| ccggtcgggt cgatgccgac cagttggggg ccgtcggcag ggtagccgct cagcagtgtc | 81720 |
| gcgtcgttgc tgccgatgtc gacgaccagg tcgtccgggc cgaggccac cagctcgcgg | 81780 |
| atggcggcga ccttgccgtg gaggtggtcg accatgaacg gccggatgcc cgagcggtag | 81840 |
| ccgtagccct ctccgtacat gaggtccgga tcggggtgt ggcgcagttg cacgaggccg | 81900 |
| catccggccg gggaacagac gacgagttcg agcgggaccg acggcacaac ctgttcgcgg | 81960 |
| ctcgtcggga acactccggt gagcgcttgt tcgcccaggt cgagtacgga gagcagctcc | 82020 |
| ttgttgccgc agacgcggca cgcggtgcga atcatgggt cctttcggaa tccgggccgg | 82080 |
| ggcgccggcc cggggccagg tcgggggctt cgagacggag ggtgtcgggg gtgggctggg | 82140 |

```
gggacggcat caggtgcagg cggccgatcg caccggtggg ggcggacgcg tcctggcacg    82200 ggcagggggtc atcggtgaat ccggcgaagc ggtaggccac ttccatcatt cggttgcgtt    82260
cggtggcgcg gaagtccgcg ccgaggtgca ccccggcccg gtgtgcctgg tcggtcagcc    82320
agcgcaggat cgccgtgccg gcgccgaggg acaccacccg gcacgaggtg ccagcagct     82380 tgatccgcca ggcgtcgggg ctgcgccgca gcagcacgac gccgaccgct ccgtagggggc   82440 cgaagcgatc ggtgaccgtg gtgaccagca cctcgtggtc ggggtcgtcg atgagggcgc    82500
gcagatcgtc ctcggagtag tgcactccgg tggcgttcat ctggctggtg cgcagggtga    82560
gttcctcgac ccgggacagc tcgtgggggg tggcgcggct gatccgcatc ctgatgtcca    82620
gcgagcgcag gaagtccgcg tcgggcccgg tgaagtcgga ccgttcggcg tctcgccgga    82680
aggacgcctg gtacatcgag cggcggcgcc gcgagtcgac ggtgacggtg tccgggctga    82740
actccggcag gtcggtcaac ccggtcgcct gtccggcggt gtaggtgcgg acctccggca    82800
actcgtgtgt cacctcggcg cgttcgaagg gctggtcgtc gatgaaggcg agggtgccga    82860
gcgcgaagtt gagccggtcg gcgatctcgc ggaccgactt cgacttcggc ccccagccga    82920
tctgcgggag cacgaagtat tcggcgacgc cgagctgttc cagtttcgcc caggcgtggt    82980
cgtggtcgtt cttgctggcc acggcctgga ggatgccgcg cgcgtccagc tcggcgatgg    83040
tccgcaggac gtccggggtg agccggacct cgtcctcctc caggagtgtg ccctgccaga    83100
gggtgttgtc cagatcccag accaggcatt tgaccagggg ctcggcggcg ttgtcccggt    83160
gcacgtcgtt cctttctctc gatacggcgg atgcgaccgc gactgtctcg atacggcgga    83220
tgcggccgcg actcttcgac aggcggacac cgccgggacc agaaggatta cggcccgttc    83280
atcccgcggc ggacaccgca tgccgggcca ggatcagctc gcagatctcg ttgctgccct    83340
cgatgatttc catgagcttg gcgtcgcggt gcgcccgggc gacgacatgc ccgtcgcggg    83400
ccccggccga cgccagcacc tgcacggccc gctcggcgcc gcgtgcggcg ccggtggccg    83460
cgacgtgctt ggccaggacg gcggcgatca ccatgtcggg gctgccctcg tcccactggg    83520
cgctggcgta ctcgcacgcc ctggcggcgt gctgttcggc gatgaacagt tcggcgaggt    83580
gccgggcgac gagttggtgt tccgaaagcc gcgtgccgaa ctgctcccgt ccgctggtgt    83640
gccgcacggc ggcggccaga cagccgcgca ggatgcccag ggagcccat gccacggaca    83700 tccgccgta gctcagcgcg gtggtgacca gcagggcggg ggtgcggtcg tggccctgca    83760
ggagggcgtc ggccggcagc cggaccccgt ccaggtggat gttcgcatga ccggccgcgc    83820
ggcagccgtg cgcgtcggcg atgcgctcga tccgtacgcc gggggccgag gcgggcacca    83880
cgacggcccc cgcgccctcc tccgtgcgcc cgaagaccac cagcaggtcc gcgtaggcgg    83940
cgttggtcgc ccacaccttg accccgtcga cgacgatctc gtccccgtcg aaggcgatac    84000
gggtccgcaa ggcggacagg tcactgccgg cgccggcttc ggtgaaggcc acggcggcca    84060
gttcgccact ggtcaaccgg gaagtcagcg gggcctgttg gtccgctccg gcgagtcggc    84120
gcagcgtcca ggccgccatg ccctgcgagg tcatgacgct ccgcagggag ctgcacaggg    84180
cgcccacgtg cgcggtgagt tcgccgttgc gccgactgga ccagccgagg ccgccgtggg    84240
ccgcgggcgc ctgcgcgcac agcaggcccc gggagccgag atcgcgcagc agggagaggg    84300
gcagctcgcc cgtacggtcc cactcggccg cccggtcgcc gaccagctcg gtgaacagtt    84360
cctcggcctc ggatgcggcg gcatgcggcg cgtcagccac cggcgggccc ggtcgcctcg    84420
ccggtcggac cgggcgcggc cagccgtccg accagccgga ccatcgcgtc gacggtgcgg    84480
```

```
aagttgtcga gcatcaggtc ggcgccgctg atgacgattc cgtgggtctt ctccaggtgc    84540
acgacgagct gcatggcgaa cagcgaggac atgccaccga cggcgaacag gtcctggtcg    84600
cgctcccagg tggtcttggt gttggccgcg aggaaaccga gcagttcctc ggccacctcg    84660
tcgtcggcgg gcgtcgtgcc ggtcgaatcc ggccggccgg aagtcgtggt cattgcatgg    84720
tctcctggta gtcgtagaat ccccggccgc tcttgcggcc gagcaggccc tgccggacct    84780
tgtccagcag cagttcactc gggcggagag ccggatctcc ggtccgttcg tgcatcaccc    84840
gcagcgagtc ggccaggttg tccagcccga tcagatcggc cgtggccagt ggtccggtgc    84900
ggtggccgat gcagtcgcgc atcagcgcgt ccacggtttc cggggtggcc ctgccctcgt    84960
gcaccaccgc gatggcgtcg ttgagcatcc ggtgcaggag gcggctggtc acgaacccgg    85020
cgccgtcgcc gacgacgatg ccccggcggc ccagtccgga cagcagttcc cgggtcgact    85080
ccgcggccgc ctctccgctg cgtggtccca ggaccacctc gaccgtgcgg atcacgtacg    85140
cggggttcat gaagtgcacg ccgaccaggt cctcggggcg ggggacggca tcggccagtt    85200
cgtcgatggg aacgcccgag gtgttgctga tgagcagcgt tccggggcgt gccgcggacg    85260
ccaggtccgc caggacctcc gccttcctct tggggtcctc ggtgacggcc tcgatcacgg    85320
cggtcacggc ggcgatggcg ttcagggcgt cctcgacggt cagttcgccg ggcggccggt    85380
cgtggggcag cgcgcccatc agccgggccg tccgcagatg gagtgcgacc gtgtcggggg    85440
cggcggcgcg cgcctcgacg gacgtgtcga tcagggtgac cgggtgtccg tgtccgacgg    85500
cgagtgcggc gatggccgtg cccatgacac ccgctccgag cacgacgagc ggagaatttt    85560
cattggaatt gggcacagag cctccagaat cccgggacga cggctgtgcg aaatgctgtc    85620
ccgaatcgct tctgtgctcc atcacttggc cgtgactttg tcacctagga agcggtgcgg    85680
gcctggcgga ggctatgtca tctccggctt gtccaccccg gagttccgta cctaaagtgc    85740
gcccggcgaa cgcgcggcgg aattaccgcc gtttcctgcc aagggcccgt ggtttgaacg    85800
acctcgacgt atgaagggtt tcacatggct catatcgcat tcttcatcct tccggttgcc    85860
gggcatgtga atccgacgct gggagtcgcc gaggagctgg tggcgcgcgg ccaccgggtg    85920
acgtacgcgc tgtccgggga gctcgccgag cgggcccggc tgatcggcgc cgaggtggtc    85980
acctatcccg tggacaagca acggttcctg gaccagatgg tgcctcggca ggacgcggac    86040
gagtacacgg acgagggcga gttcgtacgg gtcctggagt ggctgctgga catgacggcg    86100
cagaccctgg aaccgctgga gcggcacttc gccgagaacc gtcccgatgt cgtcgtcaac    86160
gacccgtcgt cgctgtggac ggggcggctg ctggcggacc ggtgggacat cccggtcatc    86220
cgcagcactc cgacctacgc cgccaacgag cactggtcgc tgcatccgcc cgtcgactcg    86280
gccgagccgc cggacgatcc cgagctgcac aagctgctcg cgcggatcga gcggctgctg    86340
gaggagcagg gcgtcgagca cgacctggcc gccttcaccg gggtcctgca cggcggcccg    86400
gccctgctgt acatgccgcg ctcgttccag tacgcgggcg agaccttcga cgaacagcac    86460
cacttcgtcg gcccctgccc gccccggacc gcgttccacg gcgagtggac gccgacggac    86520
gacgacggcc ggcccttggt gctggtgagc ctgggaaccc tctacaacga ccggccggac    86580
ttcttccgca cctgcctgga ggcgttccgc gacgagccct ggaacgtcct tctggtgctg    86640
ggcggcgggg tgcccgccgc cgacctgggc ccgcttcccg acaacgtccg ggtgcacgac    86700
ttcgtgtcgc tgcgcgatgt gctcccgcac accgccgtgg tggtgaacca cggcgggatg    86760
agcaccgcca tggaggtgtt ctcgcacgag gtgccggtgg tggcgatccc ggtgatgccg    86820
gagcctcggg ccaccgcgcg gcggatcgtc gaactgggtc tcggtgacca gctcctgaac    86880
```

```
tcggagctga cggccgagtc cctgcgtgcc accgtgcggc gggtgctgga ggactcccgg    86940
atcccggcga acatgcggaa gatccgtgag cagatcacgg cggccggcgg ggcgaatgcg    87000
gcggccgacg cggtcgaggg actgctgccc caggggagct gaggcgtcct cgcatccgaa    87060
acgcgttcac cttccgaccg gcgggatcgc tccatgctca tcaccgaaac gaccgtgccc    87120
gacgtcttcc gcattgatcc ggagcccatt cccgaccatc ggggccggtt ctacgaagcc    87180
gtgcgccaga ggccgctgga ggctgccgtc ggtcactcga tcgcggtccg gcaggtcaac    87240
ttcaccgtct ccgggcgcaa tgtgctgcgc ggtctccacg ccaccacact gccgccgggc    87300
cagggcaaga tcctcacctg cgtgcggggt tcggtactga ccatggtggt cgacatgagg    87360
gtggggtcgc cgagcttcgg acggtacgag gccgtccggc aggatccgcg gtcgggcacc    87420
gccctctacc tgccggacgg catcggcctg ggctatgtgg cactcgtgga cgacacctgt    87480
atgaactatc tgtgcacaca cgaatacgtc ccgggcatgg tcatcgacgt cgatgcgctg    87540
gaccccgaac tcgacctgcc ctgggacctg gccgacactc cgatccggtc cgccagggac    87600
gccgcggcgc cgtccctgcg ggcggccgtc tccgcgggga tcctgccgac gtacgaggag    87660
tgcctgcggg tccgtgagcc cctacccgcc gctcttgact gaatgcgttc ccaaaaagcc    87720
ttgccggggt cggggtcgac gccgacgccg acgccggcag ggacaaacgc gtaaaagacc    87780
tgcggcgcca tgaaaacagg gcgccaagga aaaggaacgg ttgcgaagtc ggcccgcaac    87840
cgctcatgca attccggaac tgacagccgc cgccccgctg gacgagaacg gccgagttct    87900
tcgcgcagac cgcgcgcgag gacgccgccc ggcattcccc gccgaccgcg cgccactcgt    87960
ccgactcccc ctgcggctgc accagttgcg cggcgggcgc acttcgggcg gcagcagcac    88020
tcgtggagga cggtctccgc cctccacgag tgcaccgggc gactcggccc cgtgcgaacg    88080
acacacgagc tcggccccgt gcgaccggca cgcgtaccgg gccggtcgca cctgccggaa    88140
cgtcacaccg ccgcgacccc acggaagtcg acccgcgcgg agggctgcgc cagccgcagc    88200
gtgtgggcga tggacgccag cgtcacgtgc cggtgccagc cctggaacga ccgtccttcg    88260
aagtcgcgca tgcccacgcc cacactcacc cgttcgaagt cggcgtccac ctgctcggtg    88320
agcatggcca gccgcaacaa cgcgccgcgg tcccaggacg tgaggtcggt cagccacagg    88380
tcggccgggc gccggcggtt gccccgccac accccatca gcaccagggt ccgcctcggg    88440
accacgcccg gcagcaccac ggcgtgcggg gcgacgagac tgagggagcc ctgccactcc    88500
acggggcgac tcaaccgctt catctgctcc attagttgct gggccgaggt ggtcgcggtg    88560
tggtggtcca ccaggccgcg cccacctgcc gacgccaatt ggaggttccc gcccacacgc    88620
accatgaagg gcagacccac gagactgagc ccacgcacca agcgcggcag aacggcggcg    88680
cgcgcgtcca tcaccacggg tcgcgccgag gtccggctgg cctgggcggc ctcggccacc    88740
aggcgaacga cgttctcctc ctcaccgagc gcaccgggcg cgccgagttg ccgggaaccg    88800
ccgtcgccgc cccggccgcc gcccagcgtc aggtgccagc tgaccggggc gccgtcgcg    88860
cccgaggcca gccacagtcc gtggctctgc tggcagctca ccacccgccc cagatcgggc    88920
acgaaccgcc ggctcacccc gaccgagcgc accccgcct tggagaccac catcggccag    88980
atcacccagg cctcggggtt cagcctgtcg tccacgtagc gggccagcgc ggcccgcacc    89040
gcgcccagt cccaggtcga cccggcgacg aaatggtgca ggctctgctc cgccgcgcct    89100
tctccgacga aggcggcgag gttccgggcg gtcttgcgcc cctgggcggt gagcagcccg    89160
cgtatgtact gctcaccct tctgcgctgg tccgcccggc ggagcgagcc gagtaactcc    89220
```

```
gcacatccct cggagacgag cgagtcgaag tcgtggcccg cggcggggcc cgtcagggc    89280 gccgtaccgg cgggttcaag cgtacgaaat ttcat                              89315

<210> SEQ ID NO 2
<211> LENGTH: 2337
<212> TYPE: DNA
<213> ORGANISM: Streptomyces spiramyceticus WSJ-1

<400> SEQUENCE: 2
ggatcatcac tgacgaatcg aggtcgagga accgagcgtc cgaggaacag aggcgcttat     60
cggttggccg cgagattcct gtcgatcctc tcgtgcagcg cgattccgag ggaaacggaa    120
acgttgagag actcggtctg gctcatcatg gggatggaaa ccgaggcgga agacgcctcc    180
tcgaacaggt cggaaggccc accctttccg ctgccgaaca gcaaggccag ccgatccgga    240
ttgtccccga gttccttcac ggaaatgtcg ccatccgcct tgagcgtcat cagctgcata    300
ccgctgtccc gaatgaaggc gatggcctcc tcgcgaccgg agagaacgac gggaagggag    360
aagacgtaac ctcggctggc cctttggaga cgccggtccg cgatgctggt gatgtcactg    420
tcgaccagga tgatccccga cgctccgagc gcgagcgacg tgcgtactat cgcgccgatg    480
ttcccgacga tcttcacccc gtcgagaacg acgacgtccc cacgccggct cgcgatatcg    540
ccgaacctgg ccgggcgagg gacgcgggcg atgccgaatg tcttggcctt ccgctccccc    600
ttgaacaact ggttgacgat cgaggagtcg atgaggcgga ccgtatgtt ctgccgcccg     660 cacagatcca gcaactcaga tggaaaagga ctgctgtcgc tgccgtagac ctcgatgaac    720
tccaccccgg ccgcgatgct gtgcatgagg ggctcgacgt cctcgatcaa cgttgtcttt    780
atgttggatc gcgacggctt ggtgacatcg atgatccgct gcaccgcggg atcggacgga    840
tttgcgatgt gtccaactc agtcatggtc gtcctaccgg ctgctgtgtt cagtgacgcg     900
attcctgggg tgtgacaccc tacgcgacga tggcggatgg ctgccctgac cggcaatcac    960
caacgcaagg ggaagtcgtc gctctctggc aaagctcccc gctcttcccc gtccgggacc   1020
cgcgcggtcg atccccgcat atgaagtatt cgccttgatc cccggggga ccgtcacaga    1080 tccactagtt ctagaaactc cacgggcgct gacgcacacc ggtgcgggc gcgcccgagg    1140 gcgcgccccg caccggtcgt cccgcgtcgg ctacggagtg ccggacgggg cgggttcgga   1200
cctgggtgtc gagccggcgt ccggggaccg ccgcggccgt cccagggttc gcatgaccgg   1260
cttctccacg aagaagtgca ggaacgccga ctgccccagc gccagcgtga aggcgagcag   1320
ggtcagcccg acgcggccg tgtgtccca ctgccggtaa tagccctgct tcccgccggc     1380
gaagcggtgc ccgtactgga tgatcaggta gtgcacgagg tagaaggcga aggtgagttc   1440
ccccagcagc accatcgtcc tggtccccag ccaggagcgg acgccgcgca catcaccgac   1500
ggccaccgag gcgagcagca gcgcgatcac cgggacggtc aacgcgccgg ggtcgtagtg   1560
gttcggcacc gcgaacgtca ccgcgaacac cgctgagaac agcgcgacgc aggccagggg   1620
acgcgggccc ctccagcgtc cccggatcac gatctgggcc atgagcatcc cgagcacgaa   1680
ctccagcagc cgcaccggcg ggaacatgta gatgaaccac caccgcagct gcggcatgtc   1740
cgggtcccac ggcaggggcg ggctggccgg cagcagcagt gcgaccaggg ggatggagac   1800
ggcggccacg gacaccgcgg cggcccaccg ccagagccgg tccgtacgga ccttggtgaa   1860
gaaggcgaag aggaacggga acatggcgta gaagaacagc tcgcaggaga gcgaccacgc   1920
caccgggttc atgctgccgt actcgtggtg gtcgggaac catgcctgga tcagcagcag   1980
gttcgtgagc agtccgtccc acaccgatcg gcccatgttg ggctcgttga gggccagcac   2040
```

-continued

```
gatcagcagc gtcaccagca gcacgggcag gtgcagcgag tacgcgcgga ccgtgcgccg    2100
ccgccagaag ttcaccttgg acttgtcggg cagacccgcc caggtgagga cgaaaccgct    2160
gagcatgaag aagaacgaga ccgtcagcgg gcccagccgg ttcagcggga actgcagcgc    2220
ggaattgatc tcggtgttct tgaagaacgg ctgtgtcgat atatgggagg tgaataccag    2280
tagagcggag atgaaacgca tcccgccgag cgcgggaaga tgtttcggca ggggcat      2337
```

<210> SEQ ID NO 3
<211> LENGTH: 214
<212> TYPE: PRT
<213> ORGANISM: Streptomyces spiramyceticus WSJ-1

<400> SEQUENCE: 3

Met Glu Ser Arg Gly Gly Asp Glu Ala Asp Tyr Ala Ala Leu His Pro
1               5                   10                  15

Glu Glu Glu Ala Val Val Ala Gln Ala Val Asp Lys Arg Arg Arg Glu
                20                  25                  30

Phe Thr Ala Val Arg Ala Cys Ala Arg Arg Ala Met Glu Lys Leu Gly
            35                  40                  45

Phe Pro Pro Gln Pro Ile Leu Pro Ser Glu Arg Gly Ala Pro Arg Trp
        50                  55                  60

Pro Glu Gly Leu Leu Gly Ser Met Thr His Cys Asp Gly Tyr Arg Ala
65                  70                  75                  80

Ala Ala Leu Val Arg Ala Thr Asp Leu Ala Ser Leu Gly Ile Asp Ala
                85                  90                  95

Glu Pro His Gly Ser Leu Pro Asp Gly Ala Leu His Ser Val Ala Leu
            100                 105                 110

Pro Ala Glu Arg Glu Arg Leu Ala Leu Leu Ala Gly Gln Pro Gly
        115                 120                 125

Val His Trp Asp Arg Leu Leu Phe Ser Ala Lys Glu Ser Val Tyr Lys
130                 135                 140

Ala Trp Phe Pro Leu Thr Gly Lys Trp Leu Gly Phe Glu Glu Ala Tyr
145                 150                 155                 160

Ile Asp Leu His Gln Asp Ser Gly Thr Ala Gln His Gly Arg Phe Arg
                165                 170                 175

Ala Glu Leu Leu Val Pro Gly Pro Leu Val Gly Gly Arg Arg Ile Lys
            180                 185                 190

His Phe Glu Gly Arg Trp Ile Val Arg Glu Gly Leu Val Thr Thr Ala
        195                 200                 205

Leu Thr Val Pro His Pro
    210

<210> SEQ ID NO 4
<211> LENGTH: 200
<212> TYPE: PRT
<213> ORGANISM: Streptomyces spiramyceticus WSJ-1

<400> SEQUENCE: 4

Met Ser Ser His Arg Ala Pro Glu Thr Ala His Arg Ser Arg Arg Ala
1               5                   10                  15

His Arg Ala Ile Leu Gly Ala Thr Leu Glu Leu Val His Glu Val Gly
                20                  25                  30

Tyr Pro Arg Val Thr Ile Glu Gly Val Ala Ala Arg Ala Gly Val Gly
            35                  40                  45

Lys Gln Thr Ile Tyr Arg Arg Trp Pro Ser Lys Ala Ala Ile Leu Arg

```
                   50                  55                  60
Asp Ala Val Val Ser Leu Thr Glu Asp Ile Ala Arg Ala Gly Gly Ala
 65                  70                  75                  80

Val Arg Asp Thr Gly Asp Leu Glu Ala Asp Leu Lys Ala Val Leu Arg
                 85                  90                  95

Ser Ala Val Asp Thr Met Thr Asp Pro Gly Tyr Asp Val Pro Ala Arg
                100                 105                 110

Ala Leu Val Ala Ala Gly Ile Ala Asp Pro Ala Leu Gly Lys Glu Leu
                115                 120                 125

Thr Ala Arg Leu Val Glu Pro Pro Leu Arg Leu Cys Leu Glu Arg Leu
130                 135                 140

Gly Ser Ala Arg Gly Ala Gly Gln Ile Ala Gln Asp Val Asp Pro Arg
145                 150                 155                 160

Ile Ala Val Leu Met Leu Ala Gly Pro Val Ala Gln His Trp Leu Met
                165                 170                 175

Gly Asp Gly Pro Leu Thr His Glu Tyr Thr Asp Ala Leu Val Asp Leu
                180                 185                 190

Ala Leu Arg Gly Leu Ala Pro Arg
                195                 200

<210> SEQ ID NO 5
<211> LENGTH: 282
<212> TYPE: PRT
<213> ORGANISM: Streptomyces spiramyceticus WSJ-1

<400> SEQUENCE: 5

Met Lys Ser Lys Ser Pro Arg Pro Arg Ser Ala Ser Ala Pro Ala
 1               5                  10                  15

Ala Ser Arg Cys Val Ala Arg Arg Glu Trp Gly Gln Asn Phe Phe Arg
                 20                  25                  30

Ala Ala Ala Ala Cys Arg Phe Ser Ala Gln Leu Asp Ser Ser Asp
                 35                  40                  45

Ala Ile Ala Pro Gly Ser Pro Asn Asp Leu Leu Thr Val Glu Ile Gly
 50                  55                  60

Ala Gly Ser Gly Arg Val Thr Lys Ala Leu Ala Ser Thr Gly Ser Pro
 65                  70                  75                  80

Leu Leu Ala Val Glu Ile Asp Thr Gln Trp Ala Arg Arg Leu Ala Ala
                 85                  90                  95

Glu Ser Leu Pro Asp Val Thr Val Asn Glu Asp Phe Leu Thr Leu
                100                 105                 110

Gln Leu Pro Gly Gln Pro Val Arg Leu Ile Gly Asn Leu Pro Phe Val
                115                 120                 125

Ser Gly Thr Lys Ile Leu Arg Arg Cys Leu Glu Leu Gly Pro Asp Arg
            130                 135                 140

Met Arg Gln Gly Val Phe Leu Leu Gln Arg Glu Tyr Val Gly Lys Arg
145                 150                 155                 160

Thr Gly Ala Trp Gly Gly Asn Leu Phe Asn Ala Gln Trp Glu Pro Trp
                165                 170                 175

Tyr Ala Phe Glu Lys Gly Leu Ala Phe Ser Arg Gln Glu Phe Asn Pro
                180                 185                 190

Val Pro Arg Ala Asp Thr Gln Thr Leu Met Val Thr Pro His Arg Lys
                195                 200                 205

Pro Pro Val Pro Trp Arg Glu Thr Ala Tyr Gln Arg Phe Thr Gln
            210                 215                 220
```

```
Gln Val Phe Asp Thr Gly Gln Met Thr Ile Gly Glu Ala Ala Arg Lys
225                 230                 235                 240

Val Leu Arg Arg Gly His Ala Gln Phe Val Arg Gly Ala Gly Val Arg
                245                 250                 255

Pro Ala Asp Arg Val Lys Asp Leu Thr Val Pro Glu Trp Thr Ala Leu
                260                 265                 270

Phe Arg Ala His Gln Arg Thr Ala Asp Cys
                275                 280

<210> SEQ ID NO 6
<211> LENGTH: 408
<212> TYPE: PRT
<213> ORGANISM: Streptomyces spiramyceticus WSJ-1

<400> SEQUENCE: 6

Met Leu His Arg Val Asp Leu Ser Ser Leu Thr Gly Leu Arg Trp Tyr
1               5                   10                  15

Ala Ala Leu Thr Val Phe Ala Cys His Ile Ala Gln Gln Gly Phe Phe
                20                  25                  30

Ala Asp Gln Gln Val Gly Ser Ala Leu Leu His Ile Thr Thr Leu Gly
            35                  40                  45

Ser Met Ala Val Ser Val Phe Phe Ile Leu Ser Gly Phe Val Leu Ala
        50                  55                  60

Trp Ser Ala Arg Asp Glu Asp Ser Thr Pro Thr Phe Trp Arg Arg Arg
65                  70                  75                  80

Ile Ala Lys Ile Tyr Pro Leu His Ile Val Thr Phe Gly Ile Ala Ala
                85                  90                  95

Leu Ile Ile Phe Ser Leu Ser Glu Pro Val Leu Pro Gly Gly Ser Val
                100                 105                 110

Trp Asp Gly Leu Val Pro Asn Ile Leu Leu Val Gln Ser Trp Leu Pro
            115                 120                 125

Asp Ala Ser Leu Ala Ala Ser Phe Asn Thr Pro Ser Trp Ser Leu Ser
130                 135                 140

Cys Glu Leu Ala Phe Tyr Leu Ser Phe Pro Leu Trp Tyr Arg Leu Val
145                 150                 155                 160

Arg Lys Ile Pro Val Gly Arg Leu Trp Trp Cys Ala Ala Gly Ile Ala
                165                 170                 175

Thr Ala Val Met Cys Val Pro Phe Val Thr Gly Leu Leu Pro Ala Ser
                180                 185                 190

Glu Glu Ala Ala Pro Gly Met Pro Leu Asn Glu Val Trp Phe Ala Tyr
            195                 200                 205

Trp Leu Pro Pro Val Arg Met Leu Glu Phe Val Leu Gly Ile Val Met
210                 215                 220

Ala Leu Ile Leu Arg Ala Gly Val Trp Arg Gly Pro Arg Ala Gly Thr
225                 230                 235                 240

Cys Thr Leu Leu Leu Ala Ala Ser Tyr Gly Leu Thr Gln Val Val Pro
                245                 250                 255

Pro Met Phe Thr Leu Ala Ala Cys Ser Ile Val Pro Ala Ala Leu Leu
                260                 265                 270

Ile Thr Ala Leu Ala Asp Ala Asp Val His Gly Arg Arg Thr Gly Leu
            275                 280                 285

Arg Ser Ala Met Leu Val Arg Leu Gly Gln Trp Ser Phe Ala Phe Tyr
290                 295                 300

Leu Val His Phe Met Val Ile Arg Tyr Gly His Arg Leu Met Gly Gly
305                 310                 315                 320
```

```
Glu Ser Gly Tyr Glu Arg Gln Trp Ser Thr Pro Ala Ala Ile Ala Leu
                325                 330                 335

Ser Leu Ala Met Leu Met Val Ala Ile Leu Val Gly Gly Leu Leu His
            340                 345                 350

Thr Val Val Glu Gln Pro Cys Met Arg Leu Phe Gly Ser Arg Thr Pro
            355                 360                 365

Ser Ala Val Pro Lys Pro Gly Thr Ala Pro Ala Pro Arg Ser Ser Pro
370                 375                 380

Gly Pro Asp Val Thr Gly Val Pro Val Val Thr His Thr Pro Asp Val
385                 390                 395                 400

Thr Asn Glu Leu Ser Pro Lys Gly
                405

<210> SEQ ID NO 7
<211> LENGTH: 221
<212> TYPE: PRT
<213> ORGANISM: Streptomyces spiramyceticus WSJ-1

<400> SEQUENCE: 7

Met Ala Asp Gln Thr Ala Leu Ser Pro Ala Leu Leu Glu Tyr Ala Arg
1               5                   10                  15

Ser Val Ala Leu Arg Asp Asp Gly Leu Leu Arg Glu Leu His Gly Val
            20                  25                  30

Thr Ala Gly Leu Pro Gly Gly Arg Ala Met Gln Ile Met Pro Glu Glu
        35                  40                  45

Ala Gln Phe Leu Ala Leu Leu Ile Arg Leu Val Gly Ala Arg Arg Val
50                  55                  60

Leu Glu Ile Gly Thr Phe Thr Gly Tyr Ser Thr Leu Cys Met Ala Arg
65                  70                  75                  80

Ala Leu Pro Ala Asp Gly Arg Ile Val Thr Cys Asp Ile Ser Asp Lys
                85                  90                  95

Trp Pro Gly Val Gly Ala Pro Phe Trp Arg Arg Ala Gly Val Asp Ser
            100                 105                 110

Leu Ile Asp Leu Arg Val Gly Asp Ala Ala Arg Thr Leu Ala Glu Leu
        115                 120                 125

Arg Glu His Glu Gly Asp Gly Val Phe Asp Leu Val Phe Val Asp Ala
130                 135                 140

Asp Lys Thr Gly Tyr Pro His Tyr Tyr Glu Gln Ala Leu Ala Leu Val
145                 150                 155                 160

Arg Pro Gly Gly Leu Val Ala Ile Asp Asn Thr Leu Phe Phe Gly Arg
                165                 170                 175

Val Ala Asp Pro Ala Val Asp Asp Ala Asp Thr Val Ala Val Arg Arg
            180                 185                 190

Leu Asn Asp Leu Leu Arg Asp Asp Glu Arg Val Asp Ile Ala Leu Leu
        195                 200                 205

Thr Ile Ala Asp Gly Ile Thr Leu Ala Arg Arg Glu
210                 215                 220

<210> SEQ ID NO 8
<211> LENGTH: 449
<212> TYPE: PRT
<213> ORGANISM: Streptomyces spiramyceticus WSJ-1

<400> SEQUENCE: 8

Met Pro Glu Ser His Ala Gln Ser Ala Leu Leu Ala Ala Ile Thr Ala
1               5                   10                  15
```

```
Pro Asp Arg Thr Pro Glu Asp Ile Ala Ala Leu Arg Leu Pro Glu Ser
            20                  25                  30

Phe Arg Ala Val Thr Val Arg Lys Glu Asp Thr Asp Met Phe Arg Gly
            35                  40                  45

Met Thr Ser Thr Asp Lys Asp Pro Arg Lys Ser Leu Arg Val Asp Glu
 50                  55                  60

Val Pro Leu Pro Glu Leu Gly Pro Gly Glu Ala Leu Ile Ala Val Met
 65                  70                  75                  80

Ala Ser Ser Val Asn Tyr Asn Thr Val Trp Ser Ser Ile Phe Glu Pro
                85                  90                  95

Leu Pro Thr Phe Gly Phe Leu Glu Arg Tyr Gly Arg Thr Ser Pro Ser
            100                 105                 110

Ala Ala Arg His Asp Leu Pro Tyr His Ile Leu Gly Ser Asp Leu Ala
            115                 120                 125

Gly Val Val Leu Arg Thr Gly Pro Gly Val Asn Val Trp Lys Pro Gly
130                 135                 140

Asp Glu Val Val Ala His Cys Leu Ser Val Glu Leu Glu Ser Ala Asp
145                 150                 155                 160

Gly His Asp Asp Thr Met Leu Asp Pro Ala Gln Arg Ile Trp Gly Phe
                165                 170                 175

Glu Thr Asn Phe Gly Leu Ala Glu Val Ala Leu Val Lys Ser Asn
            180                 185                 190

Gln Leu Met Pro Lys Ala Ala His Leu Thr Trp Glu Ala Ala Ala
            195                 200                 205

Pro Gly Leu Val Asn Ser Thr Ala Tyr Arg Gln Leu Val Ser Arg Asn
210                 215                 220

Gly Ala Gly Met Lys Gln Gly Asp Asn Val Leu Ile Trp Gly Ala Ser
225                 230                 235                 240

Gly Gly Leu Gly Ser Tyr Ala Thr Gln Leu Ala Leu Ala Gly Gly Ala
                245                 250                 255

Asn Pro Val Cys Val Val Ser Ser Glu Arg Lys Ala Gln Val Cys Arg
            260                 265                 270

Ala Met Gly Ala Glu Ala Ile Ile Asp Arg Ser Ala Glu Asp Tyr Arg
            275                 280                 285

Phe Trp Thr Asp Glu Asp Thr Gln Asn Pro Arg Glu Trp Lys Arg Phe
290                 295                 300

Gly Gly Arg Ile Arg Glu Leu Thr Gly Gly Glu Asp Val Asp Ile Val
305                 310                 315                 320

Phe Glu His Pro Gly Arg Glu Thr Phe Gly Ala Ser Val Tyr Val Thr
            325                 330                 335

Arg Arg Gly Gly Thr Ile Val Thr Cys Ala Ser Thr Ser Gly Phe Arg
            340                 345                 350

His Glu Phe Asp Asn Arg Tyr Leu Trp Met His Leu Lys Arg Ile Val
            355                 360                 365

Gly Thr His Phe Ala Asn Tyr Arg Glu Ala Trp Glu Ala Asn Arg Leu
            370                 375                 380

Val Ala Lys Gly Lys Ile His Pro Thr Leu Ser Cys Thr Tyr Pro Leu
385                 390                 395                 400

Ala Asp Thr Ala Leu Ala Val His Asp Val His Ser Asn Leu His Gln
                405                 410                 415

Gly Lys Val Gly Val Leu Cys Leu Ala Pro Thr Glu Gly Leu Gly Val
            420                 425                 430
```

```
Arg Asp Glu Glu Lys Arg Ala Lys His Ile Asp Ala Ile Asn Arg Phe
            435                 440                 445

Arg
```

<210> SEQ ID NO 9
<211> LENGTH: 421
<212> TYPE: PRT
<213> ORGANISM: Streptomyces spiramyceticus WSJ-1

<400> SEQUENCE: 9

```
Met Arg Val Leu Leu Thr Ser Leu Ala His Asn Thr His Tyr Tyr Ser
1               5                   10                  15

Leu Val Pro Leu Ala Trp Ala Leu Arg Ala Ala Gly His Glu Val Arg
            20                  25                  30

Val Ala Ser Pro Pro Ser Leu Thr Asp Val Ile Thr Ser Thr Gly Leu
        35                  40                  45

Thr Ala Val Pro Val Gly Asp Asp Arg Pro Ala Ala Glu Leu Leu Ala
    50                  55                  60

Glu Met Gly Ser Asp Leu Val Pro Tyr Gln Arg Gly Phe Glu Phe Gly
65                  70                  75                  80

Glu Val Glu Ser Glu Glu Glu Thr Thr Trp Glu Tyr Leu Leu Gly Gln
                85                  90                  95

Gln Ser Met Met Ala Ala Leu Cys Phe Ala Pro Phe Asn Gly Ala Ala
            100                 105                 110

Thr Met Asp Glu Ile Val Asp Phe Ala Arg Gly Trp Arg Pro Asp Leu
        115                 120                 125

Val Val Trp Glu Pro Trp Thr Tyr Ala Gly Pro Val Ala Ala Arg Ala
    130                 135                 140

Cys Gly Ala Ala His Ala Arg Ile Leu Trp Gly Pro Asp Ala Ile Gly
145                 150                 155                 160

Arg Ser Arg Arg Arg Phe Leu Ala Ala Leu Glu Gln Val Pro Glu Glu
                165                 170                 175

Leu Arg Glu Asp Pro Ile Ala Glu Trp Leu Gly Trp Thr Leu Asp Arg
            180                 185                 190

Tyr Gly Tyr Ala Phe Asp Glu Arg Asp Val Leu Gly His Trp Val Ile
        195                 200                 205

Asp Pro Gly Pro Arg Ser Thr Arg Leu Asp Leu Gly Gln Thr Met Val
    210                 215                 220

Pro Met Cys Tyr Val Pro Tyr Asn Gly Arg Ser Val Ile Glu Pro Trp
225                 230                 235                 240

Leu Ala Lys Lys Pro Asp Arg Pro Arg Val Cys Leu Thr Leu Gly Val
                245                 250                 255

Ser Ala Arg Glu Thr Tyr Gly Arg Asp Ala Val Ser Tyr Ser Glu Leu
            260                 265                 270

Leu Glu Ala Leu Gly Arg Leu Asp Ile Glu Val Val Ala Thr Leu Asp
        275                 280                 285

Ala Ser Gln Arg Glu Arg Leu Gly Val Leu Pro Asp Asn Val Val Pro
    290                 295                 300

Val Asp Phe Val Pro Leu Asp Ala Leu Leu Pro Ser Cys Ala Ala Ile
305                 310                 315                 320

Ile His His Gly Gly Ala Gly Thr Trp Ser Thr Ala Leu Leu His Gly
                325                 330                 335

Val Pro Gln Ile Leu Leu Pro Ser Leu Trp Asp Ala Pro Leu Lys Ala
            340                 345                 350
```

Gln Gln Leu Gln Arg Leu Ser Ala Gly Phe Asp Leu Pro Ala Ala Thr
            355                 360                 365

Leu Thr Ala Arg Gly Leu Ala Asp Ala Val His Thr Ala Val His Asp
    370                 375                 380

Pro Ala Ile Lys Ala Gly Ala Arg Arg Leu Ser Glu Glu Met Leu Ala
385                 390                 395                 400

Asp Pro Thr Pro Ala Gly Ile Val Pro Thr Leu Glu Arg Leu Thr Ala
                405                 410                 415

Leu His Arg Ala Thr
            420

<210> SEQ ID NO 10
<211> LENGTH: 415
<212> TYPE: PRT
<213> ORGANISM: Streptomyces spiramyceticus WSJ-1

<400> SEQUENCE: 10

Met Glu Pro Ala Pro Ala Ser Ala Gly Thr Arg Glu Leu Gly Arg Arg
1               5                   10                  15

Leu Gln Leu Thr Arg Ala Ala His Trp Cys Ala Gly Asn Gln Gly Asp
            20                  25                  30

Pro Tyr Ala Leu Ile Leu Arg Ala Val Ser Asp Pro Glu Pro Leu Glu
        35                  40                  45

Arg Glu Ile Cys Ala Ala Gly Pro Trp Phe His Ser Glu Leu Leu Gly
    50                  55                  60

Ala Trp Val Thr Ala Asp Pro Glu Val Ala Ala Val Leu Ala Asp
65                  70                  75                  80

Pro Arg Phe Gly Thr Leu Asp Arg Ala Gly Arg Arg Pro Asp Glu Glu
                85                  90                  95

Leu Leu Pro Leu Ala Glu Ala Phe Pro Arg His Glu Arg Ala Glu Leu
            100                 105                 110

Val Arg Leu Arg Ala Leu Ala Asp Pro Val Leu Asn Arg Cys Ala Pro
        115                 120                 125

Ala Glu Ala Pro Cys Ala Ala Arg Thr Thr Ala Arg Arg Val Leu Arg
    130                 135                 140

Arg Leu Leu Pro Thr Gly Gly Ala Gly Phe Asp Leu Val Thr Glu Val
145                 150                 155                 160

Ala Arg Pro Tyr Ala Val Glu Leu Val Leu Gly Phe Leu Gly Val Pro
                165                 170                 175

Asp Arg Asp Arg Asp Ala Ala Ala Arg Ala Leu Ala Ala Cys Ala Pro
            180                 185                 190

Gln Leu Asp Ala Arg Leu Ala Pro Gln Ile Leu Ala Val Ala Arg Glu
        195                 200                 205

Ser Ala Asp Ala Val Arg Thr Leu Ala Asp Leu Val Pro Glu Leu Val
    210                 215                 220

Ala Glu Lys Leu Arg Ala Val Glu Ser Gly Gly Pro Arg Pro Asp Asp
225                 230                 235                 240

Val Leu Ala Leu Leu Leu Arg Asp Gly Val Ala Pro Arg Asp Val Glu
                245                 250                 255

Arg Ile Ala Leu Val Leu Ala Ile Gly Ala Pro Glu Pro Ala Ala Thr
            260                 265                 270

Ala Val Ala His Thr Val His Arg Leu Leu Gly Arg Pro Gly Glu Trp
        275                 280                 285

Glu Arg Ala Arg Arg Thr Pro Ala Ala Ala Arg Ala Val Glu Gln Thr
    290                 295                 300

```
Leu Arg His Arg Pro Pro Ala Arg Leu Glu Ser Arg Val Ala His Thr
305                 310                 315                 320

Asp Leu Glu Leu Gly Gly Arg Arg Ile Ala Ala Asp Glu His Ile Val
            325                 330                 335

Val Leu Ala Ala Ala Gly Arg Glu Thr Pro Gly Pro Glu Pro Leu Gly
        340                 345                 350

Gly Pro Asp Gly Pro His Leu Ala Leu Ala Leu Pro Leu Ile Arg Leu
    355                 360                 365

Ala Thr Thr Thr Ala Val Gln Val Met Ala Gly Arg Leu Pro Gly Leu
370                 375                 380

Arg Ala Glu Gly Ala Pro Leu Thr Arg Pro Arg Ser Pro Val Val Gly
385                 390                 395                 400

Ala Cys Ala Arg Leu Arg Val His Pro Gly Arg Val His Pro Gly
                405                 410                 415

<210> SEQ ID NO 11
<211> LENGTH: 237
<212> TYPE: PRT
<213> ORGANISM: Streptomyces spiramyceticus WSJ-1

<400> SEQUENCE: 11

Met Tyr Ala Asn Asp Ile Ala Ala Val Tyr Asp Leu Val His Glu Gly
1               5                   10                  15

Lys Gly Lys Asp Tyr Arg Gln Glu Ala Glu Ile Ala Ala Leu Val
            20                  25                  30

Arg Val His Arg Pro Asp Thr Arg Ser Leu Leu Asp Val Ala Cys Gly
        35                  40                  45

Thr Gly Gln His Leu Arg His Leu Asp Gly Leu Phe Asp His Val Glu
    50                  55                  60

Gly Leu Glu Leu Ser His Asp Met Leu Ala Leu Ala Thr Asp Arg Asn
65                  70                  75                  80

Pro Gly Val Thr Phe His Glu Gly Asp Met Arg Ser Phe Ala Leu Gly
                85                  90                  95

Arg Arg Phe Asp Ala Val Ile Cys Met Phe Ser Ser Ile Gly His Leu
            100                 105                 110

Arg Thr Thr Asp Glu Leu Asp Ser Thr Leu Arg Ser Phe Thr Asp His
        115                 120                 125

Leu Glu Pro Gly Gly Val Ile Val Glu Pro Trp Trp Phe Pro Ser
    130                 135                 140

Ser Phe Thr Pro Gly Tyr Val Gly Ala Ser Val Thr Glu Ala Gly Glu
145                 150                 155                 160

Arg Thr Ile Cys Arg Val Ser His Ser Val Arg Glu Gly Asn Ala Thr
                165                 170                 175

Arg Ile Glu Val His Tyr Leu Val Ala Glu Pro Gly Gly Gly Ile Arg
            180                 185                 190

His Leu Thr Glu Asp His Ala Ile Thr Leu Phe Pro Arg Ala Asp Tyr
        195                 200                 205

Glu Ala Ala Phe Glu Arg Ala Gly Cys Asp Val Val Tyr Gln Glu Gly
    210                 215                 220

Gly Pro Ser Gly Arg Gly Leu Phe Ile Gly Thr Arg Arg
225                 230                 235

<210> SEQ ID NO 12
<211> LENGTH: 1890
<212> TYPE: PRT
```

<213> ORGANISM: Streptomyces spiramyceticus WSJ-1

<400> SEQUENCE: 12

```
Met Ser Pro Ser Met Asp Glu Val Leu Gly Ala Leu Arg Thr Ser Val
1               5                   10                  15

Lys Glu Thr Glu Arg Leu Arg Arg His Asn Arg Glu Leu Leu Ala Ala
            20                  25                  30

Ala His Glu Pro Val Ala Ile Val Gly Met Ala Cys Arg Tyr Pro Gly
        35                  40                  45

Gly Val Thr Thr Pro Asp Asp Leu Trp Glu Leu Ala Ala Asp Gly Val
    50                  55                  60

Asp Ala Ile Thr Arg Phe Pro Ala Asp Arg Gly Trp Asp Glu Ala Ala
65                  70                  75                  80

Val Tyr Ser Pro Asp Pro Asp Thr Pro Gly Thr Thr Tyr Cys Arg Glu
                85                  90                  95

Gly Gly Phe Leu Thr Gly Val Gly Asp Phe Asp Ala Ala Phe Phe Gly
            100                 105                 110

Val Ser Pro Asn Glu Ala Leu Val Met Asp Pro Gln Gln Arg Leu Leu
        115                 120                 125

Leu Glu Thr Ser Trp Glu Ala Leu Glu Arg Ala Gly Val Val Pro Ala
    130                 135                 140

Ser Leu Arg Gly Ser Arg Thr Gly Val Phe Val Gly Ala Ala His Thr
145                 150                 155                 160

Gly Tyr Val Ala Asp Thr Ala Arg Ala Pro Glu Gly Thr Glu Gly Tyr
                165                 170                 175

Leu Leu Thr Gly Asn Ala Asp Ala Val Met Ser Gly Arg Ile Ala Tyr
            180                 185                 190

Thr Leu Gly Leu Glu Gly Pro Ala Leu Thr Ile Glu Thr Ala Cys Ser
        195                 200                 205

Ser Ser Leu Val Ala Leu His Leu Ala Val Gln Ser Leu Arg Arg Gly
    210                 215                 220

Glu Cys Asp Leu Ala Leu Ala Gly Gly Val Ala Val Met Pro Asp Pro
225                 230                 235                 240

Thr Val Phe Val Glu Phe Ser Arg Gln Arg Gly Leu Ala Ser Asp Gly
                245                 250                 255

Arg Cys Lys Ala Phe Ala Glu Gly Ala Asp Gly Thr Val Trp Ala Glu
            260                 265                 270

Gly Val Gly Val Leu Leu Val Glu Arg Leu Ser Asp Ala Arg Arg Tyr
        275                 280                 285

Gly His Arg Val Leu Ala Val Val Arg Gly Ser Ala Val Asn Gln Asp
    290                 295                 300

Gly Ala Ser Asn Gly Leu Thr Ala Pro Ser Gly Pro Ala Gln Arg Arg
305                 310                 315                 320

Val Ile Arg Glu Ala Leu Ala Asp Ala Gly Leu Ala Pro Gly Asp Val
                325                 330                 335

Asp Ala Val Glu Ala His Gly Thr Gly Thr Ala Leu Gly Asp Pro Ile
            340                 345                 350

Glu Ala Gly Ala Leu Leu Ala Thr Tyr Gly Arg Glu Arg Val Gly Asp
        355                 360                 365

Pro Leu Trp Leu Gly Ser Leu Lys Ser Asn Ile Gly His Ala Gln Ala
    370                 375                 380

Ala Ala Gly Val Gly Gly Val Ile Lys Met Val Glu Ala Met Arg His
385                 390                 395                 400
```

```
Ser Ser Leu Pro Arg Thr Leu His Val Asp Ala Pro Ser Ser Lys Val
                405                 410                 415

Glu Trp Gly Ser Gly Ser Val Glu Leu Leu Thr Glu Ala Arg Ser Trp
            420                 425                 430

Pro Arg Arg Ala Gly Arg Val Arg Ala Ala Val Ser Ala Phe Gly
            435                 440                 445

Val Ser Gly Thr Asn Ala His Val Val Ile Glu Glu Pro Ser Glu
450                 455                 460

Ala Asp Gly Ser Asp Gly Pro Ala Pro Asp Arg Ile Thr Ala Ala
465                 470                 475                 480

Thr Pro Leu Pro Trp Val Ile Ser Ala Arg Ser Glu Glu Ala Leu Arg
                485                 490                 495

Gly Gln Ala Asp Arg Leu Ala Ala Leu Ala Arg Arg Gly Pro Thr Glu
                500                 505                 510

Asp Thr Asp Ala Asp Leu Thr Thr Ala Val Asp Leu Gly Tyr Ser Leu
                515                 520                 525

Ala Thr Thr Arg Glu Ala Leu Glu His Arg Ala Val Ala Leu Val His
                530                 535                 540

Asp Ala Arg Ala Ala Arg Glu Asp Leu Ala Ala Leu Ala Ala Gly Arg
545                 550                 555                 560

Thr Pro Glu Asn Met Val Thr Gly Val Ala Arg Gly Arg Gly Ile
                565                 570                 575

Ala Phe Leu Cys Ser Gly Gln Gly Ala Gln Arg Leu Gly Ala Gly Gln
                580                 585                 590

Glu Leu Arg Arg Arg Phe Pro Val Phe Ala Asp Ala Leu Asp Glu Ile
                595                 600                 605

Ala Ala Glu Phe Asp Ala His Leu Glu Arg Pro Leu Leu Ser Val Met
610                 615                 620

Phe Ala Glu Pro Ser Ala Pro Asp Ala Thr Leu Leu Asp Arg Thr Asp
625                 630                 635                 640

Tyr Thr Gln Pro Ala Leu Phe Ala Val Glu Thr Ala Leu Phe Arg Leu
                645                 650                 655

Phe Glu Ser Trp Gly Leu Val Pro Asp Val Leu Val Gly His Ser Ile
            660                 665                 670

Gly Gly Leu Val Ala Ala His Ala Ala Gly Val Phe Ser Ala Ala Asp
            675                 680                 685

Ala Ala Arg Leu Val Ala Ala Arg Gly Arg Leu Met Arg Ala Leu Pro
            690                 695                 700

Glu Gly Gly Ala Met Ala Ala Val Gln Ala Thr Glu Arg Glu Val Ala
705                 710                 715                 720

Ala Leu Glu Pro Val Val Ala Gly Gly Ala Val Ile Ala Ala Val Asn
                725                 730                 735

Gly Pro Gln Ala Leu Val Leu Ser Gly Asp Glu Ala Ala Val Leu Ala
                740                 745                 750

Ala Ala Gly Glu Leu Ala Ala Arg Gly Arg Thr Lys Arg Leu Arg
            755                 760                 765

Val Ser His Ala Phe His Ser Pro Arg Met Asp Ala Met Leu Ala Asp
770                 775                 780

Phe Arg Val Ile Ala Glu Thr Val Asp Tyr His Ala Pro Arg Leu Pro
785                 790                 795                 800

Val Val Ser Glu Val Thr Gly Glu Leu Ala Thr Ala Ala Gln Leu Arg
                805                 810                 815

Asp Pro Gly Tyr Trp Thr Arg Gln Val Arg Glu Pro Val Arg Phe Ala
```

```
            820                 825                 830
Asp Ala Val Arg Thr Ala Arg Ala Arg Asp Ala Thr Thr Phe Ile Glu
            835                 840                 845
Leu Gly Pro Asp Ala Val Leu Ser Gly Met Ala Glu Glu Ser Leu Ala
            850                 855                 860
Asp Glu Ala Asp Thr Val Phe Ala Pro Ala Leu Arg Arg Gly Arg Pro
865                 870                 875                 880
Glu Gly Asp Thr Ala Leu Arg Ala Ala Arg Ala Phe Val Arg Gly
                885                 890                 895
Ala Asp Leu Asp Trp Ser Ala Leu Tyr Ser Gly Thr Gly Ala Arg Arg
            900                 905                 910
Thr Asp Leu Pro Thr Tyr Ala Phe Gln His Ser Arg Tyr Trp Leu Ala
            915                 920                 925
Pro Thr Ala Ala Ser Pro Thr Val Ala Pro Ala Thr Ser Ala Pro Ser
            930                 935                 940
Ala Gly Pro Val Ala Glu Ala Glu Gln Asp Asp Ala Leu Trp Ala Ala
945                 950                 955                 960
Val His Ala Gly Asp Ala Ala Ser Ala Ala Arg Leu Gly Ala Asp
                965                 970                 975
Gly Ala Gly Ile Glu Ser Gln Leu Gln Ala Val Leu Pro His Leu Ala
            980                 985                 990
Ala Trp His Asp Arg Arg Thr Thr Ala Gln Thr Ala Gly Leu Arg
            995                 1000                1005
Tyr Arg Val Ala Trp Gln Ala Ile Ala Pro Asp Ala Val Arg Phe Ser
    1010                1015                1020
Pro Ser Asp Arg Trp Leu Met Val Glu His Gly Gln Cys Thr Asp Ser
1025                1030                1035                1040
Ala Asp Ala Ala Glu Arg Ala Leu Arg Ala Ala Gly Ala Glu Val Ile
                1045                1050                1055
Arg Leu Val Arg Pro Leu Gly Gln Ala Ala Gly Ala Pro Arg Thr Asp
            1060                1065                1070
Ala Leu Asp Arg Asp Ala Leu Ala Ala Arg Leu Ala Glu Leu Ala Arg
            1075                1080                1085
Ser Pro Glu Ser Leu Ala Gly Val Leu Leu Pro Asp Thr Gly Gly
            1090                1095                1100
Ala Thr Leu Ala Gly His Pro Gly Leu Asp Glu Gly Thr Thr Ala Val
1105                1110                1115                1120
Leu Leu Met Val Gln Ala Met Ala Asp Ala Ala Val Glu Thr Pro Leu
                1125                1130                1135
Trp Val Ala Thr Arg Gly Ala Val Ala Val Gly Pro Gly Glu Val Pro
            1140                1145                1150
Cys Ala Met Gly Ala Arg Val Trp Gly Leu Gly Arg Val Ala Ala Leu
            1155                1160                1165
Glu Ala Pro Val Gln Trp Gly Gly Leu Val Asp Leu Pro Ala Glu Pro
            1170                1175                1180
Gly Gly Arg Asp Trp Arg Arg Leu Ala Ala Val Val Ser Gly Arg Gly
1185                1190                1195                1200
Gly Glu Asp Gln Val Ala Ile Arg Gly Ser Gly Leu Phe Gly Arg Arg
                1205                1210                1215
Leu Leu Pro Ala Ala Val Pro Ser Ala Ser Arg Ser Trp Arg Pro Arg
            1220                1225                1230
Gly Cys Val Leu Val Thr Gly Gly Leu Gly Gly Val Gly Gly His Val
            1235                1240                1245
```

-continued

```
Ala Arg Trp Leu Ala Arg Gly Gly Ala Glu His Val Val Leu Ala Gly
        1250                1255                1260

Arg Arg Gly Gly Gly Ala Pro Gly Ala Val Glu Leu Glu Arg Glu Leu
1265                1270                1275                1280

Val Gly Leu Gly Ala Lys Val Thr Phe Val Ala Cys Asp Val Ala Asp
                1285                1290                1295

Arg Ala Ser Val Val Gly Leu Leu Gly Val Glu Gly Leu Gly Val
                1300                1305                1310

Pro Leu Cys Gly Val Phe His Ala Ala Gly Val Ala Gln Val Ser Ala
            1315                1320                1325

Leu Gly Glu Val Ser Leu Ala Glu Ala Ala Gly Val Leu Ala Gly Lys
        1330                1335                1340

Ala Val Gly Ala Glu Leu Leu Asp Glu Leu Thr Ala Gly Val Asp Leu
1345                1350                1355                1360

Asp Val Phe Val Leu Phe Ser Ser Gly Ala Ala Val Trp Gly Ser Gly
                1365                1370                1375

Gly Gln Ser Val Tyr Ala Ala Ala Asn Ala His Leu Asp Ala Leu Ala
                1380                1385                1390

Glu Arg Arg Arg Ala Gln Gly Arg Pro Ala Thr Ser Val Ala Trp Gly
            1395                1400                1405

Val Trp Asp Gly Gly Met Gly Glu Met Ala Pro Glu Gly Tyr Leu
        1410                1415                1420

Ala Arg His Gly Leu Val Pro Leu Arg Pro Glu Thr Ala Leu Thr Ala
1425                1430                1435                1440

Leu His Gln Ala Val Asp Ser Gly Asp Ala Thr Val Thr Val Ala Asp
                1445                1450                1455

Leu Asp Trp Glu Arg Phe Ala Pro Gly Phe Thr Ala Phe Arg Pro Ser
            1460                1465                1470

Pro Leu Ile Ser Gly Ile Pro Val Ala Arg Thr Ala Leu Ala Ala Ala
            1475                1480                1485

Gly Gln Pro Ala Asp Asp Thr Pro Thr Ala Pro Asp Leu Val Arg Ala
            1490                1495                1500

Arg Pro Glu Asp Arg Pro Arg Leu Ala Leu Glu Leu Val Leu Arg His
1505                1510                1515                1520

Ile Ala Ala Val Leu Gly His Thr Glu Glu Asn Arg Gly Asp Ala Gln
                1525                1530                1535

Ala Pro Phe Arg Asp Ile Gly Phe Asp Ser Leu Ala Ala Val Arg Leu
            1540                1545                1550

Arg Gly Arg Leu Ala Glu Asp Thr Gly Leu Asp Leu Pro Ser Thr Leu
        1555                1560                1565

Val Phe Asp His Glu Asp Pro Thr Ala Leu Ala His His Leu Ala Gly
    1570                1575                1580

Leu Ala Asp Ala Gly Ala Thr Gly Arg His Glu Ser Ala Val Pro Ala
1585                1590                1595                1600

Glu Ser Gly Leu Leu Ala Ser Phe Arg Ala Ala Val Glu Gln Ser Arg
            1605                1610                1615

Ser Gly Glu Ala Val Glu Leu Met Ala Ser Leu Ala Ala Phe Arg Pro
            1620                1625                1630

Ala Tyr Ser Arg Glu Gln Pro Gly Ser Ala Arg Pro Ala Pro Val Leu
            1635                1640                1645

Leu Ala Thr Gly Pro Thr Thr His Pro Thr Leu Tyr Cys Cys Ala Gly
        1650                1655                1660
```

```
Thr Ala Val Gly Ser Gly Pro Gly Glu Tyr Val Pro Phe Ala Glu Gly
1665                1670                1675                1680

Leu Arg Asp Ser Arg Glu Thr Val Val Leu Pro Leu Ser Gly Phe Gly
                1685                1690                1695

Gly Pro Ala Glu Pro Leu Pro Ala Ser Leu Asp Ala Leu Leu Asp Val
            1700                1705                1710

Gln Ala Asp Val Leu Leu Glu His Ala Ala Gly Lys Pro Phe Ala Leu
        1715                1720                1725

Ala Gly His Ser Ala Gly Ala Asn Val Ala His Ala Leu Ala Ala Arg
    1730                1735                1740

Leu Glu Glu Arg Gly Thr Gly Pro Thr Ala Val Leu Met Asp Val
1745                1750                1755                1760

Tyr Arg Pro Glu Asp Pro Gly Ala Met Gly Val Trp Arg Asp Leu
                1765                1770                1775

Leu Ser Arg Ala Leu Glu Arg Ser Thr Val Pro Leu Glu Asp His Arg
            1780                1785                1790

Leu Thr Ala Met Ala Gly Tyr His Arg Leu Leu Gly Ala Arg Leu
        1795                1800                1805

Thr Ala Leu Asn Ala Pro Val Leu Leu Val Arg Ala Ser Glu Pro Leu
1810                1815                1820

Arg Glu Trp Pro Val Gly Glu Ala Gln Gly Asp Trp Arg Ser Arg Val
1825                1830                1835                1840

Pro Phe Ala Arg Thr Val Ala Asp Val Pro Gly Asn His Phe Thr Met
                1845                1850                1855

Leu Thr Glu His Ala Arg His Thr Ala Ser Val Val His Asp Trp Leu
            1860                1865                1870

Glu Ala Val Pro His Pro Ala Gly Pro Pro Ala Leu Leu Thr Gly Gly
        1875                1880                1885

Glu His
    1890

<210> SEQ ID NO 13
<211> LENGTH: 1582
<212> TYPE: PRT
<213> ORGANISM: Streptomyces spiramyceticus WSJ-1

<400> SEQUENCE: 13

Met Ala Asn Glu Glu Lys Leu Arg Ala Tyr Leu Lys Arg Val Thr Gly
1               5                   10                  15

Glu Leu His Arg Ala Thr Glu Gln Leu Arg Thr Leu Asp Glu Arg Ala
            20                  25                  30

His Glu Pro Ile Ala Ile Val Gly Ala Ala Cys Arg Leu Pro Gly Gly
        35                  40                  45

Val Arg Ser Pro Asp Glu Leu Trp Asp Leu Leu Ala Gly Thr Asp
    50                  55                  60

Ala Val Ser Leu Ala Pro Ala Asp Arg Gly Trp Asp Val Glu Ala Met
65                  70                  75                  80

Tyr Ser Pro Asp Pro Asp Thr Pro Gly Thr Thr Tyr Cys Arg Glu Gly
                85                  90                  95

Gly Phe Val Gln Gly Ala Asp Arg Phe Asp Pro Gly Leu Phe Gly Ile
            100                 105                 110

Ser Pro Asn Glu Ala Leu Thr Met Asp Pro Gln Gln Arg Leu Leu Leu
        115                 120                 125

Glu Thr Ser Trp Glu Ala Leu Glu Arg Ala Gly Leu Asp Pro Gln Ser
    130                 135                 140
```

```
Leu Ala Gly Ser Arg Thr Gly Val Phe Ala Gly Ala Trp Glu Ser Gly
145                 150                 155                 160

Tyr Gln Lys Gly Val Glu Gly Leu Glu Ala Glu Leu Glu Ala Gln Leu
                165                 170                 175

Leu Ala Gly Ile Val Ser Phe Thr Ala Gly Arg Val Ala Tyr Ala Leu
                180                 185                 190

Gly Leu Glu Gly Pro Ala Leu Thr Ile Asp Thr Ala Cys Ser Ser Ser
                195                 200                 205

Leu Val Ala Leu His Leu Ala Val Gln Ser Leu Arg Arg Gly Glu Cys
                210                 215                 220

Asp Leu Ala Leu Ala Gly Gly Ala Thr Val Ile Ala Asp Phe Ala Leu
225                 230                 235                 240

Phe Thr Gln Phe Ser Arg Gln Arg Gly Leu Ala Pro Asp Gly Arg Cys
                245                 250                 255

Lys Ala Phe Ala Glu Ala Ala Asp Gly Phe Gly Pro Ala Glu Gly Ala
                260                 265                 270

Gly Met Leu Leu Val Glu Arg Leu Ser Glu Ala Gln Lys Lys Gly His
                275                 280                 285

Pro Val Leu Ala Val Val Arg Gly Ser Ala Val Asn Gln Asp Gly Ala
                290                 295                 300

Ser Asn Gly Leu Thr Ala Pro Ser Gly Pro Ala Gln Gln Lys Val Ile
305                 310                 315                 320

Arg Asp Ala Leu Ala Asp Ala Gly Leu Thr Pro Ala Asp Val Asp Ala
                325                 330                 335

Val Glu Ala His Gly Thr Gly Thr Pro Leu Gly Asp Pro Ile Glu Ala
                340                 345                 350

Ser Ala Leu Met Ala Thr Tyr Gly Arg Glu Arg Ala Gly Asp Pro Leu
                355                 360                 365

Trp Leu Gly Ser Leu Lys Ser Asn Ile Gly His Thr Gln Ala Ala Ala
                370                 375                 380

Gly Val Ala Gly Val Ile Lys Met Val Glu Ala Met Arg His Gly Thr
385                 390                 395                 400

Leu Pro Arg Thr Leu His Ala Thr Ala Ser Ser Lys Ile Glu Trp
                405                 410                 415

Gly Ala Gly Ala Val Glu Leu Leu Ala Glu Ala Arg Pro Trp Pro Gln
                420                 425                 430

Arg Ala Asp Gly Pro Arg Arg Ala Ala Ile Ser Ser Phe Gly Ile Ser
                435                 440                 445

Gly Thr Asn Ala His Ile Val Val Glu Glu Ala Pro Thr Ala Arg Ala
                450                 455                 460

Glu Pro Glu Glu Pro Glu Glu Pro Pro Val Ser Pro Thr Thr Val Leu
465                 470                 475                 480

Pro Leu Ser Ala Ala Gly Ala Gln Pro Leu Arg Glu Gln Ala Arg Arg
                485                 490                 495

Leu Ala Ala His Leu Ala Asp His Glu Ile Thr Ala Ala Asp Ala
                500                 505                 510

Ala Tyr Ser Ala Ala Thr Thr Arg Ala Ala Leu Ser Asn Arg Ala Ser
                515                 520                 525

Val Leu Ala Asp Asp Arg Glu Ser Leu Ile Ala Arg Leu Thr Ala Leu
                530                 535                 540

Ala Glu Gly Arg Arg Asp Val Asp Val Ala Val Gly Glu Ala Gly Ser
545                 550                 555                 560
```

```
Gly Arg Pro Pro Val Phe Val Phe Pro Gly Gln Gly Ser Gln Trp Thr
            565                 570                 575

Gly Met Gly Ala Glu Leu Leu Glu Ser Ala Pro Ala Phe Arg Val Lys
        580                 585                 590

Ala Glu Glu Cys Ala Arg Ala Leu Ala Ala His Leu Asp Trp Ser Val
    595                 600                 605

Leu Asp Val Leu Arg Gly Gly Pro Asp Ala Pro Pro Ile Asp Arg Ala
    610                 615                 620

Asp Val Val Gln Pro Thr Leu Phe Thr Met Met Val Ser Leu Ala Ala
625                 630                 635                 640

Leu Trp Glu Ala His Gly Val Arg Pro Ala Val Val Gly His Ser
                645                 650                 655

Gln Gly Glu Val Ala Ala Ala Tyr Ala Ala Gly Ala Leu Ser Leu Asp
            660                 665                 670

Asp Ala Ala Arg Val Ile Ala Glu Arg Ser Arg Leu Trp Gly Arg Leu
            675                 680                 685

Ala Gly Asn Gly Gly Met Val Ser Val Met Ala Pro Ala Asp Arg Val
    690                 695                 700

Arg Glu Leu Leu Glu Pro Trp Ala Glu Arg Ile Ser Val Ala Ala Val
705                 710                 715                 720

Asn Gly Pro Ala Ser Val Thr Val Ala Gly Asp Ala Gln Ala Leu Glu
                725                 730                 735

Glu Phe Gly Val Arg Leu Ser Ala Asp Gly Val Leu Arg Trp Pro Leu
            740                 745                 750

Ala Gly Val Asp Phe Ala Gly His Ser Pro Gln Val Glu Gln Phe Arg
            755                 760                 765

Thr Glu Leu Leu Gly Thr Leu Ala Asp Val Arg Pro Thr Ala Ala Arg
            770                 775                 780

Leu Pro Phe Phe Ser Thr Val Thr Ala Gly Ala His Asp Pro Glu Gly
785                 790                 795                 800

Leu Asp Ala Ala Tyr Trp Tyr Arg Asn Thr Arg Glu Pro Val Glu Phe
                805                 810                 815

Glu Ser Thr Leu Arg Ala Leu Leu Arg Gln Gly His Arg Thr Phe Val
            820                 825                 830

Glu Met Gly Pro His Pro Leu Leu Gly Ser Ser Ile Asp Glu Ile Ala
            835                 840                 845

Glu Ala Glu Gly Val His Ala Thr Ala Leu Ser Thr Leu His Arg Gly
    850                 855                 860

Ser Gly Gly Leu Asp Arg Phe Arg Ala Ser Val Gly Ala Ala Phe Ala
865                 870                 875                 880

His Gly Val Arg Val Asp Trp Ser Pro Leu Phe Glu Gly Ala Gly Ala
                885                 890                 895

Arg Arg Val Pro Leu Pro Thr Tyr Ala Phe Arg Arg Asp Arg Phe Trp
            900                 905                 910

Leu Pro Thr Ala Val Gly Arg Arg Thr Ala Lys Ala Pro Ala Asp Glu
            915                 920                 925

Ser Ala Ala Trp Arg Tyr Arg Val Thr Trp Thr Ala Leu Glu Thr Gly
    930                 935                 940

Gly Ser Gly Ala Pro Ser Gly Arg Trp Leu Val Glu Leu Pro Gly
945                 950                 955                 960

Ala Ala Pro Asp Glu Ala Asp Ala Ala Thr Ala Leu Gly Thr Ala
                965                 970                 975

Gly Ala Val Val Glu Arg Cys Pro Leu Asp Pro Ala Glu Val Ala Arg
```

```
                980             985             990
Val Ala Leu Thr Glu Arg Leu Ala  Glu Leu Ala Ala Gly Pro Gln Gly
            995             1000            1005

Leu Ala  Gly Val Leu Val Leu Pro Gly Arg Ala Ala  Asp Ala Ala Pro
    1010             1015            1020

Ala  Asp Ala Phe Pro Leu Asp Pro Gly Thr Ala  Ala Val Leu Leu Val
1025             1030            1035            1040

Thr Gln Ala Val Thr  Asp Gly Ala Pro Lys Ala Arg Val Trp Val  Ala
            1045            1050            1055

Thr Arg Gly Ala  Val Ala Val Gly Pro  Gly Glu Val Pro Cys Ala Met
            1060            1065            1070

Gly Ala Arg  Val Trp Gly Leu Gly  Arg Val Ala Ala Leu  Glu Ala Pro
        1075            1080            1085

Val Gln  Trp Gly Gly Leu Val  Asp Leu Pro Ala Glu  Pro Gly Gly Arg
        1090            1095            1100

Asp  Trp Arg Arg Leu Ala  Ala Val Val Ser Gly  Arg Gly Gly Glu  Asp
1105            1110            1115            1120

Gln Val Ala Ile Arg  Gly Ser Gly Leu Phe  Gly Arg Arg Met Leu  Pro
            1125            1130            1135

Ala Ala Pro Gly  Val Arg Arg Ser  Trp Arg Pro Arg Gly  Cys Val
            1140            1145            1150

Leu Val Thr  Gly Gly Leu Gly Gly  Val Gly Gly His Val  Ala Arg Trp
        1155            1160            1165

Leu Ala  Arg Gly Gly Ala Glu  His Val Val Leu Ala  Gly Arg Arg Gly
        1170            1175            1180

Gly  Gly Ala Pro Gly  Ala Val Glu Leu Glu  Arg Glu Leu Val Gly  Leu
1185            1190            1195            1200

Gly Ala Lys Val Thr  Phe Val Ala Cys Asp  Val Ala Asp Arg Ala  Ser
            1205            1210            1215

Val Val Gly Leu  Leu Gly Val Val Glu  Gly Leu Gly Val Pro  Leu Cys
            1220            1225            1230

Gly Val Phe  His Ala Ala Gly Val  Ala Gln Val Ser Ala  Leu Gly Glu
        1235            1240            1245

Val Ser  Leu Ala Glu Ala Ala  Gly Val Leu Ala Gly  Lys Ala Val Gly
        1250            1255            1260

Ala Glu Leu Leu Asp  Glu Leu Thr Ala Gly  Val Asp Leu Asp Val  Phe
1265            1270            1275            1280

Val Leu Phe Ser Ser  Gly Ala Ala Val Trp  Gly Ser Gly Gly  Ser
            1285            1290            1295

Val Tyr Ala Ala  Ala Asn Ala His Leu  Asp Ala Leu Ala Glu  Arg Arg
            1300            1305            1310

Arg Ala Gln  Gly Arg Pro Ala Thr  Ser Val Ala Trp Gly  Leu Trp Asp
        1315            1320            1325

Gly Gly  Gly Met Gly Ala Gly  Asp Gly Val Arg Asp  Phe Tyr Thr Glu
        1330            1335            1340

Arg  Gly Leu Ala Pro Met  Arg Pro Glu Ser Gly  Ile Glu Ala Leu  His
1345            1350            1355            1360

Thr Ala Leu Asn Gln  Asp Asp Thr Cys Val  Thr Val Ala Asp Ile  Asp
            1365            1370            1375

Trp Glu His Phe  Val Thr Gly Phe Thr  Ala Phe Arg Pro Ser  Pro Leu
            1380            1385            1390

Ile Ser Gly  Ile Pro Gln Val Arg  Ala Leu Arg Ala Ala  Gln Pro Thr
        1395            1400            1405
```

```
Val Gly Ala Ser Asp Asp Leu Arg Arg Arg Ile Asp Ala Ala Leu Thr
    1410                1415                1420

Pro Arg Glu Arg Thr Lys Val Leu Val Asp Leu Val Arg Thr Val Ala
1425                1430                1435                1440

Ala Glu Val Leu Gly His Asp Gly Ile Gly Arg Ile Gly His Asp Val
            1445                1450                1455

Ala Phe Lys Glu Leu Gly Phe Asp Ser Leu Ala Ala Val Arg Val Arg
            1460                1465                1470

Gly Arg Leu Ala Glu Ala Thr Gly Leu Val Leu Pro Ala Thr Ile Ile
        1475                1480                1485

Phe Asp His Pro Thr Val Asp Arg Leu Gly Asn Ala Leu Leu Glu Glu
    1490                1495                1500

Leu Thr Gly Ala Ser Asp Pro Glu Arg Gly Gly Ala Pro Gly Pro Ala
1505                1510                1515                1520

Gly Thr Gly Gly Asn Asp Ala Ser Pro Pro Ala Pro Glu Pro Ala Ala
            1525                1530                1535

His Asp Ala Glu Ile Asp Glu Leu Asp Ala Asp Ala Leu Val Arg Leu
            1540                1545                1550

Ala Thr Gly Gly Thr Gly Pro Ala Asp Gly Ala Pro Ala Asn Asp Gly
        1555                1560                1565

Ser Thr Glu Ala Gly Thr Thr Arg Gly Gly Ala Pro Glu Gln
    1570                1575                1580

<210> SEQ ID NO 14
<211> LENGTH: 3795
<212> TYPE: PRT
<213> ORGANISM: Streptomyces spiramyceticus WSJ-1

<400> SEQUENCE: 14

Val Ser Ala Thr Asn Glu Glu Lys Leu Arg Glu Tyr Leu Arg Arg Ala
1               5                   10                  15

Met Ala Asp Leu His Ser Ala Arg Glu Arg Leu Arg Glu Val Glu Ser
            20                  25                  30

Ala Ser Arg Glu Pro Ile Ala Ile Val Gly Met Ala Cys Arg Tyr Pro
        35                  40                  45

Gly Gly Val Ala Ser Pro Glu Asp Leu Trp Asp Leu Val Ala Ala Gly
    50                  55                  60

Thr Asp Ala Ile Ser Pro Phe Pro Ala Asp Arg Gly Trp Asp Ala Glu
65                  70                  75                  80

Gly Leu Tyr Asp Pro Glu Pro Gly Val Pro Gly Lys Ser Tyr Val Arg
                85                  90                  95

Glu Gly Gly Phe Leu His Glu Ala Ala Glu Phe Asp Ala Glu Phe Phe
            100                 105                 110

Gly Ile Ser Pro Arg Glu Ala Ala Ala Met Asp Pro Gln Gln Arg Leu
        115                 120                 125

Leu Leu Glu Thr Ser Trp Glu Ala Leu Glu Arg Ala Gly Ile Val Pro
    130                 135                 140

Asp Ser Leu Arg Gly Thr Arg Thr Gly Val Phe Thr Gly Val Met Tyr
145                 150                 155                 160

His Asp Tyr Gly Ser His Gln Val Gly Thr Ala Ala Asp Pro Ser Gly
                165                 170                 175

Gln Leu Gly Leu Gly Thr Ala Gly Ser Val Ala Ser Gly Arg Val Ala
            180                 185                 190

Tyr Thr Leu Gly Leu Gln Gly Pro Ala Val Thr Met Asp Thr Ala Cys
```

```
            195                 200                 205
Ser Ser Ser Leu Val Ala Leu His Leu Ala Val Gln Ser Leu Arg Arg
        210                 215                 220
Gly Glu Cys Asp Met Ala Leu Ala Gly Gly Val Thr Val Met Ala Thr
225                 230                 235                 240
Pro Thr Val Phe Val Glu Phe Ser Arg Gln Arg Gly Leu Ala Ser Asp
                245                 250                 255
Gly Arg Cys Lys Ala Phe Ala Glu Gly Ala Asp Gly Thr Val Trp Ala
            260                 265                 270
Glu Gly Val Gly Val Leu Leu Val Glu Arg Leu Ser Asp Ala Arg Arg
        275                 280                 285
Tyr Gly His Arg Val Leu Ala Val Val Arg Gly Ser Ala Val Asn Gln
    290                 295                 300
Asp Gly Ala Ser Asn Gly Leu Thr Ala Pro Ser Gly Pro Ala Gln Arg
305                 310                 315                 320
Lys Val Ile Arg Glu Ala Leu Ala Asp Ala Gly Leu Ala Pro Gly Asp
                325                 330                 335
Val Asp Ala Val Glu Ala His Gly Thr Gly Thr Pro Leu Gly Asp Pro
            340                 345                 350
Ile Glu Ala Gly Ala Leu Met Ala Thr Tyr Gly Ser Glu Arg Gln Gly
        355                 360                 365
Arg Asp Pro Leu Trp Leu Gly Ser Leu Lys Ser Asn Ile Gly His Thr
    370                 375                 380
Gln Ala Ala Gly Ala Ala Gly Val Ile Lys Met Val Glu Ala Ile
385                 390                 395                 400
Arg His Ser Thr Leu Pro Arg Thr Leu His Val Asp Ala Pro Ser Ala
                405                 410                 415
Lys Val Glu Trp Asp Pro Ser Ala Val Glu Leu Leu Thr Asp Ala Arg
            420                 425                 430
Pro Trp Pro Gln Arg Glu His Arg Pro Arg Ala Ala Ile Ser Ala
        435                 440                 445
Phe Gly Val Ser Gly Thr Asn Ala His Val Ile Ile Glu Glu Pro Pro
    450                 455                 460
Ala Glu Thr Ala Thr Gly Gly Ala Ala Ala Gly Asp Ala Pro Val
465                 470                 475                 480
Ala Gly Glu Glu Pro Val Thr Gly Asp Ala Pro Val Thr Gly Glu Val
                485                 490                 495
Pro Ala Ala Gly Ala Ala Ala Gly Thr Ser Val Ser Ser Val Pro Gly
            500                 505                 510
His Ala Ser Val Pro Gly His Ala Ser Ala Pro Arg Val Ala Ser Val
        515                 520                 525
Pro Gly His Ala Ser Ala Pro Arg Val Ala Ser Ala Pro Gly His Ala
    530                 535                 540
Ser Ala Pro Arg Asp Ala Ser Ala Pro Arg Pro Ala Ser Ala Pro Asp
545                 550                 555                 560
Glu Ala Ser Met Thr Gly Asp Thr Pro Ala Thr Pro Ser Thr Val Val
                565                 570                 575
Trp Pro Leu Ser Ala Glu Thr Ala Pro Ala Leu Arg Ala Gln Ala Ala
            580                 585                 590
Arg Leu Arg Ala His Leu Glu Arg Leu Pro Asp Thr Ser Pro Thr Asp
        595                 600                 605
Ile Gly His Ala Leu Ala Ala Asp Arg Ala Ala Leu Thr Gln Arg Ala
    610                 615                 620
```

```
Val Leu Leu Gly Asp Asn Gly Ala Pro Val Asp Ala Leu Ala Ala Leu
625                 630                 635                 640

Ala Ala Gly Glu Thr Thr Pro Asp Ala Val His Gly Thr Ala Ala Asp
                645                 650                 655

Ile Arg Arg Val Ala Phe Val Phe Pro Gly Gln Gly Ser Gln Trp Ala
            660                 665                 670

Gly Met Gly Ala Glu Leu Leu Asp Thr Ala Pro Ala Phe Ala Ala Glu
            675                 680                 685

Leu Glu Leu Cys Gln Ser Ala Leu Ser Pro Tyr Val Asp Trp Thr Leu
690                 695                 700

Ser Asp Val Leu Arg Gly Ala Pro Gly Ala Pro Gly Leu Asp Arg Val
705                 710                 715                 720

Asp Val Val Gln Pro Ala Thr Phe Ala Val Met Val Gly Leu Ala Ala
            725                 730                 735

Leu Trp Arg Ser Leu Gly Val Glu Pro Ala Ala Val Ile Gly His Ser
            740                 745                 750

Gln Gly Glu Ile Ala Ala Ala Cys Val Ala Gly Ala Leu Ser Leu Asp
            755                 760                 765

Asp Ala Ala Arg Ile Val Ala Leu Arg Ser Gln Val Ile Ala Arg Glu
770                 775                 780

Leu Ala Gly Arg Gly Gly Met Ala Ser Val Ala Leu Pro Ala Thr Asp
785                 790                 795                 800

Val Glu Ala Arg Leu Ala Gly Val Glu Ile Ala Ala Val Asn Gly
            805                 810                 815

Pro Gly Ser Thr Val Val Cys Gly Glu Pro Gly Ala Leu Glu Ala Leu
            820                 825                 830

Leu Val Ala Leu Glu Ala Glu Gly Ser Arg Val Arg Arg Ile Asp Val
835                 840                 845

Asp Tyr Ala Ser His Ser His Tyr Val Glu Ser Ile Arg Glu Glu Leu
850                 855                 860

Ala Thr Val Leu Ala Pro Val Arg Pro Tyr Arg Gly Asp Val Pro Phe
865                 870                 875                 880

Tyr Ser Thr Val Glu Ala Ala Leu Leu Asp Thr Ala Ala Leu Asp Ala
            885                 890                 895

Asp Tyr Trp Tyr Arg Asn Leu Arg Leu Pro Val Arg Phe Glu Pro Thr
            900                 905                 910

Val Arg Ala Met Leu Ala Asp Gly Ile Asp Ala Phe Val Glu Cys Ser
            915                 920                 925

Ala His Pro Val Leu Thr Val Gly Val Arg Gln Thr Val Glu Ser Val
            930                 935                 940

Gly Thr Ala Val Pro Ala Val Gly Ser Leu Arg Arg Asp Glu Gly Gly
945                 950                 955                 960

Leu Arg Arg Phe Leu Thr Ser Ala Ala Glu Ala Gln Val Val Gly Val
                965                 970                 975

Pro Val Asp Trp Ala Thr Leu His Pro Gly Ala Gly Arg Val Asn Leu
            980                 985                 990

Pro Thr Tyr Ala Phe Gln Arg Glu Arg Tyr Trp Val Gly Ser Ala Arg
            995                 1000                1005

Pro Asp Arg Ala Lys Thr Ala Glu Thr Gly Glu Gly Ala Pro Glu Ser
        1010                1015                1020

Gly Asp Arg Leu Gly Tyr His Val Glu Trp Lys Gly Leu Arg Ser Ala
1025                1030                1035                1040
```

-continued

Thr Gly Gly Trp Arg Pro Gly Leu Arg Leu Leu Ile Val Pro Thr Gly
             1045                1050                1055

Glu Gln His Ala Ala Leu Ala Asp Thr Val Glu Gln Ala Ile Ala Ser
         1060                1065                1070

Phe Gly Gly Thr Val Arg Arg Ile Ala Val Asp Pro Ala Arg Thr Gly
         1075                1080                1085

Arg Ala Glu Leu Leu Gly Leu Leu Glu Ser Ala Ile Asn Gly Asp Thr
         1090                1095                1100

Ala Val Thr Gly Ala Val Ser Leu Leu Gly Leu Cys Thr Asp Gly Arg
1105                1110                1115                1120

Pro Asp His Pro Ala Val Pro Thr Ala Val Thr Ala Thr Leu Ala Leu
             1125                1130                1135

Val Gln Ala Leu Ala Asp Leu Gly Ser Thr Ala Pro Leu Trp Thr Val
         1140                1145                1150

Thr Cys Gly Ala Val Ala Thr Ala Pro Asp Glu Leu Pro Cys Thr Ala
         1155                1160                1165

Gly Ala Gln Leu Trp Gly Leu Gly Arg Val Ala Ala Leu Glu Leu Pro
         1170                1175                1180

Glu Val Trp Gly Gly Leu Ile Asp Leu Pro Ala Gln Pro Asp Ala Arg
1185                1190                1195                1200

Val Leu Asp Arg Leu Ala Gly Val Leu Ala Glu Pro Gly Gly Glu Asp
             1205                1210                1215

Gln Ile Ala Ile Arg Met Ala Gly Val Phe Gly Arg Arg Val Leu Arg
         1220                1225                1230

Asn Pro Ala Asp Ala Gly Ser Pro Ala Trp Arg Ala Arg Gly Thr Val
         1235                1240                1245

Leu Ile Ala Gly Asp Ile Thr Thr Val Pro Gly Arg Leu Ile Arg Ser
1250                1255                1260

Leu Leu Glu Asp Gly Ala Asp Arg Val Val Leu Ala Gly Pro Asp Ala
1265                1270                1275                1280

Pro Ala Gln Ala Ala Ala Ala Gly Leu Thr Gly Ala Ser Val Val Pro
             1285                1290                1295

Val Arg Cys Asp Val Thr Asp Arg Thr Thr Leu Ala Gly Leu Leu Gly
         1300                1305                1310

Glu His Ala Pro Ser Val Val Val His Ala Pro Pro Leu Val Pro Leu
         1315                1320                1325

Ala Pro Leu Asn Glu Thr Ala Pro Gly Asp Ile Ala Thr Ala Leu Ala
         1330                1335                1340

Ala Lys Thr Thr Ala Ala Gly His Leu Val Asp Leu Ala Pro Ala Ala
1345                1350                1355                1360

Gly Leu Asp Ala Leu Val Leu Phe Ser Ser Val Ser Gly Val Trp Gly
             1365                1370                1375

Gly Ala Ala Gln Gly Cys Tyr Ala Ala Ala Thr Ala His Leu Asp Ala
             1380                1385                1390

Leu Ala Glu Arg Ala Arg Ala Ala Gly Val Pro Ala Leu Ser Val Ala
             1395                1400                1405

Trp Ser Pro Trp Ala Gly Gly Thr Pro Ala Asp Gly Ala Glu Ala Glu
         1410                1415                1420

Phe Leu Asn Arg Arg Gly Leu Ala Pro Leu Asp Pro Asp Glu Ala Val
1425                1430                1435                1440

Arg Thr Leu Arg Arg Met Leu Glu Arg Gly Ser Ala Cys Gly Ala Val
             1445                1450                1455

Ala Asp Val Glu Trp Asn Arg Phe Ala Ala Ser Tyr Thr Trp Val Arg

```
                 1460                1465                1470
Pro Ala Val  Leu Phe Asp Asp Ile  Pro Asp Val Gln Arg  Leu Arg Ala
         1475                1480                1485

Val Glu  Leu Ala Pro Ser Asn  Gly Asp Ser Thr Thr  Ser Glu Leu Val
    1490                1495                1500

Arg Glu Leu Thr Ala  Gln Ser Gly His Lys  Arg His Val Thr Leu Leu
1505                1510                1515                1520

Arg Leu Val Arg Ala  His Ala Ala Val  Leu Gly Gln Ser Ser  Gly
             1525                1530                1535

Asp Ala Val Asn  Ser Ala Arg Ala Phe  Arg Asp Leu Gly Phe  Asp Ser
         1540                1545                1550

Leu Thr Ala  Leu Glu Leu Arg Asp  Arg Leu Ser Thr Ala  Thr Gly Leu
         1555                1560                1565

Lys Leu  Pro Thr Ser Leu Val  Phe Asp His Ser Asn  Pro Ala Ala Leu
     1570                1575                1580

Ala  Arg His Leu Gly Glu  Glu Leu Leu Gly Arg  Gly Asp Thr Ala Asp
1585                1590                1595                1600

Arg Thr Gly Pro Glu  Thr Pro Thr Gln Thr  Asp Glu Pro Ile Ala  Ile
             1605                1610                1615

Ile Gly Met Ala  Cys Arg Leu Pro Gly  Gly Val Gln Ser  Pro Glu Asp
         1620                1625                1630

Leu Trp Asp  Leu Leu Thr Gly Glu  Val Asp Ala Ile Thr  Pro Phe Pro
         1635                1640                1645

Thr Asp  Arg Gly Trp Asn Asn  Glu Ala Leu Tyr Asp  Pro Asp Pro Gly
     1650                1655                1660

Ser  Pro Gly His His Thr  Tyr Val Arg Glu Gly  Gly Phe Leu His Asp
1665                1670                1675                1680

Ala Ala Glu Phe Asp  Pro Gly Phe Phe Gly  Ile Ser Pro Arg Glu  Ala
             1685                1690                1695

Leu Ala Met Asp  Pro Gln Gln Arg Leu  Ile Leu Glu Thr Ser  Trp Glu
         1700                1705                1710

Ser Phe Glu  Arg Ala Gly Ile Asp  Pro Val Glu Leu Arg  Gly Ser Arg
         1715                1720                1725

Thr Gly  Val Phe Val Gly Thr  Asn Gly Gln His Tyr  Val Pro Leu Leu
     1730                1735                1740

Gln  Asp Gly Asp Glu  Ser  Phe Asp Gly Tyr Ile  Ala Thr Gly Asn Ser
1745                1750                1755                1760

Ala Ser Val Met Ser  Gly Arg Leu Ser Tyr  Val Phe Gly Leu Glu  Gly
             1765                1770                1775

Pro Ala Val Thr  Val Asp Thr Ala Cys  Ser Ala Ser Leu Ala  Ala Leu
         1780                1785                1790

His Leu Ala  Val Gln Ser Leu Arg  Arg Gly Glu Cys Asp  Tyr Ala Leu
         1795                1800                1805

Ala Gly  Gly Ala Thr Val Met  Ser Thr Pro Glu Met  Leu Val Glu Phe
     1810                1815                1820

Ala  Arg Gln Arg Ala Val  Ser Pro Asp Gly Arg  Ser Lys Ala Phe Ala
1825                1830                1835                1840

Glu Thr Ala Asp Gly  Val Gly Leu Ala Glu  Gly Ala Gly Met Leu  Leu
             1845                1850                1855

Val Glu Arg Leu  Ser Glu Ala Gln Lys  Lys Gly His Pro Val  Leu Ala
         1860                1865                1870

Val Val Arg  Gly Ser Ala Val Asn  Gln Asp Gly Ala Ser  Asn Gly Leu
         1875                1880                1885
```

-continued

Thr Ala Pro Ser Gly Pro Ala Gln Gln Lys Val Ile Arg Glu Ala Leu
    1890            1895            1900

Ala Asp Ala Gly Leu Thr Pro Ala Asp Val Asp Ala Val Glu Ala His
1905            1910            1915            1920

Gly Thr Gly Thr Pro Leu Gly Asp Pro Ile Glu Ala Gly Ala Leu Leu
            1925            1930            1935

Ala Thr Tyr Gly Arg Asp Arg Arg Asp Asp Pro Leu Trp Leu Gly Ser
        1940            1945            1950

Leu Lys Ser Asn Ile Gly His Thr Gln Ala Ala Ala Gly Val Ala Gly
        1955            1960            1965

Val Ile Lys Met Val Leu Ala Leu Arg His Gly Thr Leu Pro Arg Thr
    1970            1975            1980

Leu His Ala Thr Thr Ala Ser Ser Lys Ile Glu Trp Asp Ala Gly Ala
1985            1990            1995            2000

Val Glu Leu Leu Asp Glu Ala Arg Pro Trp Pro Gln Arg Ala Asp Gly
            2005            2010            2015

Leu Arg Arg Ala Gly Ile Ser Ser Phe Gly Ile Ser Gly Thr Asn Ala
            2020            2025            2030

His Val Val Val Glu Glu Pro Pro Glu Pro Thr Ala Pro Glu Leu Leu
    2035            2040            2045

Ala Pro Glu Pro Ala Ala Asp Gly Asp Val Trp Ser Glu Glu Trp Trp
    2050            2055            2060

His Glu Val Thr Val Pro Leu Met Met Ser Ala His Asn Asp Ala Ala
2065            2070            2075            2080

Leu Arg Asp Gln Ala Arg Arg Leu Arg Ala Asp Leu Leu Ala His Pro
            2085            2090            2095

Glu Leu His Pro Ala Asp Val Gly Tyr Thr Leu Ile Thr Thr Arg Thr
        2100            2105            2110

Arg Phe Glu Gln Arg Ala Ala Val Val Gly Glu Asn Phe Thr Glu Leu
        2115            2120            2125

Ile Ala Ala Leu Asp Asp Leu Val Glu Gly Arg Pro His Pro Leu Val
    2130            2135            2140

Leu Arg Gly Thr Ala Gly Thr Ala Asp Gln Val Val Phe Val Phe Pro
2145            2150            2155            2160

Gly Gln Gly Ser Gln Trp Pro Glu Met Ala Asp Gly Leu Phe Asp Arg
            2165            2170            2175

Ser Ser Asp Ser Ser Ser Phe Leu Glu Thr Ala Arg Ala Cys Asp Ala
            2180            2185            2190

Ala Leu Arg Pro His Leu Gly Trp Ser Val Leu Asp Val Leu Cys Arg
        2195            2200            2205

Glu Pro Gly Ala Pro Ser Leu Asp Arg Val Asp Val Val Gln Pro Val
    2210            2215            2220

Leu Phe Thr Met Met Val Ser Leu Ala Glu Thr Trp Arg Ser Leu Gly
2225            2230            2235            2240

Val Glu Pro Ala Ala Val Val Gly His Ser Gln Gly Glu Ile Ala Ala
            2245            2250            2255

Ala His Val Ala Gly Ala Leu Ser Leu Asp Asp Ala Ala Arg Ile Val
        2260            2265            2270

Ala Leu Arg Ser Gln Ala Trp Leu Arg Leu Ala Gly Lys Gly Gly Met
        2275            2280            2285

Val Ala Val Thr Met Ser Glu Arg Asp Leu Arg Pro Arg Leu Glu Pro
    2290            2295            2300

```
Trp  Ser  Asp  Arg  Leu  Ala  Val  Ala  Ala  Val  Asn  Gly  Pro  Glu  Thr  Cys
2305                      2310                     2315                     2320

Ala  Val  Ser  Gly  Asp  Pro  Asp  Ala  Leu  Ala  Glu  Leu  Val  Ala  Glu  Leu
               2325                     2330                     2335

Ser  Ala  Glu  Gly  Val  His  Ala  Arg  Pro  Ile  Pro  Gly  Val  Asp  Thr  Ala
               2340                     2345                     2350

Gly  His  Ser  Pro  Gln  Val  Asp  Met  Leu  Glu  Glu  His  Leu  Arg  Glu  Val
               2355                     2360                     2365

Leu  Ala  Pro  Val  Ala  Pro  Arg  Ser  Ser  Asp  Ile  Pro  Phe  Tyr  Ser  Thr
2370                      2375                     2380

Val  Thr  Gly  Gly  Leu  Leu  Asp  Thr  Ala  Glu  Leu  Asn  Ala  Asp  Tyr  Trp
2385                      2390                     2395                     2400

Tyr  Arg  Asn  Met  Arg  Glu  Pro  Val  Glu  Phe  Glu  Lys  Ala  Thr  Arg  Ala
               2405                     2410                     2415

Leu  Ile  Ala  Asp  Gly  His  Asp  Val  Phe  Leu  Glu  Ser  Ser  Pro  His  Pro
                    2420                2425                     2430

Met  Leu  Ala  Val  Ser  Leu  Gln  Glu  Thr  Ile  Ser  Asp  Ala  Gly  Ala  Ser
               2435                     2440                     2445

Ala  Ala  Val  Leu  Gly  Thr  Leu  Arg  Arg  Gly  Gln  Gly  Gly  Pro  Arg  Cys
               2450                     2455                     2460

Leu  Ala  Val  Ala  Val  Cys  Arg  Ala  Tyr  Thr  His  Gly  Val  Glu  Ile  Asp
2465                      2470                     2475                     2480

Ala  Glu  Ala  Ile  Phe  Gly  Pro  Asp  Ser  Arg  His  Val  Glu  Leu  Pro  Thr
                    2485                2490                     2495

Tyr  Pro  Phe  Gln  Arg  Glu  Arg  Tyr  Trp  Tyr  Ser  Pro  Thr  Ser  Arg  Gly
               2500                     2505                     2510

Asp  Asp  Pro  Ala  Ser  Leu  Gly  Leu  Asp  Ala  Ala  Asp  His  Pro  Leu  Leu
               2515                     2520                     2525

Gly  Gly  Gly  Val  Glu  Leu  Pro  Asp  Ser  Gly  Ala  Gln  Met  Tyr  Thr  Ala
               2530                     2535                     2540

Arg  Leu  Gly  Thr  Asp  Ala  Thr  Pro  Trp  Leu  Ala  Asp  His  Ala  Leu  Met
2545                      2550                     2555                     2560

Gly  Ala  Ala  Leu  Leu  Pro  Gly  Ala  Ala  Phe  Ala  Asp  Leu  Ala  Leu  Trp
               2565                     2570                     2575

Ala  Gly  Arg  Gln  Ala  Gly  Thr  Gly  Arg  Ile  Glu  Glu  Leu  Thr  Leu  Ala
               2580                     2585                     2590

Ala  Pro  Leu  Ala  Leu  Pro  Glu  Ser  Gly  Gly  Val  Arg  Leu  Arg  Leu  Asn
               2595                     2600                     2605

Val  Gly  Ala  Pro  Gly  Ala  Asp  Asp  Ala  Arg  Arg  Phe  Ala  Val  His  Ala
               2610                     2615                     2620

Arg  Ala  Glu  Gly  Ala  Ala  Asp  Trp  Thr  Leu  His  Ala  Glu  Gly  Leu  Leu
2625                      2630                     2635                     2640

Thr  Ala  Glu  Asp  Ala  Ala  Asp  Val  Pro  Asp  Ala  Ser  Ala  Thr  Ala  Pro
               2645                     2650                     2655

Pro  Pro  Gly  Ala  Glu  Gln  Leu  Asp  Gly  Asp  Phe  Tyr  Glu  Arg  Phe
               2660                     2665                     2670

Ala  Glu  Leu  Gly  Tyr  Gly  Tyr  Gly  Pro  Phe  Phe  Arg  Gly  Leu  Val  Ser
               2675                     2680                     2685

Ala  His  Arg  Ser  Gly  Ser  Asp  Ile  His  Ala  Glu  Val  Ala  Leu  Pro  Val
               2690                     2695                     2700

Gln  Ala  Gln  Gly  Asp  Ala  Ala  Arg  Phe  Gly  Ile  His  Pro  Ala  Leu  Leu
2705                      2710                     2715                     2720

Asp  Ala  Ala  Leu  Gln  Thr  Met  Ser  Leu  Gly  Gly  Phe  Phe  Pro  Glu  Asp
```

```
                  2725                2730                2735
Gly Arg Ile Arg  Met Pro Phe Ala Leu  Arg Gly Val Arg Leu  Tyr Arg
              2740                2745                2750

Thr Gly Ala Glu Arg Leu His Val Arg Ile Ser Pro Val Ser Gln Asp
              2755                2760                2765

Ala Val Arg Ile Arg Cys Ala Asp Thr Glu Gly Arg Ala Val Ala Glu
           2770                2775                2780

Ile Asp Ser Phe Leu Met Arg Pro Val Asp Pro Glu Gln Leu Leu Gly
2785                2790                2795                2800

Gly Arg Pro Val Gly Ala Asp Ala Leu Phe Arg Ile Ala Trp Arg Glu
              2805                2810                2815

Leu Thr Ser Gly Ser Gly Thr Gly Leu Arg Thr Gly Asn Gly Ala Gly
              2820                2825                2830

Ala Ala Ser Ser Val Arg Trp Val Val Ala Gly Pro Asp Val Leu Gly
              2835                2840                2845

Leu Ala Glu Ala Ala Asp Ala His Leu Pro Asp Ala Leu Gly Pro Asp
              2850                2855                2860

Gly Pro Leu Pro Thr Ala Ala Gly Glu Ala Ala Pro Asp Ala Phe Val
2865                2870                2875                2880

Phe Gly Val Pro Thr Gly Thr Gly Asp Val Ala Ala Asp Ala His Ala
              2885                2890                2895

Val Ala Cys Gln Val Leu Asp Leu Val Gln Arg Arg Leu Ala Ala Pro
              2900                2905                2910

Asp Ala Pro Glu Gly Ala Arg Leu Val Val Ala Thr Arg Gly Ala Val
              2915                2920                2925

Ala Val Arg Gly Asp Ala Glu Val Ser Asp Pro Ala Ala Ala Ala Ala
              2930                2935                2940

Trp Gly Leu Leu Arg Ser Ala Gln Ala Glu Glu Pro Asp Arg Phe Leu
2945                2950                2955                2960

Leu Val Asp Leu Asp Asp Asp Pro Ala Ser Ala Arg Ala Leu Pro Thr
              2965                2970                2975

Ala Leu Ala Ser Gly Glu Pro Gln Thr Ala Val Arg Ala Gly Arg Val
              2980                2985                2990

Tyr Val Pro Arg Leu Glu Arg Ala Ala Asp Ser Thr Asp Gly Pro Leu
              2995                3000                3005

Thr Pro Pro Glu Lys Gly Ala Trp Arg Leu Gly Arg Gly Ala Asp Leu
              3010                3015                3020

Thr Leu Asp Gly Leu Ala Leu Val Pro Ala Pro Asp Ala Glu Ala Pro
3025                3030                3035                3040

Leu Glu His Gly Gln Val Arg Val Ala Val Arg Ala Ala Gly Val Asn
              3045                3050                3055

Phe Arg Asp Ala Leu Ile Ala Leu Gly Met Tyr Pro Cys Glu Ala Glu
              3060                3065                3070

Met Gly Thr Glu Gly Ala Gly Thr Val Glu Val Gly Pro Gly Val
              3075                3080                3085

Thr Gly Val Ala Pro Gly Asp Arg Val Leu Gly Leu Trp Asn Gly Gly
              3090                3095                3100

Leu Gly Pro Val Cys Val Ala Asp His Arg Leu Leu Val Pro Ile Pro
3105                3110                3115                3120

Asp Gly Trp Ser Tyr Ala Arg Ala Ala Ser Val Pro Ala Val Phe Leu
              3125                3130                3135

Ser Ala Tyr Tyr Gly Leu Val Thr Leu Ala Asp Leu Arg Pro Gly Glu
              3140                3145                3150
```

-continued

Lys Val Leu Val His Ala Ala Ala Gly Gly Val Gly Met Ala Ala Val
        3155                3160                3165

Gln Ile Ala Arg His Leu Gly Ala Glu Val Leu Ala Thr Ala Ser Thr
        3170                3175                3180

Gly Lys Trp Asp Val Leu Arg Ala Met Gly Ile Thr Asp Glu His Leu
3185                3190                3195                3200

Ala Ser Ser Arg Thr Leu Asp Phe Ala Thr Ala Phe Ala Gly Thr Asp
                3205                3210                3215

Gly Thr Ser Arg Ala Asp Val Val Leu Asn Ser Leu Thr Lys Glu Phe
                3220                3225                3230

Val Asp Ala Ser Leu Gly Leu Leu Arg Pro Gly Gly Arg Phe Leu Glu
        3235                3240                3245

Leu Gly Lys Thr Asp Val Arg Asp Pro Glu Gln Val Gly Ala Asp His
        3250                3255                3260

Pro Gly Val Arg Tyr Arg Ala Phe Asp Leu Asn Glu Ala Gly Pro Asp
3265                3270                3275                3280

Glu Leu Gly Arg Leu Leu Arg Lys Leu Met Glu Leu Phe Ala Ala Gly
                3285                3290                3295

Val Leu His Pro Leu Pro Val Val Thr His Asp Val Arg Arg Ala Ala
        3300                3305                3310

Asp Ala Leu Arg Thr Ile Ser Gln Ala Arg His Thr Gly Lys Leu Val
        3315                3320                3325

Leu Thr Met Pro Pro Ala Trp His Pro Tyr Gly Thr Val Leu Ile Thr
        3330                3335                3340

Gly Gly Thr Gly Ala Leu Gly Gly Arg Ile Ala Arg His Leu Ala Thr
3345                3350                3355                3360

His His Gly Val Arg Gln Leu Leu Ile Ala Ala Arg Arg Gly Pro Asp
                3365                3370                3375

Gly Glu Gly Ala Ala Glu Leu Val Ala Asp Leu Thr Ala Leu Gly Ala
                3380                3385                3390

Ser Ala Thr Val Val Ala Cys Asp Val Ser Asp Ala Asp Ala Val Arg
        3395                3400                3405

Arg Leu Leu Ala Gly Val Pro Ala Glu His Pro Leu Thr Ala Val Val
        3410                3415                3420

His Ser Ala Gly Val Leu Asp Asp Gly Val Leu Pro Thr Leu Thr Pro
3425                3430                3435                3440

Glu Arg Met Arg Arg Val Leu Arg Pro Lys Val Glu Ala Ala Val His
                3445                3450                3455

Leu Asp Glu Leu Thr Arg Asp Leu Asp Leu Ser Ala Phe Val Leu Phe
                3460                3465                3470

Ser Ser Ser Ala Gly Leu Leu Gly Ser Pro Ala Gln Gly Asn Tyr Ala
        3475                3480                3485

Ala Ala Asn Ala Thr Leu Asp Ala Leu Ala Val Arg Arg Arg Ala Leu
        3490                3495                3500

Gly Leu Pro Ala Val Ser Leu Ala Trp Gly Leu Trp Ser Asp Thr Ser
3505                3510                3515                3520

Arg Met Ala Gly Gly Leu Asp Gln Glu Ser Leu Gln Arg Arg Phe Ala
                3525                3530                3535

Arg Asn Gly Phe Pro Pro Leu Ser Ala Thr Leu Gly Ala Ala Leu Phe
                3540                3545                3550

Asp Ala Ala Leu Arg Val Asp Glu Ala Val Gln Ile Pro Met Arg Phe
        3555                3560                3565

```
Asp Pro Ala Ala Leu Arg Ala Thr Gly Thr Val Pro Ala Leu Leu Ser
    3570                3575                3580

Asp Leu Val Gly Pro Ala Pro Ala Gly Ser Ala Thr Pro Ala Ala
3585                3590                3595                3600

Gly Pro Tyr Pro Thr Pro Asp Ala Gly His Thr Gly Glu Pro Leu Ala
            3605                3610                3615

Glu Arg Leu Ala Arg Leu Ser Ala Glu Glu Arg His Asp Gln Leu Leu
            3620                3625                3630

Ser Leu Val Ser Glu His Val Ala Ala Val Leu Gly His Gly Ser Ala
        3635                3640                3645

Ala Glu Val Arg Ser Asp Arg Pro Phe Arg Glu Val Gly Phe Asp Ser
3650                3655                3660

Leu Thr Ala Val Glu Leu Arg Asn Arg Met Gly Ala Val Thr Gly Val
3665                3670                3675                3680

Arg Leu Pro Ala Thr Leu Val Phe Asp His Pro Thr Pro Ala Ala Leu
                3685                3690                3695

Ala Ala His Leu Asp Gly Leu Leu Ala Pro Gln Arg Pro Pro Thr Thr
        3700                3705                3710

Ala Pro Leu Leu Ser Glu Leu Asp Arg Ile Glu Glu Ala Leu Ala Ala
    3715                3720                3725

Leu Thr Pro Glu Gly Leu Ala Val Ala Pro Ala Pro Asp Ala Arg
3730                3735                3740

Ala Glu Val Ala Leu Arg Leu Asp Ala Leu Ala Asp Arg Trp Arg Ala
3745                3750                3755                3760

Leu His Asp Gly Ala Ala Gly Val Asp Asp Asp Ile Ala Asp Val Leu
                3765                3770                3775

Ser Thr Ala Asp Asp Asp Glu Ile Phe Ala Phe Ile Asp Glu Arg Tyr
            3780                3785                3790

Gly Ala Ser
        3795

<210> SEQ ID NO 15
<211> LENGTH: 2004
<212> TYPE: PRT
<213> ORGANISM: Streptomyces spiramyceticus WSJ-1

<400> SEQUENCE: 15

Met Thr Ala Glu Asn Asp Lys Ile Arg Ser Tyr Leu Lys Arg Ala Thr
1               5                   10                  15

Ala Glu Leu His Lys Thr Lys Ser Arg Leu Ala Glu Val Glu Ser Ala
            20                  25                  30

Ser Arg Glu Pro Ile Ala Ile Val Gly Met Ala Cys Arg Tyr Pro Gly
        35                  40                  45

Gly Val Ala Ser Pro Glu Asp Leu Trp Asp Leu Ala Ala Ala Gly Ala
    50                  55                  60

Asp Ala Ile Ser Pro Phe Pro Val Asp Arg Gly Trp Asp Val Glu Gly
65                  70                  75                  80

Leu Tyr Asp Pro Asp Pro Glu Ala Val Gly Arg Ser Tyr Val Arg Glu
                85                  90                  95

Gly Gly Phe Leu His Gly Ala Ala Glu Phe Asp Ala Glu Phe Phe Gly
            100                 105                 110

Ile Ser Pro Arg Glu Ala Ala Ala Met Asp Pro Gln Gln Arg Leu Leu
        115                 120                 125

Leu Glu Thr Ser Trp Glu Ala Leu Glu Arg Ala Gly Ile Val Pro Asp
    130                 135                 140
```

```
Ser Leu Arg Gly Thr Arg Thr Gly Val Phe Thr Gly Val Met Tyr Asp
145                 150                 155                 160

Asp Tyr Gly Ser Gln Phe Asp Ser Ala Pro Pro Glu Tyr Glu Gly Tyr
                165                 170                 175

Leu Val Asn Gly Ser Ala Gly Ser Ile Ala Ser Gly Arg Val Ala Tyr
            180                 185                 190

Val Leu Gly Leu Glu Gly Pro Ala Leu Thr Val Asp Thr Ala Cys Ser
        195                 200                 205

Ser Ser Leu Val Ala Leu His Leu Ala Val Gln Ser Leu Arg Arg Gly
    210                 215                 220

Glu Cys Asp Met Ala Leu Ala Gly Gly Val Thr Val Met Ala Thr Pro
225                 230                 235                 240

Thr Val Phe Val Glu Phe Ser Arg Gln Arg Gly Leu Ala Ser Asp Gly
                245                 250                 255

Arg Cys Lys Ala Phe Ala Glu Gly Ala Asp Gly Thr Val Trp Ala Glu
            260                 265                 270

Gly Val Gly Val Leu Leu Val Glu Arg Leu Ser Asp Ala Arg Arg Tyr
        275                 280                 285

Gly His Arg Val Leu Ala Val Arg Gly Ser Ala Val Asn Gln Asp
    290                 295                 300

Gly Ala Ser Asn Gly Leu Thr Ala Pro Ser Gly Ala Ala Gln Arg Arg
305                 310                 315                 320

Val Ile Arg Glu Ala Leu Ala Asp Ala Gly Leu Ala Pro Gly Asp Val
                325                 330                 335

Asp Ala Val Glu Ala His Gly Thr Gly Thr Ala Leu Gly Asp Pro Ile
            340                 345                 350

Glu Ala Gly Ala Leu Leu Ala Thr Tyr Gly Arg Glu Arg Val Gly Asp
        355                 360                 365

Pro Leu Trp Leu Gly Ser Leu Lys Ser Asn Ile Gly His Ala Gln Ala
    370                 375                 380

Ala Ala Gly Val Gly Gly Val Ile Lys Met Val Glu Ala Met Arg His
385                 390                 395                 400

Ser Ser Leu Pro Arg Thr Leu His Val Asp Ala Pro Ser Ser Arg Val
                405                 410                 415

Glu Trp Gly Ser Gly Ala Val Glu Leu Leu Thr Glu Ala Arg Ser Trp
            420                 425                 430

Pro Arg Arg Ala Gly Arg Val Arg Arg Ala Ala Val Ser Ala Phe Gly
        435                 440                 445

Val Ser Gly Thr Asn Ala His Val Val Ile Glu Glu Pro Ser Val Glu
    450                 455                 460

Glu Ser Ala Glu Ala Glu Ala Val Val Thr Ala Ala Ala Glu Ser Ser
465                 470                 475                 480

Ser Val Leu Ala Trp Pro Val Ser Ala Arg Ser Glu Glu Ala Leu Arg
                485                 490                 495

Gly Gln Ala Val Arg Leu Arg Glu His Val Glu Arg Val Gly Ala Asp
            500                 505                 510

Pro Val Asp Val Ala His Ser Leu Val Val Ser Arg Ala Ser Phe Gly
        515                 520                 525

Glu Arg Ala Val Val Val Gly Arg Glu Arg Gly Glu Leu Leu Ala Gly
    530                 535                 540

Leu Asp Ala Val Ala Ala Gly Val Val Ala Ala Gly Gly Ala Ala Ser
545                 550                 555                 560
```

Gly Val Val Arg Gly Ser Ala Val Arg Gly Arg Val Gly Val Leu
            565                 570                 575

Phe Thr Gly Gln Gly Ala Gln Trp Val Gly Met Gly Arg Glu Leu Tyr
        580                 585                 590

Gly Ala Gly Gly Val Phe Ala Gly Val Leu Asp Glu Val Leu Gly Val
            595                 600                 605

Val Gly Glu Val Gly Gly Arg Ser Leu Arg Glu Val Met Phe Ala Glu
    610                 615                 620

Ala Gly Ser Val Asp Ala Gly Leu Leu Gly Cys Thr Glu Phe Ala Gln
625                 630                 635                 640

Pro Ala Leu Phe Ala Leu Glu Val Ala Leu Phe Arg Ala Leu Glu Ala
                645                 650                 655

Arg Gly Val Gly Val Ser Val Val Leu Gly His Ser Val Gly Glu Val
                660                 665                 670

Ala Ala Ala Tyr Val Ala Gly Val Phe Ser Leu Ala Asp Ala Val Arg
            675                 680                 685

Leu Val Val Ala Arg Gly Arg Leu Met Gly Ala Leu Pro Val Gly Gly
    690                 695                 700

Ala Met Val Ser Val Gly Ala Ser Glu Ala Glu Leu Ala Gly Leu Val
705                 710                 715                 720

Ala Gly Leu Gly Gly Arg Val Ser Val Ala Ala Val Asn Gly Pro Ala
                725                 730                 735

Ser Val Val Leu Ser Gly Glu Ala Gly Val Leu Asp Gly Val Val Ala
                740                 745                 750

Gly Leu Val Gly Arg Gly Val Glu Cys Arg Trp Leu Glu Val Ser His
            755                 760                 765

Ala Phe His Ser Val Leu Met Asp Pro Met Leu Glu Glu Phe Arg Arg
    770                 775                 780

Val Ala Ala Ser Val Glu Phe His Arg Pro Arg Ser Gly Val Ala Val
785                 790                 795                 800

Val Ser Ser Val Thr Gly Ala Val Ala Gly Leu Asp Glu Leu Gly Asp
                805                 810                 815

Pro Glu Tyr Trp Val Arg His Val Arg Glu Ala Val Arg Phe Ala Asp
            820                 825                 830

Gly Val Gly Ala Ala Arg Asp Val Gly Val Asp Thr Phe Val Glu Val
    835                 840                 845

Gly Pro His Ala Val Leu Thr Val Met Ala Gly Gln Cys Leu Asp Gly
850                 855                 860

Asp Glu Gly Asp Leu Ala Phe Val Pro Val Leu Arg Arg Asp Arg Pro
865                 870                 875                 880

Glu Leu Glu Thr Phe Thr Thr Ala Leu Ala Thr Leu Tyr Ala Arg Gly
                885                 890                 895

Leu Pro Val Pro Pro Ala Pro Ser Glu Pro Ala Gly Arg Arg Val Asp
            900                 905                 910

Leu Pro Thr Tyr Ala Phe His Arg Asp Arg Tyr Trp Leu Ala Ala Leu
    915                 920                 925

Pro Arg Leu Thr Thr Gly Gly Val Ser Ala Ala Gly Leu His Gly Val
930                 935                 940

Glu His Pro Leu Leu Ala Ala Val Glu Leu Pro Gly Ala Glu Thr
945                 950                 955                 960

Glu Val Trp Thr Gly Arg Ile Ser Ala Ala Asp Leu Pro Trp Leu Ala
                965                 970                 975

Asp His Leu Val Trp Asp Arg Gly Val Val Pro Gly Ser Ala Leu Leu

```
            980                 985                 990
Glu Met Leu Leu Gln Val Gly Ser Arg Ile Gly Leu Pro Arg Val Ala
            995                1000               1005
Glu Leu Ala Phe Glu Thr Ala Leu Thr Trp Ala Ala Asp Asn Pro Val
           1010                1015               1020
Gln Ile Arg Val Val Val Ala Ala Pro Ala Ser Gly Pro Gly Gly Ala
1025               1030                1035               1040
Arg Glu Val Ser Leu His Ser Arg Pro Glu Pro Val Ala Asp Pro Ser
               1045                1050               1055
His Ser Thr Arg Ser Pro His Leu Ala Ala Gln Asp Arg Asp Asn Gly
           1060                1065               1070
Trp Thr Arg His Ala Ser Gly Leu Leu Ala Pro Ala Ala Asp His Ala
           1075                1080               1085
Asp His Thr His Glu Ala Gly His Pro His Gly Ala Pro His Pro His
           1090                1095               1100
Glu Ser Gly His Pro His Gly Ala Asp Arg Thr Gly Ala Asp Ala Phe
1105               1110                1115               1120
Ala Glu Leu Thr Gly Ala Trp Pro Pro Ala Gly Ala Glu Pro Leu Asp
               1125                1130               1135
Ile Ala Gly Gln Tyr Pro Leu Phe Ala Ala Gly Val Arg Tyr Glu
           1140                1145               1150
Gly Ala Phe Arg Gly Leu Arg Ala Ala Trp Arg Arg Gly Asp Glu Ile
           1155                1160               1165
Phe Ala Glu Val Arg Leu Pro Asp Ala His Ala Ala Asp Ala Ala Arg
           1170                1175               1180
Tyr Gly Val His Pro Ala Leu Leu Asp Ala Ala Leu His Pro Ile Ala
1185               1190                1195               1200
Leu Leu Asp Pro Leu Gly Asp Gly Gly His Gly Leu Leu Pro Phe Ser
               1205                1210               1215
Trp Thr Asp Val Arg Arg His Asp Ala Ala Gly His Ala Leu Arg Val
           1220                1225               1230
Arg Val Ala Ala Val Asp Gly Gly Ala Val Ser Ile Ala Ala Val Asp
           1235                1240               1245
Arg Glu Gly Ser Pro Val Leu Ser Ala Arg Ser Leu Ala Leu Arg Arg
           1250                1255               1260
Ile Pro Ala Asp Arg Leu Pro Ala Ala Pro Ala Ala Pro Leu Tyr Arg
1265               1270                1275               1280
Val Asp Trp Val Pro Leu Pro Gly Arg Val Ser Val Ala Ala Val Thr
               1285                1290               1295
Arg Trp Ala Val Val Gly Pro Glu Ala Glu Ala Thr Ala Ala Gly Leu
           1300                1305               1310
Arg Ala Val Gly Ile Asp Ala Arg Thr His Val Leu Pro Phe Asp Glu
           1315                1320               1325
Pro Leu Pro Pro Gln Val Gly Ala Asp Ala Glu Val Ile Leu Leu Asp
           1330                1335               1340
Leu Thr Thr Ala Thr Ala Thr Ala Thr Ala Thr Ala Ser Arg Thr Ala
1345               1350                1355               1360
Pro His Gly Arg Leu Leu Gly Leu Leu Asp Glu Leu Arg Ala Thr Val
               1365                1370               1375
Arg Arg Thr Leu Glu Ala Val Gln Ala Arg Leu Ala Asp Thr Asp Thr
           1380                1385               1390
Asp Thr Asp Thr Asn Ala Asp Ala Gly Ala Asp Ser Gly Val Arg Thr
           1395                1400               1405
```

-continued

Asp Ala Arg Thr Ala Thr Arg Pro Gly Gly Arg Pro Arg Leu Val Val
     1410             1415             1420

Leu Thr Arg Gly Ala Ala Gly Pro Glu Gly Gly Ala Ala Asp Pro Ala
1425             1430             1435             1440

Gly Ala Ala Val Trp Gly Leu Val Arg Val Ala Gln Ala Glu Gln Pro
             1445             1450             1455

Gly Arg Phe Thr Leu Val Asp Val Asp Gly Ala Gln Ala Ser Leu Arg
             1460             1465             1470

Ala Leu Pro Gly Leu Leu Ala Thr Asp Thr Ala Gln Leu Ala Val Arg
             1475             1480             1485

Asp Gly Arg Ala Ala Val Pro Arg Leu Val Arg Val Ala Asp Val Ala
         1490             1495             1500

Asp Val Ala Asp Leu Asp Thr Gly Ser Asp Thr Ala Ala Asp Glu Thr
1505             1510             1515             1520

Gly Ala Gly Glu Pro Ala Glu Thr Leu Asp Pro Asn Gly Thr Val Leu
             1525             1530             1535

Ile Thr Gly Gly Thr Gly Ala Leu Ala Ala Glu Thr Ala Arg His Leu
             1540             1545             1550

Val Glu Arg His Lys Ala Arg His Leu Leu Leu Val Ser Arg Arg Gly
         1555             1560             1565

Pro Asp Ala Pro Gly Ala Ala Glu Leu Ala Ala Glu Leu Thr Asn Leu
         1570             1575             1580

Gly Ala Glu Val Thr Val Arg Ala Cys Asp Val Ala Asp Arg Asp Ala
1585             1590             1595             1600

Leu Arg Arg Leu Leu Gly Glu Leu Pro Ala Glu His Pro Leu Thr Cys
             1605             1610             1615

Val Val His Thr Ala Gly Val Leu Asp Asp Gly Val Leu Ser Val Gln
             1620             1625             1630

Thr Ala Glu Arg Ile Asp Ala Val Leu Arg Pro Lys Ala Asp Ala Ala
         1635             1640             1645

Val His Leu Asp Glu Leu Thr Arg Glu Leu Gly Pro Val Pro Leu Val
1650             1655             1660

Leu Tyr Ser Ser Val Ser Ala Ala Leu Gly Ser Ala Gly Gln Ala Gly
1665             1670             1675             1680

Tyr Ala Ala Ala Asn Ala Phe Leu Asp Ala Leu Ala Ala Arg Arg Arg
             1685             1690             1695

Ala Ala Gly His Pro Ala Leu Ser Leu Gly Trp Gly Trp Trp Ser Gly
             1700             1705             1710

Leu Gly Leu Ala Thr Gly Leu Glu Arg Ala Asp Ala Ala Arg Ile Arg
             1715             1720             1725

Arg Ser Gly Val Ala Pro Leu Asp Pro Arg Ala Ala Leu Glu Leu Phe
         1730             1735             1740

Asp Arg Ala Leu Val Arg Pro Glu Pro Ala Leu Leu Pro Val Arg Leu
1745             1750             1755             1760

Asp Leu Arg Ala Ala Ala Arg Ala Thr Val Leu Pro Glu Val Leu Arg
             1765             1770             1775

Asp Leu Val Gly Val Pro Ala Asp Gly Gly Ser Ala Pro Gly Ala Val
             1780             1785             1790

Ala Gly Ala Gly Gly Glu Ala Gly Thr Gly His Arg Pro Pro Ala Pro
             1795             1800             1805

Ala Asp Ala Ala Ala Ala Leu Ala Thr Arg Leu Ala Gly Arg Ser Ala
     1810             1815             1820

```
Pro Glu Arg Thr Ala Leu Leu Asp Leu Val Arg Thr Glu Val Ala
1825                1830                1835                1840

Ala Val Leu Gly His Gly Asp Thr Ala Ala Val Gly Ala Ala Arg Ser
            1845                1850                1855

Phe Lys Asp Ala Gly Phe Asp Ser Leu Thr Ala Val Asp Leu Arg Asn
        1860                1865                1870

Arg Leu Asn Ala Arg Thr Gly Leu Arg Leu Pro Ala Thr Leu Val Phe
        1875                1880                1885

Asp His Pro Thr Pro Leu Ser Leu Ala Glu Leu Leu Leu Gly Glu Leu
        1890                1895                1900

Thr Ala Ala Gly Arg Ala Glu Pro Ala Gly Pro Val Pro Asp Glu Pro
1905                1910                1915                1920

Ala Gly Ala Glu Asp Leu Ser Ser Ala Phe Asp Arg Leu Glu Arg Ser
            1925                1930                1935

Leu Ala Ala Thr Asp Asp Gly Asp Ala Arg Val Arg Ala Ala Gln Arg
            1940                1945                1950

Leu Arg Gly Leu Leu Ala Ala Leu Thr Val Gly Ser Gly Glu Gln Ser
        1955                1960                1965

Gly Pro Gly Ala Gly Glu Ser Pro His Gly Pro Gly Asp Val Val Ile
        1970                1975                1980

Asp Arg Leu Arg Ser Ala Ser Asp Asp Asp Leu Phe Asp Leu Leu Asp
1985                1990                1995                2000

Ser Asp Phe Gln

<210> SEQ ID NO 16
<211> LENGTH: 4538
<212> TYPE: PRT
<213> ORGANISM: Streptomyces spiramyceticus WSJ-1

<400> SEQUENCE: 16

Met Ser Cys Arg Phe Pro Ser Ala Pro Gly Ile Gln Glu Phe Trp Lys
1               5                   10                  15

Leu Leu Thr Asp Gly Thr Glu Ala Ile Gly Arg Ala Ala Asp Gly Arg
            20                  25                  30

Arg Arg Gly Met Ile Glu Ala Val Gly Asp Phe Asp Ala Ala Phe Phe
        35                  40                  45

Gly Met Ser Pro Arg Glu Ala Ala Glu Thr Asp Pro Gln Gln Arg Leu
    50                  55                  60

Met Leu Glu Leu Gly Trp Glu Ala Leu Glu Asp Ala Gly Ile Val Pro
65                  70                  75                  80

Gly Ser Leu Arg Gly Glu Ala Val Gly Val Phe Val Gly Ala Met Asn
                85                  90                  95

Asp Asp Tyr Ala Thr Leu Leu His Arg Ala Gly Ala Pro Ile Gly Ala
            100                 105                 110

His Thr Ala Thr Gly Leu Gln Arg Ala Met Leu Ala Asn Arg Leu Ser
        115                 120                 125

Tyr Val Leu Gly Thr Arg Gly Pro Ser Leu Ala Val Asp Thr Ala Gln
    130                 135                 140

Ser Ser Ser Leu Val Ala Val Ala Leu Ala Val Glu Ser Leu Arg Ala
145                 150                 155                 160

Gly Thr Ser Arg Ile Ala Val Ala Gly Gly Val Asn Leu Ile Leu Ala
                165                 170                 175

Asp Glu Gly Ser Ala Ala Met Glu Arg Leu Gly Ala Leu Ser Pro Asp
            180                 185                 190
```

-continued

```
Gly Arg Cys His Thr Phe Asp Ala Arg Ala Asn Gly Tyr Val Arg Gly
            195                 200                 205

Glu Gly Gly Ala Ala Val Val Leu Lys Pro Leu Ala Asp Ala Leu Ala
    210                 215                 220

Asp Gly Asp Pro Val Tyr Cys Val Val Arg Gly Val Ala Ile Gly Asn
225                 230                 235                 240

Asp Gly Gly Gly Pro Gly Leu Thr Ala Pro Asp Arg Glu Gly Gln Glu
                245                 250                 255

Ala Val Leu Arg Ser Ala Cys Ala Gln Ala Gly Val Asp Pro Ala Glu
                260                 265                 270

Val His Phe Val Glu Leu His Gly Thr Gly Thr Pro Val Gly Asp Pro
            275                 280                 285

Val Glu Ala His Ala Leu Gly Ala Val His Gly Ser Gly Arg Ser Ala
    290                 295                 300

Asp Thr Pro Leu Leu Val Gly Ser Val Lys Thr Asn Ile Gly His Leu
305                 310                 315                 320

Glu Gly Ala Ala Gly Ile Ala Gly Leu Val Lys Ala Val Leu Cys Leu
                325                 330                 335

Arg Glu Arg Thr Leu Pro Gly Ser Leu Asn Phe Asp Thr Pro Asn Pro
            340                 345                 350

Ala Ile Pro Leu Asp Arg Leu Arg Leu Lys Val Gln Thr Ala Pro Thr
    355                 360                 365

Glu Leu His Pro Gly Pro Ser Gly Ala Pro Leu Leu Ala Gly Val Ser
370                 375                 380

Ser Phe Gly Ile Gly Gly Thr Asn Cys His Val Val Leu Glu His Leu
385                 390                 395                 400

Pro Gln Pro Ala Pro Ala Gly Pro Asp Ala Ile Pro Ser Ser Ala Ser
            405                 410                 415

Glu Ala Ala Ala Pro His Pro Ala Pro Pro Leu Leu Leu Ser Ala Arg
    420                 425                 430

Ser Arg Ala Ala Leu Arg Ala Gln Ala Ala Arg Leu His Asp His Leu
            435                 440                 445

Gly Arg Thr Gly Ala Asp Pro Arg Asp Ile Ala Tyr Ser Leu Ala Thr
    450                 455                 460

Thr Arg Thr Leu Phe Glu His Arg Ala Ala Leu Arg Cys Gly Asp Arg
465                 470                 475                 480

Glu Glu Leu Ala Ala Ser Leu Asp Ala Phe Ala Arg Gly Lys Thr Ser
                485                 490                 495

Ala Gly Val Arg Thr Gly Thr Ala Val Ser Gly Gly Thr Ala Val Leu
            500                 505                 510

Phe Thr Gly Gln Gly Ala Gln Trp Val Gly Met Gly Arg Glu Leu Tyr
    515                 520                 525

Gly Ala Gly Gly Val Phe Ala Gly Val Leu Asp Glu Val Leu Gly Val
    530                 535                 540

Val Gly Glu Val Gly Gly Arg Ser Leu Arg Glu Val Met Phe Ala Glu
545                 550                 555                 560

Ala Gly Ser Val Gly Ala Gly Leu Leu Gly Cys Thr Glu Phe Ala Gln
                565                 570                 575

Pro Ala Leu Phe Ala Leu Glu Val Ala Leu Phe Arg Ala Leu Glu Ala
            580                 585                 590

Arg Gly Val Gly Val Ser Val Val Leu Gly His Ser Val Gly Glu Val
    595                 600                 605

Ala Ala Ala Tyr Val Ala Gly Val Phe Ser Leu Ala Asp Ala Val Arg
```

```
            610                 615                 620
Leu Val Ala Arg Gly Arg Leu Met Gly Ala Leu Pro Val Gly Gly
625                 630                 635                 640

Ala Met Val Ser Val Gly Ala Ser Glu Ala Glu Leu Ala Gly Leu Val
                    645                 650                 655

Ala Gly Leu Gly Gly Arg Val Ser Val Ala Ala Val Asn Gly Pro Ala
                660                 665                 670

Ser Val Val Leu Ser Gly Glu Ala Gly Val Leu Asp Gly Val Ala
                675                 680                 685

Gly Leu Val Gly Arg Gly Val Glu Cys Arg Trp Leu Glu Val Ser His
690                 695                 700

Ala Phe His Ser Val Leu Met Asp Pro Met Leu Glu Glu Phe Arg Arg
705                 710                 715                 720

Val Ala Ala Ser Val Glu Phe His Arg Pro Arg Ser Gly Val Ala Val
                    725                 730                 735

Val Ser Ser Val Thr Gly Ala Val Ala Gly Leu Asp Glu Leu Gly Asp
                740                 745                 750

Pro Glu Tyr Trp Val Arg His Val Arg Glu Ala Val Arg Phe Ala Asp
                755                 760                 765

Gly Val Gly Ala Ala Arg Asp Val Gly Val Asp Thr Phe Val Glu Val
770                 775                 780

Gly Pro His Ala Val Leu Thr Val Met Ala Gly Gln Cys Leu Asp Gly
785                 790                 795                 800

Asp Glu Gly Asp Leu Ala Phe Val Pro Val Leu Arg Arg Asp Arg Pro
                805                 810                 815

Glu Leu Glu Thr Phe Thr Thr Ala Leu Ala Thr Leu Tyr Thr Arg Asp
                820                 825                 830

Ala Glu Leu Asp Val Ala Ala Leu His Ser Gly Phe Gly Gly Arg Arg
                835                 840                 845

Val Asp Leu Pro Thr Tyr Pro Phe Gln Arg Arg Thr His Trp Ser Pro
                850                 855                 860

Ala Leu Ser Arg Gly Ile Ala Ala Asp Ala Gly Pro Gly Leu Thr Thr
865                 870                 875                 880

Thr Asp Ala Ala Gly Asn Thr Ala Pro Pro Glu Ser Thr Glu Ala Pro
                    885                 890                 895

Leu Arg Asp Pro Asp Asp Glu Pro Leu Thr Ala Ser Pro Glu Pro Met
                900                 905                 910

Ser Pro Glu Gln Leu Val Arg Leu Val Arg Glu Thr Thr Ala Thr Val
                915                 920                 925

Leu Gly His Asp Asp Pro Asp Glu Ile Ala Leu Asp Arg Thr Phe Thr
930                 935                 940

Ser Gln Gly Leu Glu Ser Ala Thr Ala Val Glu Leu His Asp Leu Leu
945                 950                 955                 960

Asn Arg Ala Thr Gly Leu Thr Leu Ala Ala Thr Leu Val Tyr Asp Leu
                    965                 970                 975

Pro Thr Pro Arg Ala Val Ala Glu His Leu Val Ala Ala Leu His Gly
                980                 985                 990

Thr Lys Ser Ala His Pro Gly Glu His Glu Ala Val Gly Ala Ala Ala
                995                 1000                1005

Ala Arg Gly Gly Thr Arg Asp Asp Asp Pro Ile Ala Ile Val Gly Val
                1010                1015                1020

Gly Cys Arg Leu Pro Gly Gly Val Asp Ser Arg Ala Ala Leu Trp Asp
1025                1030                1035                1040
```

Leu Leu Ala Ser Gly Thr Asp Ala Ile Ser Ser Phe Pro Ala Asp Arg
            1045                1050                1055

Gly Trp Asp Leu Asp Gly Leu Tyr Asp Ala Glu Pro Gly Val Pro Gly
            1060                1065                1070

Lys Thr Tyr Val Arg Gln Gly Gly Phe Leu His Gln Ala Ala Glu Phe
            1075                1080                1085

Asp Ala Glu Phe Phe Gly Ile Ser Pro Arg Glu Ala Thr Ala Met Asp
            1090                1095                1100

Pro Gln Gln Arg Leu Leu Leu Glu Thr Ser Trp Glu Ala Leu Glu Asp
1105                1110                1115                1120

Ala Gly Val Leu Pro Glu Ser Leu Arg Gly Gly Asp Thr Gly Val Phe
            1125                1130                1135

Ile Gly Ala Val Ala Pro Glu Tyr Gly Pro Arg Leu His Glu Gly Ala
            1140                1145                1150

Asp Gly Tyr Glu Gly Tyr Leu Leu Thr Gly Thr Thr Ala Ser Val Ala
            1155                1160                1165

Ser Gly Arg Ile Ala Tyr Thr Leu Gly Thr Arg Gly Pro Ala Leu Thr
            1170                1175                1180

Val Asp Thr Ala Cys Ser Ser Leu Val Ala Leu His Leu Ala Val
1185            1190                1195                1200

Gln Ala Leu Arg Arg Gly Glu Cys Gly Leu Ala Leu Ala Gly Gly Ala
            1205                1210                1215

Thr Val Met Ser Gly Pro Gly Met Phe Val Glu Phe Ser Arg Gln Arg
            1220                1225                1230

Gly Leu Ala Pro Asp Gly Arg Cys Met Pro Phe Ser Ala Asp Ala Asp
            1235                1240                1245

Gly Thr Ala Trp Ser Glu Gly Val Ala Val Leu Ala Leu Glu Arg Leu
            1250                1255                1260

Ser Asp Ala Arg Arg Ala Gly His Arg Val Leu Ala Val Val Arg Gly
1265                1270                1275                1280

Ser Ala Val Asn Gln Asp Gly Ala Ser Asn Gly Leu Thr Ala Pro Asn
            1285                1290                1295

Gly Ser Ala Gln Glu Gly Val Ile Arg Ala Ala Leu Ala Asp Ala Gly
            1300                1305                1310

Leu Ala Pro Gly Asp Val Asp Ala Val Glu Ala His Gly Thr Gly Thr
            1315                1320                1325

Ala Leu Gly Asp Pro Ile Glu Ala Gly Ala Leu Leu Ala Thr Tyr Gly
            1330                1335                1340

Arg Glu Arg Val Gly Glu Pro Leu Trp Leu Gly Ser Leu Lys Ser Asn
1345                1350                1355                1360

Val Gly His Thr Gln Ala Ala Ala Gly Ala Ala Gly Val Ile Lys Met
            1365                1370                1375

Leu Leu Ala Met Arg His Gly Thr Leu Pro Arg Thr Leu His Ala Asp
            1380                1385                1390

Arg Pro Ser Thr His Val Asp Trp Ser Ser Gly Thr Val Glu Leu Leu
            1395                1400                1405

Ala Glu Ala Arg Arg Trp Pro Glu Arg Ala Gly Arg Pro Arg Arg Ala
            1410                1415                1420

Ala Val Ser Ser Phe Gly Ile Ser Gly Thr Asn Ala His Leu Val Ile
1425                1430                1435                1440

Glu Glu Ala Pro Ala Glu Thr Pro Thr Glu Pro Pro Thr Val Thr Ala
            1445                1450                1455

```
Pro Thr Ala Glu  Leu Ala Pro Thr Leu  Ala Trp Pro Val Ser  Ala Arg
             1460              1465                  1470

Ser Glu Glu  Ala Leu Arg Ala Gln  Ala Ala Arg Leu Arg  Glu His Val
         1475              1480               1485

Glu Arg Val Gly Ala Asp Pro  Val Asp Val Ala His  Ser Leu Ala Val
        1490              1495                1500

Thr Arg Glu Ser Phe  Gly Glu Arg Ala Val  Val Gly Gly Asp Arg
1505                 1510                 1515                1520

Ala Glu Leu Met Ala  Gly Leu Asp Ala Leu  Ala Ala Gly His Thr  Arg
                1525                 1530                1535

Pro Lys Thr Val  Arg Gly Thr Ala Val  Ser Gly Gly Thr Ala  Val Leu
            1540                 1545               1550

Phe Thr Gly  Gln Gly Ala Gln Trp  Val Gly Met Gly Arg  Glu Leu Tyr
         1555              1560                 1565

Gly Ala  Gly Gly Val Phe Ala  Gly Val Leu Asp Glu  Val Leu Gly Val
         1570             1575                1580

Val Gly Glu Val Gly  Gly Arg Ser Leu Arg  Glu Val Met Phe Ala  Glu
1585                 1590                 1595                1600

Ala Gly Ser Val Asp  Ala Gly Leu Leu Gly  Cys Thr Glu Phe Ala  Gln
                1605                 1610                1615

Pro Ala Leu Phe  Ala Leu Glu Val Ala  Leu Phe Arg Ala Leu  Glu Ala
            1620                 1625                1630

Arg Gly Val  Gly Val Ser Val Val  Leu Gly His Ser Val  Gly Glu Val
         1635              1640                1645

Ala Ala  Ala Tyr Val Ala Gly  Val Phe Ser Leu Ala  Asp Ala Val Arg
         1650             1655                1660

Leu Val Val Ala Arg  Gly Arg Leu Met Gly  Ala Leu Pro Val Gly  Gly
1665                 1670                 1675                1680

Ala Met Val Ser Val  Gly Ala Ser Glu Ala  Glu Leu Ala Gly Leu  Val
                1685                 1690                1695

Ala Gly Leu Gly  Gly Arg Val Ser Val  Ala Ala Val Asn Gly  Pro Ala
            1700                 1705                1710

Ser Val Val  Leu Ser Gly Glu Ala  Gly Val Leu Asp Gly  Val Val Ala
         1715              1720                1725

Gly Leu  Val Gly Arg Gly Val  Glu Cys Arg Trp Leu  Glu Val Ser His
         1730             1735                1740

Ala Phe His Ser Val  Leu Met Asp Pro Met  Leu Glu Glu Phe Arg  Arg
1745                 1750                 1755                1760

Val Ala Ala Ser Val  Glu Phe His Arg Pro  Arg Ser Gly Val Ala  Val
                1765                 1770                1775

Val Ser Ser Val  Thr Gly Ala Val Ala  Gly Leu Asp Glu Leu  Gly Asp
            1780                 1785                1790

Pro Glu Tyr  Trp Val Arg His Val  Arg Glu Ala Val Arg  Phe Ala Asp
         1795              1800                1805

Gly Val  Gly Ala Ala Arg Asp  Val Gly Val Asp Thr  Phe Val Glu Val
         1810             1815                1820

Gly Pro His Ala Val  Leu Thr Val Met Ala  Gly Gln Cys Leu Asp  Gly
1825                 1830                 1835                1840

Asp Glu Gly Asp Leu  Ala Phe Val Pro Val  Leu Arg Arg Asp Arg  Pro
                1845                 1850                1855

Glu Leu Glu Thr  Phe Thr Thr Ala Leu  Ala Thr Leu Tyr Ala  Arg Gly
            1860                 1865                1870

Ala Gln Ile  Asp Trp Asp Ala Pro  Asn Arg Lys Arg Asp  Ala Arg Arg
```

-continued

```
            1875                1880                1885
Ile Asp Leu Pro Thr Tyr Pro Phe Gln Arg Ala Arg Phe Trp Leu Asp
            1890                1895                1900
Pro Ala Pro Ala Ala Val Pro Thr Ala Met Ala Ala Gly Ser Ser Glu
1905                1910                1915                1920
Asp Val Pro Thr Ala Ala Gln Gly Val Thr Ser Ala Thr Ala Gly Leu
                1925                1930                1935
Arg Tyr Arg Val Thr Trp Gln Pro Ala Ala Val Gly Cys Gly Val Pro
                1940                1945                1950
Arg Pro Ala Gly Arg Met Leu Leu Leu Ala Ser Asp Asp Thr Thr
                1955                1960                1965
Asp Ser Gly Leu Ala Thr Ala Ile Ala Arg Glu Leu Ala Val Arg Gly
            1970                1975                1980
Thr Glu Val His Thr Ala Val Val Pro Val Gly Thr Gly Arg Glu Ala
1985                1990                1995                2000
Ala Ala Asp Leu Leu Arg Ala Ala Gly Asp Gly Ala Ala Arg Ser Thr
                2005                2010                2015
His Val Leu Trp Leu Ala Pro Ala Glu Pro Asp Thr Ala Asp Ala Val
                2020                2025                2030
Ala Leu Ile Gln Ala Leu Gly Glu Ala Gly Pro Asp Ala Pro Leu Trp
                2035                2040                2045
Ile Thr Thr Arg Asp Ala Val Ala Ala Gln Pro Gly Glu Ala Pro Ser
                2050                2055                2060
Val Ala Gly Ala Gln Leu Trp Gly Leu Gly Gln Val Ala Ala Leu Glu
2065                2070                2075                2080
Leu Ala Gln Arg Trp Gly Gly Leu Ala Asp Leu Pro Gly Glu Pro Ser
                2085                2090                2095
Pro Ala Ala Leu Arg Ala Phe Val Gly Thr Leu Leu Ala Glu Gly Glu
                2100                2105                2110
Asp Asn Gln Phe Ala Val Arg Pro Ser Gly Val His Val Arg Arg Val
                2115                2120                2125
Val Pro Val Pro Val Arg Ala Ala Thr Thr Ala Ala Ala Arg Asp Ala
                2130                2135                2140
Gln Gly Asp Thr Pro Asp Gly Val Val Pro Gly Asn Arg Arg Ser Ser
2145                2150                2155                2160
Gly Thr Val Leu Ile Thr Gly Gly Thr Gly Ala Leu Gly Ala Gln Val
                2165                2170                2175
Ala Arg Arg Leu Ala Arg Ala Gly Ala Pro His Leu Leu Leu Val Gly
                2180                2185                2190
Arg Arg Gly Ala Ala Gly Pro Gly Ala Gly Glu Leu Val Glu Glu Leu
                2195                2200                2205
Thr Ala Leu Gly Thr Glu Val Thr Val Ala Ala Cys Asp Val Ala Asp
                2210                2215                2220
Arg Asp Ala Leu Ala Ala Leu Leu Ala Gly Ile Pro Glu Asp Arg Pro
2225                2230                2235                2240
Leu Ala Ala Val Leu His Ala Ala Gly Val Leu Asp Asp Gly Val Leu
                2245                2250                2255
Asp Ser Leu Thr Ser Asp Arg Ile Asp Ala Val Leu Arg Ala Lys Val
                2260                2265                2270
Thr Ala Ala Arg His Leu Asp Glu Leu Thr Ala Asp Leu Pro Leu Asp
                2275                2280                2285
Ala Phe Val Leu Phe Ser Ser Ile Val Gly Val Trp Gly Asn Gly Gly
                2290                2295                2300
```

```
Gln  Ala  Ala  Tyr  Ala  Ala  Ala  Asn  Ala  Ala  Leu  Asp  Ala  Leu  Ala  His
2305                 2310                 2315                 2320

Arg  Arg  Arg  Ala  Arg  Gly  Gly  Arg  Ala  Thr  Ser  Ile  Ala  Trp  Gly  Pro
            2325                 2330                 2335

Trp  Ala  Gly  Ala  Gly  Met  Ala  Ser  Gly  Thr  Ala  Thr  Lys  Ser  Phe  Glu
            2340                 2345                 2350

Arg  Asp  Gly  Val  Ala  Leu  Asp  Pro  Glu  His  Ala  Leu  Asp  Val  Leu
            2355                 2360                 2365

Asp  Asp  Ala  Val  Gly  Ala  Gly  Thr  Ser  Ala  Ala  Ala  Gly  Ala  Ser
     2370                 2375                 2380

Ala  Ala  Val  Ala  Thr  Ser  Leu  Ile  Val  Ala  Asp  Val  Asp  Trp  Glu  Thr
2385                 2390                 2395                 2400

Phe  Val  Gly  Arg  Ser  Val  Thr  Arg  Arg  Thr  Trp  Ala  Leu  Phe  Asp  Gly
            2405                 2410                 2415

Val  Pro  Ala  Ala  Arg  Ser  Ala  Arg  Ser  Ala  Arg  Ala  Ala  Gln  Gly  Arg
            2420                 2425                 2430

Ala  Thr  Leu  Pro  Arg  Gly  Thr  Arg  Pro  Gly  His  Gly  Gly  Pro  Gly  Gly
            2435                 2440                 2445

Ser  Gly  Ala  Gly  Ala  Asp  Glu  Gly  Arg  Pro  Trp  Leu  Ser  Val  Gly  Pro
            2450                 2455                 2460

Ser  Ser  Thr  Glu  Arg  Arg  Arg  Ala  Leu  Leu  Asp  Leu  Val  Cys  Ser  Glu
2465                 2470                 2475                 2480

Ala  Ala  Glu  Ile  Leu  Arg  His  Ala  Ser  Ala  Asp  Ala  Val  Asp  Pro  Glu
            2485                 2490                 2495

Ile  Ala  Phe  Arg  Ser  Ala  Gly  Phe  Asp  Ser  Leu  Thr  Val  Leu  Glu  Leu
            2500                 2505                 2510

Arg  Asn  Arg  Leu  Thr  Ala  Ala  Thr  Gly  Leu  Asn  Leu  Pro  Ser  Thr  Leu
            2515                 2520                 2525

Leu  Phe  Asp  His  Pro  Asn  Pro  Thr  Ser  Leu  Ala  Ala  His  Leu  His  Asp
            2530                 2535                 2540

Glu  Leu  Phe  Gly  Thr  Asp  Ser  Glu  Ala  Glu  Pro  Val  Ala  Asp  Thr  Arg
2545                 2550                 2555                 2560

Ala  Arg  Ala  Thr  Ala  Asp  Glu  Arg  Glu  Pro  Ile  Ala  Ile  Val  Gly  Met
            2565                 2570                 2575

Ala  Cys  Arg  Tyr  Pro  Gly  Gly  Val  Ser  Ser  Pro  Glu  Asp  Leu  Trp  Arg
            2580                 2585                 2590

Leu  Val  Ala  Glu  Asp  Gly  His  Thr  Leu  Ser  Pro  Phe  Pro  Val  Asp  Arg
            2595                 2600                 2605

Gly  Trp  Asp  Val  Glu  Gly  Leu  Tyr  Asp  Pro  Asp  Pro  Glu  Ala  Val  Gly
            2610                 2615                 2620

Arg  Ser  Tyr  Val  Arg  Glu  Gly  Gly  Phe  Leu  His  Gly  Ala  Ala  Glu  Phe
2625                 2630                 2635                 2640

Asp  Ala  Glu  Phe  Phe  Gly  Ile  Ser  Pro  Arg  Glu  Ala  Ala  Ala  Met  Asp
            2645                 2650                 2655

Pro  Gln  Gln  Arg  Leu  Leu  Leu  Glu  Thr  Ser  Trp  Glu  Ala  Leu  Glu  Arg
            2660                 2665                 2670

Ala  Gly  Ile  Val  Pro  Asp  Ala  Leu  Arg  Gly  Thr  Arg  Thr  Gly  Val  Phe
            2675                 2680                 2685

Thr  Gly  Ile  Ser  Gln  Gln  Asp  Tyr  Ala  Ser  Gln  Leu  Gly  Asp  Ala  Ala
            2690                 2695                 2700

Glu  Thr  Tyr  Gly  Gly  His  Val  Leu  Thr  Gly  Thr  Leu  Gly  Ser  Val  Ile
2705                 2710                 2715                 2720
```

```
Ser Gly Arg Val Ala  Tyr Val Leu Gly Leu  Glu Gly Pro Ala Leu  Thr
                2725                 2730                 2735

Val Asp Thr Ala Cys  Ser Ser Ser Leu Val  Ala Leu His Leu Ala  Val
            2740                 2745                 2750

Gln Ser Leu Arg Arg  Gly Glu Cys Asp Met  Ala Leu Ala Gly Gly  Val
            2755                 2760                 2765

Thr Val Met Ala Thr  Pro Thr Val Phe Val  Glu Phe Ser Arg Gln  Arg
            2770                 2775                 2780

Gly Leu Ala Ser Asp  Gly Arg Cys Lys Ala  Phe Ala Glu Gly Ala  Asp
2785                 2790                 2795                 2800

Gly Thr Val Trp Ala  Glu Gly Val Gly Val  Leu Leu Val Glu Arg  Leu
            2805                 2810                 2815

Ser Asp Ala Arg Arg  Tyr Gly His Arg Val  Leu Ala Val Val Arg  Gly
            2820                 2825                 2830

Ser Ala Val Asn Gln  Asp Gly Ala Ser Asn  Gly Leu Thr Ala Pro  Ser
            2835                 2840                 2845

Gly Ala Ala Gln Arg  Arg Val Ile Arg Glu  Ala Leu Ala Asp Ala  Gly
            2850                 2855                 2860

Leu Ala Pro Gly Asp  Val Asp Ala Val Glu  Ala His Gly Thr Gly  Thr
2865                 2870                 2875                 2880

Ala Leu Gly Asp Pro  Ile Glu Ala Gly Ala  Leu Leu Ala Thr Tyr  Gly
            2885                 2890                 2895

Arg Glu Arg Val Gly  Asp Pro Leu Trp Leu  Gly Ser Leu Lys Ser  Asn
            2900                 2905                 2910

Ile Gly His Ala Gln  Ala Ala Ala Gly Val  Gly Gly Val Ile Lys  Met
            2915                 2920                 2925

Val Glu Ala Met Arg  His Ser Ser Leu Pro  Arg Thr Leu His Val  Asp
            2930                 2935                 2940

Ala Pro Ser Ser Arg  Val Glu Trp Gly Ser  Gly Ala Val Glu Leu  Leu
2945                 2950                 2955                 2960

Thr Glu Ala Arg Ser  Trp Pro Arg Arg Ala  Gly Arg Val Arg Arg  Ala
            2965                 2970                 2975

Ala Val Ser Ala Phe  Gly Val Ser Gly Thr  Asn Ala His Val Val  Ile
            2980                 2985                 2990

Glu Glu Pro Ser Val  Glu Glu Ser Ala Glu  Ala Glu Ala Val Val  Thr
            2995                 3000                 3005

Ala Ala Ala Glu Ser  Ser Ser Val Leu Ala  Trp Pro Val Ser Ala  Arg
3010                 3015                 3020

Ser Glu Glu Ala Leu  Arg Gly Gln Ala Val  Arg Leu Arg Glu His  Val
3025                 3030                 3035                 3040

Glu Arg Val Gly Ala  Asp Pro Val Asp Val  Ala His Ser Leu Val  Val
            3045                 3050                 3055

Ser Arg Ala Ser Phe  Gly Glu Arg Ala Val  Val Gly Arg  Glu Arg
            3060                 3065                 3070

Gly Glu Leu Leu Ala  Gly Leu Asp Ala Val  Ala Ala Gly Val Val  Ala
            3075                 3080                 3085

Ala Gly Gly Ala Ala  Ser Val Val Arg Gly  Ser Ala Val Arg Gly
            3090                 3095                 3100

Arg Arg Val Gly Val  Leu Phe Thr Gly Gln  Gly Ala Gln Trp Val  Gly
3105                 3110                 3115                 3120

Met Gly Arg Glu Leu  Tyr Gly Ala Gly Gly  Val Phe Ala Gly Val  Leu
            3125                 3130                 3135

Asp Glu Val Leu  Gly Val Val Gly Glu  Val Gly Gly Arg Ser  Leu Arg
```

```
                 3140              3145              3150
Glu Val Met  Phe Ala Glu Ala  Gly Ser Val Asp  Ala Gly Leu Leu Gly
             3155              3160             3165

Cys Thr Glu  Phe Ala Gln Pro  Ala Leu Phe Ala  Leu Glu Val Ala Leu
        3170              3175             3180

Phe Arg Ala Leu Glu  Ala Arg Gly Val  Gly Val Ser Val  Val Leu Gly
3185             3190              3195              3200

His Ser Val Gly Glu  Val Ala Ala Ala Tyr  Val Ala Gly Val Phe  Ser
             3205                 3210                 3215

Leu Ala Asp Ala  Val Arg Leu Val Val  Ala Arg Gly Arg Leu  Met Gly
             3220                 3225                 3230

Ala Leu Pro  Val Gly Gly Ala Met  Val Ser Val Gly Ala  Ser Glu Ala
        3235                 3240                 3245

Glu Leu  Ala Gly Leu Val Ala  Gly Leu Gly Arg  Val Ser Val Ala
         3250                 3255             3260

Ala  Val Asn Gly Pro Ala  Ser Val Val Leu Ser  Gly Glu Ala Gly Val
3265                 3270                 3275                 3280

Leu Asp Gly Val Val  Ala Gly Leu Val Gly  Arg Gly Val Glu Cys  Arg
                3285                 3290                 3295

Trp Leu Glu Val  Ser His Ala Phe His  Ser Val Leu Met Asp  Pro Met
                3300                 3305                 3310

Leu Glu Glu  Phe Arg Arg Val Ala  Ala Ser Val Glu Phe  His Arg Pro
        3315                 3320                 3325

Arg Ser  Gly Val Ala Val Val  Ser Ser Val Thr Gly  Ala Val Ala Gly
         3330                 3335                 3340

Leu Asp Glu Leu Gly  Asp Pro Glu Tyr Trp  Val Arg His Val Arg  Glu
3345                 3350                 3355                 3360

Ala Val Arg Phe Ala  Asp Gly Val Gly Ala  Ala Arg Asp Val Gly  Val
                3365                 3370                 3375

Asp Thr Phe Val  Glu Val Gly Pro His  Ala Val Leu Thr Val  Met Ala
            3380                 3385                 3390

Gly Gln Cys  Leu Asp Gly Asp Glu  Gly Asp Leu Ala Phe  Val Pro Val
        3395                 3400                 3405

Leu Arg  Arg Asp Arg Pro Glu  Leu Glu Thr Phe Thr  Thr Ala Leu Ala
         3410                 3415                 3420

Thr  Leu Tyr Thr Arg Asp  Ala Glu Leu Asp Val  Ala Ala Leu His Ser
3425                 3430                 3435                 3440

Gly Phe Gly Gly Arg  Arg Val Asp Leu Pro  Thr Tyr Pro Phe Gln  Arg
                3445                 3450                 3455

Arg Gly Tyr Trp  Ala Thr Gly Ser Val  Ser Gly Ser Thr Gly  Ser Ser
            3460                 3465                 3470

Ala Ala Ala  Arg Phe Gly Leu Glu  Trp Lys Asp His Pro  Phe Leu Ser
        3475                 3480                 3485

Gly Ala  Thr Pro Ile Val Gly  Ser Gly Ala Leu Leu  Leu Thr Gly Arg
         3490                 3495                 3500

Val Ala Leu Ser Thr  His Pro Trp Leu Ala  Asp His Ala Ile Ser  Gly
                3505                 3510                 3515                 3520

Thr Val Leu Leu Pro  Gly Thr Ala Ile Ala  Asp Leu Leu Leu Arg  Ala
                3525                 3530                 3535

Ala Glu Glu Val  Gly Ala Gly Gly Val  Glu Glu Leu Thr Leu  His Ala
            3540                 3545                 3550

Pro Leu Leu  Leu Pro Glu Gln Gly  Gly Leu Arg Leu Gln  Val Leu Val
        3555                 3560                 3565
```

```
Glu Ala Ala Asp Gly Gln Gly Arg Arg Ala Val Ala Leu Ala Ala Arg
        3570                3575                3580

Pro Glu Thr Pro Gly Trp Asp Gly Glu Pro Glu Trp Thr Lys His
3585                3590                3595                3600

Ala Glu Gly Val Leu Ala Pro Ala Glu Pro Ala Val Pro Asp Thr Ala
            3605                3610                3615

Trp Ala Ala Gly Ala Trp Pro Pro Gly Ala Glu Pro Val Asp Val
        3620                3625                3630

Gly Glu Leu Tyr Glu Gly Phe Ala Ala Asp Gly Tyr Asp Tyr Gly Pro
            3635                3640                3645

Ala Phe Ser Gly Leu Ser Gly Ala Trp Arg Leu Gly Asn Glu Leu Phe
        3650                3655                3660

Ala Glu Val Arg Leu Ser Ala Thr Gly Thr Ala Gly Asp Gly Phe Gly
3665                3670                3675                3680

Ile His Pro Ala Leu Phe Asp Ala Ala Leu His Pro Trp Arg Ala Gly
            3685                3690                3695

Gly Leu Leu Pro Asp Thr Gly Gly Thr Thr Leu Ala Pro Phe Ser Trp
        3700                3705                3710

Gln Gly Ile Ala Leu His Ala Thr Gly Ala Glu Thr Leu Arg Val Arg
        3715                3720                3725

Leu Ala Pro Ala Gly Ser Gly Ala Glu Ser Ala Phe Ser Val Arg Ala
        3730                3735                3740

Ala Asp Pro Ala Gly Ala Pro Val Leu Thr Leu Asp Ala Leu Leu Leu
3745                3750                3755                3760

Arg Pro Val Ala Leu Gly Thr Ala Gly Ala Pro Glu Pro Leu Tyr Arg
            3765                3770                3775

Val Asp Trp Gln Pro Val Pro Gln Arg Ser Asp Thr Pro Gly Ala His
        3780                3785                3790

Gly Trp Thr Val Leu Gly Pro Ala Ala Gly Glu Thr Ala Ala Glu Gln
        3795                3800                3805

Ala Ala Thr Glu Glu Cys Ala Thr Leu Arg Ala Leu Pro Gly Ala Glu
        3810                3815                3820

Pro Ala Ala His Ala Asp Leu Ala Ala Leu Arg Thr Ala Leu Thr Ala
3825                3830                3835                3840

Gly Thr Pro Val Pro Gly Leu Val Val Val Pro Ala Thr Asp Ile Arg
            3845                3850                3855

Pro Ala Glu Ser Ser Ala Gly Ala Gly Ala Gly Val Asp Ala Gly Ala
            3860                3865                3870

Asp Ala Arg Val Arg Arg Gly Lys Ala His Val Arg Thr Ala Thr Ala
            3875                3880                3885

His Ala Arg Thr Gly Thr Asp Trp Gly Asp Asp Pro Val Arg Val Ala
        3890                3895                3900

Leu Gly Arg Gly Leu Ala Leu Val Arg Glu Trp Thr Glu Asp Glu Arg
3905                3910                3915                3920

Leu Ala Asp Ser Arg Leu Val Val Leu Thr Arg Gly Ala Val Glu Ala
            3925                3930                3935

Gly Ser Gly Glu Val Pro Asp Leu Ala Gly Ala Ala Leu Trp Gly Leu
            3940                3945                3950

Leu Arg Ser Ala Gln Ser Glu Tyr Pro Asp Arg Phe Thr Leu Val Asp
            3955                3960                3965

Val Asp Asp Ser Pro Glu Ser Arg Ala Ala Leu Pro Arg Ala Leu Glu
        3970                3975                3980
```

```
Ser  Gly Glu Pro Gln  Leu Ala Leu Arg Ala  Gly Ala Leu Leu Ala  Pro
3985                  3990                 3995                 4000

Ala  Leu Val Pro Ile  Thr Thr Pro Ala Thr  Ala Ala Thr Pro Ala  Thr
          4005                  4010                      4015

Ala  Val Asp Ser Ala  Ala Ala Val  Ala Ala Gln Ser Val  Ala Pro
          4020                4025                4030

Glu  Ala Ala  Gly Pro Ala Glu Arg  Gly Gly Ala Ala Thr  Gly Gly Pro
          4035                4040                4045

Ala  Ser  Asp Gly Ala  Phe Asp  Pro Asp Gly Ser Ala  Val Asp Ala  Val
          4050                  4055                 4060

Phe  Asp Pro Ala Gly  Thr  Val Leu Ile Thr  Gly  Cys Thr Gly Ala  Leu
4065                  4070                 4075                   4080

Gly Arg Arg Val Ala   Pro His Leu Ala Arg   Arg His Gly Val Arg   His
          4085                  4090                     4095

Met  Leu Leu Val  Ser Arg Arg Gly Pro  Asp Ala Pro Glu Ala  Ala Leu
          4100                 4105                 4110

Leu  Glu Arg  Glu Leu Val Gly Leu  Gly Val Thr Ala Thr  Phe Leu Ala
          4115                4120                4125

Cys  Asp  Leu Ala Asp  Pro Ala  Ala Val Arg Lys Ala  Val Val Ala  Val
4130                   4135                4140

Ser  Pro Glu His Pro  Leu  Thr Gly Val Val  His  Thr Ala Gly Val  Leu
4145                  4150                 4155                   4160

Asp Asp Gly Ala Leu   Thr Gly Leu Thr Gln   Glu Arg Leu Asp Thr   Val
          4165                  4170                     4175

Leu Arg Ser Lys  Ala  Asp Ala Val Arg  Asn Leu His Glu Ala   Thr Leu
          4180                4185                 4190

Asp Arg Pro  Leu Arg Ala Phe Val  Leu Phe Ser Ala Ala   Ala Gly Leu
          4195                4200                4205

Leu Gly  Arg Pro Gly Gln Gly  Ser Tyr Ala Ala Ala   Asn Ala Val Leu
          4210                 4215                 4220

Asp  Ala Leu Ala Gly  Ala  Arg Arg Ala Ala  Gly  Leu Pro Ala Val  Ser
4225                  4230                 4235                   4240

Leu Ala Trp Gly Leu   Trp Asp Glu Arg Ala   Gly Met Ala Gly Gly   Leu
          4245                  4250                     4255

Asp  Asp Val Ala  Leu His Arg Leu Arg  Arg Glu Gly Ile Ala   Ala Met
          4260                4265                 4270

Pro Pro Glu  Gln Gly Leu Gly  Leu Leu Asp Gln Ala  Leu  Thr Ala His
          4275                4280                 4285

Arg Asp  Gly Pro Ala Val Leu  Val Pro Leu Leu Leu   Asp Gly Ala  Ala
          4290                4295                 4300

Leu  Arg Arg Thr Ala  Lys  Glu Arg Gly Ala  Ala  Ala Val Pro Pro  Leu
4305                  4310                 4315                   4320

Leu Arg Gly Leu Leu   Pro Ala Ala Leu Arg   His Ser Ser Thr Gly   Thr
          4325                  4330                     4335

Pro Ala Ala Ala  Asp Arg His Gly Lys  Gly Ala Glu Ser Gly  Thr Gly
          4340                4345                 4350

Arg  Ile Ala  Arg Ile Val Ala Leu  Asp Ala Ala Glu Arg  Ser Thr Ala
          4355                4360                4365

Val Leu  Asp Leu Val  Thr Glu  Gln Val Ala Glu Val  Leu Gly His Ala
          4370                 4375                 4380

Ser  Ala Ala Glu Ile  Glu  Pro Glu Arg Pro  Phe  Arg Glu Ile Gly  Val
4385                  4390                 4395                   4400

Asp Ser Leu Ala Ala   Val Glu Leu Arg Asn   Arg Leu Ser Arg Leu   Val
```

```
                    4405               4410               4415
Gly Leu Arg Leu Pro Thr Thr Leu Ala Phe Asp His Pro Thr Pro Lys
            4420               4425               4430

Asp Met Ala Glu Trp Ile Asp Gly Glu Leu Pro Arg Pro Ala Gly Ala
        4435               4440               4445

Pro Val Val Asp Ala Ala Leu Glu Gly Ile Gly Glu Leu Ala Arg Ala
    4450               4455               4460

Val Ala Leu Leu Gly Ser Asp Asp Ala Arg Arg Val Glu Val Arg Gln
4465               4470               4475               4480

Arg Leu Val Gly Leu Leu Thr Ala Leu Asp Thr Pro Gly Arg Gly Val
            4485               4490               4495

Val Gly Pro Gln Gly Arg Thr Ala Pro Ala Ala Pro Ala Ala Ala Asp
        4500               4505               4510

Gly Ala Gly Ala Thr Val Thr Asp Arg Leu Asp Glu Ala Thr Asp Asp
    4515               4520               4525

Glu Ile Phe Ala Phe Leu Asp Glu Gln Leu
    4530               4535

<210> SEQ ID NO 17
<211> LENGTH: 403
<212> TYPE: PRT
<213> ORGANISM: Streptomyces spiramyceticus WSJ-1

<400> SEQUENCE: 17

Met Gly Glu Ala Val Ser Gly Pro Met Glu Leu Ser Lys Asp Ala Asp
1               5                   10                  15

Ala Arg Gly Leu Leu Asp Trp Phe Ala Phe Asn Arg Thr Arg His Pro
            20                  25                  30

Val Phe Trp Asp Glu Gly Arg Gln Ala Trp Gln Val Phe Gly Tyr Asp
        35                  40                  45

Asp Tyr Val Thr Val Ser Asn Asn Pro Gln Phe Phe Ser Ser Asp Phe
    50                  55                  60

Asn Met Val Met Pro Thr Pro Pro Glu Leu Glu Met Ile Ile Gly Pro
65                  70                  75                  80

Gly Thr Ile Gly Ala Leu Asp Pro Pro Ala His Gly Pro Met Arg Lys
                85                  90                  95

Leu Val Ser Gln Ala Phe Thr Pro Arg Arg Ile Ala Arg Leu Glu Pro
            100                 105                 110

Arg Val Arg Ala Ile Thr Glu Glu Leu Leu Asp Lys Val Arg Glu Gln
        115                 120                 125

Asn Val Ile Asp Ala Val Gly Asp Leu Ser Tyr Ala Leu Pro Val Ile
    130                 135                 140

Val Ile Ala Glu Leu Leu Gly Val Pro Thr Gly Asp Arg Asp Leu Phe
145                 150                 155                 160

Arg Glu Trp Val Asp Thr Leu Leu Thr Asn Glu Gly Leu Glu Tyr Pro
                165                 170                 175

Asn Leu Pro Asp Asn Phe Thr Glu Thr Ile Ala Pro Ala Leu Lys Glu
            180                 185                 190

Met Thr Asp Tyr Leu Leu Glu Gln Ile His Ala Lys Arg Glu Ala Pro
        195                 200                 205

Ala Asp Asp Leu Ile Ser Gly Leu Val Gln Ala Glu Gln Asp Gly Arg
    210                 215                 220

Arg Leu Thr Asp Val Glu Ile Val Asn Ile Val Ala Leu Leu Leu Thr
225                 230                 235                 240
```

```
Ala Gly His Val Ser Ser Ser Thr Leu Leu Ser Asn Leu Phe Leu Val
                245                 250                 255

Leu Glu Glu Asn Pro Gln Ala Leu Glu Asp Leu Arg Ala Asp Arg Thr
260                 265                 270

Leu Val Pro Gly Ala Ile Glu Glu Thr Leu Arg Tyr Arg Ser Pro Phe
            275                 280                 285

Asn Asn Ile Phe Arg Phe Val Lys Gln Asp Thr Thr Ile Leu Gly Pro
290                 295                 300

Leu Met Glu Lys Gly Gln Met Val Ile Ala Trp Ser Gln Ser Ala Asn
305                 310                 315                 320

Arg Asp Pro Arg His Phe Pro Asp Pro Asp Thr Phe Asp Ile Arg Arg
                325                 330                 335

Ser Asp Gly Thr Arg His Met Ala Phe Gly His Gly Ile His His Cys
            340                 345                 350

Leu Gly Ala Ala Leu Ala Arg Leu Glu Gly Lys Val Met Leu Glu Leu
        355                 360                 365

Leu Leu Glu Arg Val Asp Gly Phe Arg Ile Asp His Glu Asn Thr Leu
370                 375                 380

Phe Tyr Glu Ala Asp Gln Leu Thr Pro Lys Tyr Leu Pro Val Arg Val
385                 390                 395                 400

Asp Trp Asn

<210> SEQ ID NO 18
<211> LENGTH: 116
<212> TYPE: PRT
<213> ORGANISM: Streptomyces spiramyceticus WSJ-1

<400> SEQUENCE: 18

Met Val Glu Ser Gly Val Thr Val Asp Phe Pro Val Gln Arg Val Tyr
1               5                   10                  15

Tyr Met His Gly Gln Thr Gln Ser Ser Pro Pro Arg Gly Leu His Ala
            20                  25                  30

His Arg Thr Leu Glu Gln Leu Val Ile Ala Val His Gly Ala Phe Ser
        35                  40                  45

Ile Thr Leu Asp Asp Gly Phe Gln His Ala Thr Tyr Arg Leu Asp Glu
    50                  55                  60

Pro Gly Ala Gly Leu Cys Ile Gly Pro Met Val Trp Arg Val Leu Lys
65                  70                  75                  80

Asp Phe Ala Pro Asp Thr Val Ala Leu Val Leu Ala Ser Gln His Tyr
                85                  90                  95

Glu Glu Ser Asp Tyr Tyr Arg Asp Tyr Asp Thr Phe Leu His Asp Ala
            100                 105                 110

Arg Ser Leu Thr
        115

<210> SEQ ID NO 19
<211> LENGTH: 399
<212> TYPE: PRT
<213> ORGANISM: Streptomyces spiramyceticus WSJ-1

<400> SEQUENCE: 19

Met Thr Ile Pro Phe Leu Asp Ala Gly Ala Gly Tyr Arg Glu Leu Arg
1               5                   10                  15

Ala Asp Ile Asp Ala Ala Leu Gln Arg Val Ser Ala Ser Gly Arg Tyr
            20                  25                  30

Leu Leu Gly Ala Glu Leu Glu Gly Phe Glu Glu Glu Phe Ala Ala Tyr
```

```
            35                  40                  45
Cys Asp Asn Gly His Cys Val Ala Val Gly Ser Gly Cys Asp Ala Leu
 50                  55                  60
Glu Leu Ser Leu Arg Ala Leu Asp Ile Gly Pro Gly Asp Glu Val Val
 65                  70                  75                  80
Val Pro Ala His Thr Phe Ile Gly Thr Trp Leu Ala Val Ser Ala Thr
                 85                  90                  95
Gly Ala Gln Pro Val Ala Val Asp Pro Thr Pro Asp Gly Leu Ser Leu
                100                 105                 110
Asp Pro Ala Leu Val Glu Ala Val Thr Pro Arg Thr Lys Ala Leu
                115                 120                 125
Met Pro Val His Leu His Gly His Pro Ala Asp Leu Asp Pro Leu Leu
                130                 135                 140
Ala Val Ala Glu Arg His Gly Leu Ala Val Val Glu Asp Ala Ala Gln
145                 150                 155                 160
Ala His Gly Ala Arg Tyr Arg Gly Arg Ile Gly Ser Gly His Val
                165                 170                 175
Val Ala Phe Ser Phe Tyr Pro Gly Lys Asn Leu Gly Ala Met Gly Asp
                180                 185                 190
Gly Gly Ala Val Val Thr Arg Asp Ala Gly Val Ala Asp Arg Ile Arg
                195                 200                 205
Leu Leu Arg Asn Cys Gly Ser Arg Glu Lys Tyr Arg His Glu Val Arg
210                 215                 220
Ala Thr Asn Ser Arg Leu Asp Glu Leu Gln Ala Ala Val Leu Arg Ala
225                 230                 235                 240
Lys Leu Pro Arg Leu Asp Ala Trp Asn Ala Arg Arg Ala Arg Thr Ala
                245                 250                 255
Glu Arg Tyr Thr Arg Ala Leu Gly Ser Leu Pro Gln Ile Ala Val Pro
                260                 265                 270
Val Thr Ala Arg Trp Ala Asp Pro Ala Trp His Leu Tyr Val Ile Arg
                275                 280                 285
Cys Ala Glu Arg Asp Glu Leu Arg Arg Arg Leu Glu Arg Ala Gly Val
290                 295                 300
Gln Thr Leu Ile His Tyr Pro Val Pro Pro His Arg Ser Pro Ala Tyr
305                 310                 315                 320
Ala Asp Ala Pro Ala Gly Ala Pro Ala Gly Ala His Pro Arg Ser Glu
                325                 330                 335
Arg Leu Ala Ala Gln Ser Leu Ser Leu Pro Leu Gly Pro His Leu Gly
                340                 345                 350
Asp Asp Glu Ser Arg Ala Val Val Ala Ala Val Arg Ala Ala Ala Ala
                355                 360                 365
Gly Leu Ala Ala Tyr Pro Thr Pro Asp Gly Thr Pro Thr Pro Arg
                370                 375                 380
Thr Thr Pro Asp Gly Gln Arg Phe Pro Leu Ala Thr Glu Lys Arg
385                 390                 395

<210> SEQ ID NO 20
<211> LENGTH: 302
<212> TYPE: PRT
<213> ORGANISM: Streptomyces spiramyceticus WSJ-1

<400> SEQUENCE: 20

Met Thr Glu Val Met Ser Gly Arg Ser Gly Met Lys Gly Ile Ile Leu
 1               5                  10                  15
```

Ala Gly Gly Gly Gly Thr Arg Leu Arg Pro Leu Thr Gly Thr Leu Ser
            20                  25                  30

Lys Gln Leu Leu Pro Val Tyr Asp Lys Pro Met Ile Tyr Tyr Pro Leu
         35                  40                  45

Ser Val Leu Met Leu Gly Gly Ile Arg Glu Ile Leu Val Ile Ser Ser
 50                  55                  60

Thr Gln His Ile Glu Leu Phe Gln Gln Leu Leu Gly Asp Gly Ser Arg
65                  70                  75                  80

Leu Gly Leu Asp Ile Thr Tyr Ala Glu Gln Pro Glu Pro Gln Gly Ile
                 85                  90                  95

Ala Gln Ala Leu Thr Ile Gly Thr Asp His Ile Gly Asp Ser Pro Val
            100                 105                 110

Ala Leu Ile Leu Gly Asp Asn Ile Phe His Gly Pro Gly Phe Ser Ser
        115                 120                 125

Val Leu Arg Gly Ser Ile Arg His Leu Asp Gly Cys Val Leu Phe Gly
    130                 135                 140

Tyr Pro Val Ser Asp Pro Gln Arg Tyr Gly Val Gly Glu Ile Asp Asp
145                 150                 155                 160

Gln Gly Met Leu Leu Ser Leu Glu Glu Lys Pro Ala Arg Pro Arg Ser
                165                 170                 175

Asn Leu Ala Val Thr Gly Leu Tyr Leu Tyr Asp Asn Asp Val Val Asp
            180                 185                 190

Ile Ala Lys Asn Ile Arg Pro Ser Ala Arg Gly Glu Leu Glu Ile Thr
        195                 200                 205

Asp Val Asn Gln Val Tyr Leu Glu Gln Lys Arg Ala Arg Leu Ile Glu
    210                 215                 220

Leu Gly His Gly Phe Ala Trp Leu Asp Met Gly Thr His Asp Ser Leu
225                 230                 235                 240

Leu Gln Gly Gly Gln Tyr Val Gln Leu Leu Glu Arg Gln Gly Val
                245                 250                 255

Arg Ile Ala Cys Ile Glu Glu Ile Ala Leu Arg Met Gly Phe Ile Asp
            260                 265                 270

Ala Asp Thr Leu Tyr Trp Leu Gly Arg Glu Leu Gly Thr Ser Gly Tyr
        275                 280                 285

Gly Ala Tyr Leu Met Glu Val Ala Thr His Ala Gly Ala Ala
    290                 295                 300

<210> SEQ ID NO 21
<211> LENGTH: 345
<212> TYPE: PRT
<213> ORGANISM: Streptomyces spiramyceticus WSJ-1

<400> SEQUENCE: 21

Met Gln Ala Pro His Glu Ser Pro His Arg Pro Thr Arg Phe Ala Asp
1               5                   10                  15

Gly Arg Gln Pro Ala Arg Ile Leu Val Thr Gly Gly Ala Gly Phe Ile
            20                  25                  30

Gly Ser Arg Phe Val Asn Ala Leu Leu Asp Gly Ser Leu Pro Glu Phe
        35                  40                  45

Gly Lys Pro Glu Val Arg Val Leu Asp Ala Leu Thr Tyr Ala Gly Asn
    50                  55                  60

Leu Ala Asn Leu Ala Pro Val Gly Asp Cys Pro Arg Leu Arg Ile Phe
65                  70                  75                  80

Gln Gly Asp Ile Cys Asp Arg Ser Ala Val Ala Gln Ala Met Ala Gly
                85                  90                  95

```
Val Asp Leu Val Val His Phe Ala Ala Glu Ser His Val Asp Arg Ser
            100                 105                 110

Ile Asp Asp Ala Asp Ala Phe Val Arg Thr Asn Val Leu Gly Thr Gln
            115                 120                 125

Val Leu Leu Gln Glu Ala Leu Ala Ile Arg Pro Gly Leu Phe Val His
    130                 135                 140

Val Ser Thr Asp Glu Val Tyr Gly Ser Ile Pro Val Gly Ser Trp Pro
145                 150                 155                 160

Glu Asp His Pro Leu Ser Pro Asn Ser Pro Tyr Ala Ala Ser Lys Ala
                165                 170                 175

Ser Ser Asp Leu Leu Ala Leu Ala Tyr His Arg Thr His Gly Leu Pro
            180                 185                 190

Val Cys Val Thr Arg Cys Ser Asn Asn Tyr Gly Pro Tyr Gln Tyr Pro
        195                 200                 205

Glu Lys Ile Ile Pro Leu Phe Thr Ser Asn Leu Leu Asp Gly Arg Thr
    210                 215                 220

Val Pro Leu Tyr Gly Asp Gly Gly Asn Arg Arg Asp Trp Leu His Val
225                 230                 235                 240

Asn Asp His Cys Arg Gly Ile Ala Leu Val Ala Arg Gly Gly Arg Pro
                245                 250                 255

Gly Glu Val Tyr Asn Ile Gly Gly Gly Ala Glu Leu Thr Asn Val Glu
            260                 265                 270

Leu Thr Glu Arg Leu Leu Lys Leu Cys Gly Ala Asp Trp Ser Ala Val
        275                 280                 285

Arg Gln Val Pro Asp Arg Lys Gly His Asp Gln Arg Tyr Ser Val Asp
    290                 295                 300

Tyr Thr Lys Ile Ala Thr Glu Leu Gly Tyr Ala Pro Arg Ile Thr Ile
305                 310                 315                 320

Asp Glu Gly Leu Glu Gln Thr Val Arg Trp Tyr Arg Glu Asn His Ala
                325                 330                 335

Trp Trp Thr Pro Val Lys Arg Gly Arg
            340                 345

<210> SEQ ID NO 22
<211> LENGTH: 745
<212> TYPE: PRT
<213> ORGANISM: Streptomyces spiramyceticus WSJ-1

<400> SEQUENCE: 22

Met Val Asp Ala Cys Glu Glu Gly Thr Met Thr Leu Met Ser Ala Ser
1               5                   10                  15

Val Asp Pro Arg Asp Leu Trp Leu Arg Arg Tyr Gln Pro Ser Ala Ser
            20                  25                  30

Pro Ala Val Arg Leu Val Cys Phe Pro His Ala Gly Gly Ser Ala Ser
        35                  40                  45

Ser Phe Leu Pro Phe Thr Arg Gln Leu Pro Asp Arg Ile Glu Val Ser
    50                  55                  60

Ala Val Gln Tyr Pro Gly Arg Gln Asp Arg Arg Ser Glu Pro Leu Ile
65                  70                  75                  80

Asp Thr Ile Glu Gly Leu Ala Lys Pro Leu Ala Asp Met Leu Glu Thr
                85                  90                  95

Arg Ala Gly Pro Pro Val Val Leu Phe Gly His Ser Met Gly Ala Leu
            100                 105                 110

Val Ala Tyr Glu Val Ala Arg Val Leu Gln Gln Arg Gly Ala Ala Pro
```

-continued

```
            115                 120                 125
Val Arg Leu Val Val Ser Gly Arg Ala Pro Ala Ser Asp Arg Pro
130                 135                 140
Met Thr Val His Leu Tyr Asp Asp Arg Leu Val Glu Glu Leu Arg
145                 150                 155                 160
Thr Leu Asp Gly Thr Asp Ser Gln Val Phe Ala Asp Pro Glu Leu Leu
                165                 170                 175
Gln Leu Val Leu Pro Ala Ile Arg Asn Asp Tyr Arg Ala Val Gly Thr
                180                 185                 190
Tyr Thr His Arg Pro Gly Ala Pro Leu Asp Cys Pro Leu Thr Val Phe
                195                 200                 205
Thr Gly Ala Asp Asp Pro Thr Val Thr Ala Ala Glu Ala Ala Ala Trp
                210                 215                 220
His Glu Val Ala Ala Ala Gly Ala Glu Met Arg Thr Phe Pro Gly Gly
225                 230                 235                 240
His Phe Phe Pro Tyr Gln Arg Thr Ala Glu Val Cys Gly Ala Leu Val
                245                 250                 255
Asp Thr Leu Ala Pro Leu Leu Ser Thr Gly Thr Arg Gly Val Arg Arg
                260                 265                 270
Val Arg Pro Gly Asp Val Gly Thr Val Glu Tyr Ala Gly His Arg Arg
                275                 280                 285
Thr Ala Glu Arg Val Leu Leu Ser Ala Asp Thr Leu Asp Ser Pro Val
                290                 295                 300
Thr Ser Leu Ala Asp Val Pro Arg Trp Leu Glu Ala Tyr Arg Arg Ala
305                 310                 315                 320
His Arg Phe His Val Glu Pro Ile Pro Phe Asp Arg Leu Arg Arg Trp
                325                 330                 335
Ser Phe Glu Pro Gly Thr Gly Asp Leu Arg His Glu Thr Gly Arg Phe
                340                 345                 350
Phe Ser Val Glu Gly Leu Arg Thr Ser Ser Asp Ala Asp Pro Val Ala
                355                 360                 365
Arg Val Gln Pro Ile Ile Val Gln Pro Glu Val Gly Leu Leu Gly Ile
                370                 375                 380
Leu Ala Arg Glu Phe Asp Gly Val Leu His Phe Leu Met Gln Ala Lys
385                 390                 395                 400
Pro Glu Pro Gly Asn Val Asn Gly Leu Gln Leu Ser Pro Thr Val Gln
                405                 410                 415
Ala Thr Arg Ser Asn Phe Asp Glu Val His His Gly Arg Ser Thr Pro
                420                 425                 430
Phe Leu Asp His Phe Ile His Arg Pro Gly Arg Arg Val Leu Ile Asp
                435                 440                 445
Thr Ile Gln Ser Glu Gln Gly Asp Trp Phe Leu His Lys Arg Asn Arg
                450                 455                 460
Asn Met Val Val Glu Ile Asp Thr Asp Ile Glu Ala Asp Ala Thr Phe
465                 470                 475                 480
Arg Trp Leu Thr Leu Gly Gln Ile Arg Arg Leu Met Leu Gln Asp Asp
                485                 490                 495
Leu Val Asn Met Asp Thr Arg Ser Val Leu Ala Cys Leu Pro Thr Ala
                500                 505                 510
His Gly Ala Pro Asp Asp Glu Asp Phe Pro Ala Ala Leu Arg Arg
                515                 520                 525
Ser Phe Tyr Gly Glu Ala Ala Pro Leu His Asp Leu His Ala Ile Thr
530                 535                 540
```

```
Ser Cys Leu Thr Asp Val Arg Ala Leu Arg Val Leu Arg Gln Gln Ser
545                 550                 555                 560

Val Pro Leu Asp Asp Ala Arg Arg Asp Gly Trp Glu Arg Thr Glu Ser
                565                 570                 575

Thr Ile Arg His Arg Ser Gly Lys His Phe Glu Ile Met Ala Val Glu
            580                 585                 590

Val Thr Ala Glu Arg Arg Glu Val Ala Ser Trp Thr Gln Pro Leu Leu
                595                 600                 605

Arg Pro Cys Ser Gln Gly Leu Val Ala Leu Ile Thr Arg Arg Ile Asn
            610                 615                 620

Gly Val Leu His Ala Leu Val Glu Ala Arg Ser Asp Val Gly Thr Leu
625                 630                 635                 640

Asn Val Ala Glu Phe Gly Pro Thr Val Gln Cys Arg Pro Ala Glu Ser
                645                 650                 655

Asp Gly Met Ser Pro Pro Tyr Leu Asp Gln Val Leu Thr Ala Gly Ala
            660                 665                 670

Asp Arg Ile Arg Tyr Asp Val Gln Ser Glu Glu Gly Gly Arg Phe
            675                 680                 685

Tyr His Ala Arg Asn Arg Tyr Met Val Val Glu Ala Gly Pro Glu Leu
            690                 695                 700

Asp Thr Gly Cys Pro Pro Gly Phe Cys Trp Ala Thr Phe Gly Gln Leu
705                 710                 715                 720

Thr Glu Leu Leu Ala His Gly Asn Tyr Leu Asn Val Glu Leu Arg Thr
                725                 730                 735

Leu Val Ala Cys Ala His Ala Ser Tyr
                740                 745

<210> SEQ ID NO 23
<211> LENGTH: 382
<212> TYPE: PRT
<213> ORGANISM: Streptomyces spiramyceticus WSJ-1

<400> SEQUENCE: 23

Met Ile Asn Leu Phe Gln Pro Gln Met Gly Ala Glu Glu Leu Ala Ala
1               5                   10                  15

Ile Ala Gly Val Phe Asp Asp Gln Trp Leu Gly His Gly Pro Arg Thr
                20                  25                  30

Lys Ala Phe Glu Ser Ala Phe Ala Asp His Leu Gly Val Gly Pro Glu
            35                  40                  45

His Val Val Phe Leu Asn Ser Gly Thr Ala Gly Leu Phe Leu Ala Leu
        50                  55                  60

Glu Ser Leu Gly Leu Gln Pro Asp Asp Glu Val Val Leu Pro Ser Pro
65              70                  75                  80

Ser Phe Leu Ala Ala Ala Asn Ala Val Gln Leu Thr Gly Ala Arg Pro
                85                  90                  95

Val Phe Cys Asp Val Asp Pro Arg Thr Leu Asn Pro Ala Leu Glu His
            100                 105                 110

Ile Glu Gln Ala Val Thr Ala Arg Thr Arg Ala Val Ile Ala Leu His
        115                 120                 125

Tyr Gly Gly Tyr Pro Gly Asp Ile Val Arg Ile Ala Glu His Cys Arg
    130                 135                 140

Asn Gln Gly Ile Thr Leu Ile Glu Asp Ala Ala Cys Ser Val Ala Ser
145                 150                 155                 160

Arg Ile Asp Gly Arg Val Val Gly Thr Phe Gly Asp Leu Ala Met Trp
```

```
                   165                 170                 175
Ser Phe Asp Ala Met Lys Val Leu Val Thr Gly Asp Gly Met Ile
                180                 185                 190

Tyr Val Lys Asp Pro Gly Ala Ala Arg Ile Arg Arg Leu Ala Tyr
            195                 200                 205

His Gly Leu Thr Gln Ser Ser Gly Leu Gly Tyr Ala Arg Val Ser Ala
        210                 215                 220

Arg Trp Trp Glu Met Asp Val Pro Glu Pro Gly Arg Arg Val Ile Gly
225                 230                 235                 240

Asn Asp Leu Thr Ala Ala Ile Gly Ala Val Gln Leu Arg Arg Leu Pro
                245                 250                 255

Asp Phe Val Ala Arg Arg Lys Glu Ile Val Ala Leu Tyr Glu Ser Glu
            260                 265                 270

Leu Arg Thr Met Glu Gly Val Ser Thr Pro Pro Ala Leu Pro Glu Gly
        275                 280                 285

His Glu Ser Thr His Tyr Phe Tyr Trp Ile Gln Leu Pro Pro Gly Val
    290                 295                 300

Arg Asp Arg Val Ala Arg Asp Leu Leu Thr Asp Gly Ile Tyr Thr Thr
305                 310                 315                 320

Phe Arg Tyr Ala Pro Leu His Lys Val Pro Ala Tyr Gly His Ala Gly
                325                 330                 335

Arg Glu Leu Pro Gly Val Glu Trp Ala Ser Glu Arg Thr Leu Cys Leu
            340                 345                 350

Pro Leu His Pro Gly Leu Ser Asp Ala Asp Val Leu Thr Val Val Ser
        355                 360                 365

Ser Leu Arg Lys Ala Leu Asn Ala Gly Ala Gln Ala Pro Ala
    370                 375                 380

<210> SEQ ID NO 24
<211> LENGTH: 239
<212> TYPE: PRT
<213> ORGANISM: Streptomyces spiramyceticus WSJ-1

<400> SEQUENCE: 24

Met Tyr Glu Asn Asp Ser Ala Ala Glu Val Tyr Asp Leu Leu Tyr Gln
1               5                   10                  15

Asp Arg Lys Asp Tyr Ala Gly Glu Ala Ala Arg Val Thr Gly Leu Ile
            20                  25                  30

Arg Glu Arg Thr Pro Asn Ala Ser Ser Leu Leu Asp Ile Ala Cys Gly
        35                  40                  45

Thr Gly Thr His Leu Glu Ala Phe Ala Lys Leu Tyr Asp Arg Val Ser
    50                  55                  60

Gly Leu Glu Leu Ser Glu Trp Met Ala Ala Arg Ala Glu Glu Arg Leu
65                  70                  75                  80

Ser Asp Val Thr Leu His Arg Gly Asp Met Arg Ser Phe Asn Leu Gly
                85                  90                  95

Glu Thr Phe Asp Ala Val Val Cys Met Phe Ser Ser Ile Gly Tyr Leu
            100                 105                 110

Glu Thr Ala Ala Asp Leu Glu Asp Ala Ile Ala Ala Met Ser Arg His
        115                 120                 125

Leu Ser Ala Asp Gly Val Leu Ala Val Glu Pro Trp Tyr Phe Pro Asp
    130                 135                 140

Thr Phe Leu Asp Gly Tyr Val Ser Thr His Ala Leu Arg Thr Glu Ser
145                 150                 155                 160
```

```
Gly Asp Gln Gly Val Ala Arg Val Ala His Ser Thr Arg Glu Gly Lys
            165                 170                 175

Lys Thr Arg Met Glu Ile His Tyr Leu Ile Ala His Thr Thr Asp Gly
        180                 185                 190

Ile Arg His Arg Ser Glu Val Asp Tyr Leu Thr Leu Phe Ser Arg Ala
            195                 200                 205

Glu Tyr Glu Thr Ala Tyr Arg Lys Ala Gly Leu His Val Glu Tyr Val
        210                 215                 220

Glu Thr Gly Asn Gly Ser Pro Gly Phe Phe Leu Gly Thr Arg Ala
225                 230                 235

<210> SEQ ID NO 25
<211> LENGTH: 670
<212> TYPE: PRT
<213> ORGANISM: Streptomyces spiramyceticus WSJ-1

<400> SEQUENCE: 25

Met Ser Tyr Leu Asp Tyr Gly Glu Glu Ala Ser Glu Glu Asp Glu Ser
1               5                   10                  15

Asp Asp Ala Leu Thr Phe Leu Glu Phe Val Ala Arg Ser Ala Pro Arg
            20                  25                  30

Ser Glu Tyr Asp Arg Leu Met Ala Arg Ala Glu Arg Ala Gly Ala Asp
        35                  40                  45

Glu Glu Arg Met Arg Arg Leu Glu Arg Phe Asn Arg Leu Ala Leu Thr
50                  55                  60

Ala Gln Ser Met Ile Glu Tyr Arg Arg Asp Arg Glu Ala Glu Leu Ala
65                  70                  75                  80

Ala Leu Val Asp Ala Ala His Glu Phe Val Ala Ala Gln Gln Tyr Lys
                85                  90                  95

Asp Leu Leu Glu Ser Val Ala Arg Arg Ala Arg Leu Leu Leu Lys Leu
            100                 105                 110

Asp Val Ala Tyr Val Ser Leu His Gln Glu Asp Leu His His Glu Asp
        115                 120                 125

Arg Pro Gly Thr Val Val Leu Ser Ala Asp Gly Asn Ala Val Lys Val
    130                 135                 140

Ala Asp Ser Tyr Arg Leu Pro Ala Asp Gly Leu Gly Gly Met Val
145                 150                 155                 160

Arg Thr Cys His Ala Pro Phe Trp Thr Pro Asp Tyr Leu Gly Asp Ser
                165                 170                 175

Ser Phe Val His Val Glu Thr Val Asp Asp Ile Val Arg Ala Glu Gly
            180                 185                 190

Leu Arg Ala Val Leu Ala Val Pro Leu Cys Val Gly Asp Asp Ser Val
        195                 200                 205

Gly Val Leu Tyr Val Ala Asp Arg Gln Val Arg His Leu Thr Pro Asn
    210                 215                 220

Glu Val Thr Leu Leu Cys Ser Leu Ala Asp Leu Ala Ala Val Ala Ile
225                 230                 235                 240

Glu Arg Ile Arg Leu Val Glu Glu Leu Arg Asp Thr Ile Gly Arg Leu
                245                 250                 255

Arg Glu Asp Val Gly Glu Ala Arg Ala Leu Ala Gly Thr Arg Arg
            260                 265                 270

Ser Ala Asp Leu Gln Ser His Leu Ile Thr Gln Val Leu Glu Arg Arg
        275                 280                 285

Gly Ala Asp Ala Leu Leu Ala Ala Ala Glu Ser Leu Gly Gly Gly
    290                 295                 300
```

Thr Ser Leu Cys Ser Pro Leu Gly Arg Pro Leu Ala Glu Tyr Gly Asn
305                 310                 315                 320

Leu Arg Pro Val Ala Pro Ala Asp Leu Arg Ala Ala Cys Arg Arg Ala
            325                 330                 335

Ala Glu Thr Gly Arg Pro Thr Pro Val Ala Pro Gly Tyr Trp Thr Val
        340                 345                 350

Pro Leu Tyr Pro Gly Glu Tyr Asn Ala Gly Phe Leu Leu Thr Asp Val
    355                 360                 365

Gly Pro Glu Ala Asp His Thr Val Val Pro Leu Leu Pro Met Val Ala
370                 375                 380

Arg Thr Leu Ala Leu His Leu Arg Ile Gln Arg Asn Asp Ser Thr Lys
385                 390                 395                 400

Ala Gln Ser His Gln Asp Phe Phe Asp Asp Leu Val Gly Ala Pro Arg
            405                 410                 415

Ser Pro Ala Leu Leu Arg Glu Arg Ala Leu Leu Phe Ser Leu Ser Phe
        420                 425                 430

Arg Arg Pro His Val Val Leu Val Ala Ser Gly Pro His Gly Ala Ser
    435                 440                 445

Ala Arg Leu Glu Ser Ser Gly Ala Asp Tyr Ala Lys Glu Leu Gly Gly
450                 455                 460

Leu Cys Ser Val Arg Asp Gly Ala Val Val Leu Leu Leu Pro Gly Asp
465                 470                 475                 480

Asp Pro Val Ala Val Ala Gln Thr Ala Ala Pro Glu Leu Thr Asp Arg
            485                 490                 495

Val Gly His Pro Val Thr Val Gly Ala Ala Gly Pro Ala Ser Thr Val
        500                 505                 510

Asp Gly Ile Ser Asp Ala His Arg Glu Ala Ala Gln Cys Leu Glu Thr
    515                 520                 525

Leu Arg Ala Leu Gly Gly Asp Gly Gly Thr Ala Cys Ala Ser Asp Leu
530                 535                 540

Gly Phe Leu Gly Met Leu Leu Ala Glu Glu Asn Asp Val Pro Gly Tyr
545                 550                 555                 560

Ile Lys Thr Thr Ile Gly Pro Val Ile Asp Tyr Asp Thr His Arg Phe
            565                 570                 575

Thr Asp Leu Ile Pro Thr Leu Arg Val Tyr Leu Glu Ser Gly Arg Ser
        580                 585                 590

Pro Thr Arg Ala Ala Glu Thr Leu Arg Val His Pro Asn Thr Val Ser
    595                 600                 605

Arg Arg Leu Glu Arg Ile Gly Gln Leu Leu Gly Glu Asp Trp Gln Gly
610                 615                 620

Pro Glu Arg Val Leu Asp Ile Gln Leu Ala Leu Arg Leu Tyr Gln Val
625                 630                 635                 640

Arg Ser Ala Leu Ser Ser Arg Ser Ala Ser Leu Pro Arg
            645                 650                 655

Pro Ala Pro Ala Ser Arg Thr Val Leu Gly Ser Gln Arg Glu
        660                 665                 670

<210> SEQ ID NO 26
<211> LENGTH: 354
<212> TYPE: PRT
<213> ORGANISM: Streptomyces spiramyceticus WSJ-1

<400> SEQUENCE: 26

Met His Arg Arg Val Gln Arg Arg Leu Ser His Ala Leu Thr Arg Ala

```
  1               5                  10                 15
Arg Asp Leu Val Pro Lys Gly Pro Arg Ser Arg Leu Lys Thr Arg Pro
             20                  25                 30

Pro Asp Gly Asp Pro Arg Arg Arg Ala Gly Ala Gly Ala Leu Ala Ala
             35                  40                 45

Pro Leu Phe Pro Glu Pro Gly Arg Leu Arg Lys Arg Gln Asp Leu Pro
             50                  55                 60

Met Asn Gly Cys Gln Val Ala Val Gly Ala Val Val Arg Pro Arg Asn
 65                  70                  75                 80

Phe Ala Arg Leu Arg Ala Pro Ser Cys Gly Lys Gly Glu Ala Ser Val
                 85                  90                 95

Asn Phe Arg Arg Arg Tyr Gly Asn Ser Cys Pro Pro Val Arg Cys Ala
                100                 105                110

Gly Ser Gly Arg Arg Phe Arg Gln Arg Arg Pro Leu Cys His Val Arg
                115                 120                125

Leu Ala Asp Cys Leu Gly Ala Ser Tyr Val Pro Leu Thr Ser Thr Gly
                130                 135                140

Ser Asp Ala Gly Ser Arg Thr Pro Asp Arg Val His Arg Ser Thr Arg
145                 150                 155                160

Ala Thr Ser Ser Leu Arg Ser Thr Cys Pro Ser Ala Ser Thr Gly Thr
                165                 170                175

Glu Pro Glu Gly Ser Val Pro Gly Pro Gly Pro Ser Arg Ala Gly Arg
                180                 185                190

Gly Pro His Asp Arg Pro Ile Arg Ser Ala Ala Ile Ala Glu Asn Thr
                195                 200                205

Ala Glu Pro Pro Ala Arg Arg Val Gly Arg Ile Lys Pro Cys Arg Leu
210                 215                 220

Ile Arg Leu Glu Gln His Ile Asp Pro Arg Gly Ser Leu Ser Val Val
225                 230                 235                240

Glu Ser Gly Val Thr Val Asp Phe Pro Val Gln Arg Val Tyr Tyr Met
                245                 250                255

His Gly Gln Thr Gln Ser Ser Pro Pro Arg Gly Leu His Ala His Arg
                260                 265                270

Thr Leu Glu Gln Leu Val Ile Ala Val His Gly Ala Phe Ser Ile Thr
                275                 280                285

Leu Asp Asp Gly Phe Gln His Ala Thr Tyr Arg Leu Asp Glu Pro Gly
                290                 295                300

Ala Gly Leu Cys Ile Gly Pro Met Val Trp Arg Val Leu Lys Asp Phe
305                 310                 315                320

Ala Pro Asp Thr Val Ala Leu Val Leu Ala Ser Gln His Tyr Glu Glu
                325                 330                335

Ser Asp Tyr Tyr Arg Asp Tyr Asp Thr Phe Leu His Asp Ala Arg Ser
                340                 345                350

Leu Thr

<210> SEQ ID NO 27
<211> LENGTH: 550
<212> TYPE: PRT
<213> ORGANISM: Streptomyces spiramyceticus WSJ-1

<400> SEQUENCE: 27

Met Ser Ile Ala Gln Phe Ala Leu His Asp Val Ile Lys Arg Tyr His
 1               5                  10                 15

Asp Cys Val Val Leu Asp Arg Val Gly Phe Ser Ile Lys Pro Gly Glu
```

```
            20                  25                  30
Lys Val Gly Val Ile Gly Asp Asn Gly Ser Gly Lys Ser Thr Leu Leu
            35                  40                  45
Lys Val Leu Ala Gly Arg Glu Gln Pro Asp Asn Gly Met Leu Thr Val
        50                  55                  60
Val Ala Pro Gly Gly Ile Gly Tyr Leu Ala Gln Thr Leu Glu Leu Pro
65                  70                  75                  80
Leu Asp Ala Thr Val Gln Asp Ala Val Asp Leu Ala Leu Ser Asp Leu
                85                  90                  95
Arg Glu Leu Glu Ala Ser Met His Glu Val Glu Ala Glu Leu Thr Glu
            100                 105                 110
Arg Asp Glu Asp Gly Ser Glu Arg Glu Leu Ser Ala Leu Leu Gln Arg
        115                 120                 125
Tyr Ala Gly Leu Val Glu Gln Tyr Gln Ala Arg Gly Gly Tyr Glu Ala
    130                 135                 140
Asp Val Arg Val Glu Val Ala Leu His Gly Leu Gly Leu Pro Ser Leu
145                 150                 155                 160
Asp Arg Asp Arg Lys Leu Gly Thr Leu Ser Gly Gly Glu Arg Ser Arg
                165                 170                 175
Leu Ala Leu Ala Ala Thr Leu Ala Ser Ala Pro Glu Leu Leu Leu Leu
            180                 185                 190
Asp Glu Pro Thr Asn Asp Leu Asp Arg Ala Met Glu Trp Leu Glu
        195                 200                 205
Asn His Leu Gln Gly His Arg Gly Thr Val Ile Ala Val Thr His Asp
    210                 215                 220
Arg Val Phe Leu Asp Arg Leu Thr Thr Thr Ile Leu Glu Val Asp Ser
225                 230                 235                 240
Gly Arg Val Thr Arg Tyr Gly Asn Gly Tyr Glu Gly Tyr Leu Thr Ala
                245                 250                 255
Lys Ala Val Glu Arg Glu Arg Leu Arg Glu Tyr Glu Glu Trp Arg
            260                 265                 270
Ala Glu Leu Glu Arg Asn Gln Gly Leu Ile Thr Ser Asn Val Ala Arg
        275                 280                 285
Met Asp Asn Ile Pro Arg Lys Met Ser Leu Ser Val Phe Gly His Gly
    290                 295                 300
Ala Tyr Arg Arg Gly Arg Asp His Gly Ala Met Val Arg Ile Arg
305                 310                 315                 320
Asn Ala Lys Gln Arg Val Ala Gln Leu Thr Glu Asn Pro Ala Leu Ala
                325                 330                 335
Pro Ala Asp Pro Leu Ser Phe Ala Ala Arg Ile Asp Thr Ala Gly Pro
            340                 345                 350
Glu Ala Glu Glu Ala Val Ala Glu Leu Thr Asp Val Arg Val Ala Asp
        355                 360                 365
Arg Leu Asp Val Asp Ser Leu Lys Ile Arg Pro Gly Glu Arg Leu Leu
    370                 375                 380
Ile Thr Gly Pro Asn Gly Ala Gly Lys Ser Thr Leu Leu Arg Val Leu
385                 390                 395                 400
Ser Gly Glu Leu Ala Pro Asp Ser Gly Ser Val Arg Val Gly Cys Arg
                405                 410                 415
Val Gly His Leu Arg Gln Asp Glu Thr Pro Trp Ser Pro Glu Leu Thr
            420                 425                 430
Val Leu Arg Ala Phe Ala His Gly Arg Glu Gly Tyr Leu Glu Asp His
        435                 440                 445
```

```
Ala Glu Lys Leu Leu Ser Leu Gly Leu Phe Ser Pro Ser Asp Leu Arg
    450                 455                 460

Arg Arg Val Lys Asp Leu Ser Tyr Gly Gln Arg Arg Ile Glu Ile
465                 470                 475                 480

Ala Arg Leu Val Ser Asp Pro Met Asp Leu Leu Leu Asp Glu Pro
                485                 490                 495

Thr Asn His Leu Thr Pro Val Leu Val Glu Glu Leu Glu Gln Ala Leu
            500                 505                 510

Val Asp Tyr Arg Gly Ala Val Val Val Thr His Asp Arg Arg Met
        515                 520                 525

Arg Ser Arg Phe Thr Gly Ala Arg Leu Ala Met Asp His Gly Cys Ile
        530                 535                 540

Ala Glu Phe Ser Ala Gly
545                 550

<210> SEQ ID NO 28
<211> LENGTH: 433
<212> TYPE: PRT
<213> ORGANISM: Streptomyces spiramyceticus WSJ-1

<400> SEQUENCE: 28

Met Gly Glu Thr Lys Asn Arg Ile Thr Glu Leu Val Arg Ala Tyr His
1               5                   10                  15

Arg Glu Gln Ala Thr Gly Asn Phe Val Pro Gly Thr Thr His Val Pro
            20                  25                  30

Val Ser Gly Ala Val Leu Ser Glu Asp Asp Arg Leu Ala Leu Val Glu
        35                  40                  45

Thr Ala Leu Glu Met Arg Ile Ala Ala Gly Pro Ala Ser Arg Ser Phe
    50                  55                  60

Glu Arg Gln Phe Ala Arg Tyr Leu Gly Leu Arg Lys Ala His Leu Thr
65                  70                  75                  80

Asn Ser Gly Ser Ser Ala Asn Leu Leu Ala Leu Ser Ala Leu Thr Ser
                85                  90                  95

Pro Gln Leu Glu Asp Arg Arg Leu Lys Pro Gly Asp Glu Val Val Thr
            100                 105                 110

Val Ala Ala Gly Phe Pro Thr Thr Val Asn Pro Ile Phe His Asn Glu
        115                 120                 125

Leu Val Pro Val Phe Val Asp Val Glu Leu Gly Thr Tyr Asn Thr Thr
130                 135                 140

Pro Glu Arg Ile Glu Arg Ala Ile Gly Pro Arg Thr Arg Ala Ile Met
145                 150                 155                 160

Ile Ala His Ala Leu Gly Asn Pro Phe Glu Ala Glu Glu Val Ala Arg
                165                 170                 175

Leu Ala Asp Glu Arg Gly Leu Phe Leu Val Glu Asp Asn Cys Asp Ala
            180                 185                 190

Val Gly Ser Arg Tyr Arg Gly Arg Leu Thr Gly Ser Phe Gly Asp Leu
        195                 200                 205

Ser Thr Val Ser Phe Tyr Pro Ala His His Ile Ala Met Gly Glu Gly
    210                 215                 220

Gly Cys Val Leu Thr Asp Asn Leu Ala Leu Ala Arg Ile Val Glu Ser
225                 230                 235                 240

Leu Arg Asp Trp Gly Arg Asp Cys Trp Cys Glu Pro Gly Glu Asp Asn
                245                 250                 255

Arg Cys Leu Lys Arg Phe Asp Gln Lys Met Gly Asp Leu Pro Pro Gly
```

```
                260                 265                 270
Tyr Asp His Lys Tyr Ile Phe Ser His Val Gly Tyr Asn Leu Lys Ser
            275                 280                 285

Thr Asp Leu Gln Ala Ala Leu Gly Leu Ser Gln Leu Thr Arg Ile Glu
        290                 295                 300

Glu Phe Thr Asp Ala Arg Arg Ala Asn Trp Arg Met Arg Glu Thr
305                 310                 315                 320

Leu Asp Gly Leu Pro Gly Leu Leu Pro Glu Ala Thr Pro Gly Ser
            325                 330                 335

Asp Pro Ser Trp Phe Gly Phe Leu Ile Thr Val Asp Pro Asp Ala Thr
            340                 345                 350

Tyr Ser Arg Ala Ala Leu Val Asp His Leu Glu Ser Arg Arg Ile Ser
            355                 360                 365

Thr Arg Arg Leu Phe Gly Gly Asn Leu Val Arg His Pro Ala Tyr Thr
            370                 375                 380

Gly Arg Gln Tyr Arg Val Ser Gly Ala Leu Glu Asn Ser Asp Leu Ile
385                 390                 395                 400

Thr Asp Gln Thr Phe Trp Ile Gly Val Phe Pro Gly Ile Thr Thr Glu
            405                 410                 415

Met Val Asp Tyr Val Thr Asp Thr Val Arg Glu Phe Val Leu Lys His
            420                 425                 430

Ser

<210> SEQ ID NO 29
<211> LENGTH: 482
<212> TYPE: PRT
<213> ORGANISM: Streptomyces spiramyceticus WSJ-1

<400> SEQUENCE: 29

Met Thr His Pro Glu Asp Ser Ala Gly Thr Ser Gln Arg Ala Asp Ala
1               5                   10                  15

Leu Met Asn Asp Thr Leu Ala Ala Asp Ala Glu Gly Trp Asp Gly
            20                  25                  30

Glu Gln Phe Asp Arg Glu Asp Arg Ala Ser Leu Arg Arg Val Ala Gly
        35                  40                  45

Leu Ser Thr Glu Leu Thr Asp Val Ser Glu Val Glu Tyr Arg Lys Leu
50                  55                  60

Arg Leu Glu Arg Val Val Leu Val Gly Ile Trp Thr Ser Gly Thr Ala
65                  70                  75                  80

Ala Glu Ala Glu Ser Ser Leu Ala Glu Leu Ala Ala Leu Ala Glu Thr
            85                  90                  95

Ala Gly Ala Leu Val Leu Asp Gly Val Val Gln Arg Arg Gln Lys Pro
            100                 105                 110

Asp Pro Ala Thr Tyr Ile Gly Ser Gly Lys Ala Ser Gln Leu Arg Asp
            115                 120                 125

Ile Val Glu Glu Thr Gly Ala Asp Thr Val Val Cys Asp Gly Glu Leu
            130                 135                 140

Ser Pro Ser Gln Leu Met His Leu Glu Glu Val Val Gly Val Lys Val
145                 150                 155                 160

Val Asp Arg Thr Ala Leu Ile Leu Asp Ile Phe Ala Gln His Ala Gln
                165                 170                 175

Ser Arg Glu Gly Lys Ala Gln Val Ala Leu Ala Gln Met Gln Tyr Met
            180                 185                 190

Leu Pro Arg Leu Arg Gly Trp Gly Gln Ser Leu Ser Arg Gln Met Gly
```

```
            195                 200                 205
Gly Gly Gly Gly Gly Met Ala Thr Arg Gly Pro Gly Glu Thr Lys
    210                 215                 220
Ile Glu Thr Asp Arg Arg Ile Asn Asp Lys Met Ala Arg Leu Arg
225                 230                 235                 240
Arg Glu Leu Glu Gln Leu Lys Thr Gly Arg Asp Val Lys Arg Glu Glu
                245                 250                 255
Arg Arg Arg Asn Lys Val Leu Ser Val Ala Leu Ala Gly Tyr Thr Asn
            260                 265                 270
Ala Gly Lys Ser Ser Leu Leu Asn Arg Leu Thr Gly Ala Gly Val Leu
        275                 280                 285
Val Glu Asn Ala Leu Phe Ala Thr Leu Asp Thr Thr Val Arg Arg Ala
    290                 295                 300
Thr Thr Pro Ser Gly Arg Thr Tyr Thr Ile Ala Asp Thr Val Gly Phe
305                 310                 315                 320
Val Arg His Leu Pro His His Leu Val Glu Ala Phe Arg Ser Thr Ile
                325                 330                 335
Glu Glu Val Ala Asp Ala His Leu Val Leu His Val Val Asp Gly Ser
            340                 345                 350
His Pro Asp Pro Gly Ala Gln Leu Ala Ser Val Arg Glu Val Leu Arg
        355                 360                 365
Asp Val Gly Ala Ala Glu Ser Thr Glu Ile Val Val Asn Lys Ala
    370                 375                 380
Asp Val Ala Asp Pro Asp Val Leu Ala Arg Leu Leu Glu Gln Glu Pro
385                 390                 395                 400
Asp Ala Ile Val Val Ser Ala Arg Ser Gly Gln Gly Ile Asp Glu Leu
                405                 410                 415
Gln Glu Leu Ile Asp Arg Leu Leu Pro His Pro Ala Val Glu Val Glu
            420                 425                 430
Val Val Ile Pro Tyr Asp Glu Gly Leu Val Ala Arg Ala His Asp
        435                 440                 445
Glu Gly Glu Val Leu Ser Ala Glu His Thr Pro Glu Gly Thr Leu Leu
    450                 455                 460
Thr Ala Leu Val His Pro Asp Leu Ala Ser Glu Leu Gln Ala His Pro
465                 470                 475                 480
Arg Pro

<210> SEQ ID NO 30
<211> LENGTH: 346
<212> TYPE: PRT
<213> ORGANISM: Streptomyces spiramyceticus WSJ-1

<400> SEQUENCE: 30

Met Arg Val Leu Ile Ile Gly Gly Ser Gln Phe Val Gly Arg Ala Tyr
1               5                   10                  15
Ala Ala Glu Ala Leu Ala Ala Gly His Glu Val Thr Thr Phe Asn Arg
            20                  25                  30
Gly Val Ser Gly Thr Asp Leu Pro Gly Val Glu Ala Val Arg Gly Asp
        35                  40                  45
Arg Glu Ala Ala Gly Asp Leu Glu Arg Leu Val Ser Gly Arg Arg Trp
    50                  55                  60
Asp Ala Val Val Asp Thr Cys Gly Tyr Val Pro Arg Thr Val Gly Ala
65                  70                  75                  80
Ser Ala Ala Ala Leu Ser Gly His Ala Asp Ala Tyr Leu Tyr Val Ser
```

```
            85                  90                  95
Ser Ile Ala Cys Leu Pro Asp Trp Thr Gln Ala Val Arg Pro Val Asp
            100                 105                 110

Asp Asp Ser Pro Ala Tyr Asp Cys Pro Pro Asp Ala Gly Pro Asp His
            115                 120                 125

Ala Asp Gly Asp Tyr Gly Thr Leu Lys Ala Gly Cys Glu Arg Ala Val
145         130                 135                 140

Asp Gln His Phe Val Gly Arg Thr Leu His Leu Arg Ala Gly Val Ile
145                 150                 155                 160

Leu Gly Pro His Asp Asn Met Arg Met Leu Asp Ala Trp Leu Trp Arg
                165                 170                 175

Met Arg Ala Ala Glu Gly Glu His Arg Arg Val Leu Ala Pro Gly Gly
            180                 185                 190

Pro Glu Val Gly Met Arg Leu Ile Asp Val Arg Asp Val Ala Ala Phe
            195                 200                 205

Gly Leu Asp Cys Leu Ala Glu Gly Arg Thr Gly Ala Tyr Ile Val Asn
210                 215                 220

Pro Pro Glu Lys Asn Thr Thr Phe Gly Asn Leu Leu Thr Glu Cys Val
225                 230                 235                 240

Lys Ala Thr Gly Ser Ala Ala Glu Pro Val Trp Val Asp Asp Arg Phe
            245                 250                 255

Phe Ala Asp His Gly Val Ser Pro Trp Thr Asp Leu Pro Leu Trp Val
            260                 265                 270

Pro Asp Thr Ala Gln Asp Thr Leu Val Trp Ala Ala Gly Ala Pro Arg
            275                 280                 285

Ala Arg Ala Ala Gly Leu Ala Cys Arg Pro Ile Ser Glu Thr Val Arg
            290                 295                 300

Asp Ala Trp Glu Val Ile Arg Asp Gln Pro Val Pro Glu Leu Pro Leu
305                 310                 315                 320

Ala Ala Gly Cys Gly Leu Ser Leu Ala Arg Glu Arg Glu Leu Leu Ala
                325                 330                 335

Ala Trp Asp Ala Arg Gly Gly Ala Ala Gly
                340                 345

<210> SEQ ID NO 31
<211> LENGTH: 346
<212> TYPE: PRT
<213> ORGANISM: Streptomyces spiramyceticus WSJ-1

<400> SEQUENCE: 31

Met Thr Ala Leu Gly Thr Pro Ala Glu Pro Ser Ala Ala Pro Gly Pro
1               5                   10                  15

Pro Trp Pro Glu Ala Ser Pro Val Leu Arg Phe Gly Ala Ile Gly Cys
            20                  25                  30

Gly Asp Ile Ala Gly Arg Arg Thr Leu Pro Ala Leu Leu Ser Thr Pro
            35                  40                  45

Gly Thr Val Leu Thr Cys Val Gly Ser Arg Glu Pro Glu Arg Ala Lys
        50                  55                  60

Ala Leu Gly Glu His Phe Gly Cys Glu Ala Val Ala Pro Tyr Glu Ala
65                  70                  75                  80

Leu Leu Glu Arg Pro Asp Val Asp Ala Val Tyr Ile Ala Val Pro Ser
                85                  90                  95

Met Leu His Ala Lys Trp Ala Ala Ala Leu Arg Ala Gly Lys His
            100                 105                 110
```

```
Val Leu Val Glu Lys Pro Ala Ala Asn His Ala Asp Ala Ala Arg
            115                 120                 125

Leu Phe Ala Met Ala Arg Glu Arg Gly Leu Val Leu Met Glu Asn Phe
130                 135                 140

Met Phe Leu His His Ser Gln His Ala Thr Val Lys Val Leu Leu Glu
145                 150                 155                 160

Thr Gly Ala Ile Gly Asp Leu Arg Thr Phe Ser Ala Ala Phe Thr Ile
                165                 170                 175

Pro Pro Arg Pro Asp Asp Met Arg Tyr Arg Pro Asp Ile Gly Gly
            180                 185                 190

Gly Ala Leu Leu Asp Asn Gly Val Tyr Pro Leu Arg Ala Ala Ile His
            195                 200                 205

Phe Leu Gly Pro Glu Leu Arg Leu Met Gly Ala Val Leu Arg Arg Glu
210                 215                 220

Arg Arg Arg Gly Val Val Ser Gly Ser Val Leu Leu Ala Ala Pro
225                 230                 235                 240

Thr Gly Val Ala Ala His Leu Ala Phe Gly Met Glu His Gly Tyr Arg
                245                 250                 255

Ser Ala Tyr Glu Leu His Gly Ser Thr Gly Ser Leu Ala Leu Asn His
            260                 265                 270

Val Phe Thr Thr Pro Asp Ser His His Pro Val Leu Arg Leu Ser Arg
275                 280                 285

Gln Asp His Arg Glu Glu Arg Val Leu Pro Val Asp Arg His Phe Val
            290                 295                 300

Asn Ile Leu Ser Val Phe Arg Arg Ala Val Thr Arg Ala Glu Asn Ile
305                 310                 315                 320

Ser Ala Glu Ser Tyr Ala Ala Leu Arg Gln Ala Ala Leu Val Asp Glu
                325                 330                 335

Ile Val Ala Arg Ala Glu Thr Val Thr Val
            340                 345

<210> SEQ ID NO 32
<211> LENGTH: 415
<212> TYPE: PRT
<213> ORGANISM: Streptomyces spiramyceticus WSJ-1

<400> SEQUENCE: 32

Met Ala Asp Ala Ile Thr Thr Glu Leu Ala Asp Arg Glu Leu Gly Arg
1               5                   10                  15

Arg Leu His Arg Ile Arg Gly Ala His Trp Tyr Phe Gly Asn His Gly
                20                  25                  30

Asp Pro Tyr Ala Leu Ile Leu Arg Gly Gln Ala Asp Asp Pro Ser Ala
            35                  40                  45

Tyr Glu Glu Arg Val Arg Asp Gly Gly Pro Leu Phe Arg Ser His Ile
        50                  55                  60

Gly Thr Trp Val Thr Ala Asp Pro Glu Val Gly Ala Ala Val Leu Gly
65                  70                  75                  80

Asp Pro Arg Phe Gly Ala Leu Asp Arg Ala Gly Arg Arg Pro Glu Glu
                85                  90                  95

Tyr Leu Gln Pro Ser Pro Ala Ser Cys Leu Gly Leu Arg Ala Ala
            100                 105                 110

Tyr Leu Arg Leu Arg Arg Val Ala Glu Pro Val Leu Gly Ala Gly Ala
        115                 120                 125

Ala Asp Glu Trp Arg Arg Leu Ala Glu Asp Leu Gly Arg Arg Leu Leu
130                 135                 140
```

```
Asp Gly Arg Gly Ser Gly Phe Asp Leu Thr Ala Asp Phe Ala Arg Arg
145                 150                 155                 160

Leu Pro Ala Leu Val Leu Ala Ala Trp Leu Gly Val Pro Asp Glu Arg
                165                 170                 175

Arg Glu Glu Trp Glu Glu Leu Leu Arg Glu Ala Gly Pro Leu Leu Asp
            180                 185                 190

Ser Leu Leu Cys Pro Gln Thr Leu Ala Ala Thr Arg Ala Ala Asp Ser
        195                 200                 205

Ala Ala Glu Gly Leu Arg Thr Leu Leu Gly Lys Val Ala Val Ala Arg
    210                 215                 220

Ser Asp Gly Ala Gly Asp Gly Ala Leu Gly Arg Met Val Ala Ala Gly
225                 230                 235                 240

Ala Ala Pro Asp Asp Ala Val Ala Ala Met Cys Leu Val Leu Ser
                245                 250                 255

Ala Ala Glu Thr Thr Thr Thr Leu Val Cys Asp Ala Val Arg Leu Leu
                260                 265                 270

Leu Asp Arg Pro Arg Trp Trp Arg Ala Leu Cys Asp Ser Pro Ala Leu
            275                 280                 285

Ala Pro Ala Ala Val Arg His Thr Leu Arg Tyr Val Pro Pro Val Arg
    290                 295                 300

Leu Glu Ser Arg Val Ala His Glu Asp Val Ala Pro Thr Gly His Pro
305                 310                 315                 320

Leu Pro Ala Gly Ser His Val Val Leu Val Ser Ala Ala Arg Arg
                325                 330                 335

Gly Ala Ala Pro Asp Ala Gly Pro Ala Asp Leu Thr Asn Val Pro Thr
                340                 345                 350

Ala Ala Gly Ala Gly Leu Pro Asp Asp Leu Tyr Phe Ala Leu Ser Gly
            355                 360                 365

Glu Phe Val Gly Arg Thr Ala Glu Thr Ala Leu Gly Val Leu Ala Glu
370                 375                 380

Val Ala Pro Arg Leu Arg Arg Glu Gly Asp Ile Val Arg Arg Arg Arg
385                 390                 395                 400

Ser Pro Val Leu Gly Arg Tyr Ala Arg Phe Pro Val Ala Tyr Ser
                405                 410                 415

<210> SEQ ID NO 33
<211> LENGTH: 422
<212> TYPE: PRT
<213> ORGANISM: Streptomyces spiramyceticus WSJ-1

<400> SEQUENCE: 33

Met Arg Val Leu Val Thr Ser Ile Pro His His Thr His Tyr Tyr His
1               5                   10                  15

Leu Val Pro Leu Ile Trp Ala Leu Arg Ala Ser Gly His Glu Val Val
                20                  25                  30

Ala Ala Gly Gln Pro Ser Leu Ile Asp Ala Ile Thr Ser Ser Gly Ile
            35                  40                  45

Pro Gly Phe Pro Leu Ala Glu Glu Ser Leu Ala Gln Ile Phe Glu
        50                  55                  60

Glu Val Glu Gly Asp Leu Gln Pro Tyr Gln His Gly Ile Asp Glu Phe
65                  70                  75                  80

Asp Phe Leu Gly Thr Leu Gln Asp Ala Leu Asp Trp Glu Lys Leu Leu
                85                  90                  95

Ala Gln Gln Val Ile Leu Ser Gly Leu Trp Leu Glu Pro Leu Asn Gly
```

```
            100                 105                 110
Ala Thr Thr Leu Asp Ser Ile Val Asp Phe Ala Arg Ser Trp Lys Pro
            115                 120                 125

Asp Leu Val Leu Trp Glu Pro Phe Thr Tyr Ala Gly Pro Val Ala Ala
            130                 135                 140

Arg Ala Cys Gly Ala Ala His Ala Arg Val Leu Trp Gly Pro Asp Thr
145                 150                 155                 160

Ile Gly Leu Met Arg Thr Lys Phe Leu Gln Ala Gln Ala Gln Gln Pro
                165                 170                 175

Glu Glu His Arg Asp Asp Pro Ile Ala Glu Trp Leu Thr Trp Ala Leu
            180                 185                 190

Glu Arg Tyr Gly Cys Asp Phe Arg Glu Glu Asp Val Leu Gly Gln Trp
            195                 200                 205

Ser Val Asp Pro Met Ala Glu Gly Val Ser Leu Gly Leu Asp Leu Pro
210                 215                 220

Thr Val Pro Met Arg Tyr Thr Pro Tyr Asn Gly Ser Ala Val Ile Pro
225                 230                 235                 240

Asp Trp Leu Thr Glu Glu Pro Lys Arg Pro Arg Val Cys Leu Thr Leu
                245                 250                 255

Gly Val Ser Ser Arg Glu Tyr Gly Glu Asp Glu Val Pro Val Gln Lys
            260                 265                 270

Phe Ile Glu Ala Leu Ala Asp Leu Asp Ile Glu Leu Val Ala Thr Leu
            275                 280                 285

Asp Asp Ala Gln Arg Asp Leu Leu Pro Arg Ile Pro Asp Asn Thr Arg
            290                 295                 300

Ile Val Asp Phe Val Pro Met Asp Ala Leu Leu Pro Thr Cys Ser Ala
305                 310                 315                 320

Ile Ile Asn His Ser Gly Ser Gly Thr Cys Asn Thr Ala Ala Leu His
                325                 330                 335

Gly Val Pro Gln Ile Ile Leu Gly Asn Ile Leu Asp Ala Ala Val Arg
            340                 345                 350

Gln His Met Phe Ala Gln Ser Ser Ala Ala Leu Thr Phe Ala Pro Glu
            355                 360                 365

Glu Val Thr Gly Glu Ser Leu Arg Ser Ala Leu Val Arg Leu Leu Gly
            370                 375                 380

Glu Pro Lys Phe Arg Asp Gly Ala Gln Arg Leu Lys Glu Arg Met Arg
385                 390                 395                 400

Ala Met Pro Ser Pro Ala Gly Ile Val Pro Thr Leu Glu Ser Leu Thr
                405                 410                 415

Ala Arg His Arg Arg Ala
            420

<210> SEQ ID NO 34
<211> LENGTH: 391
<212> TYPE: PRT
<213> ORGANISM: Streptomyces spiramyceticus WSJ-1

<400> SEQUENCE: 34

Met Arg Ala Leu Phe Thr Thr Ala Pro Leu Ala Gly His Leu Leu Pro
1               5                   10                  15

Leu Val Pro Thr Ala Trp Ala Leu Arg Ala Ala Gly His Asp Val Leu
            20                  25                  30

Val Thr Thr Arg Glu Asn Phe Val Pro Val Ala Leu Arg Ser Gly Leu
            35                  40                  45
```

```
Pro Ser Ser Cys Gly Pro Ala Val Asp Phe Thr Gly Thr Val Ala
    50                  55                  60

Asp Gly Pro Leu Ala Pro Ser Arg Asp Glu Ala Gly Gln Arg Gly Val
 65                  70                  75                  80

Leu Gly Gly Ala Leu Ala Arg Val Ala Arg Gly Ser Leu Ala Gly Val
                 85                  90                  95

Arg Arg Leu Ala Asp Val Trp Arg Pro Asp Leu Ile Val Ser Glu Arg
                100                 105                 110

Ala Glu Phe Ala Gly Pro Leu Val Ala Ala Leu Gly Ile Pro Trp
            115                 120                 125

Val Arg Tyr His Trp Ser Val Ser Cys Leu Glu Tyr Arg Arg Ala
130                 135                 140

Ala Glu Glu Glu Phe Ala Pro Glu Leu Thr Ala Leu Gly Leu Asp Arg
145                 150                 155                 160

Phe Pro Asp Pro Ala Arg Val Leu Asp Pro Trp Pro Val Ser Leu Arg
                165                 170                 175

Arg Pro Asp Ala Val Ala His Asp Gly Ile Arg His Val Pro Ala His
            180                 185                 190

Gly Asp Ala Pro Val Pro Glu Trp Ala Phe Thr Arg Gly Arg Arg Pro
            195                 200                 205

Arg Ile Cys Val Thr Leu Gly Thr Met Leu Pro Arg Tyr Gly Ala Phe
210                 215                 220

Gly Val Arg Asp Phe Leu Ala Glu Leu Val Glu Thr Arg Gly Ser
225                 230                 235                 240

Asp Cys Glu Leu Leu Ile Ala Val Asp Asp Ile Val Ala Arg Trp
                245                 250                 255

Pro Pro Leu Pro Ala Ala Val Arg His Ala Gly Arg Leu Pro Leu Ala
            260                 265                 270

Glu Val Leu Pro Ala Cys Asp Val Val His His Gly Gly Gln Gly
            275                 280                 285

Thr Ser Leu Thr Ala Leu Ala Ala Gly Arg Pro Gln Val Val Met Pro
290                 295                 300

Arg Leu Asp Asp Gln Phe Asp Asn Ala Gln Ala Leu Ala Ala Ala Asp
305                 310                 315                 320

Ala Ala Leu Leu Val Pro Pro Ser Leu Ala Thr Pro Ala Ala Val Ala
                325                 330                 335

Ala Gly Cys Ala Glu Leu Leu Glu Asn Ala Leu Tyr Ala Lys Ala Ala
            340                 345                 350

Ala Gly Leu Ala Glu Thr Met Ala Leu Leu Pro Ser Pro Ser Ala Ala
            355                 360                 365

Val Gly Pro Leu Glu His Leu Gly Pro Ala Pro Gly Met Leu Arg Ser
370                 375                 380

His Ala Asn Glu Asp Ala Val
385                 390

<210> SEQ ID NO 35
<211> LENGTH: 330
<212> TYPE: PRT
<213> ORGANISM: Streptomyces spiramyceticus WSJ-1

<400> SEQUENCE: 35

Met Ile Ser Glu Val Leu Asn Arg Ser Asn Asp Pro Arg Gly Pro Leu
 1               5                  10                  15

Ile Thr Val Val Gly Ala Ser Gly Phe Ile Gly Ser Ala Leu Val Ala
                 20                  25                  30
```

```
Glu Leu Ala Arg Thr Pro Val Arg Leu Arg Ala Val Ser Arg Arg Glu
        35                  40                  45

Ala Pro Val Pro Ala Gly Thr Pro Ala Ala Val Glu Val Arg Arg Ala
    50                  55                  60

Asp Leu Ala Arg Pro Gly Glu Val Arg Asp Ala Val Glu Gly Ala Asp
65                  70                  75                  80

Ala Val Val His Leu Ala Ala His Ile Gly Gly Ala Gln Ser Trp Arg
                85                  90                  95

Ala Ala Asp Glu Arg Ser Ala Arg Val Asn Val Gly Leu Leu His Asp
            100                 105                 110

Leu Val Asp Ala Phe Arg Gly Arg Ser Gly Thr Leu Pro Ala Val Val
        115                 120                 125

Phe Ala Ser Thr Leu Gln Ala Gly Ala Asp Val Ala Arg Gln Gly Ala
    130                 135                 140

Tyr Ala Arg Gln Lys Ser Ala Ala Glu Glu Val Leu Leu Arg Ala Ala
145                 150                 155                 160

Ser Glu Gly Val Val Arg Gly Val Val Leu Arg Leu Pro Thr Val Tyr
                165                 170                 175

Gly Arg Ser Pro Leu Thr Gly Trp Thr Gly Arg Gly Val Val Ala Ser
            180                 185                 190

Val Ala Arg Arg Ala Val Glu Asp Gly Pro Val Thr Met Trp His Asp
        195                 200                 205

Gly Thr Val Gly Arg Asp Leu Leu His Val Glu Asp Ala Ala Arg Ala
    210                 215                 220

Phe Val Ala Ala Leu Asp His Ala Ala Arg Leu Asp Gly Gly Thr Trp
225                 230                 235                 240

Ser Val Gly Thr Gly Arg Leu Glu Pro Leu Gly Glu Val Phe Ser Thr
                245                 250                 255

Ile Ala Gly Leu Val Ser Glu Arg Thr Gly Arg Pro Pro Val Pro Val
            260                 265                 270

Val Ser Thr Glu Pro Pro Asp His Ala Glu Ala Gly Asp Phe Asp Ser
        275                 280                 285

Pro Val Ser Asp Pro Ser Ala Phe Arg Ala Val Thr Gly Trp Ser Pro
    290                 295                 300

Arg Val Pro Leu Gln Ala Gly Leu Ser Ala Val Val Glu Thr Met Val
305                 310                 315                 320

Ala Ala Glu Ser Arg Gly Gly Ile Arg Gly
                325                 330

<210> SEQ ID NO 36
<211> LENGTH: 335
<212> TYPE: PRT
<213> ORGANISM: Streptomyces spiramyceticus WSJ-1

<400> SEQUENCE: 36

Met Ser Thr Asp Arg Asn Gln Ala Ala His Thr Arg Leu Gly Arg Ser
1               5                   10                  15

Ala Thr Leu Val Ser Arg Leu Trp Leu Gly Thr Val Asn Phe Ser Gly
            20                  25                  30

Arg Val Glu Asp Ala Asp Ala Met His Leu Met Glu Thr Ala Val Asp
        35                  40                  45

Arg Gly Ile Asn Cys Ile Asp Thr Ala Asp Ile Tyr Gly Trp Arg Val
    50                  55                  60

His Lys Gly His Thr Glu Glu Leu Val Gly Arg Trp Leu Ala Lys Ser
```

```
            65                  70                  75                  80
Ala Ala Arg Arg Glu Asp Val Leu Leu Ala Thr Lys Val Gly Gly Asp
                85                  90                  95

Met Ser Glu Arg Leu Asn Asp Gly Gly Leu Ser Ala Arg His Ile Ile
            100                 105                 110

Thr Ala Cys Glu Gln Ser Leu Arg Leu Arg Val Asp His Ile Asp
        115                 120                 125

Leu Tyr Gln Met His Arg Ile Asp His Ala Ala Pro Trp Asp Glu Ile
    130                 135                 140

Trp Gln Ala Met Asp Arg Leu Val Ala Ser Gly Lys Val Thr Tyr Val
145                 150                 155                 160

Gly Ser Ser Asn Phe Ala Gly Trp Asn Val Ala Ala Gln Asp Ala
                165                 170                 175

Ala Arg Arg Arg Ser Leu Gly Leu Val Ser Glu Gln Cys Leu Tyr
            180                 185                 190

Asn Leu Ala Val Arg His Ala Glu Leu Glu Leu Pro Ala Ala Gln
        195                 200                 205

Ala Tyr Gly Leu Gly Val Phe Ala Trp Ser Pro Leu His Gly Gly Leu
    210                 215                 220

Leu Ser Gly Val Leu Arg Lys Leu Ala Ala Gly Thr Ala Val Lys Ser
225                 230                 235                 240

Ala Gln Gly Arg Ala Gln Leu Leu Leu Pro Glu Leu His Ala Thr Ile
                245                 250                 255

Glu Ala Tyr Glu Gly Phe Cys Asp Arg Ile Gly Ala Asp Pro Ala Glu
            260                 265                 270

Val Gly Leu Ala Trp Val Leu Ser Arg Pro Gly Ile Ser Gly Ala Val
        275                 280                 285

Ile Gly Pro Arg Thr Val Glu Gln Leu Asp Ser Ala Leu Arg Ala Leu
    290                 295                 300

Asp Leu Val Leu Gly Glu Ala Glu Leu Ala Glu Leu Asp Ala Ile Phe
305                 310                 315                 320

Pro Ala Leu Gly Asn Gly Gly Arg Ala Pro Asp Ala Trp Ile Ser
                325                 330                 335

<210> SEQ ID NO 37
<211> LENGTH: 410
<212> TYPE: PRT
<213> ORGANISM: Streptomyces spiramyceticus WSJ-1

<400> SEQUENCE: 37

Met Ile Ala Thr Ala Cys Arg Val Cys Gly Asn Lys Glu Leu Leu Ser
1               5                   10                  15

Val Leu Asp Leu Gly Glu Gln Ala Leu Thr Gly Val Phe Pro Thr Ser
            20                  25                  30

Arg Glu Gln Val Val Pro Ser Val Pro Leu Glu Leu Val Val Cys Ser
        35                  40                  45

Pro Ala Gly Cys Gly Leu Val Gln Leu Arg His Thr Pro Asp Pro Asp
    50                  55                  60

Leu Met Tyr Gly Glu Gly Tyr Gly Tyr Arg Ser Gly Ile Arg Pro Phe
65                  70                  75                  80

Met Val Asp His Leu His Gly Lys Val Ala Ala Ile Arg Glu Leu Val
                85                  90                  95

Asp Leu Gly Pro Asp Asp Leu Val Val Asp Ile Gly Ser Asn Asp Ala
            100                 105                 110
```

Thr Leu Leu Ser Gly Tyr Pro Ala Asp Gly Pro Gln Leu Val Gly Ile
            115                 120                 125

Asp Pro Thr Gly Gly Lys Phe Arg Glu Leu Tyr Pro Arg Asn Ala Glu
130                 135                 140

Leu Ile Val Asp Tyr Phe Thr Arg Glu Thr Phe Glu Ser Arg Phe Gly
145                 150                 155                 160

Ala Arg Arg Ala Lys Val Val Thr Ser Ile Ala Met Phe Tyr Asp Leu
                165                 170                 175

Pro Asp Pro Leu Arg Phe Met Ser Asp Val Arg Asp Val Leu Thr Glu
            180                 185                 190

Asp Gly Ile Trp Met Met Glu Gln Ser Tyr Leu Pro Ala Met Leu Glu
        195                 200                 205

Ala Asp Ala Tyr Asp Ile Val Cys His Glu His Leu Glu Tyr Tyr Ala
    210                 215                 220

Leu Arg Gln Ile Glu Trp Met Ala Glu Arg Val Gly Leu Thr Val Ile
225                 230                 235                 240

Arg Ala Glu Leu Thr Glu Val Tyr Gly Gly Ser Leu Cys Val Thr Leu
                245                 250                 255

Ala Arg Ser Gly Ser Gln His Arg Lys Asp Asp Ala Gly Leu Ala Arg
            260                 265                 270

Ile Arg Ala Arg Glu Ala Ala Ala Gly Leu Asp Gly Met Ala Pro Phe
        275                 280                 285

Glu Gly Phe Ala Arg Arg Val Val Asn Gln Arg Gly Ala Leu Arg Asp
    290                 295                 300

Phe Leu Asp Arg Ser Arg Glu Glu Gly Arg Leu Thr Leu Gly Tyr Gly
305                 310                 315                 320

Ala Ser Thr Lys Gly Asn Val Ile Leu Gln Tyr Cys Gly Ile Thr Glu
                325                 330                 335

Arg Asp Leu Pro Cys Ile Gly Glu Val Ser Glu Lys Ala Gly Arg
            340                 345                 350

Phe Thr Pro Gly Thr Ala Ile Pro Ile Val Ser Glu Gln Asp Ala Lys
        355                 360                 365

Ala Gln Lys Pro Asp Gln Leu Leu Val Leu Pro Trp Ile Tyr Arg Asp
    370                 375                 380

Gly Phe Val Glu Arg Glu Arg Asp Phe Leu Asp Gly Gly Arg Leu
385                 390                 395                 400

Ile Phe Pro Leu Pro Ala Leu Asp Val Val
            405                 410

<210> SEQ ID NO 38
<211> LENGTH: 370
<212> TYPE: PRT
<213> ORGANISM: Streptomyces spiramyceticus WSJ-1

<400> SEQUENCE: 38

Met His Arg Asp Asn Ala Ala Glu Pro Leu Val Lys Cys Leu Val Trp
1               5                   10                  15

Asp Leu Asp Asn Thr Leu Trp Gln Gly Thr Leu Leu Glu Glu Asp Glu
            20                  25                  30

Val Arg Leu Thr Pro Asp Val Leu Arg Thr Ile Ala Glu Leu Asp Ala
        35                  40                  45

Arg Gly Ile Leu Gln Ala Val Ala Ser Lys Asn Asp His Asp His Ala
    50                  55                  60

Trp Ala Lys Leu Glu Gln Leu Gly Val Ala Glu Tyr Phe Val Leu Pro
65                  70                  75                  80

```
Gln Ile Gly Trp Gly Pro Lys Ser Lys Ser Val Arg Glu Ile Ala Asp
                85                  90                  95

Arg Leu Asn Phe Ala Leu Gly Thr Leu Ala Phe Ile Asp Asp Gln Pro
            100                 105                 110

Phe Glu Arg Ala Glu Val Thr His Glu Leu Pro Glu Val Arg Thr Tyr
        115                 120                 125

Thr Ala Gly Gln Ala Thr Gly Leu Thr Asp Leu Pro Glu Phe Ser Pro
    130                 135                 140

Asp Thr Val Thr Val Asp Ser Arg Arg Arg Ser Met Tyr Gln Ala
145                 150                 155                 160

Ser Phe Arg Arg Asp Ala Glu Arg Ser Asp Phe Thr Gly Pro Asp Ala
                165                 170                 175

Asp Phe Leu Arg Ser Leu Asp Ile Arg Met Arg Ile Ser Arg Ala Thr
            180                 185                 190

Pro His Glu Leu Ser Arg Val Glu Glu Leu Thr Leu Arg Thr Ser Gln
        195                 200                 205

Met Asn Ala Thr Gly Val His Tyr Ser Glu Asp Asp Leu Arg Ala Leu
    210                 215                 220

Ile Asp Asp Pro Asp His Glu Val Leu Val Thr Thr Val Thr Asp Arg
225                 230                 235                 240

Phe Gly Pro Tyr Gly Ala Val Gly Val Leu Leu Arg Arg Ser Pro
                245                 250                 255

Asp Ala Trp Arg Ile Lys Leu Leu Ala Thr Ser Cys Arg Val Val Ser
            260                 265                 270

Leu Gly Ala Gly Thr Ala Ile Leu Arg Trp Leu Thr Asp Gln Ala His
        275                 280                 285

Arg Ala Gly Val His Leu Gly Ala Asp Phe Arg Ala Thr Glu Arg Asn
    290                 295                 300

Arg Met Met Glu Val Ala Tyr Arg Phe Ala Gly Phe Thr Asp Asp Pro
305                 310                 315                 320

Cys Pro Cys Gln Asp Ala Ser Ala Pro Thr Gly Ala Ile Gly Arg Leu
                325                 330                 335

His Leu Met Pro Ser Pro Gln Pro Thr Pro Asp Thr Leu Arg Leu Glu
            340                 345                 350

Ala Pro Asp Leu Ala Pro Gly Arg Arg Pro Gly Pro Asp Ser Glu Arg
        355                 360                 365

Thr Pro
    370

<210> SEQ ID NO 39
<211> LENGTH: 373
<212> TYPE: PRT
<213> ORGANISM: Streptomyces spiramyceticus WSJ-1

<400> SEQUENCE: 39

Met Ala Asp Ala Pro His Ala Ala Ala Ser Glu Ala Glu Glu Leu Phe
1               5                   10                  15

Thr Glu Leu Val Gly Asp Arg Ala Ala Glu Trp Asp Arg Thr Gly Glu
            20                  25                  30

Leu Pro Leu Ser Leu Leu Arg Asp Leu Gly Ser Arg Gly Leu Leu Cys
        35                  40                  45

Ala Gln Ala Pro Ala Ala His Gly Gly Leu Gly Trp Ser Ser Arg Arg
    50                  55                  60

Asn Gly Glu Leu Thr Ala His Val Gly Ala Leu Cys Ser Ser Leu Arg
```

```
                65                  70                  75                  80
Ser Val Met Thr Ser Gln Gly Met Ala Ala Trp Thr Leu Arg Arg Leu
                    85                  90                  95

Ala Gly Ala Asp Gln Gln Ala Pro Leu Thr Ser Arg Leu Thr Ser Gly
                    100                 105                 110

Glu Leu Ala Ala Val Ala Phe Thr Glu Ala Gly Ala Ser Asp Leu
                    115                 120                 125

Ser Ala Leu Arg Thr Arg Ile Ala Phe Asp Gly Asp Glu Ile Val Val
                130                 135                 140

Asp Gly Val Lys Val Trp Ala Thr Asn Ala Ala Tyr Ala Asp Leu Leu
145                 150                 155                 160

Val Val Phe Gly Arg Thr Glu Glu Gly Ala Gly Ala Val Val Pro
                    165                 170                 175

Ala Ser Ala Pro Gly Val Arg Ile Glu Arg Ile Ala Asp Ala His Gly
                    180                 185                 190

Cys Arg Ala Ala Gly His Ala Asn Ile His Leu Asp Gly Val Arg Leu
                195                 200                 205

Pro Ala Asp Ala Leu Leu Gln Gly His Asp Arg Thr Pro Ala Leu Leu
                210                 215                 220

Val Thr Thr Ala Leu Ser Tyr Gly Arg Met Ser Val Ala Trp Gly Ser
225                 230                 235                 240

Leu Gly Ile Leu Arg Gly Cys Leu Ala Ala Val Arg His Thr Ser
                    245                 250                 255

Gly Arg Glu Gln Phe Gly Thr Arg Leu Ser Glu His Gln Leu Val Ala
                260                 265                 270

Arg His Leu Ala Glu Leu Phe Ile Ala Glu Gln His Ala Ala Arg Ala
                275                 280                 285

Cys Glu Tyr Ala Ser Ala Gln Trp Asp Glu Gly Ser Pro Asp Met Val
                290                 295                 300

Ile Ala Ala Val Leu Ala Lys His Val Ala Ala Thr Gly Ala Ala Arg
305                 310                 315                 320

Gly Ala Glu Arg Ala Val Gln Val Leu Ala Ser Ala Gly Ala Arg Asp
                    325                 330                 335

Gly His Val Val Ala Arg Ala His Arg Asp Ala Lys Leu Met Glu Ile
                340                 345                 350

Ile Glu Gly Ser Asn Glu Ile Cys Glu Leu Ile Leu Ala Arg His Ala
                355                 360                 365

Val Ser Ala Ala Gly
        370

<210> SEQ ID NO 40
<211> LENGTH: 106
<212> TYPE: PRT
<213> ORGANISM: Streptomyces spiramyceticus WSJ-1

<400> SEQUENCE: 40

Met Thr Thr Thr Ser Gly Arg Pro Asp Ser Thr Gly Thr Thr Pro Ala
1               5                   10                  15

Asp Asp Glu Val Ala Glu Glu Leu Leu Gly Phe Leu Ala Ala Asn Thr
                20                  25                  30

Lys Thr Thr Trp Glu Arg Asp Gln Asp Leu Phe Ala Val Gly Gly Met
                35                  40                  45

Ser Ser Leu Phe Ala Met Gln Leu Val Val His Leu Glu Lys Thr His
        50                  55                  60
```

```
Gly Ile Val Ile Ser Gly Ala Asp Leu Met Leu Asp Asn Phe Arg Thr
 65                  70                  75                  80

Val Asp Ala Met Val Arg Leu Val Gly Arg Leu Ala Ala Pro Gly Pro
                 85                  90                  95

Thr Gly Glu Ala Thr Gly Pro Ala Gly Gly
            100                 105

<210> SEQ ID NO 41
<211> LENGTH: 288
<212> TYPE: PRT
<213> ORGANISM: Streptomyces spiramyceticus WSJ-1

<400> SEQUENCE: 41

Met Pro Asn Ser Asn Glu Asn Ser Pro Leu Val Val Leu Gly Ala Gly
  1               5                  10                  15

Val Met Gly Thr Ala Ile Ala Ala Leu Ala Val Gly His Gly His Pro
                 20                  25                  30

Val Thr Leu Ile Asp Thr Ser Val Glu Ala Arg Ala Ala Ala Pro Asp
                 35                  40                  45

Thr Val Ala Leu His Leu Arg Thr Ala Arg Leu Met Gly Ala Leu Pro
 50                  55                  60

His Asp Arg Pro Pro Gly Glu Leu Thr Val Glu Asp Ala Leu Asn Ala
 65                  70                  75                  80

Ile Ala Ala Val Thr Ala Val Ile Glu Ala Val Thr Glu Asp Pro Lys
                 85                  90                  95

Arg Lys Ala Glu Val Leu Ala Asp Leu Ala Ser Ala Ala Arg Pro Gly
                100                 105                 110

Thr Leu Leu Ile Ser Asn Thr Ser Gly Val Pro Ile Asp Glu Leu Ala
                115                 120                 125

Asp Ala Val Pro Arg Pro Glu Asp Leu Val Gly Val His Phe Met Asn
                130                 135                 140

Pro Ala Tyr Val Ile Arg Thr Val Glu Val Val Leu Gly Pro Arg Ser
145                 150                 155                 160

Gly Glu Ala Ala Ala Glu Ser Thr Arg Glu Leu Leu Ser Gly Leu Gly
                165                 170                 175

Arg Arg Gly Ile Val Val Gly Asp Gly Ala Gly Phe Val Thr Ser Arg
                180                 185                 190

Leu Leu His Arg Met Leu Asn Asp Ala Ile Ala Val Val His Glu Gly
                195                 200                 205

Arg Ala Thr Pro Glu Thr Val Asp Ala Leu Met Arg Asp Cys Ile Gly
                210                 215                 220

His Arg Thr Gly Pro Leu Ala Thr Ala Asp Leu Ile Gly Leu Asp Asn
225                 230                 235                 240

Leu Ala Asp Ser Leu Arg Val Met His Glu Arg Thr Gly Asp Pro Ala
                245                 250                 255

Leu Arg Pro Ser Glu Leu Leu Leu Asp Lys Val Arg Gln Gly Leu Leu
                260                 265                 270

Gly Arg Lys Ser Gly Arg Gly Phe Tyr Asp Tyr Gln Glu Thr Met Gln
                275                 280                 285

<210> SEQ ID NO 42
<211> LENGTH: 405
<212> TYPE: PRT
<213> ORGANISM: Streptomyces spiramyceticus WSJ-1

<400> SEQUENCE: 42
```

```
Met Ala His Ile Ala Phe Phe Ile Leu Pro Val Ala Gly His Val Asn
 1               5                  10                 15
Pro Thr Leu Gly Val Ala Glu Glu Leu Val Ala Arg Gly His Arg Val
             20                  25                  30
Thr Tyr Ala Leu Ser Gly Glu Leu Ala Glu Arg Ala Arg Leu Ile Gly
             35                  40                  45
Ala Glu Val Val Thr Tyr Pro Val Asp Lys Gln Arg Phe Leu Asp Gln
 50                  55                  60
Met Val Pro Arg Gln Asp Ala Asp Glu Tyr Thr Asp Glu Gly Glu Phe
 65                  70                  75                  80
Val Arg Val Leu Glu Trp Leu Leu Asp Met Thr Ala Gln Thr Leu Glu
             85                  90                  95
Pro Leu Glu Arg His Phe Ala Glu Asn Arg Pro Asp Val Val Val Asn
            100                 105                 110
Asp Pro Ser Ser Leu Trp Thr Gly Arg Leu Leu Ala Asp Arg Trp Asp
            115                 120                 125
Ile Pro Val Ile Arg Ser Thr Pro Thr Tyr Ala Ala Asn Glu His Trp
            130                 135                 140
Ser Leu His Pro Pro Val Asp Ser Ala Glu Pro Pro Asp Asp Pro Glu
145                 150                 155                 160
Leu His Lys Leu Leu Ala Arg Ile Glu Arg Leu Leu Glu Glu Gln Gly
                165                 170                 175
Val Glu His Asp Leu Ala Ala Phe Thr Gly Val Leu His Gly Gly Pro
                180                 185                 190
Ala Leu Leu Tyr Met Pro Arg Ser Phe Gln Tyr Ala Gly Glu Thr Phe
                195                 200                 205
Asp Glu Gln His His Phe Val Gly Pro Cys Pro Pro Arg Thr Ala Phe
            210                 215                 220
His Gly Glu Trp Thr Pro Thr Asp Asp Gly Arg Pro Leu Val Leu
225                 230                 235                 240
Val Ser Leu Gly Thr Leu Tyr Asn Asp Arg Pro Asp Phe Phe Arg Thr
                245                 250                 255
Cys Leu Glu Ala Phe Arg Asp Glu Pro Trp Asn Val Leu Leu Val Leu
            260                 265                 270
Gly Gly Gly Val Pro Ala Ala Asp Leu Gly Pro Leu Pro Asp Asn Val
            275                 280                 285
Arg Val His Asp Phe Val Ser Leu Arg Asp Val Leu Pro His Thr Ala
            290                 295                 300
Val Val Val Asn His Gly Gly Met Ser Thr Ala Met Glu Val Phe Ser
305                 310                 315                 320
His Glu Val Pro Val Ala Ile Pro Val Met Pro Glu Pro Arg Ala
                325                 330                 335
Thr Ala Arg Arg Ile Val Glu Leu Gly Leu Gly Asp Gln Leu Leu Asn
            340                 345                 350
Ser Glu Leu Thr Ala Glu Ser Leu Arg Ala Thr Val Arg Arg Val Leu
            355                 360                 365
Glu Asp Ser Arg Ile Pro Ala Asn Met Arg Lys Ile Arg Glu Gln Ile
            370                 375                 380
Thr Ala Ala Gly Gly Ala Asn Ala Ala Asp Ala Val Glu Gly Leu
385                 390                 395                 400
Leu Pro Gln Gly Ser
            405
```

<210> SEQ ID NO 43
<211> LENGTH: 202
<212> TYPE: PRT
<213> ORGANISM: Streptomyces spiramyceticus WSJ-1

<400> SEQUENCE: 43

Met Leu Ile Thr Glu Thr Thr Val Pro Asp Val Phe Arg Ile Asp Pro
1               5                   10                  15

Glu Pro Ile Pro Asp His Arg Gly Arg Phe Tyr Glu Ala Val Arg Gln
            20                  25                  30

Arg Pro Leu Glu Ala Ala Val Gly His Ser Ile Ala Val Arg Gln Val
        35                  40                  45

Asn Phe Thr Val Ser Gly Arg Asn Val Leu Arg Gly Leu His Ala Thr
    50                  55                  60

Thr Leu Pro Pro Gly Gln Gly Lys Ile Leu Thr Cys Val Arg Gly Ser
65                  70                  75                  80

Val Leu Thr Met Val Val Asp Met Arg Val Gly Ser Pro Ser Phe Gly
                85                  90                  95

Arg Tyr Glu Ala Val Arg Gln Asp Pro Arg Ser Gly Thr Ala Leu Tyr
            100                 105                 110

Leu Pro Asp Gly Ile Gly Leu Gly Tyr Val Ala Leu Val Asp Asp Thr
        115                 120                 125

Cys Met Asn Tyr Leu Cys Thr His Glu Tyr Val Pro Gly Met Val Ile
    130                 135                 140

Asp Val Asp Ala Leu Asp Pro Glu Leu Asp Leu Pro Trp Asp Leu Ala
145                 150                 155                 160

Asp Thr Pro Ile Arg Ser Ala Arg Asp Ala Ala Ala Pro Ser Leu Arg
                165                 170                 175

Ala Ala Val Ser Ala Gly Ile Leu Pro Thr Tyr Glu Glu Cys Leu Arg
            180                 185                 190

Val Arg Glu Pro Leu Pro Ala Ala Leu Asp
        195                 200

<210> SEQ ID NO 44
<211> LENGTH: 390
<212> TYPE: PRT
<213> ORGANISM: Streptomyces spiramyceticus WSJ-1

<400> SEQUENCE: 44

Met Lys Phe Arg Thr Leu Glu Pro Ala Gly Thr Ala Pro Leu Thr Gly
1               5                   10                  15

Pro Ala Ala Gly His Asp Phe Asp Ser Leu Val Ser Glu Gly Cys Ala
            20                  25                  30

Glu Leu Leu Gly Ser Leu Arg Arg Ala Asp Gln Arg Arg Arg Gly Glu
        35                  40                  45

Gln Tyr Ile Arg Gly Leu Leu Thr Ala Gln Gly Arg Lys Thr Ala Arg
    50                  55                  60

Asn Leu Ala Ala Phe Val Gly Glu Gly Ala Ala Glu Gln Ser Leu His
65                  70                  75                  80

His Phe Val Ala Gly Ser Thr Trp Asp Trp Gly Ala Val Arg Ala Ala
                85                  90                  95

Leu Ala Arg Tyr Val Asp Asp Arg Leu Asn Pro Glu Ala Trp Val Ile
            100                 105                 110

Trp Pro Met Val Val Ser Lys Ala Gly Val Arg Ser Val Gly Val Ser
        115                 120                 125

Arg Arg Phe Val Pro Asp Leu Gly Arg Val Val Ser Cys Gln Gln Ser

```
            130                 135                 140
His Gly Leu Trp Leu Ala Ser Gly Ala Thr Ala Ala Pro Val Ser Trp
145                 150                 155                 160

His Leu Thr Leu Gly Gly Arg Gly Asp Gly Gly Ser Arg Gln
            165                 170                 175

Leu Gly Ala Pro Gly Ala Leu Gly Glu Glu Asn Val Val Arg Leu
            180                 185                 190

Val Ala Glu Ala Ala Gln Ala Ser Arg Thr Ser Ala Arg Pro Val Val
            195                 200                 205

Met Asp Ala Arg Ala Ala Val Leu Pro Arg Leu Val Arg Gly Leu Ser
210                 215                 220

Leu Val Gly Leu Pro Phe Met Val Arg Val Gly Asn Leu Gln Leu
225                 230                 235                 240

Ala Ser Ala Gly Gly Arg Gly Leu Val Asp His His Thr Ala Thr Thr
            245                 250                 255

Ser Ala Gln Gln Leu Met Glu Gln Met Lys Arg Leu Ser Arg Pro Val
            260                 265                 270

Glu Trp Gln Gly Ser Leu Ser Leu Val Ala Pro His Ala Val Val Leu
            275                 280                 285

Pro Gly Val Val Pro Arg Arg Thr Leu Val Leu Met Gly Val Trp Arg
290                 295                 300

Gly Asn Arg Arg Pro Ala Asp Leu Trp Leu Thr Asp Leu Thr Ser
305                 310                 315                 320

Trp Asp Arg Gly Ala Leu Leu Arg Leu Ala Met Leu Thr Glu Gln Val
            325                 330                 335

Asp Ala Asp Phe Glu Arg Val Ser Val Gly Val Gly Met Arg Asp Phe
            340                 345                 350

Glu Gly Arg Ser Phe Gln Gly Trp His Arg His Val Thr Leu Ala Ser
            355                 360                 365

Ile Ala His Thr Leu Arg Leu Ala Gln Pro Ser Ala Arg Val Asp Phe
            370                 375                 380

Arg Gly Val Ala Ala Val
385                 390

<210> SEQ ID NO 45
<211> LENGTH: 269
<212> TYPE: PRT
<213> ORGANISM: Streptomyces spiramyceticus WSJ-1

<400> SEQUENCE: 45

Met Thr Glu Leu Asp Thr Ile Ala Asn Pro Ser Asp Pro Ala Val Gln
1               5                   10                  15

Arg Ile Ile Asp Val Thr Lys Pro Ser Arg Ser Asn Ile Lys Thr Thr
            20                  25                  30

Leu Ile Glu Asp Val Glu Pro Leu Met His Ser Ile Ala Ala Gly Val
            35                  40                  45

Glu Phe Ile Glu Val Tyr Gly Ser Asp Ser Ser Pro Phe Pro Ser Glu
            50                  55                  60

Leu Leu Asp Leu Cys Gly Arg Gln Asn Ile Pro Val Arg Leu Ile Asp
65                  70                  75                  80

Ser Ser Ile Val Asn Gln Leu Phe Lys Gly Glu Arg Lys Ala Lys Thr
                85                  90                  95

Phe Gly Ile Ala Arg Val Pro Arg Pro Ala Arg Phe Gly Asp Ile Ala
            100                 105                 110
```

```
Ser Arg Arg Gly Asp Val Val Leu Asp Gly Val Lys Ile Val Gly
            115                 120                 125

Asn Ile Gly Ala Ile Val Arg Thr Ser Leu Ala Leu Gly Ala Ser Gly
130                 135                 140

Ile Ile Leu Val Asp Ser Asp Ile Thr Ser Ile Ala Asp Arg Leu
145                 150                 155                 160

Gln Arg Ala Ser Arg Gly Tyr Val Phe Ser Leu Pro Val Val Leu Ser
            165                 170                 175

Gly Arg Glu Glu Ala Ile Ala Phe Ile Arg Asp Ser Gly Met Gln Leu
            180                 185                 190

Met Thr Leu Lys Ala Asp Gly Asp Ile Ser Val Lys Glu Leu Gly Asp
            195                 200                 205

Asn Pro Asp Arg Leu Ala Leu Leu Phe Gly Ser Glu Lys Gly Gly Pro
210                 215                 220

Ser Asp Leu Phe Glu Glu Ala Ser Ser Ala Ser Val Ser Ile Pro Met
225                 230                 235                 240

Met Ser Gln Thr Glu Ser Leu Asn Val Ser Val Ser Leu Gly Ile Ala
            245                 250                 255

Leu His Glu Arg Ile Asp Arg Asn Leu Ala Ala Asn Arg
            260                 265

<210> SEQ ID NO 46
<211> LENGTH: 388
<212> TYPE: PRT
<213> ORGANISM: Streptomyces spiramyceticus WSJ-1

<400> SEQUENCE: 46

Met Pro Leu Pro Lys His Leu Pro Ala Leu Gly Gly Met Arg Phe Ile
1               5                   10                  15

Ser Ala Leu Leu Val Phe Thr Ser His Ile Ser Thr Gln Pro Phe Phe
            20                  25                  30

Lys Asn Thr Glu Ile Asn Ser Ala Leu Gln Phe Pro Leu Asn Arg Leu
        35                  40                  45

Gly Pro Leu Thr Val Ser Phe Phe Met Leu Ser Gly Phe Val Leu
    50                  55                  60

Thr Trp Ala Gly Leu Pro Asp Lys Ser Lys Val Asn Phe Trp Arg Arg
65                  70                  75                  80

Arg Thr Val Arg Ala Tyr Ser Leu His Leu Pro Val Leu Leu Val Thr
                85                  90                  95

Leu Leu Ile Val Leu Ala Leu Asn Glu Pro Asn Met Gly Arg Ser Val
            100                 105                 110

Trp Asp Gly Leu Leu Thr Asn Leu Leu Ile Gln Ala Trp Phe Pro
        115                 120                 125

Asp His His Glu Tyr Gly Ser Met Asn Pro Val Ala Trp Ser Leu Ser
130                 135                 140

Cys Glu Leu Phe Phe Tyr Ala Met Phe Pro Phe Leu Phe Ala Phe
145                 150                 155                 160

Thr Lys Val Arg Thr Asp Arg Leu Trp Arg Trp Ala Ala Val Ser
                165                 170                 175

Val Ala Ala Val Ser Ile Pro Leu Val Ala Leu Leu Pro Ala Ser
            180                 185                 190

Pro Pro Leu Pro Trp Asp Pro Asp Met Pro Gln Leu Arg Trp Trp Phe
            195                 200                 205

Ile Tyr Met Phe Pro Pro Val Arg Leu Leu Glu Phe Val Leu Gly Met
210                 215                 220
```

```
Leu Met Ala Gln Ile Val Ile Arg Gly Arg Trp Arg Gly Pro Arg Pro
225             230                 235             240

Leu Ala Cys Val Ala Leu Phe Ser Ala Val Phe Ala Val Thr Phe Ala
                245                 250                 255

Val Pro Asn His Tyr Asp Pro Gly Ala Leu Thr Val Pro Val Ile Ala
            260                 265             270

Leu Leu Leu Ala Ser Val Ala Val Gly Asp Val Arg Gly Val Arg Ser
            275             280             285

Trp Leu Gly Thr Arg Thr Met Val Leu Leu Gly Glu Leu Thr Phe Ala
        290             295             300

Phe Tyr Leu Val His Tyr Leu Ile Ile Gln Tyr Gly His Arg Phe Ala
305             310             315             320

Gly Gly Lys Gln Gly Tyr Tyr Arg Gln Trp Asp Thr Pro Ala Ala Val
            325             330             335

Gly Leu Thr Leu Leu Ala Phe Thr Leu Ala Leu Gly Gln Ser Ala Phe
            340             345             350

Leu His Phe Phe Val Glu Lys Pro Val Met Arg Thr Leu Gly Arg Pro
        355             360             365

Arg Arg Ser Pro Asp Ala Gly Ser Thr Pro Arg Ser Glu Pro Ala Pro
    370             375             380

Ser Gly Thr Pro
385
```